(12) United States Patent
No et al.

(10) Patent No.: US 10,672,993 B2
(45) Date of Patent: Jun. 2, 2020

(54) NITROGEN-CONTAINING POLYCYCLIC COMPOUND AND ORGANIC LIGHT EMITTING ELEMENT USING SAME

(71) Applicant: LT MATERIALS CO., LTD., Yongin, Gyeonggi-do (KR)

(72) Inventors: Young-Seok No, Osan (KR); Kee-Yong Kim, Suwon (KR); Hyo-Kyun Ham, Osan (KR); Jin-Seok Choi, Suwon (KR); Dae-Hyuk Choi, Yongin (KR); Sung-Jin Eum, Yongin (KR); Joo-Dong Lee, Seongnam (KR)

(73) Assignee: LT MATERIALS CO., LTD., Yongin-si, Gyeonggi-do (KR)

( * ) Notice: Subject to any disclaimer, the term of this patent is extended or adjusted under 35 U.S.C. 154(b) by 0 days.

(21) Appl. No.: 16/035,360

(22) Filed: Jul. 13, 2018

(65) Prior Publication Data
US 2018/0323380 A1 Nov. 8, 2018

Related U.S. Application Data

(62) Division of application No. 15/523,155, filed as application No. PCT/KR2015/011526 on Oct. 29, 2015, now Pat. No. 10,177,319.

(30) Foreign Application Priority Data

Oct. 29, 2014 (KR) .................. 10-2014-0148633

(51) Int. Cl.
| | |
|---|---|
| *C07D 221/20* | (2006.01) |
| *C07D 401/14* | (2006.01) |
| *C09K 11/06* | (2006.01) |
| *H05B 33/14* | (2006.01) |
| *H01L 51/50* | (2006.01) |
| *H01L 51/52* | (2006.01) |
| *H01L 51/00* | (2006.01) |
| *C07F 9/6512* | (2006.01) |
| *C07F 9/6521* | (2006.01) |
| *C07D 221/12* | (2006.01) |
| *C07D 401/10* | (2006.01) |
| *C07D 405/10* | (2006.01) |
| *C07D 413/10* | (2006.01) |
| *C07D 417/10* | (2006.01) |
| *C07D 471/04* | (2006.01) |
| *C07D 491/048* | (2006.01) |
| *C07D 491/147* | (2006.01) |
| *C07D 495/04* | (2006.01) |
| *C07D 495/14* | (2006.01) |
| *C07F 7/08* | (2006.01) |
| *C07F 9/576* | (2006.01) |

(52) U.S. Cl.
CPC ........ *H01L 51/0072* (2013.01); *C07D 221/12* (2013.01); *C07D 221/20* (2013.01); *C07D 401/10* (2013.01); *C07D 401/14* (2013.01); *C07D 405/10* (2013.01); *C07D 413/10* (2013.01); *C07D 417/10* (2013.01); *C07D 471/04* (2013.01); *C07D 491/048* (2013.01); *C07D 491/147* (2013.01); *C07D 495/04* (2013.01); *C07D 495/14* (2013.01); *C07F 7/0814* (2013.01); *C07F 9/5765* (2013.01); *C07F 9/6512* (2013.01); *C07F 9/6521* (2013.01); *C09K 11/06* (2013.01); *H01L 51/007* (2013.01); *H01L 51/0052* (2013.01); *H01L 51/0058* (2013.01); *H01L 51/0067* (2013.01); *H01L 51/0069* (2013.01); *H01L 51/0073* (2013.01); *H01L 51/0094* (2013.01); *H01L 51/50* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 51/5206* (2013.01); *H01L 51/5221* (2013.01)

(58) Field of Classification Search
CPC .... C07D 221/12; C07D 401/10; C09K 11/06; H05B 33/14; H01L 51/5032; H01L 51/5064; H01L 51/5296; H01L 51/0032
USPC ................ 546/18, 14, 21; 257/40, E51.019; 313/501; 428/917
See application file for complete search history.

(56) References Cited

U.S. PATENT DOCUMENTS 10,177,319 B2 * 1/2019 No ....................... C07D 221/12

FOREIGN PATENT DOCUMENTS

| KR | 10-2009-0131536 A | 12/2009 |
|---|---|---|
| KR | 10-2011-0002156 A | 1/2011 |
| KR | 10-2011-0052960 A | 5/2011 |
| KR | 10-2012-0122897 A | 11/2012 |
| KR | 10-2014-0087250 A | 7/2014 |

OTHER PUBLICATIONS

Atzrodt et al., Agnew; Chem. Int. Ed. 2007, 46, 7744-7765.
International Search Report (PCT/ISA/210) issued in PCT/KR2015/011526, dated Jun. 20, 2016.
Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials", Advanced Materials vol. 8 No. 9, 1994 pp. 677-679.

* cited by examiner

*Primary Examiner* — Venkataraman Balasubramanian
(74) *Attorney, Agent, or Firm* — Birch, Stewart, Kolasch & Birch, LLP

(57) ABSTRACT

The present application relates to a polycyclic compound including nitrogen and an organic light emitting device including the same.

16 Claims, 9 Drawing Sheets

[Figure 1]
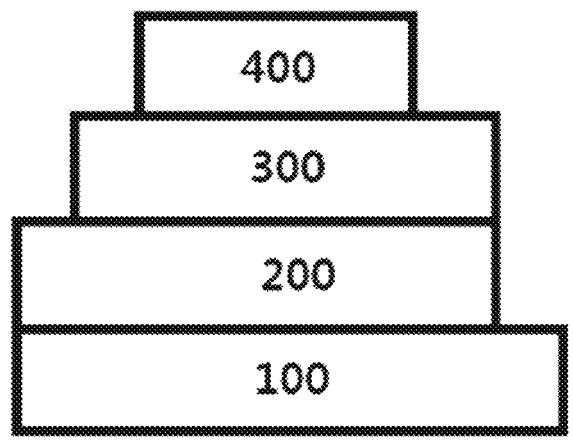
[Figure 2]
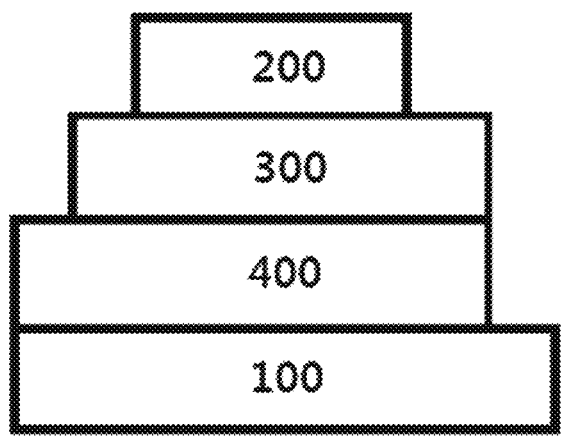

[Figure 3]
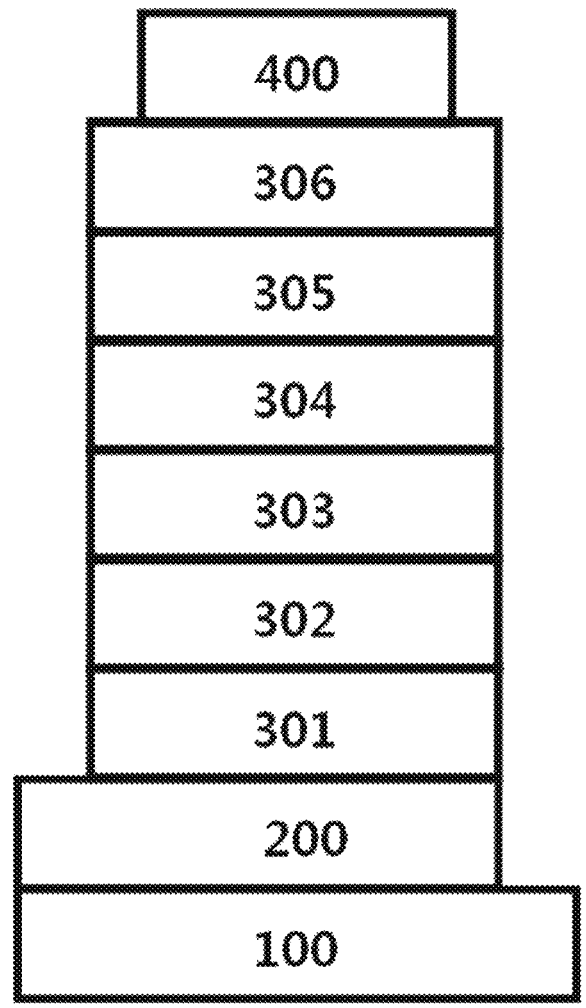

[Figure 4]
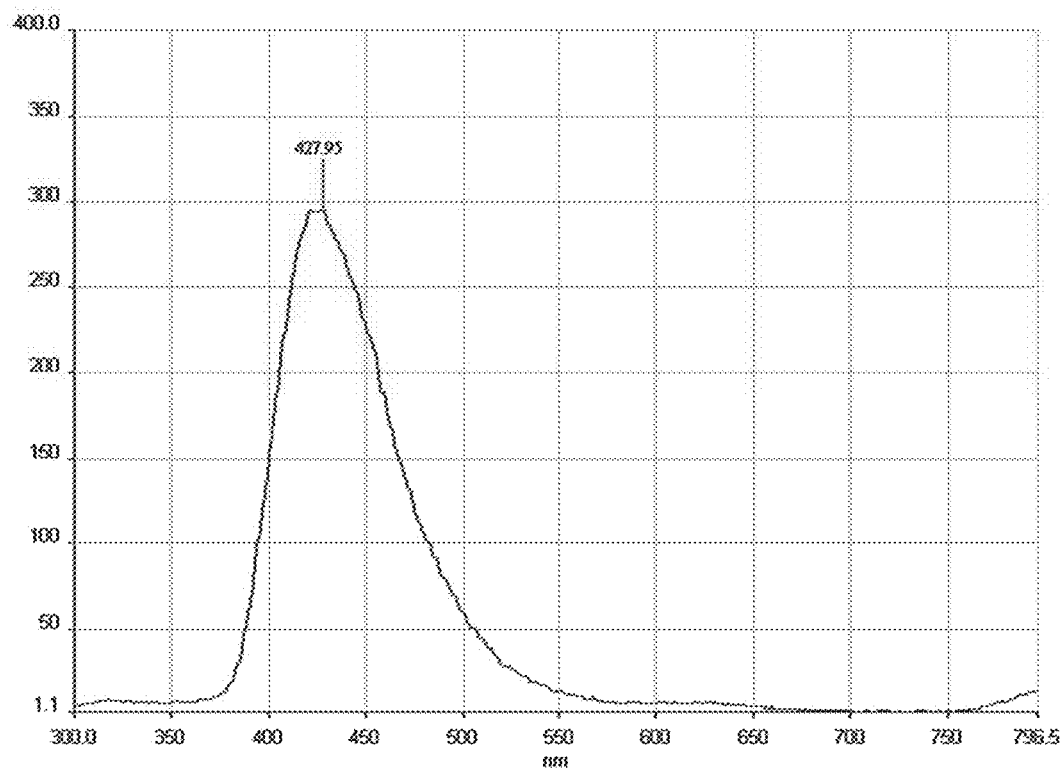
[Figure 5]
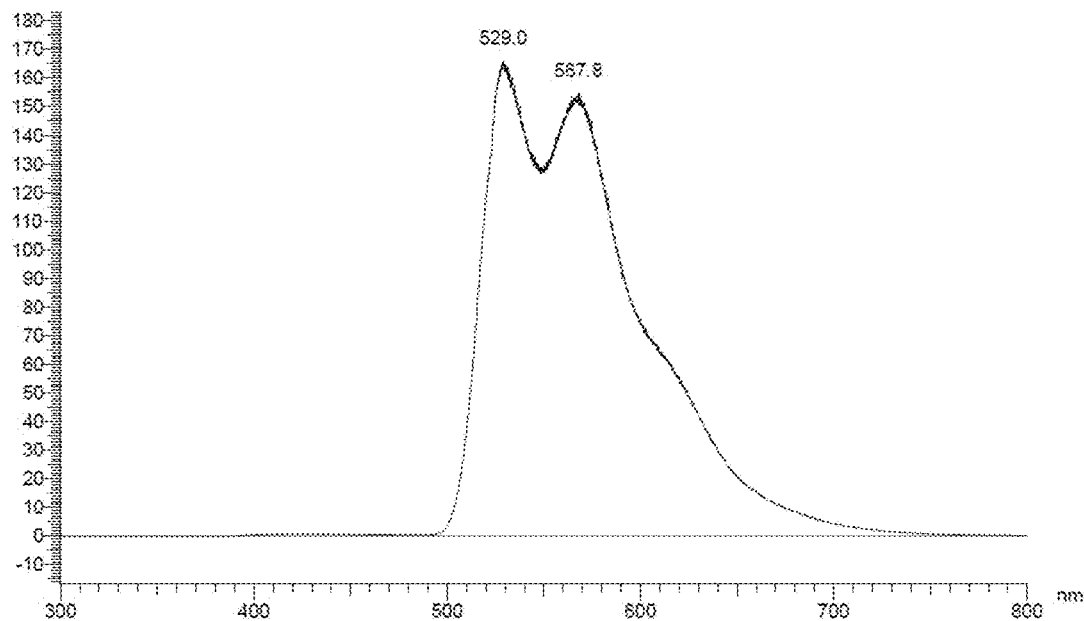

[Figure 6]
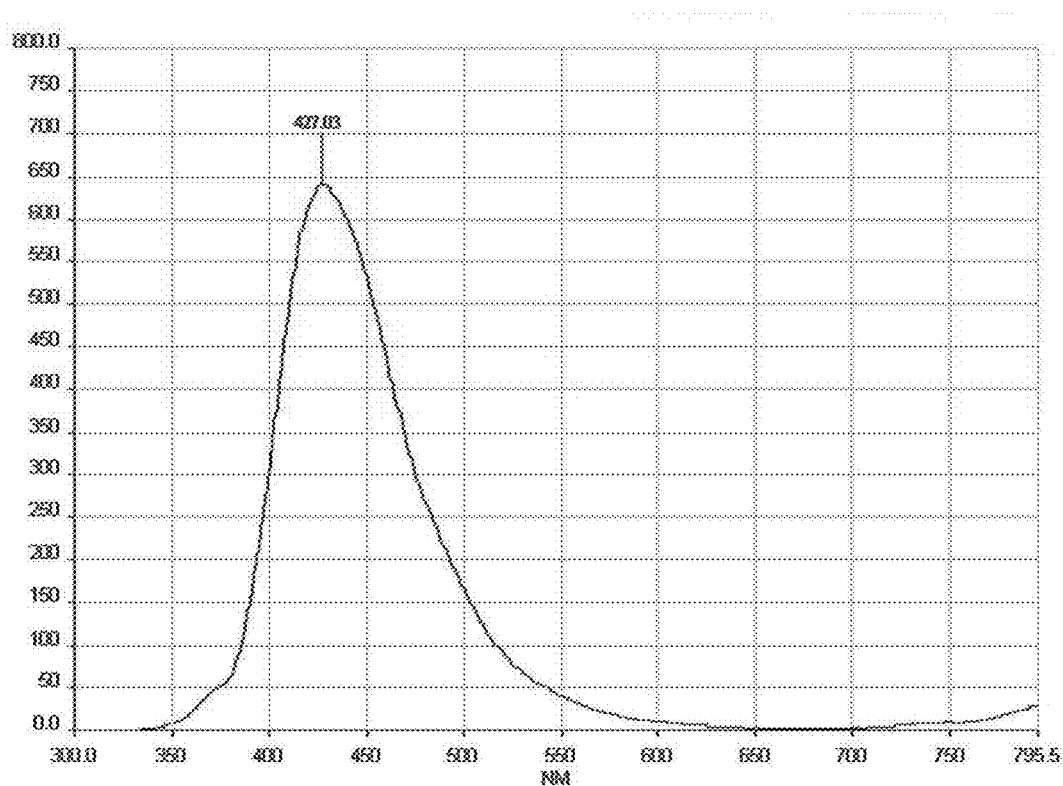
[Figure 7]
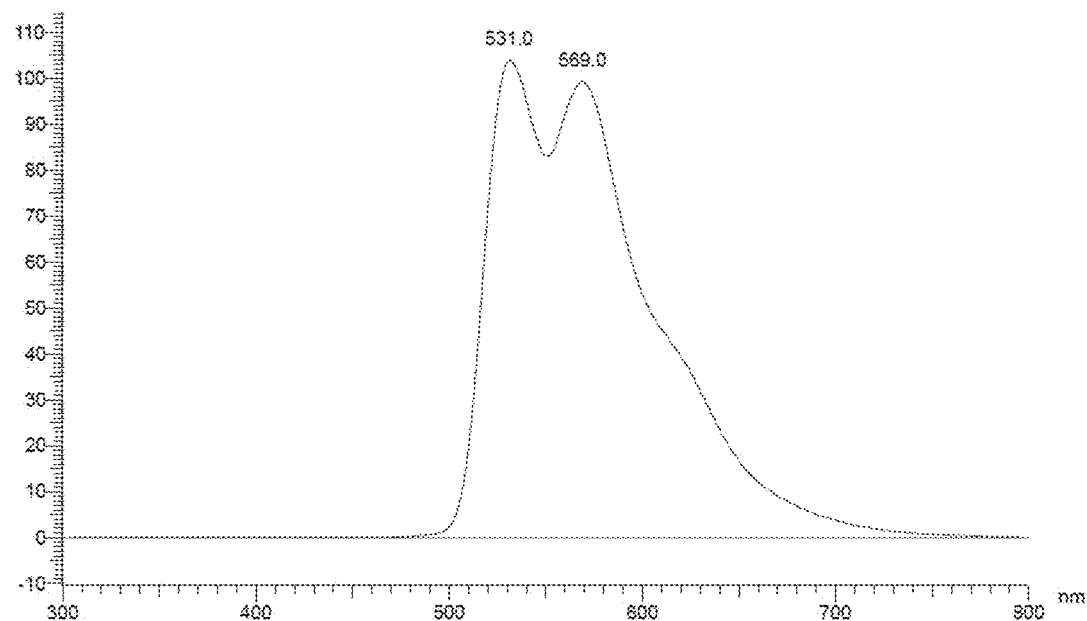

[Figure 8]
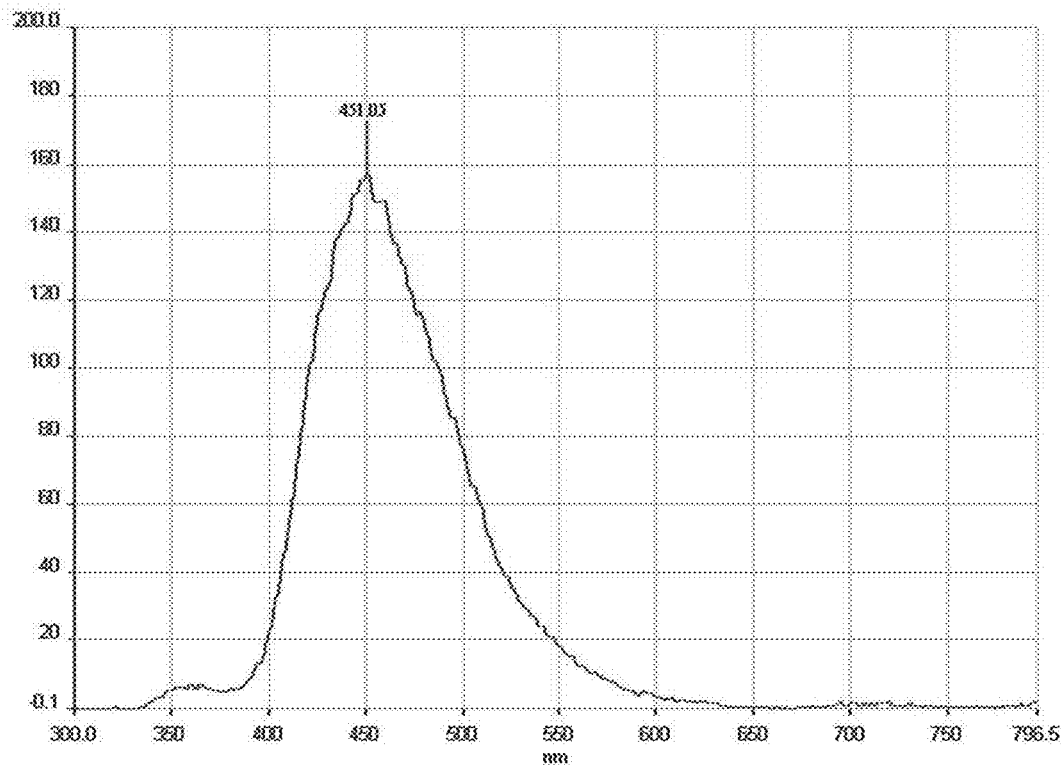
[Figure 9]
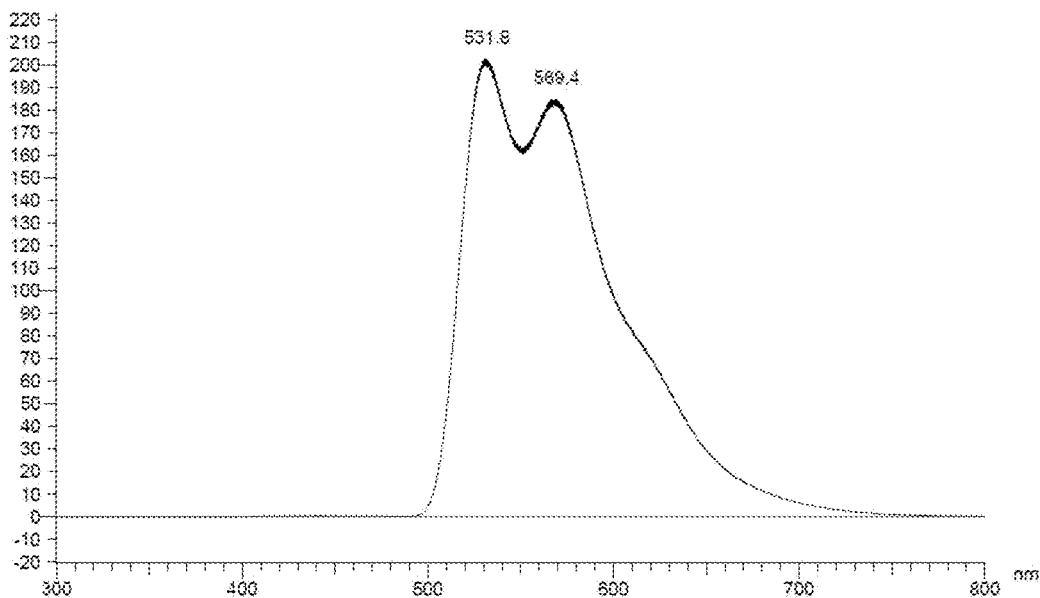

[Figure 10]
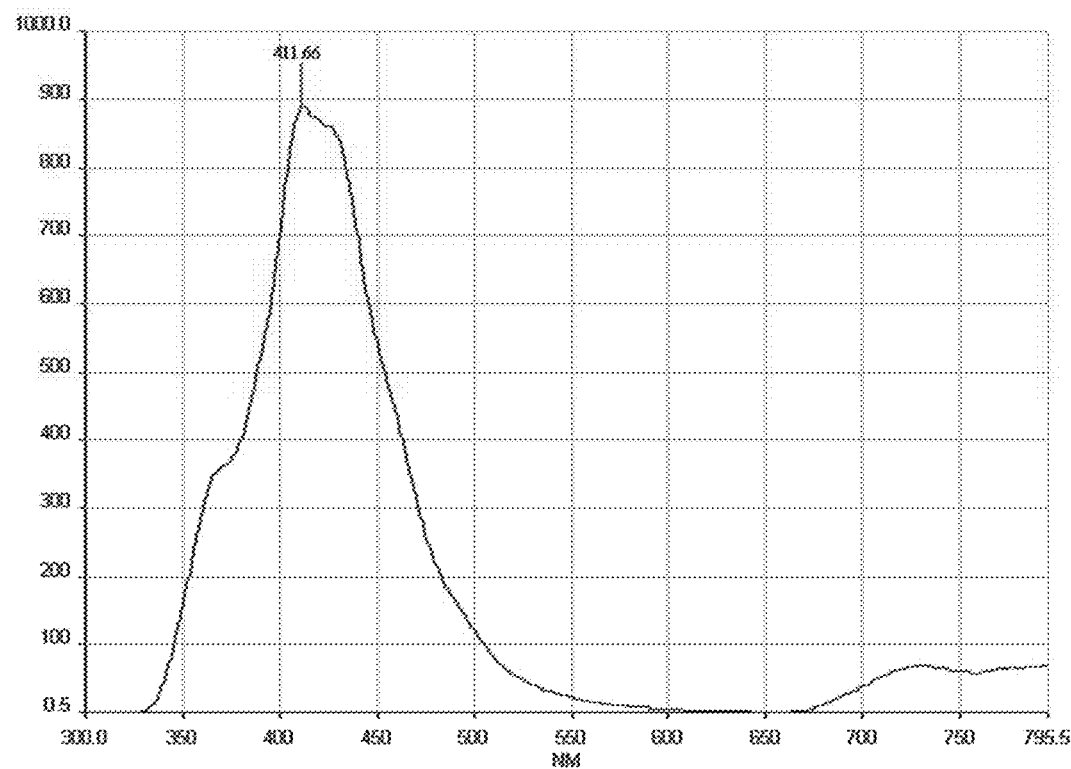
[Figure 11]
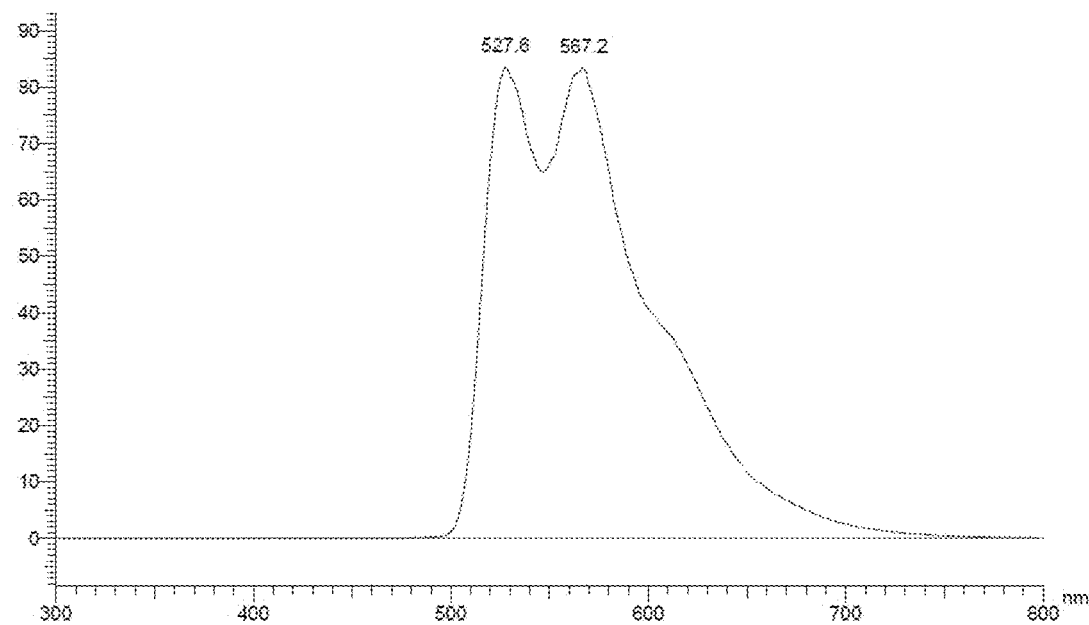

[Figure 12]
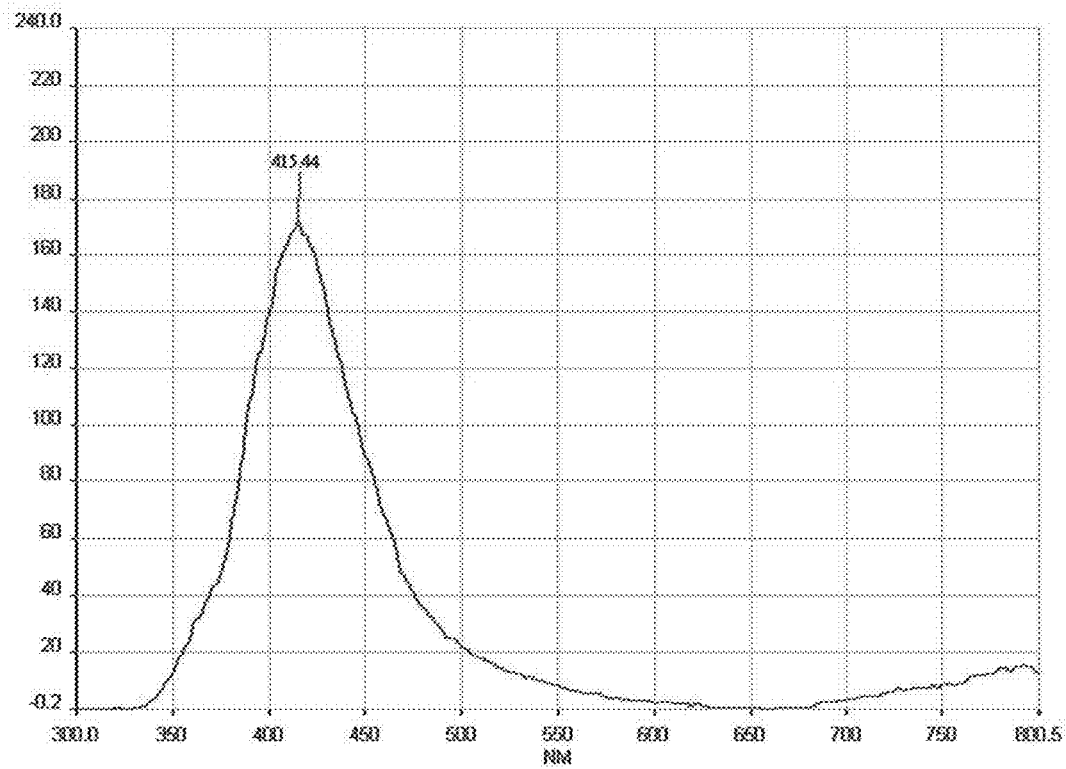
[Figure 13]
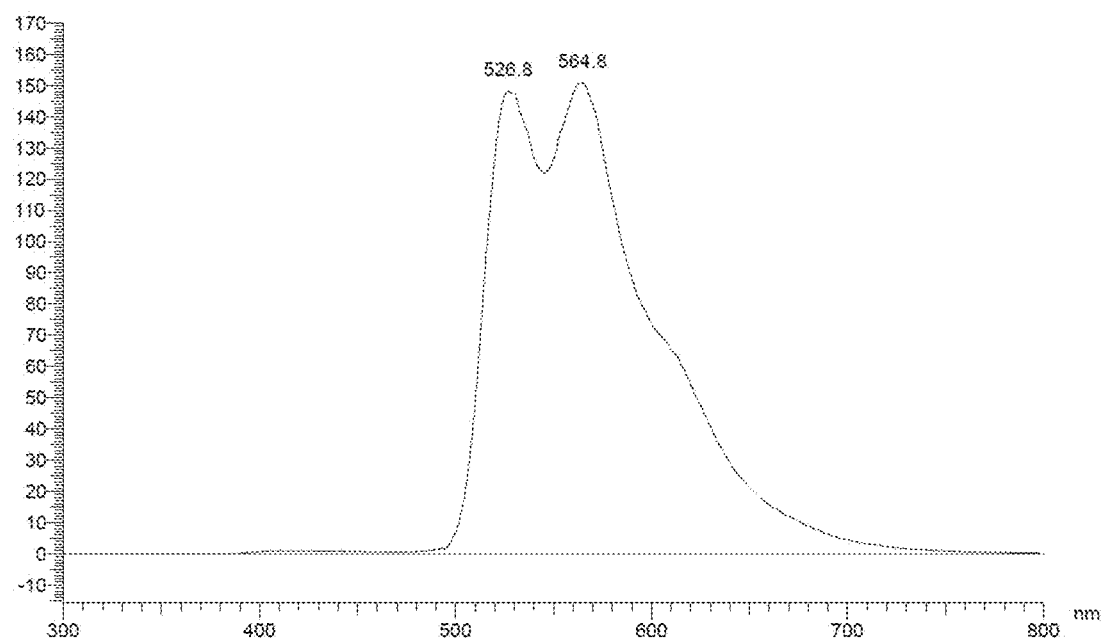

[Figure 14]
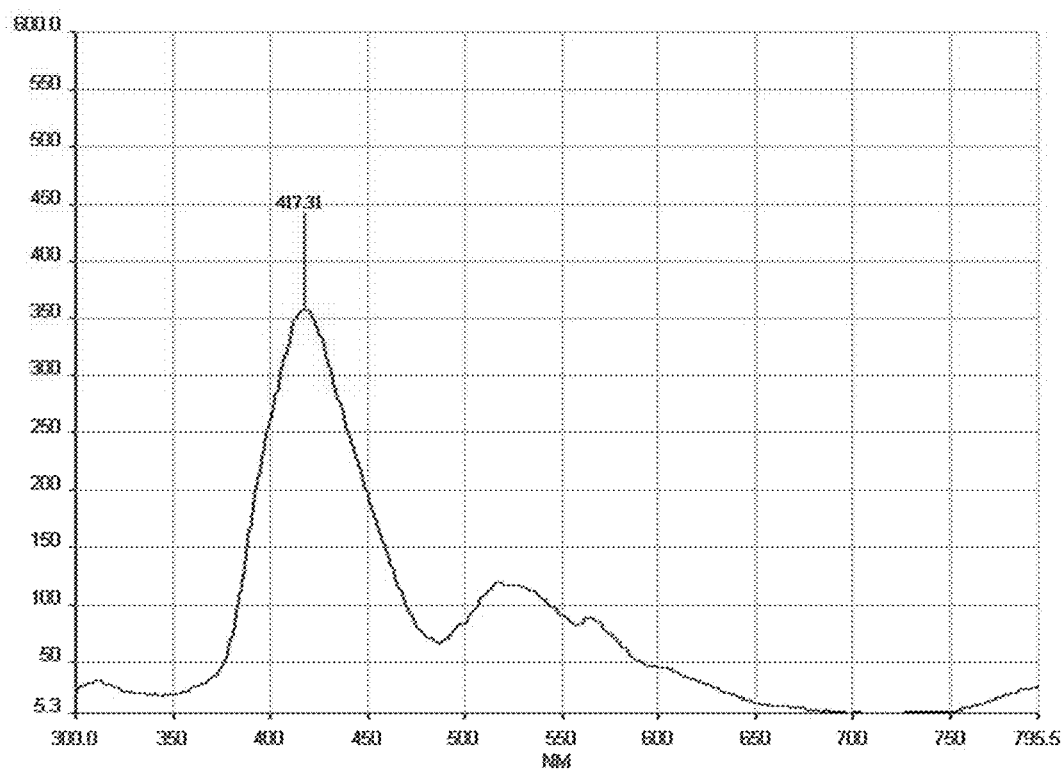
[Figure 15]
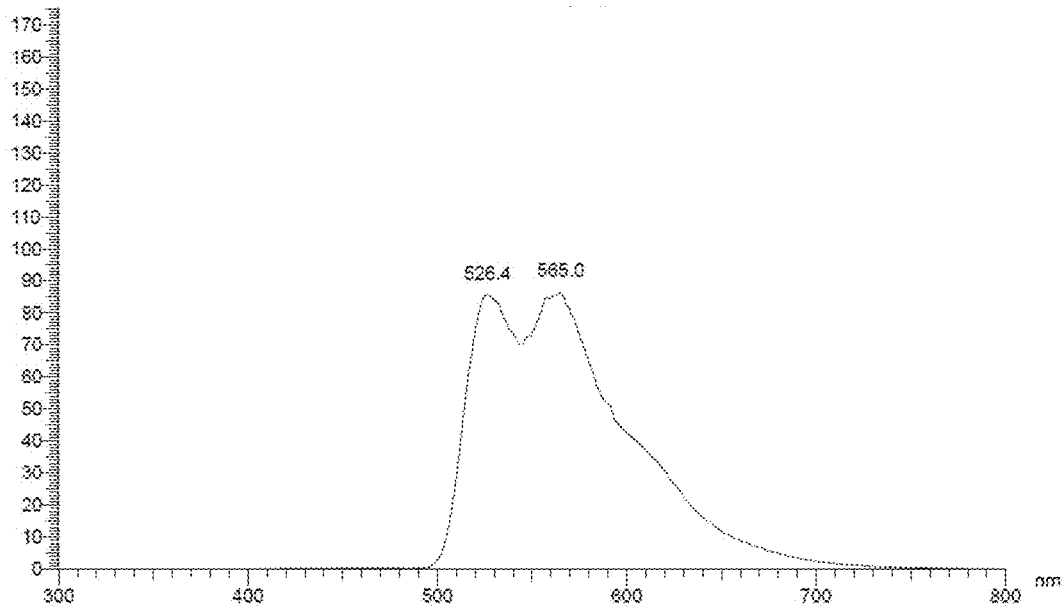

[Figure 16]
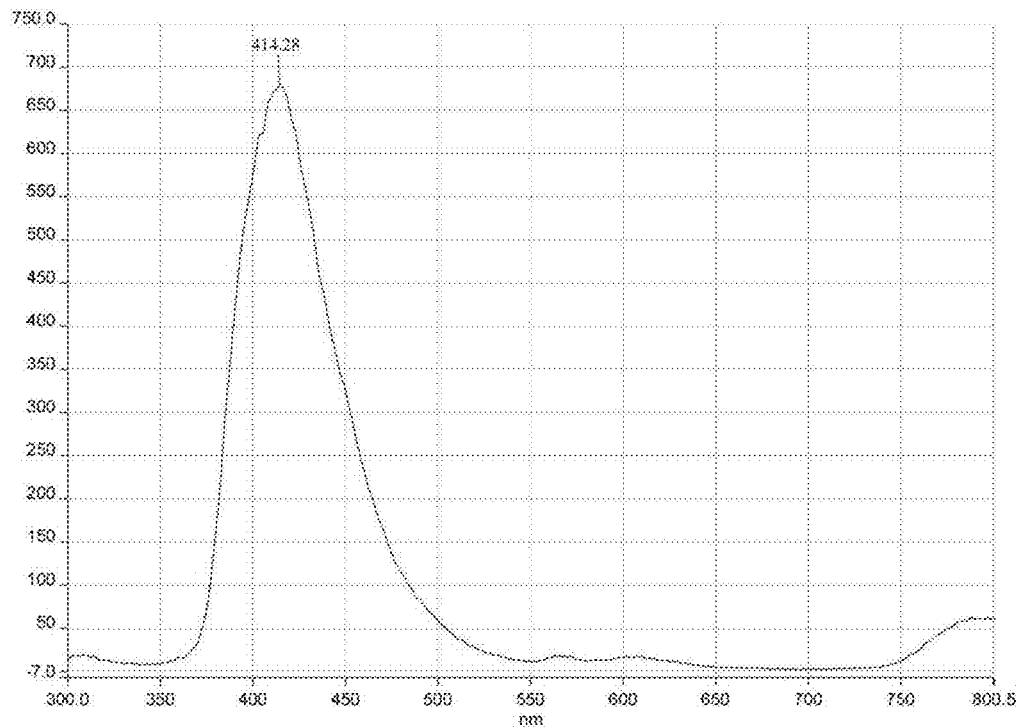
[Figure 17]
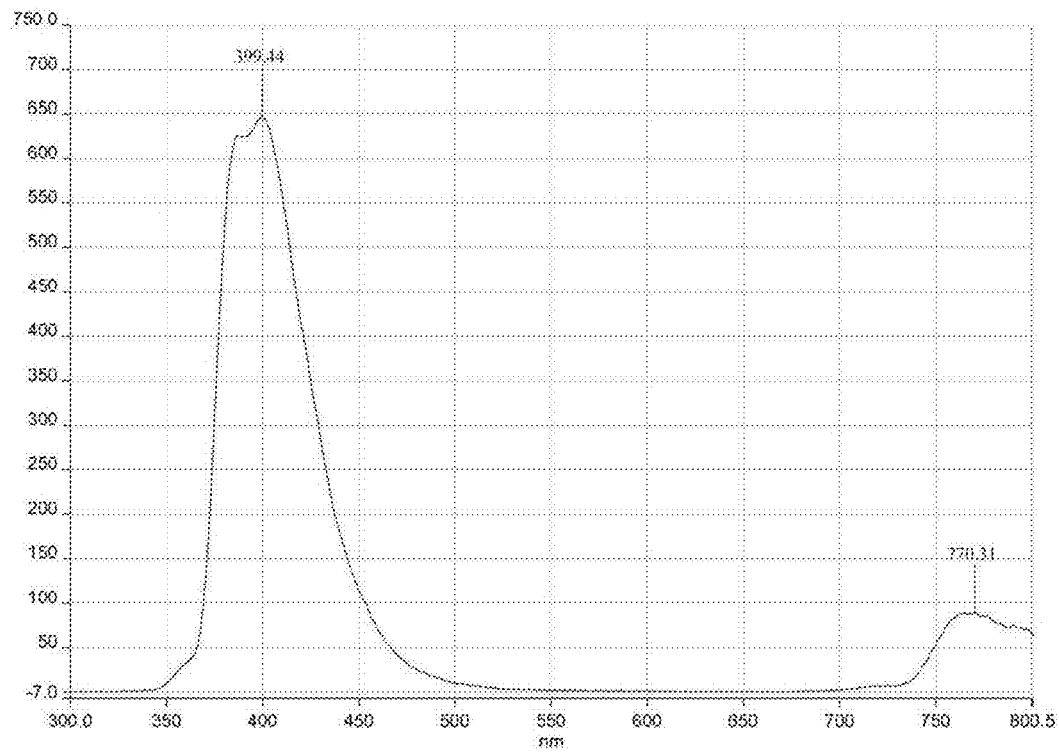

NITROGEN-CONTAINING POLYCYCLIC COMPOUND AND ORGANIC LIGHT EMITTING ELEMENT USING SAME

This application is a Divisional of U.S. application Ser. No. 15/523,155, filed on Apr. 28, 2017, which is a National Stage of PCT/KR2015/011526, filed on Oct. 29, 2015, which claims the benefit of Korean Patent Application No. 10-2014-0148633 filed in the Korean Intellectual Property Office on Oct. 29, 2014, the entire contents of which are incorporated herein by reference.

TECHNICAL FIELD

The present application relates to a novel polycyclic compound including nitrogen and an organic light emitting device including the same.

BACKGROUND ART

An electroluminescence device is a kind of self-emitting type display device, and has an advantage in that the viewing angle is wide, the contrast is excellent, and the response speed is fast.

An organic light emitting device has a structure in which an organic thin film is disposed between two electrodes. When a voltage is applied to an organic light emitting device having the structure, electrons and holes injected from the two electrodes combine with each other in an organic thin film to make a pair, and then, emit light while being extinguished. The organic thin film may be composed of a single layer or multi layers, if necessary.

A material for the organic thin film may have a light emitting function, if necessary. For example, as the material for the organic thin film, it is also possible to use a compound, which may itself constitute a light emitting layer alone, or it is also possible to use a compound, which may serve as a host or a dopant of a host-dopant-based light emitting layer. In addition, as a material for the organic thin film, it is also possible to use a compound, which may perform a function such as hole injection, hole transport, electron blocking, hole blocking, electron transport or electron injection.

In order to improve the performance, service life, or efficiency of the organic light emitting device, there is a continuous need for developing a material for an organic thin film.

DETAILED DESCRIPTION OF THE INVENTION

Technical Problem

The present application provides a novel polycyclic compound including nitrogen and an organic light emitting device including the same.

Technical Solution

The present application provides a compound of the following Chemical Formula 1.

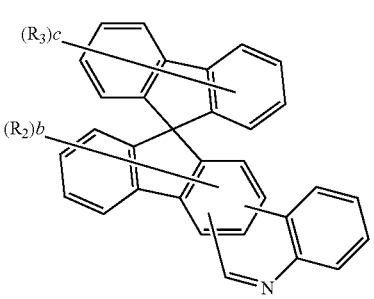

[Chemical Formula 1]

In Chemical Formula 1, $R_1$ to $R_3$ are the same as or different from each other, and are each independently selected from the group consisting of hydrogen; deuterium; halogen; a substituted or unsubstituted $C_1$ to $C_{60}$ alkyl; a substituted or unsubstituted $C_2$ to $C_{60}$ alkenyl; a substituted or unsubstituted $C_2$ to $C_{60}$ alkynyl; a substituted or unsubstituted $C_1$ to $C_{60}$ alkoxy; a substituted or unsubstituted $C_3$ to $C_{60}$ cycloalkyl; a substituted or unsubstituted $C_2$ to $C_{60}$ heterocycloalkyl; a substituted or unsubstituted $C_6$ to $C_{60}$ aryl; a substituted or unsubstituted $C_2$ to $C_{60}$ heteroaryl; —SiRR'R", and —P(=O)RR', R, R', and R" are the same as or different from each other, and are each independently selected from the group consisting of hydrogen; deuterium; a substituted or unsubstituted $C_1$ to $C_{60}$ alkyl; a substituted or unsubstituted $C_3$ to $C_{60}$ cycloalkyl; a substituted or unsubstituted $C_6$ to $C_{60}$ aryl; and a substituted or unsubstituted $C_2$ to $C_{60}$ heteroaryl, a is an integer of 1 to 5,
b is an integer of 0 to 6,
c is an integer of 0 to 8, and
when a, b, and c are each 2 or more, a plurality of $R_1$, $R_2$, and $R_3$ is each the same as or different from each other.

Further, the present application provides an organic light emitting device including a positive electrode, a negative electrode, and one or more organic material layers provided between the positive electrode and the negative electrode, in which one or more layers of the organic material layers include the compound of Chemical Formula 1.

Advantageous Effects

The compound described in the present specification may be used as a material for the organic material layer of the organic light emitting device. The compound may serve as a hole injection material, a hole transporting material, a light emitting material, a hole blocking material, an electron transporting material, an electron injection material, and the like in an organic light emitting device.

In particular, the compound of Chemical Formula 1 may be used as a material for an electron injection and/or transporting layer of an organic light emitting device.

Further, the compound of Chemical Formula 1 may be used as a material for a hole blocking layer of an organic light emitting device.

In addition, the compound of Chemical Formula 1 may be used as a material for a light emitting layer of an organic light emitting device.

BRIEF DESCRIPTION OF DRAWINGS

FIGS. 1 to 3 exemplify the stacking sequence of electrodes and organic material layers of an organic light emitting device according to exemplary embodiments of the present application.

FIG. 4 illustrates a measurement graph of PL of Compound 37 at a wavelength of 265 nm.

FIG. 5 illustrates a measurement graph of LTPL of Compound 37 at a wavelength of 279 nm.

FIG. 6 illustrates a measurement graph of PL of Compound 43 at a wavelength of 298 nm.

FIG. 7 illustrates a measurement graph of LTPL of Compound 43 at a wavelength of 308 nm.

FIG. 8 illustrates a measurement graph of PL of Compound 44 at a wavelength of 278 nm.

FIG. 9 illustrates a measurement graph of LTPL of Compound 44 at a wavelength of 307 nm.

FIG. 10 illustrates a measurement graph of PL of Compound 76 at a wavelength of 309 nm.

FIG. 11 illustrates a measurement graph of LTPL of Compound 76 at a wavelength of 327 nm.

FIG. 12 illustrates a measurement graph of PL of Compound 98 at a wavelength of 271 nm.

FIG. 13 illustrates a measurement graph of LTPL of Compound 98 at a wavelength of 271 nm.

FIG. 14 illustrates a measurement graph of PL of Compound 248 at a wavelength of 262 nm.

FIG. 15 illustrates a measurement graph of LTPL of Compound 248 at a wavelength of 307 nm.

FIG. 16 illustrates a measurement graph of PL of Compound 267 at a wavelength of 280 nm.

FIG. 17 illustrates a measurement graph of PL of Compound 275 at a wavelength of 325 nm.

EXPLANATION OF REFERENCE NUMERALS AND SYMBOLS

100 Substrate
200 Positive electrode
300 Organic material layer
301 Hole injection layer
302 Hole transporting layer
303 Light emitting layer
304 Hole blocking layer
305 Electron transporting layer
306 Electron injection layer
400 Negative electrode

BEST MODE

Hereinafter, the present application will be described in detail.

The compound described in the present specification may be represented by Chemical Formula 1. Specifically, the compound of Chemical Formula 1 may be used as a material for an organic material layer of an organic light emitting device by the structural characteristics of the core structure and the substituent as described above.

The spirobifluorene skeleton of Chemical Formula 1 has a right-angled molecular form and thus cuts a conjugation length, so that the band gap and T1 may have high values, and the planarity is so strong that the distance between molecules is short when an organic light emitting device is manufactured, thereby exhibiting an effect in which the capability of transferring electrons is excellent.

In the present specification, "substituted or unsubstituted" means being unsubstituted or substituted with one or more substituents selected from the group consisting of deuterium; halogen; —CN; a $C_1$ to $C_{60}$ alkyl; a $C_2$ to $C_{60}$ alkenyl; a $C_2$ to $C_{60}$ alkynyl; a $C_3$ to $C_{60}$ cycloalkyl; a $C_2$ to $C_{60}$ heterocycloalkyl; a $C_6$ to $C_{60}$ aryl; a $C_2$ to $C_{60}$ heteroaryl; —SiRR'R"; —P(=O)RR'; and —NRR', or being unsubstituted or substituted with a substituent to which two or more substituents among the exemplified substituents are linked, and R, R', and R" are the same as or different from each other, and are each independently hydrogen; deuterium; a substituted or unsubstituted $C_1$ to $C_{60}$ alkyl; a substituted or unsubstituted $C_3$ to $C_{60}$ cycloalkyl; a substituted or unsubstituted $C_6$ to $C_{60}$ aryl; and a substituted or unsubstituted $C_2$ to $C_{60}$ heteroaryl.

For example, "the substituent to which two or more substituents are linked" may be a biphenyl group. That is, the biphenyl group may also be an aryl group, and may be interpreted as a substituent to which two phenyl groups are linked.

In the present specification, the halogen includes F, Cl, Br, and I.

In the present specification, the alkyl includes a straight-chain or branched chain having 1 to 60 carbon atoms, and may be additionally substituted with another substituent. The number of carbon atoms of the alkyl may be 1 to 60, specifically 1 to 40, more specifically 1 to 20, and 1 to 10.

In the present specification, the alkenyl includes a straight-chain or branched chain having 2 to 60 carbon atoms, and may be additionally substituted with another substituent. The number of carbon atoms of the alkenyl may be 2 to 60, specifically 2 to 40, more specifically 2 to 20, and 1 to 10.

In the present specification, the alkynyl includes a straight-chain or branched chain having 2 to 60 carbon atoms, and may be additionally substituted with another substituent. The number of carbon atoms of the alkynyl may be 2 to 60, specifically 2 to 40, more specifically 2 to 20, and 2 to 10.

In the present specification, the cycloalkyl includes a monocycle or polycycle having 3 to 60 carbon atoms, and may be additionally substituted with another substituent. Here, the polycycle means a group in which cycloalkyl is directly linked to or fused with another cyclic group. Here, another cyclic group may also be cycloalkyl, but may also be another kind of cyclic group, for example, heterocycloalkyl, aryl, heteroaryl, and the like. The number of carbon atoms of the cycloalkyl may be 3 to 60, specifically 3 to 40, more specifically 5 to 25, 5 to 20, and 5 to 10.

In the present specification, the heterocycloalkyl includes O, S, Se, N, or Si as a heteroatom, includes a monocycle or polycycle having 2 to 60 carbon atoms, and may be additionally substituted with another substituent. Here, the polycycle means a group in which heterocycloalkyl is directly linked to or fused with another cyclic group. Here, another cyclic group may also be heterocycloalkyl, but may also be another kind of cyclic group, for example, cycloalkyl, aryl, heteroaryl, and the like. The number of carbon atoms of the heterocycloalkyl may be 2 to 60, specifically 2 to 40, more specifically 3 to 25, 3 to 20, and 3 to 10.

In the present specification, the aryl includes a monocycle or polycycle having 6 to 60 carbon atoms, and may be additionally substituted with another substituent. Here, the polycycle means a group in which aryl is directly linked to or fused with another cyclic group. Here, another cyclic group may also be aryl, but may also be another kind of cyclic group, for example, cycloalkyl, heterocycloalkyl, heteroaryl, and the like. The aryl includes a spiro group. The number of carbon atoms of the aryl may be 6 to 60, specifically 6 to 40, more specifically 6 to 25, 6 to 20, and 6 to 10. Specific examples of the aryl include phenyl, biphenyl, triphenyl, naphthyl, anthracenyl, chrysenyl, phenanthrenyl, perylenyl, fluoranthenyl, triphenylenyl, phenalenyl, pyrenyl, tetracenyl, pentacenyl, fluorenyl, indenyl, acenaphthylenyl, fluorenyl, benzofluorenyl, spirobifluorenyl and the like, or fused rings thereof, but are not limited thereto.

In the present specification, the spiro group is a group including a spiro structure, and may have 15 to 60 carbon atoms. For example, the spiro group may include a structure in which a 2,3-dihydro-1H-indene group or a cyclohexane group is spiro-bonded to a fluorene group. Specifically, the spiro group includes a group of the following structural formulae.

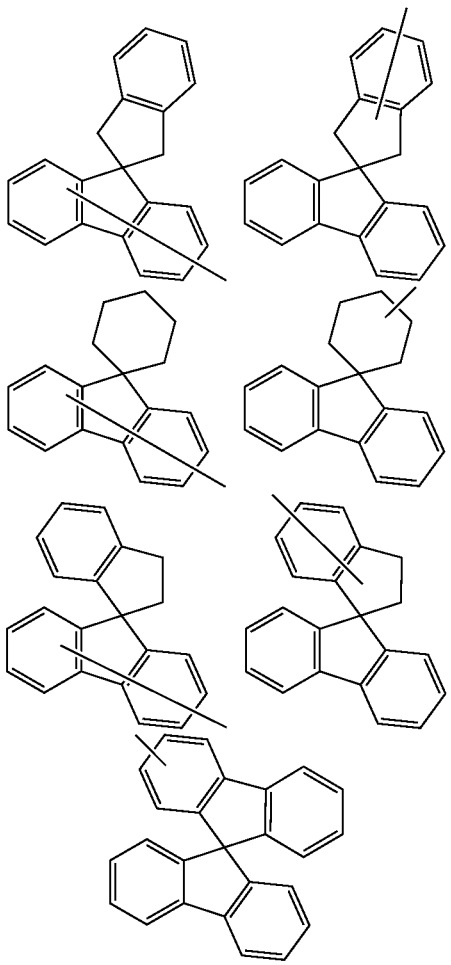

In the present specification, the heteroaryl includes S, O, Se, N, or Si as a heteroatom, includes a monocycle or a polycycle having 2 to 60 carbon atoms, and may be additionally substituted with another substituent. Here, the polycycle means a group in which heteroaryl is directly linked to or fused with another cyclic group. Here, another cyclic group may also be heteroaryl, but may also be another kind of cyclic group, for example, cycloalkyl, heterocycloalkyl, aryl, and the like. The number of carbon atoms of the heteroaryl may be 2 to 60, specifically 2 to 40, more specifically 3 to 25, 3 to 20, and 3 to 10. Specific examples of the heteroaryl include pyridyl, pyrrolyl, pyrimidyl, pyridazinyl, furanyl, thiophenyl, imidazolyl, pyrazolyl, oxazolyl, isoxazolyl, triazolyl, isothiazolyl, triazolyl, furazanyl, oxadiazolyl, thiadiazolyl, dithiazolyl, tetrazolyl, pyranyl, thiopyranyl, diazinyl, oxazinyl, oxadiazolyl, triazinyl, dioxynyl, triazinyl, tetrazinyl, cinnolinyl, quinolyl, isoquinolyl, quinoxalinyl, quinazolinyl, isoquinazolinyl, naphthyridyl, acridinyl, phenanthridinyl, imidazopyridinyl, diazanaphthalenyl, triazaindene, indolyl, indolyzinyl, benzothiazolyl, benzoxazolyl, benzimidazolyl, benzothiophenyl, benzofuranyl, dibenzothiophenyl, dibenzofuranyl, carbazolyl, benzocarbazolyl, dibenzocarbazolyl, phenazinyl, dibenzosilolyl, spirobidibenzosilolyl, dihydrophenazinyl, phenoxazinyl, phenanthridyl, pyrazolophthalazinyl, pyrazoloquinazolyl, pyridoindazolyl, and the like, or fused rings thereof, but are not limited thereto.

According to an exemplary embodiment of the present application, Chemical Formula 1 is represented by any one of the following Chemical Formulae 2 to 5.

[Chemical Formula 2]

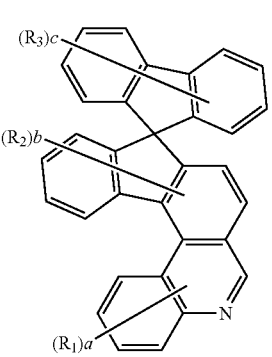

[Chemical Formula 3]

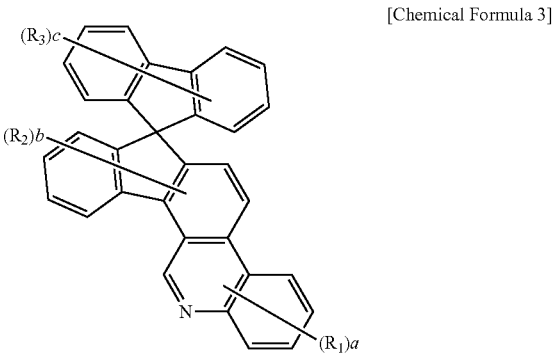

[Chemical Formula 4]

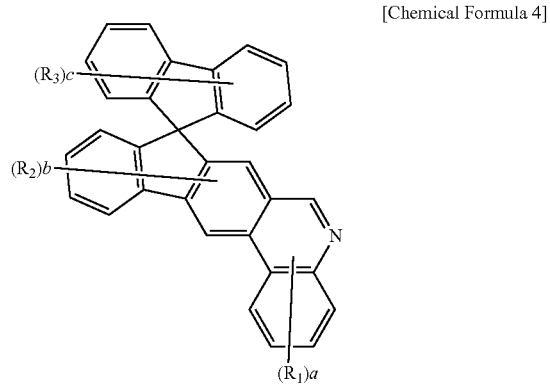

[Chemical Formula 5]

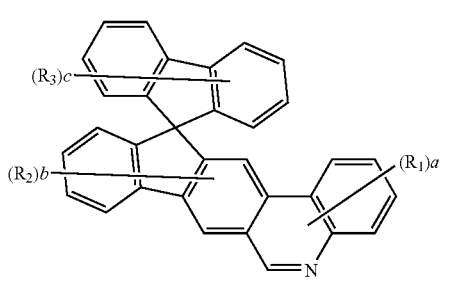

In Chemical Formulae 2 to 5,
$R_1$ to $R_3$, a, b, and c are the same as those defined in Chemical Formula 1.

According to an exemplary embodiment of the present application, Chemical Formula 1 is represented by any one of the following Chemical Formulae 2-1 to 5-1.

[Chemical Formula 2-1]

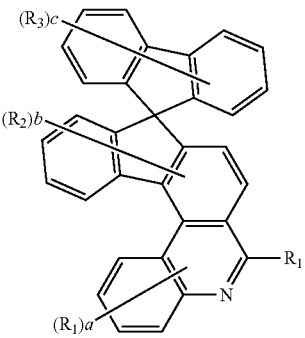

[Chemical Formula 3-1]

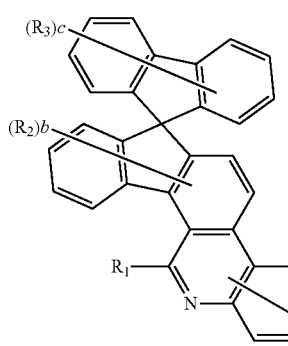

[Chemical Formula 4-1]

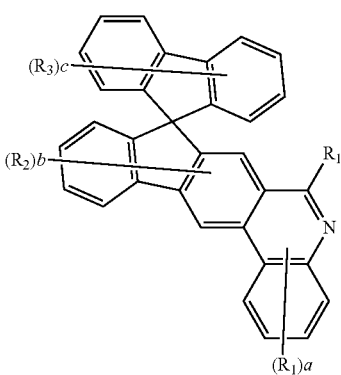

[Chemical Formula 5-1]

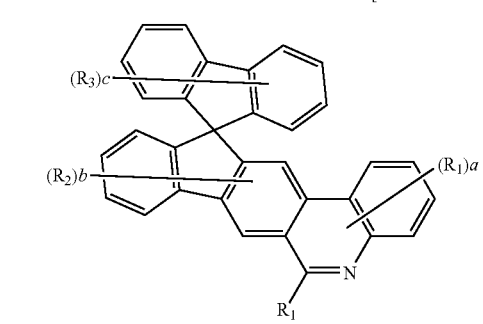

In Chemical Formulae 2-1 to 5-1, $R_4$ is the same as the definition of $R_1$ of Chemical Formula 1, d is an integer of 0 to 4, and when d is 2 or more, a plurality of $R_4$ is the same as or different from each other, and $R_1$ to $R_3$, b, and c are the same as those defined in Chemical Formula 1.

According to an exemplary embodiment of the present application, in Chemical Formulae 1 to 5 and Chemical Formulae 2-1 to 5-1, $R_1$ is -(L)m-(Z)n, L is a substituted or unsubstituted $C_6$ to $C_{60}$ arylene; or a substituted or unsubstituted $C_2$ to $C_{60}$ heteroarylene, m is an integer of 0 to 5, n is an integer of 1 to 3, Z is selected from the group consisting of a substituted or unsubstituted $C_6$ to $C_{60}$ aryl; a substituted or unsubstituted $C_2$ to $C_{60}$ heteroaryl; —SiRR'R", and —P(=O)RR', and R, R', and R" are the same as or different from each other, and are each independently selected from the group consisting of hydrogen; deuterium; a substituted or unsubstituted $C_1$ to $C_{60}$ alkyl; a substituted or unsubstituted $C_3$ to $C_{60}$ cycloalkyl; a substituted or unsubstituted $C_6$ to $C_{60}$ aryl; and a substituted or unsubstituted $C_2$ to $C_{60}$ heteroaryl.

According to an exemplary embodiment of the present application, m is 0, or an integer of 1, 2, 3, 4, or 5, and when m is an integer of 2 or more, L's are the same as or different from each other.

According to an exemplary embodiment of the present application, n is an integer of 1, 2, or 3, and when n is an integer of 2 or more, Z's are the same as or different from each other.

According to an exemplary embodiment of the present application, Z is selected from the group consisting of a substituted or unsubstituted $C_6$ to $C_{60}$ aryl; a substituted or unsubstituted $C_2$ to $C_{60}$ heteroaryl; —SiRR'R", and —P(=O)RR', and R, R', and R" are the same as or different from each other, and are each independently selected from the group consisting of hydrogen; deuterium; a substituted or unsubstituted $C_1$ to $C_{60}$ alkyl; a substituted or unsubstituted $C_3$ to $C_{60}$ cycloalkyl; a substituted or unsubstituted $C_6$ to $C_{60}$ aryl; and a substituted or unsubstituted $C_2$ to $C_{60}$ heteroaryl.

According to an exemplary embodiment of the present application, L is a substituted or unsubstituted $C_6$ to $C_{20}$ arylene; or a substituted or unsubstituted $C_2$ to $C_{20}$ heteroarylene including N.

According to an exemplary embodiment of the present application, L is a $C_6$ to $C_{20}$ arylene; or a $C_2$ to $C_{20}$ heteroarylene including N, and may be further substituted with halogen.

According to an exemplary embodiment of the present application, L is selected from phenylene; naphthylene; anthracenylene; pyridylene; pyrimidylene; triazinylene; fluorenylene; and carbazolylene, and may be further substituted with halogen.

According to an exemplary embodiment of the present application, Z is a substituted or unsubstituted monocyclic or polycyclic $C_6$ to $C_{60}$ aryl.

According to an exemplary embodiment of the present application, Z is a substituted or unsubstituted phenyl, a substituted or unsubstituted biphenyl, a substituted or unsubstituted naphthyl, a substituted or unsubstituted chrysenyl, a substituted or unsubstituted pyrenyl, a substituted or unsubstituted triphenylenyl, a substituted or unsubstituted anthracenyl, a substituted or unsubstituted phenanthrenyl, a substituted or unsubstituted fluorenyl, or a substituted or unsubstituted spirobifluorenyl.

According to an exemplary embodiment of the present application, Z is a substituted or unsubstituted phenyl, a substituted or unsubstituted biphenyl, a substituted or unsubstituted naphthyl, a substituted or unsubstituted chrysenyl, a substituted or unsubstituted pyrenyl, a substituted or unsubstituted triphenylenyl, a substituted or unsubstituted anthracenyl, a substituted or unsubstituted phenanthrenyl, a substituted or unsubstituted fluorenyl, or a substituted or unsubstituted spirobifluorenyl, and the "substituted or unsubstituted" means being unsubstituted or substituted with at least one selected from halogen, a $C_1$ to $C_{60}$ alkyl, a substituted or unsubstituted $C_3$ to $C_{60}$ cycloalkyl, a $C_6$ to $C_{60}$ aryl, and a $C_2$ to $C_{60}$ heteroaryl, or being unsubstituted or substituted with a substituent to which two or more substituents among the exemplified substituents are linked.

According to an exemplary embodiment of the present application, Z is a substituted or unsubstituted phenyl, a substituted or unsubstituted biphenyl, a substituted or unsubstituted naphthyl, a substituted or unsubstituted chrysenyl, a substituted or unsubstituted pyrenyl, a substituted or unsubstituted triphenylenyl, a substituted or unsubstituted anthracenyl, a substituted or unsubstituted phenanthrenyl, a substituted or unsubstituted fluorenyl, or a substituted or unsubstituted spirobifluorenyl, and the term "substituted or unsubstituted" means being unsubstituted or substituted with at least one selected from halogen, methyl, cyclohexyl, phenyl, biphenyl, naphthyl, pyridyl, and carbazolyl, or being unsubstituted or substituted with a substituent to which two or more substituents among the exemplified substituents are linked.

According to another exemplary embodiment of the present application, Z is a substituted or unsubstituted $C_2$ to $C_{60}$ heteroaryl, and the heteroaryl includes at least one selected from N, O, S, Si, and Se, as a heteroatom.

According to an exemplary embodiment of the present application, Z is a substituted or unsubstituted benzimidazolyl, a substituted or unsubstituted quinolyl, a substituted or unsubstituted isoquinolyl, a substituted or unsubstituted naphthyridyl, a substituted or unsubstituted quinazolinyl, a substituted or unsubstituted quinoxalinyl, a substituted or unsubstituted cinnolinyl, a substituted or unsubstituted benzothiazolyl, a substituted or unsubstituted benzoxazolyl, a substituted or unsubstituted oxadiazolyl, a substituted or unsubstituted dibenzofuranyl, a substituted or unsubstituted dibenzothiophenyl, a substituted or unsubstituted dibenzosilolyl, a substituted or unsubstituted pyridyl, a substituted or unsubstituted pyrimidyl, a substituted or unsubstituted triazinyl, a substituted or unsubstituted pyrazolophthalazinyl, a substituted or unsubstituted pyrazoloquinazolinyl, a substituted or unsubstituted pyridoindazolyl, or a substituted or unsubstituted carbazolyl.

According to an exemplary embodiment of the present application, Z is a substituted or unsubstituted benzimidazolyl, a substituted or unsubstituted quinolyl, a substituted or unsubstituted isoquinolyl, a substituted or unsubstituted naphthyridyl, a substituted or unsubstituted quinazolinyl, a substituted or unsubstituted quinoxalinyl, a substituted or unsubstituted cinnolinyl, a substituted or unsubstituted benzothiazolyl, a substituted or unsubstituted benzoxazolyl, a substituted or unsubstituted oxadiazolyl, a substituted or unsubstituted dibenzofuranyl, a substituted or unsubstituted dibenzothiophenyl, a substituted or unsubstituted dibenzosilolyl, a substituted or unsubstituted pyridyl, a substituted or unsubstituted pyrimidyl, a substituted or unsubstituted triazinyl, a substituted or unsubstituted pyrazolophthalazinyl, a substituted or unsubstituted pyrazoloquinazolinyl, a substituted or unsubstituted pyridoindazolyl, or a substituted or unsubstituted carbazolyl, and the "substituted or unsubstituted" means being unsubstituted or substituted with at least one selected from halogen, a $C_1$ to $C_{60}$ straight-chained or branched alkyl, a monocyclic or polycyclic $C_3$ to $C_{60}$ cycloalkyl, a monocyclic or polycyclic $C_6$ to $C_{60}$ aryl, and a monocyclic or polycyclic $C_2$ to $C_{60}$ heteroaryl, or being unsubstituted or substituted with a substituent to which two or more substituents among the exemplified substituents are linked.

According to an exemplary embodiment of the present application, Z is a substituted or unsubstituted benzimidazolyl, a substituted or unsubstituted quinolyl, a substituted or unsubstituted isoquinolyl, a substituted or unsubstituted naphthyridyl, a substituted or unsubstituted quinazolinyl, a substituted or unsubstituted quinoxalinyl, a substituted or unsubstituted cinnolinyl, a substituted or unsubstituted benzothiazolyl, a substituted or unsubstituted benzoxazolyl, a substituted or unsubstituted oxadiazolyl, a substituted or unsubstituted dibenzofuranyl, a substituted or unsubstituted dibenzothiophenyl, a substituted or unsubstituted dibenzosilolyl, a substituted or unsubstituted pyridyl, a substituted or unsubstituted pyrimidyl, a substituted or unsubstituted triazinyl, a substituted or unsubstituted pyrazolophthalazinyl, a substituted or unsubstituted pyrazoloquinazolinyl, a substituted or unsubstituted pyridoindazolyl, or a substituted or unsubstituted carbazolyl, and the "substituted or unsubstituted" means being unsubstituted or substituted with at least one selected from halogen, methyl, cyclohexyl, phenyl, biphenyl, naphthyl, pyridyl, and carbazolyl, or being unsubstituted or substituted with a substituent to which two or more substituents among the exemplified substituents are linked.

According to another exemplary embodiment of the present application, Z is

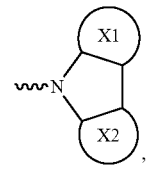

and X1 and X2 are the same as or different from each other, and are each independently a substituted or unsubstituted $C_6$ to $C_{60}$ aromatic hydrocarbon ring; or a substituted or unsubstituted $C_2$ to $C_{60}$ aromatic hetero ring.

According to an exemplary embodiment of the present application,

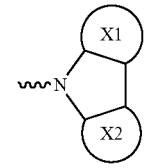

is represented by any one of the following structures.

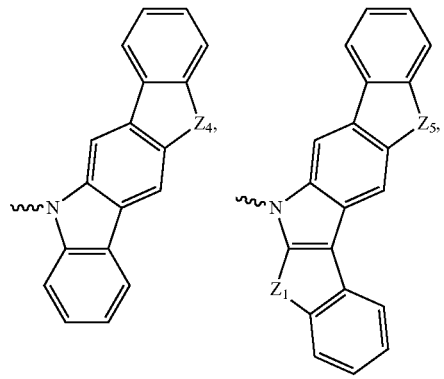

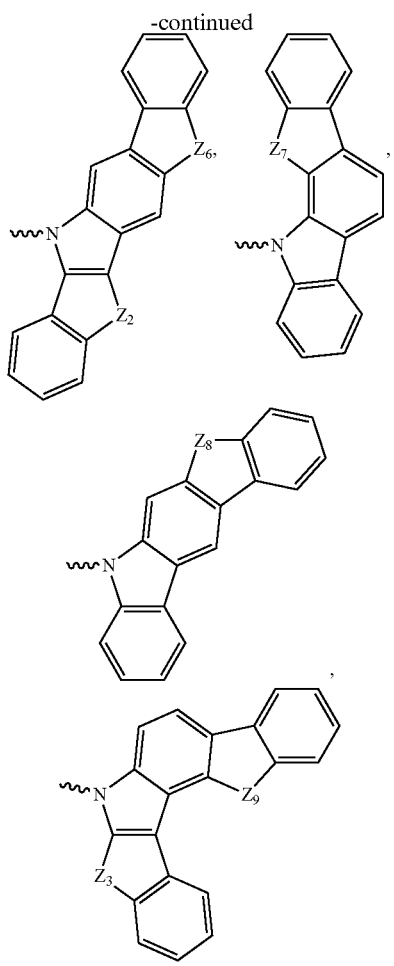

In the structural formulae, $Z_1$ to $Z_3$ are the same as or different from each other, and are each independently S or O, $Z_4$ to $Z_9$ are the same as or different from each other, and are each independently CY'Y", NY', S, or O, and Y' and Y" are the same as or different from each other, and are each independently hydrogen; deuterium; a substituted or unsubstituted $C_1$ to $C_{60}$ alkyl; or a substituted or unsubstituted $C_6$ to $C_{60}$ aryl.

According to an exemplary embodiment of the present application, Y' and Y" are the same as or different from each other, and are each independently hydrogen, deuterium, methyl, phenyl, or naphthyl.

According to another exemplary embodiment of the present application, Z is —SiRR'R", and R, R', and R" are the same as or different from each other, and are each independently selected from the group consisting of a substituted or unsubstituted $C_1$ to $C_{60}$ alkyl; a substituted or unsubstituted $C_6$ to $C_{60}$ aryl; and a substituted or unsubstituted $C_2$ to $C_{60}$ heteroaryl.

According to an exemplary embodiment of the present application, Z is —SiRR'R", and R, R', and R" are the same as or different from each other, and are a $C_6$ to $C_{60}$ aryl.

According to an exemplary embodiment of the present application, Z is —SiRR'R", and R, R', and R" are phenyl or biphenyl.

According to another exemplary embodiment of the present application, Z is —P(=O)RR', and R and R' are the same as or different from each other, and are each independently selected from the group consisting of a substituted or unsubstituted $C_1$ to $C_{60}$ alkyl; a substituted or unsubstituted $C_6$ to $C_{60}$ aryl; and a substituted or unsubstituted $C_2$ to $C_{60}$ heteroaryl.

According to an exemplary embodiment of the present application, Z is —P(=O)RR', and R and R' are the same as or different from each other, and are a $C_6$ to $C_{60}$ aryl.

According to an exemplary embodiment of the present application, Z is —P(=O)RR', and R and R' are phenyl or biphenyl.

According to an exemplary embodiment of the present application, R, R', and R" are the same as or different from each other, and are each independently a substituted or unsubstituted $C_1$ to $C_{60}$ alkyl, a substituted or unsubstituted $C_6$ to $C_{60}$ aryl, or a substituted or unsubstituted $C_2$ to $C_{60}$ heteroaryl.

According to an exemplary embodiment of the present application, R, R', and R" are the same as or different from each other, and are each independently selected from the group consisting of methyl, ethyl, propyl, isopropyl, butyl, tertbutyl, phenyl, biphenyl, naphthyl, pyridyl, pyrimidyl, anthracenyl, phenanthrenyl, chrysenyl, triphenylenyl, pyrenyl, fluorenyl, dimethylfluorenyl, carbazolyl, dibenzofuranyl, dibenzosilolyl, and dibenzothiophenyl.

According to an exemplary embodiment of the present application, in Chemical Formulae 1 to 5, $R_2$ and $R_3$ are the same as or different from each other, and are each independently hydrogen; deuterium; or a $C_6$ to $C_{60}$ aryl.

According to an exemplary embodiment of the present application, in Chemical Formulae 1 to 5, $R_2$ and $R_3$ are the same as or different from each other, and are each independently hydrogen; or deuterium.

According to an exemplary embodiment of the present application, in Chemical Formulae 2-1 to 5-1, $R_2$ to $R_4$ are the same as or different from each other, and are each independently hydrogen; deuterium; or a $C_6$ to $C_{60}$ aryl.

According to an exemplary embodiment of the present application, in Chemical Formulae 2-1 to 5-1, $R_2$ to $R_4$ are the same as or different from each other, and are each independently hydrogen; or deuterium.

According to an exemplary embodiment of the present application, in Chemical Formulae 2-1 to 5-1, b, c, and d are 0.

According to an exemplary embodiment of the present application, Chemical Formula 1 may be selected from the following compounds.

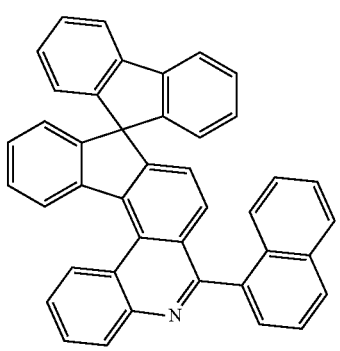

1

2
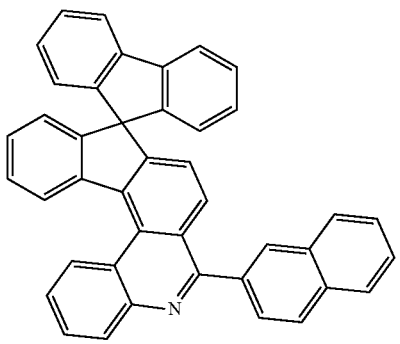
3
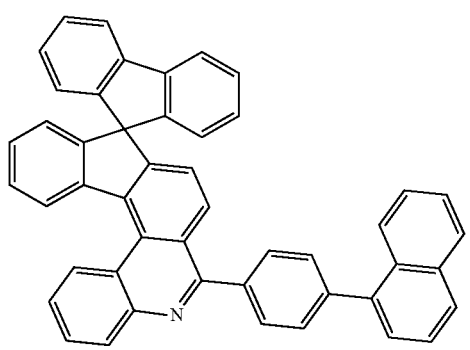
4
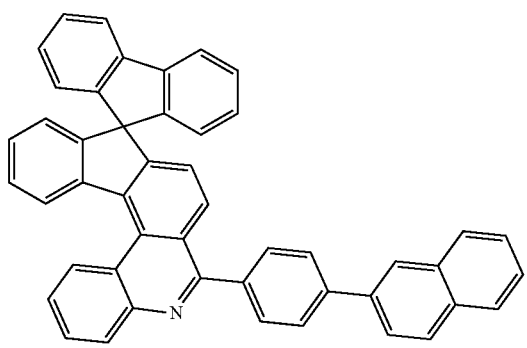
5
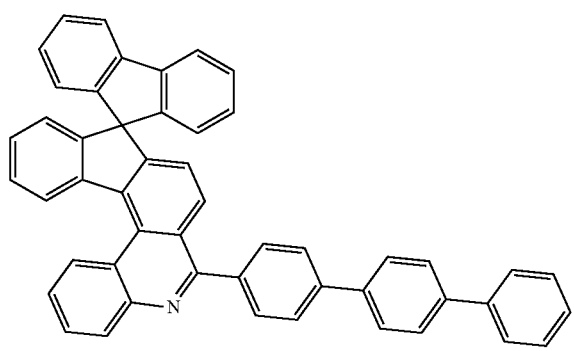
6
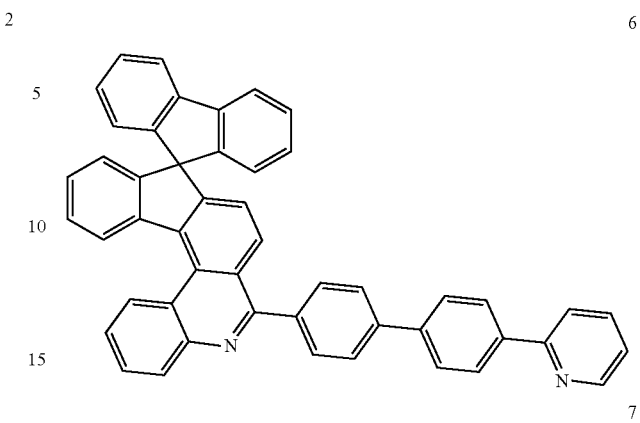
7
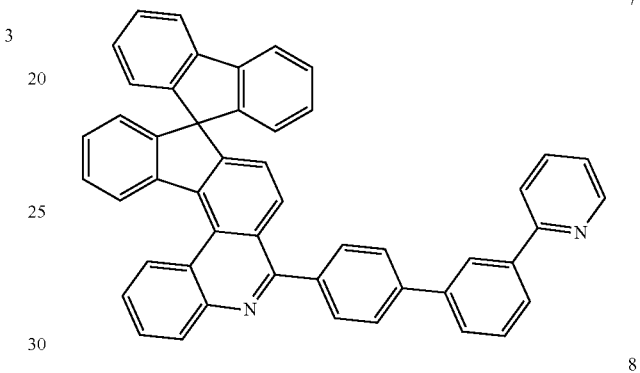
8
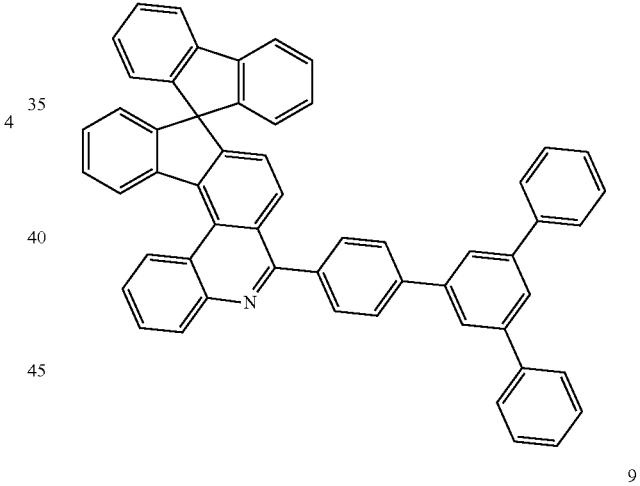
9
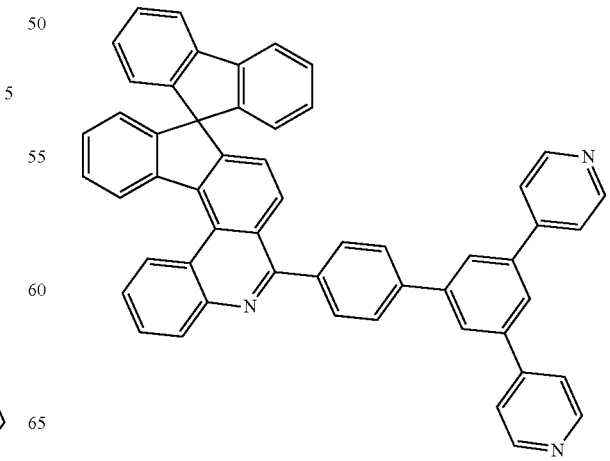

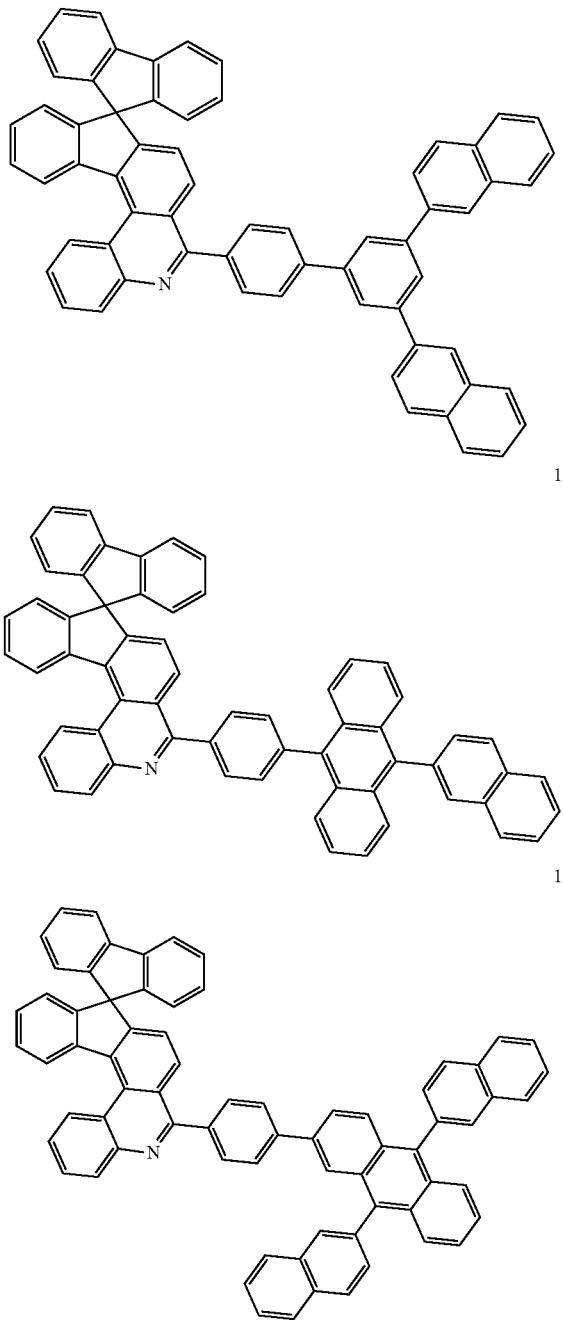
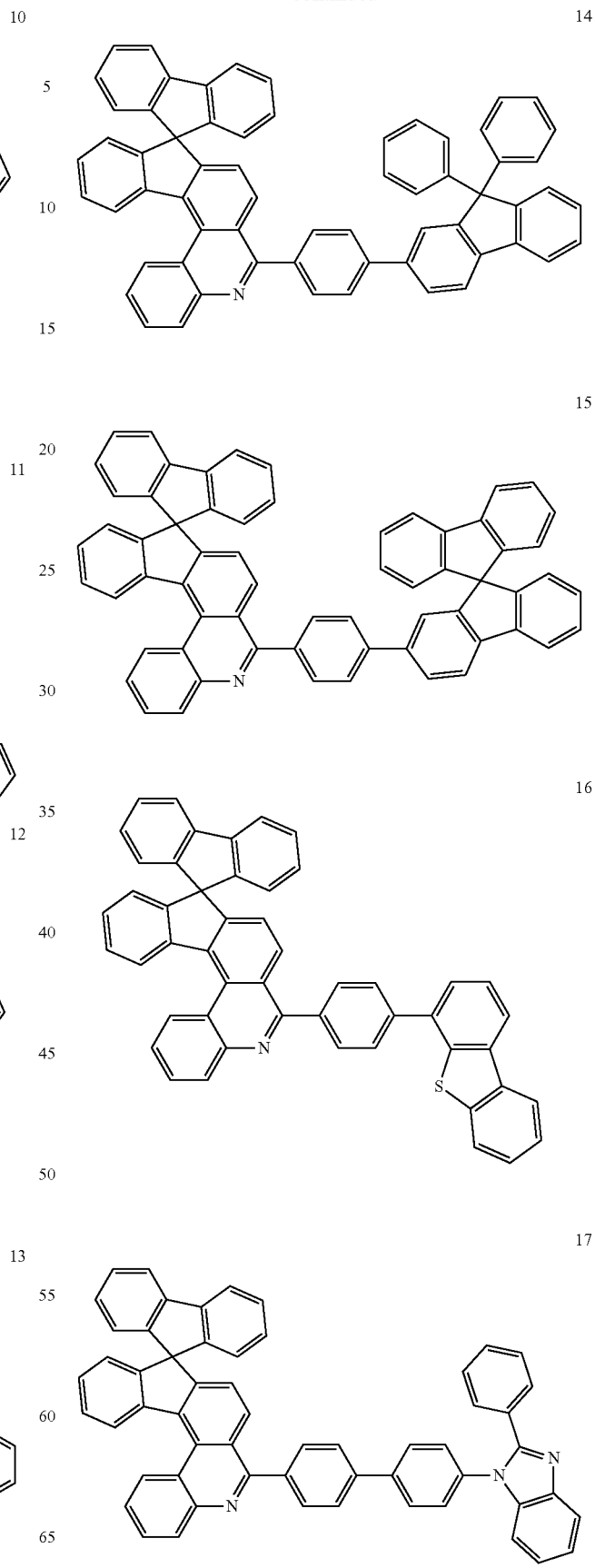

-continued
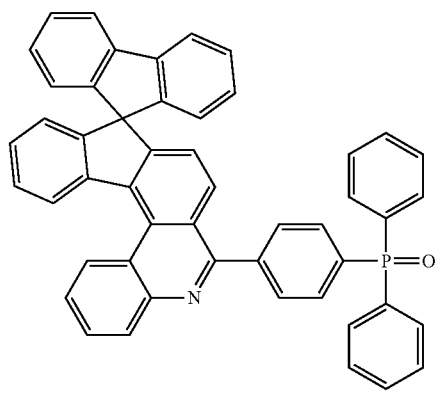
18
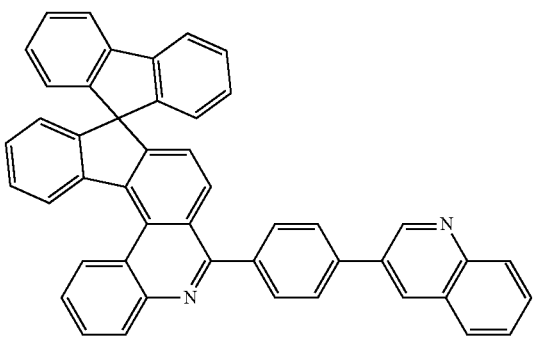
22
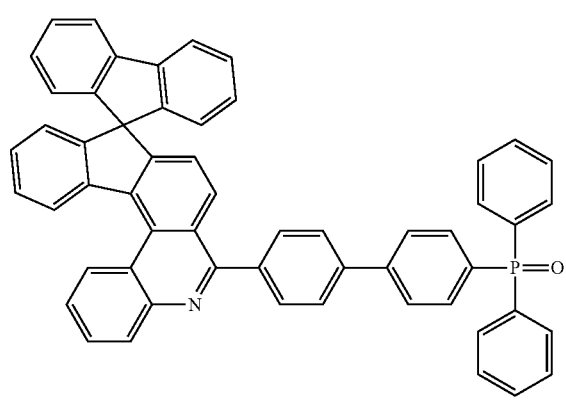
19
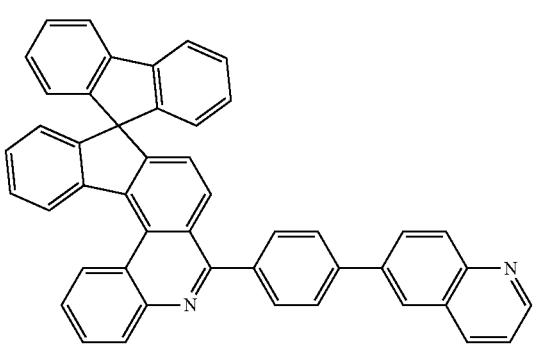
23
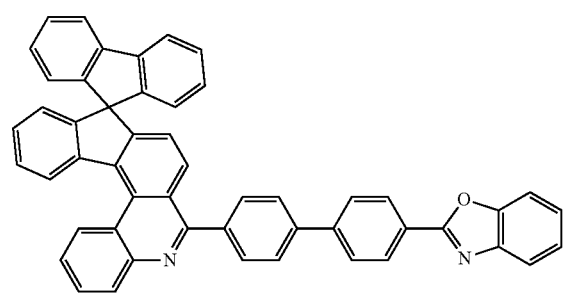
20
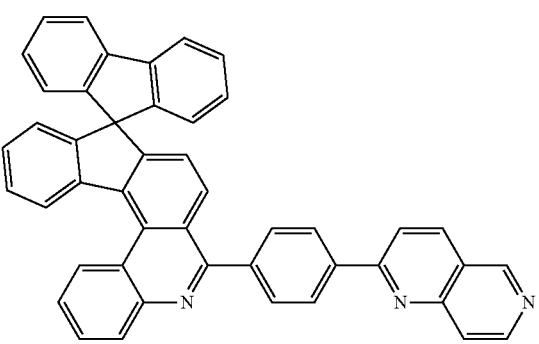
24
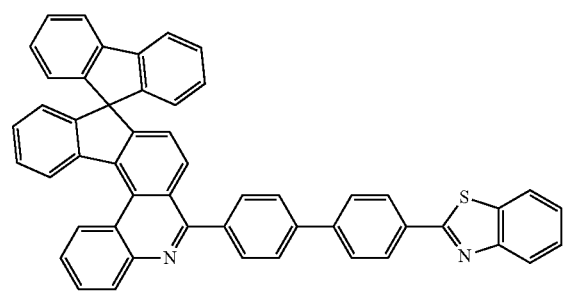
21
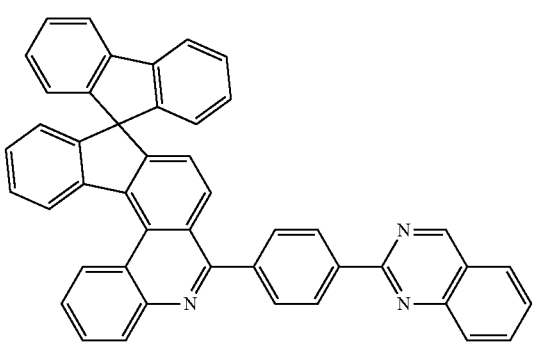
25

26
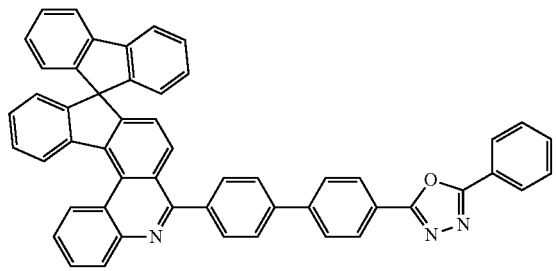
27
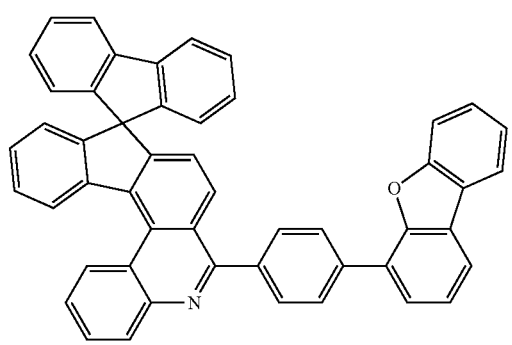
28
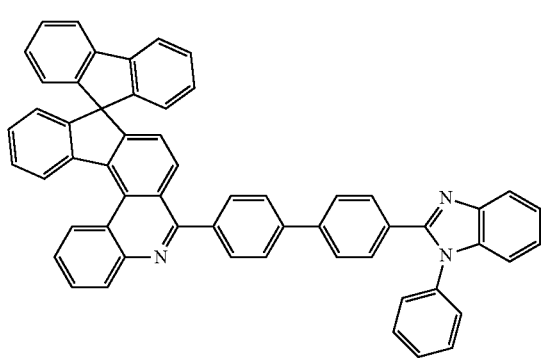
29
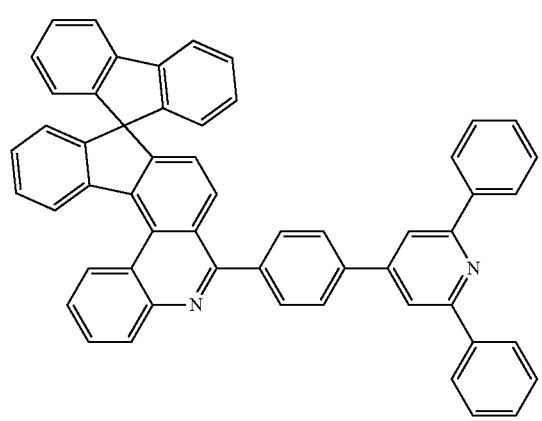
30
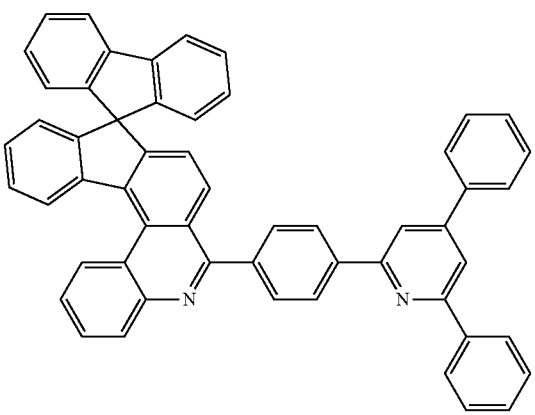
31
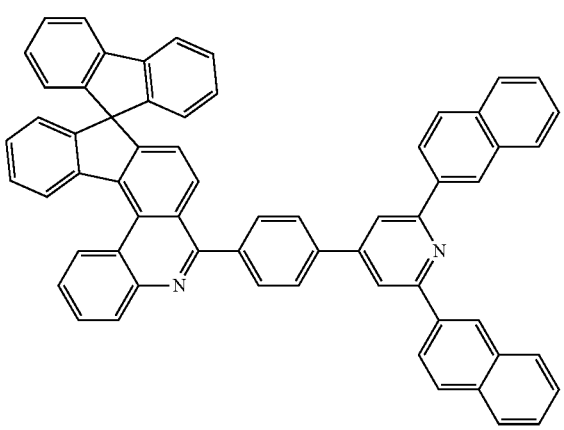
32
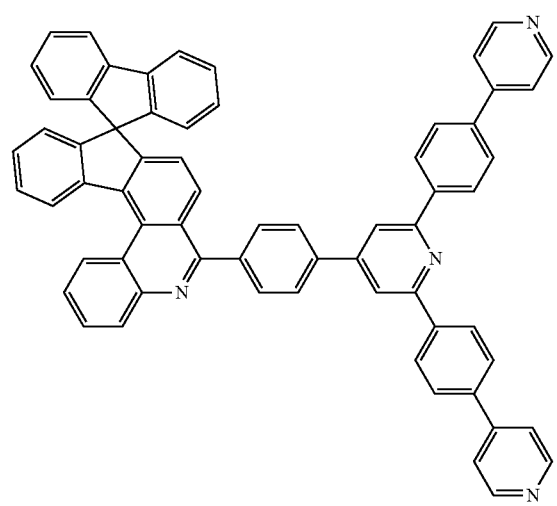

33
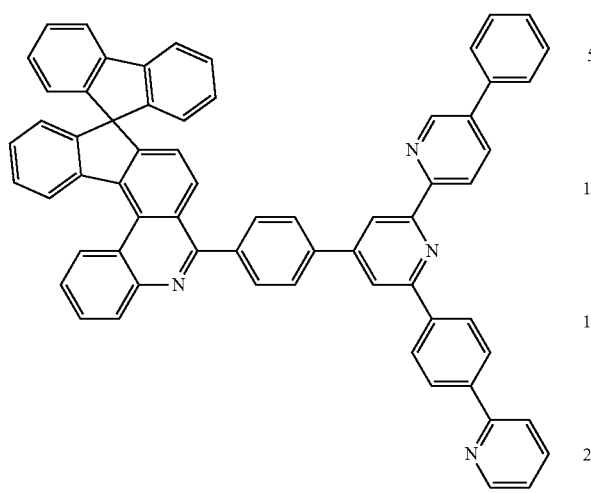
34
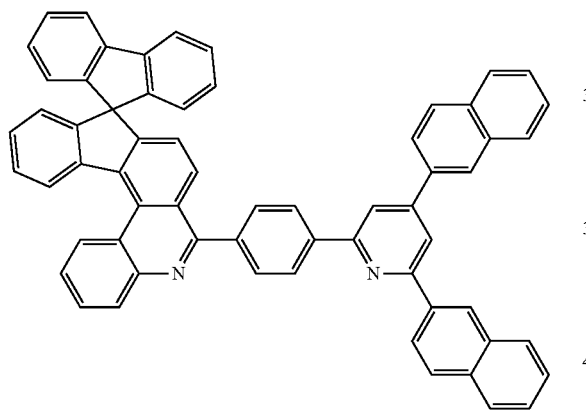
35
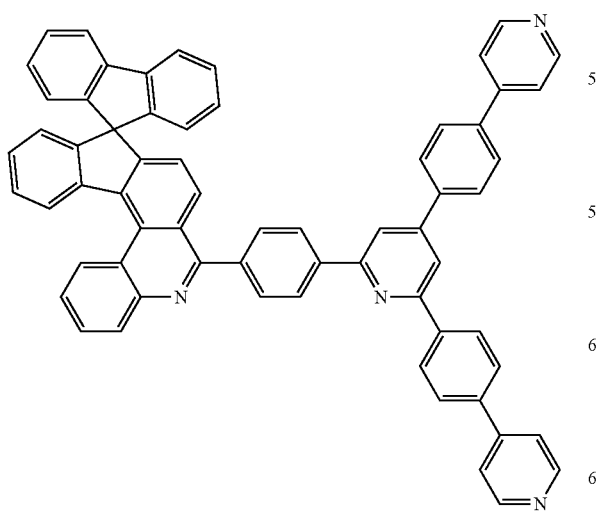
36
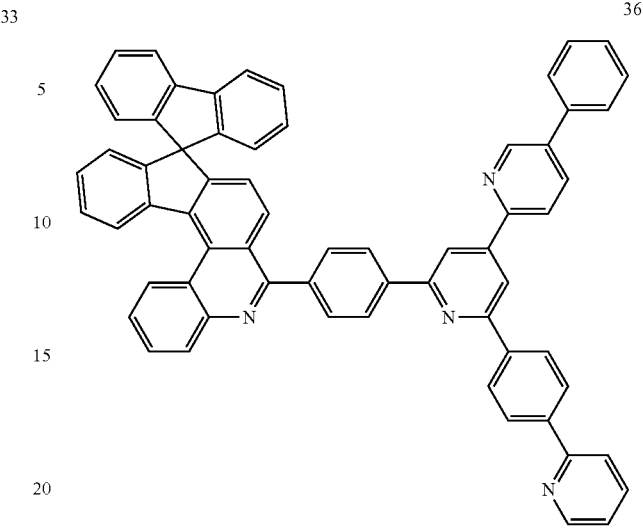
37
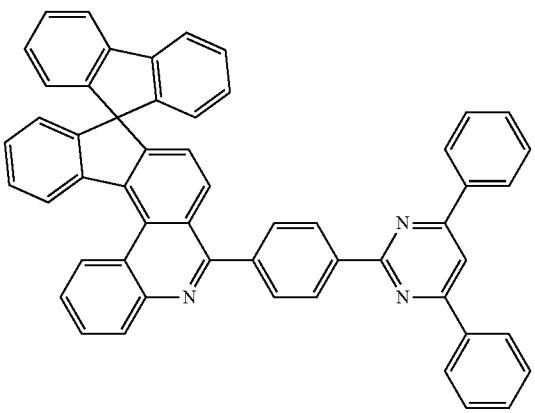
38
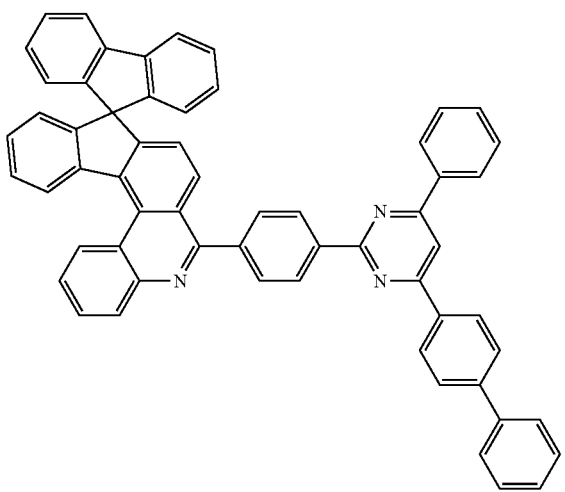

39
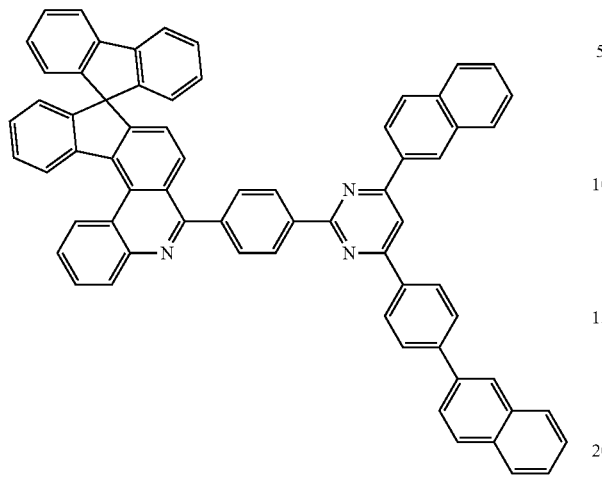
40
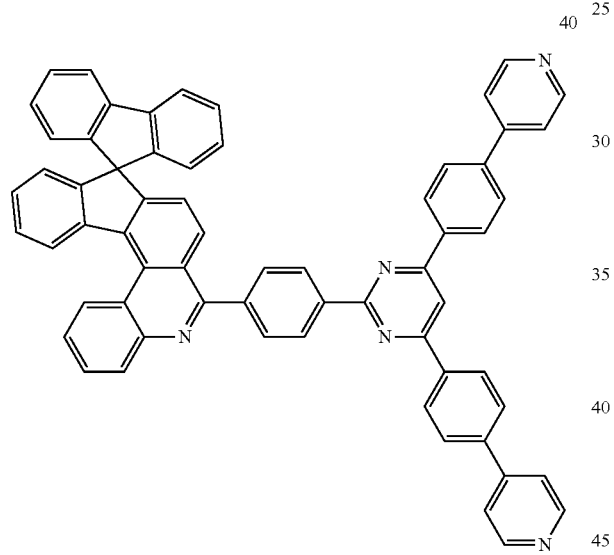
41
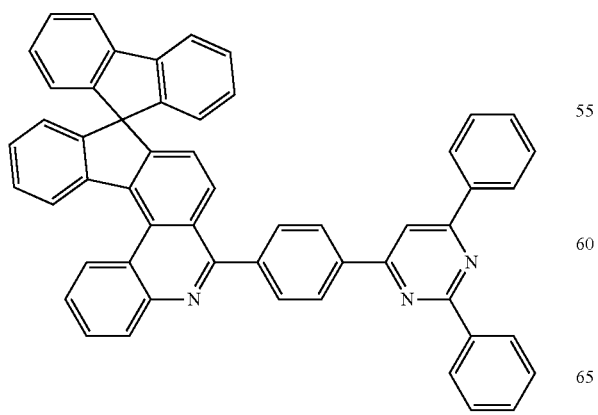
42
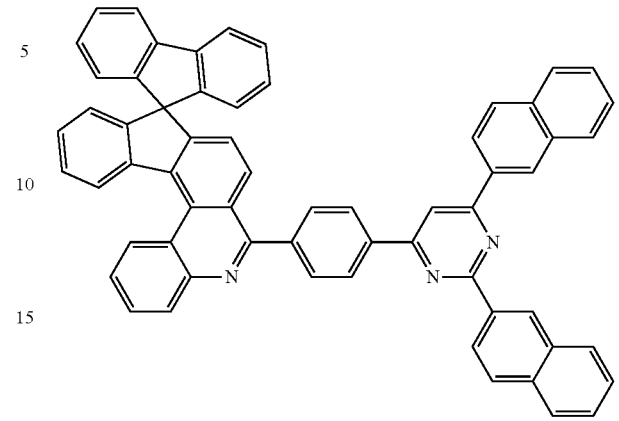
43
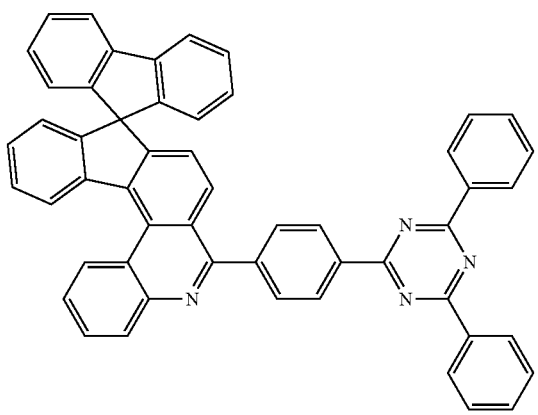
44

45
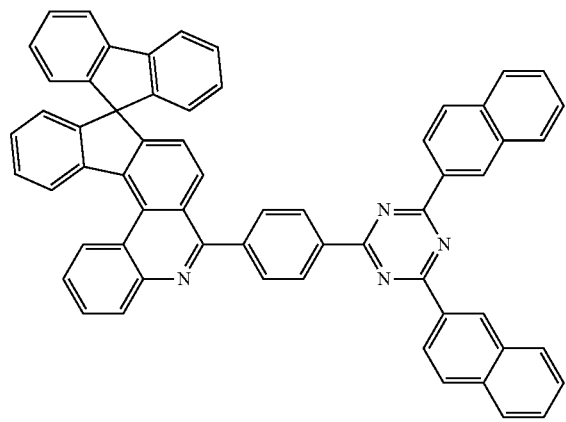
48
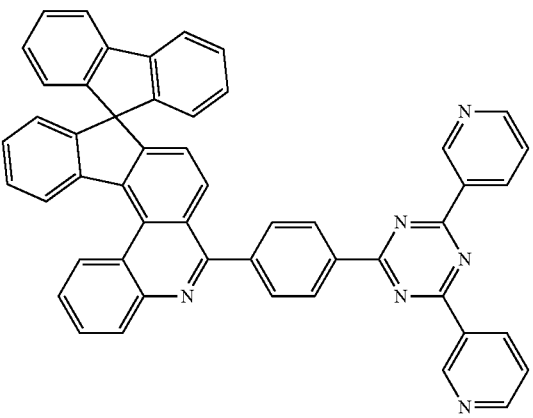
46
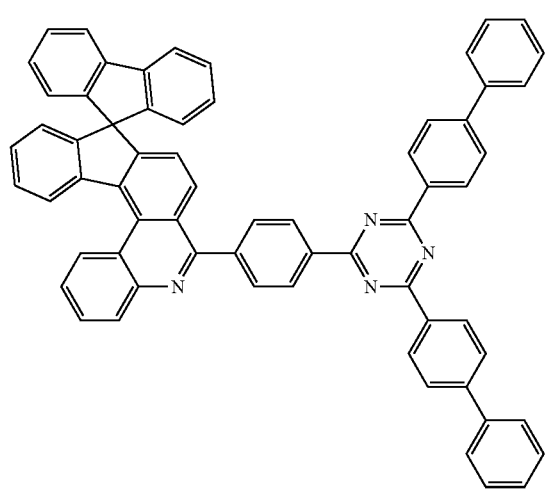
49
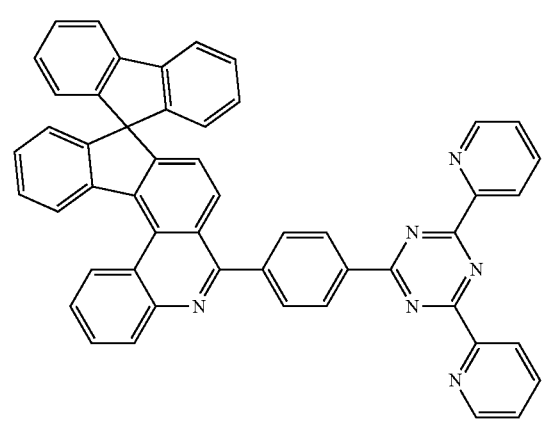
47
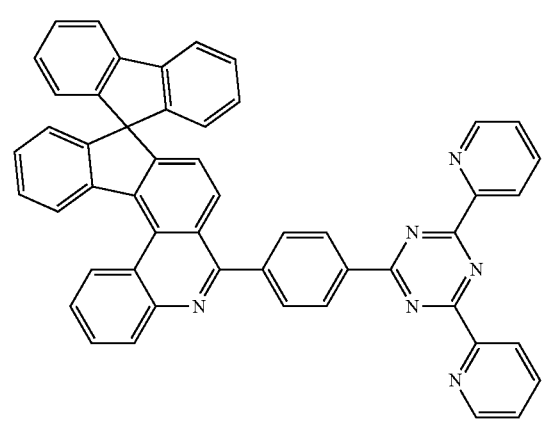
50
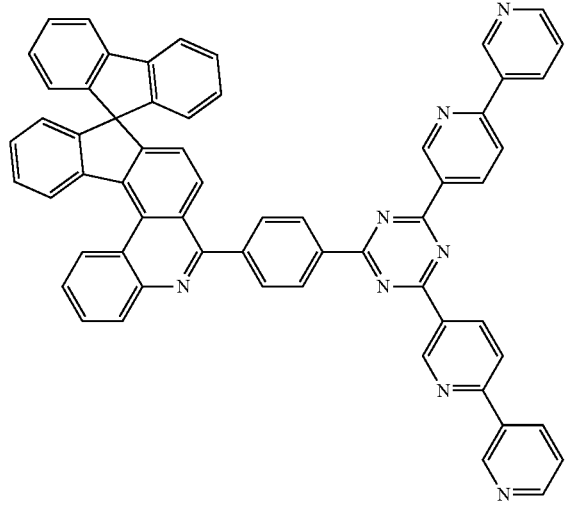

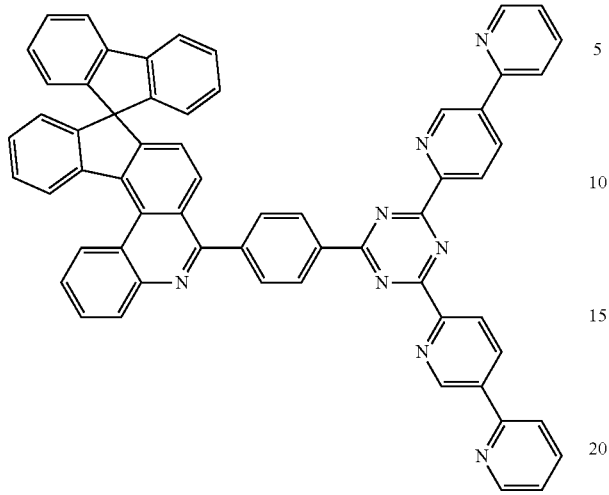
51
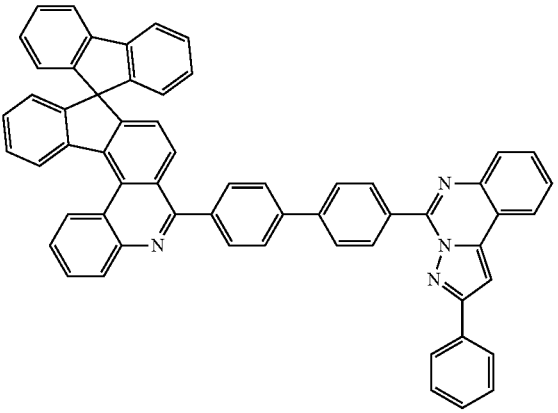
54
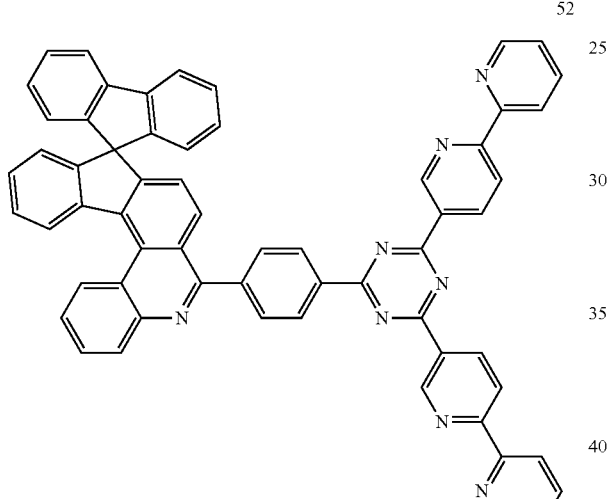
52
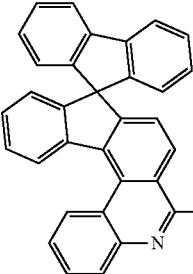
55
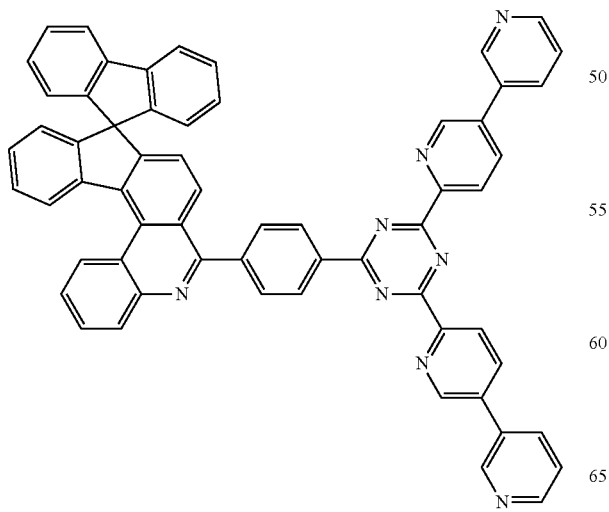
53
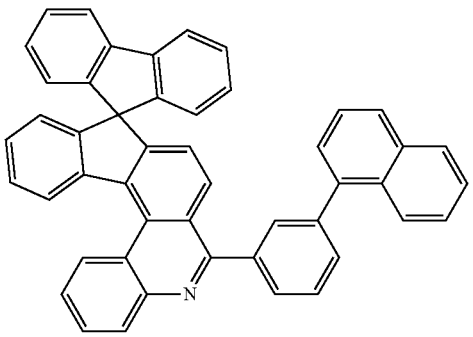
56
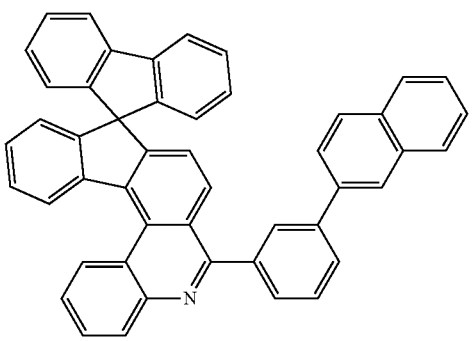
57

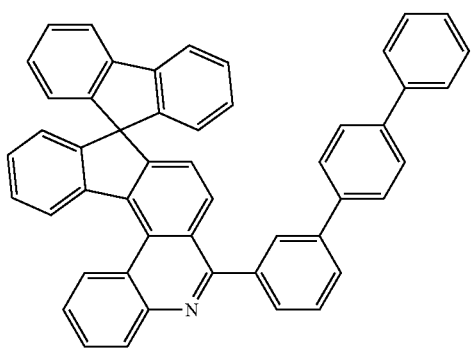
58
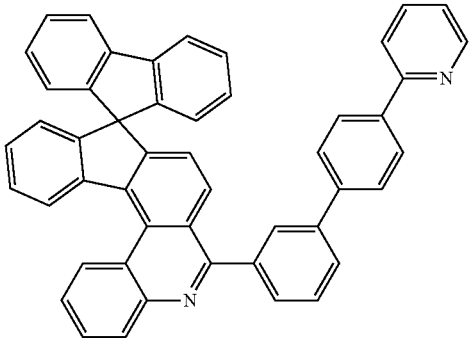
62
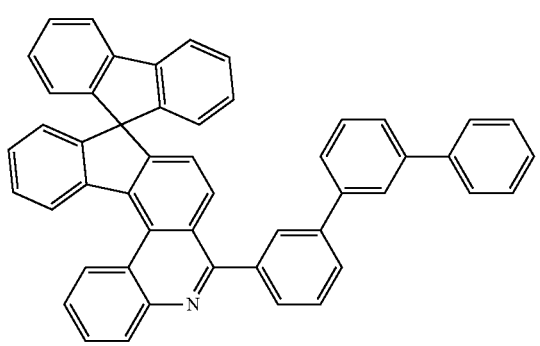
59
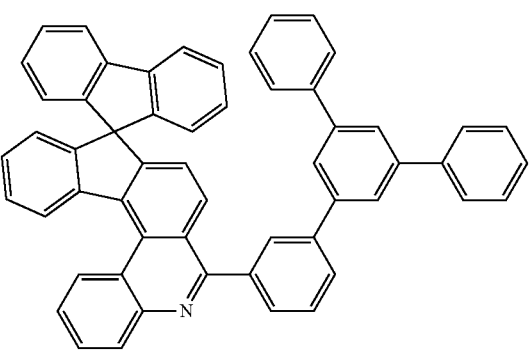
63
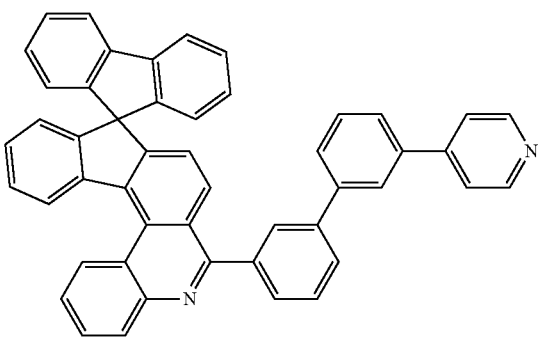
60
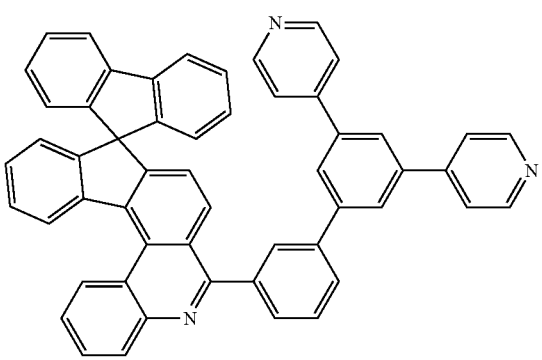
64
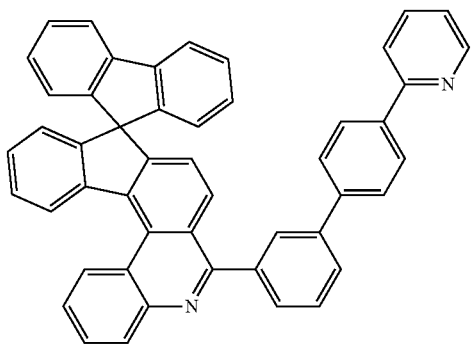
61
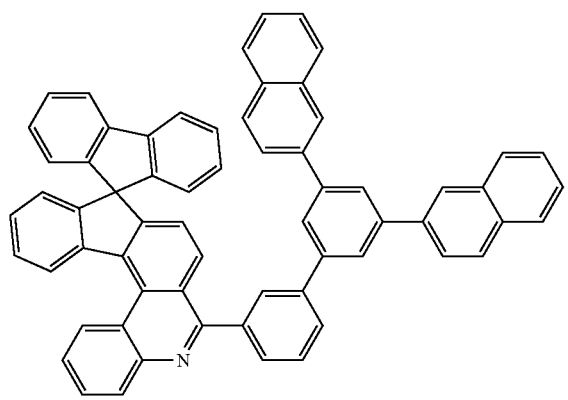
65

66
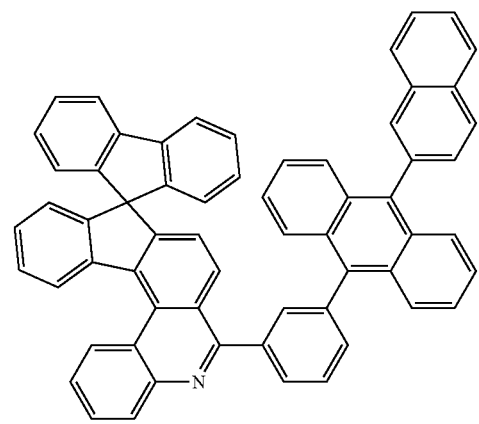
67
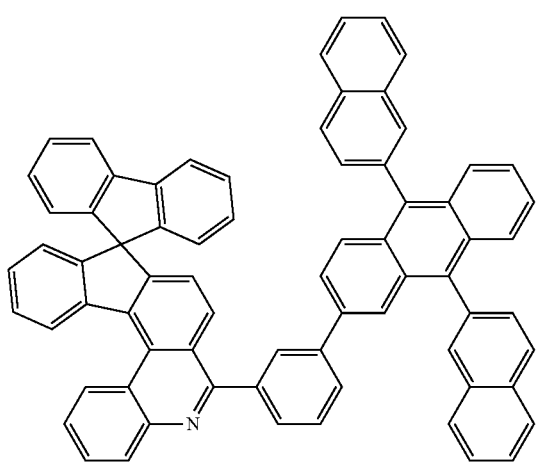
68
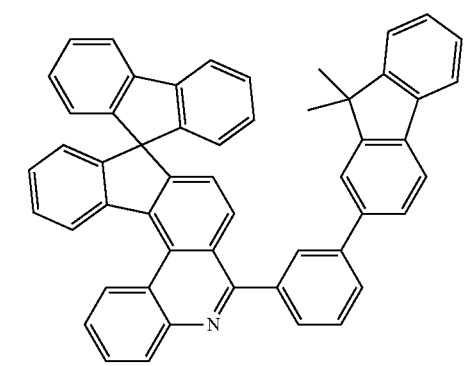
69
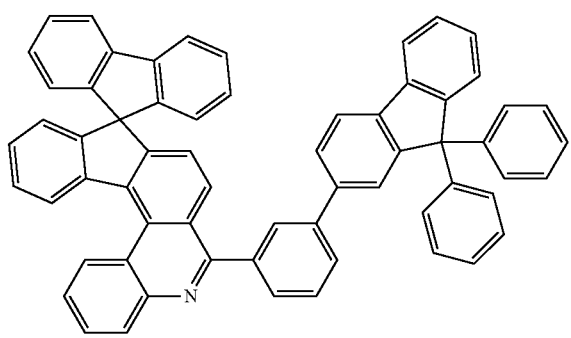
70
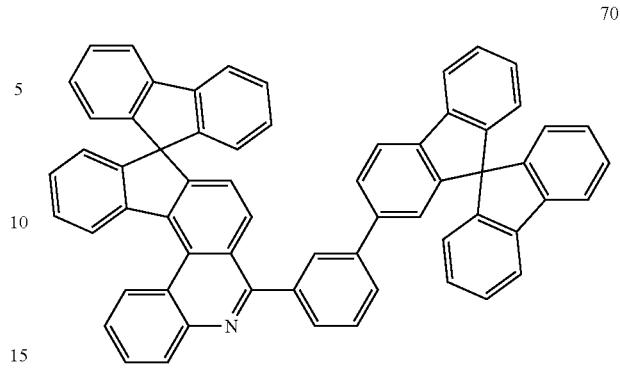
71
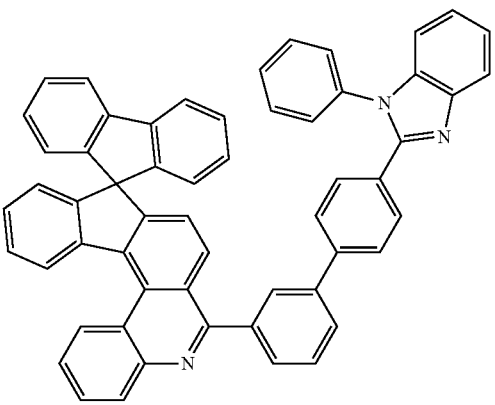
72
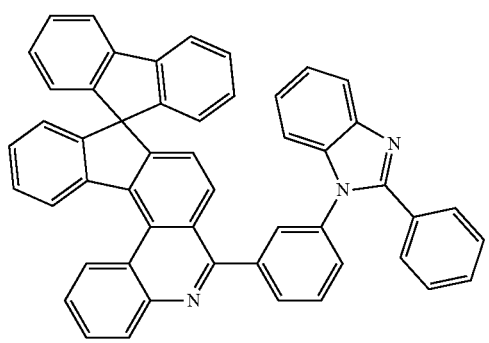
73
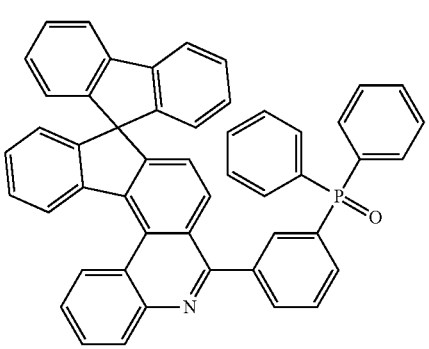

74
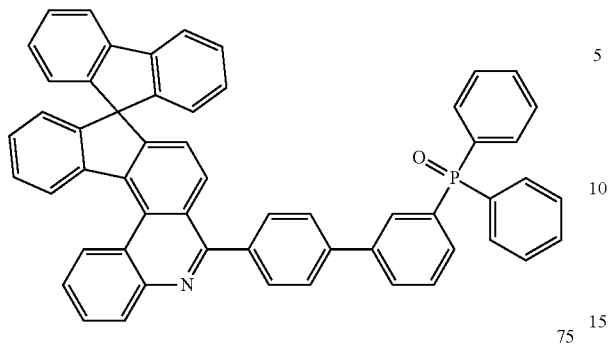
75
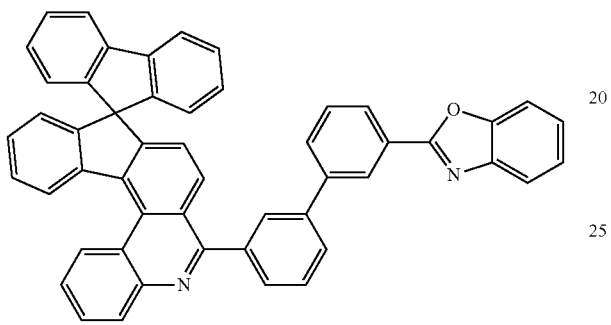
76
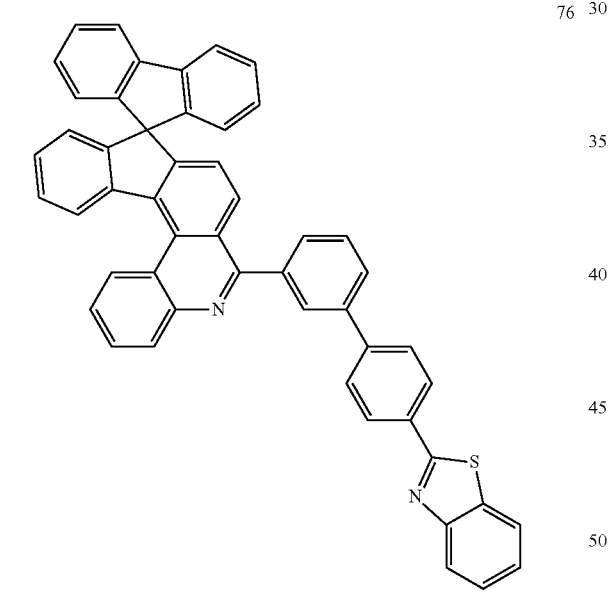
77
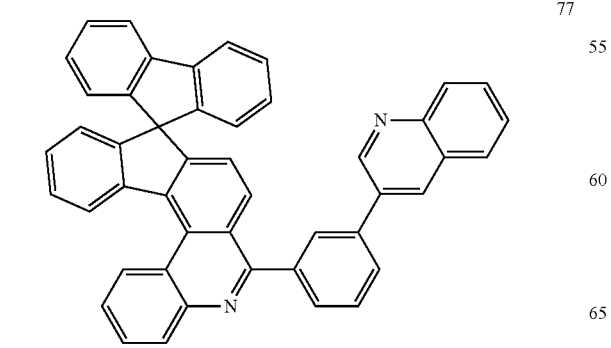
78
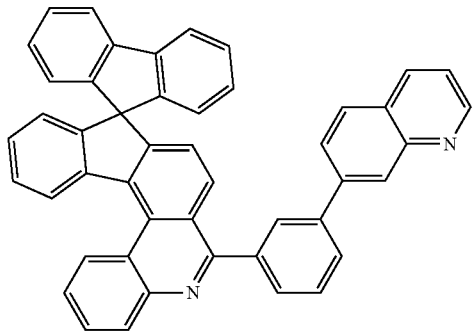
79
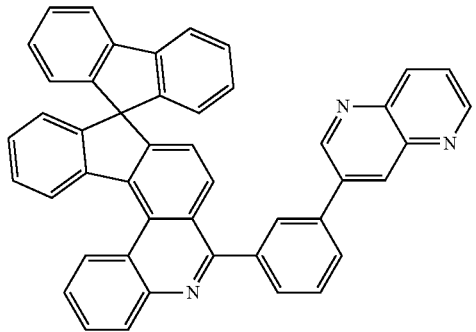
80
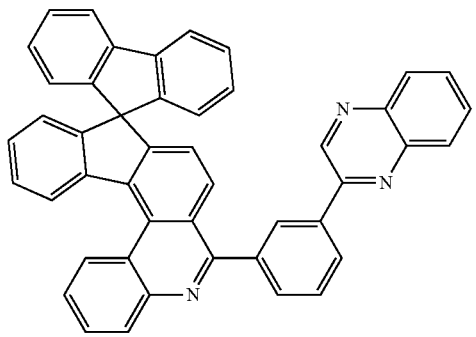
81
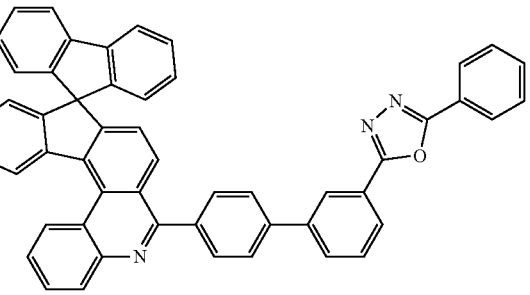

82
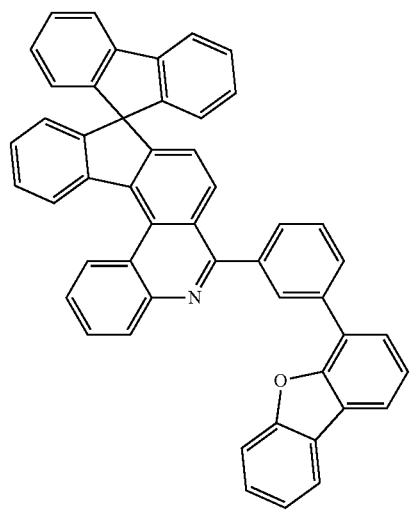
83
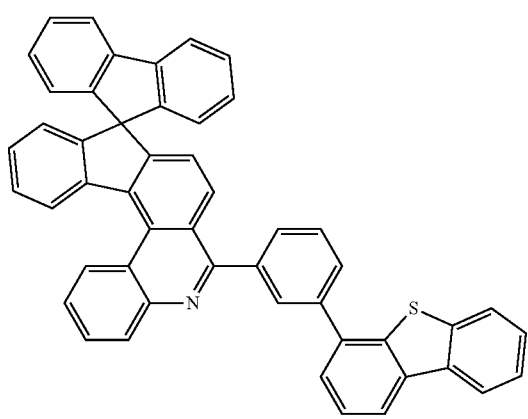
84
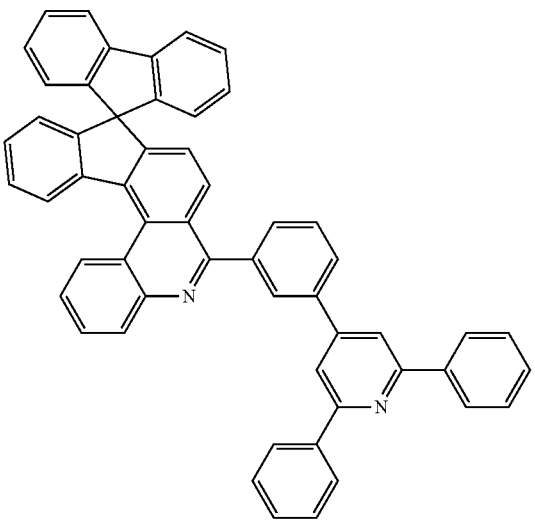
85
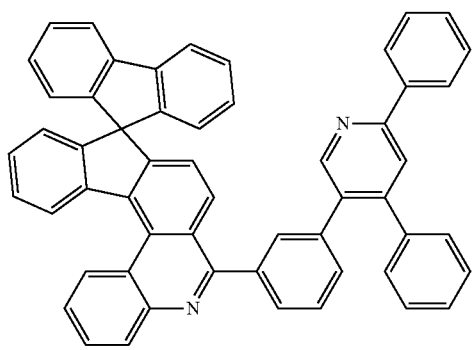
86
87
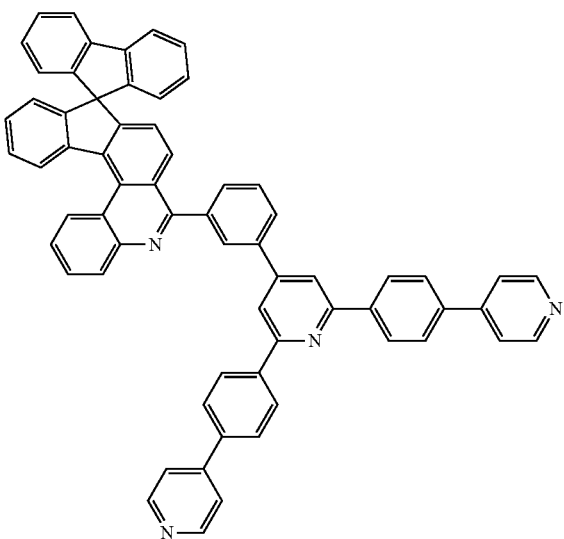

88
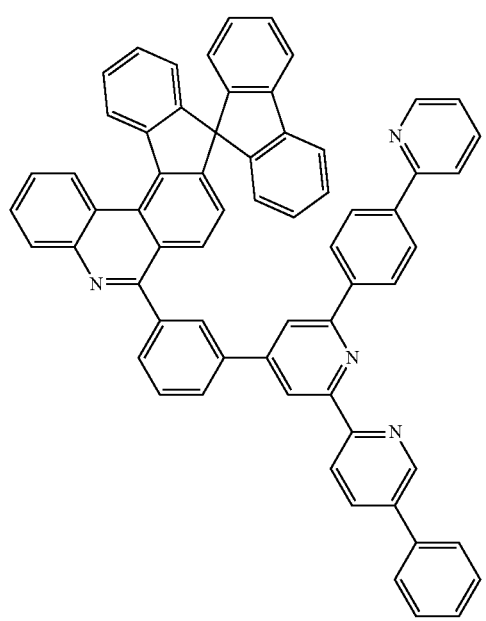
89
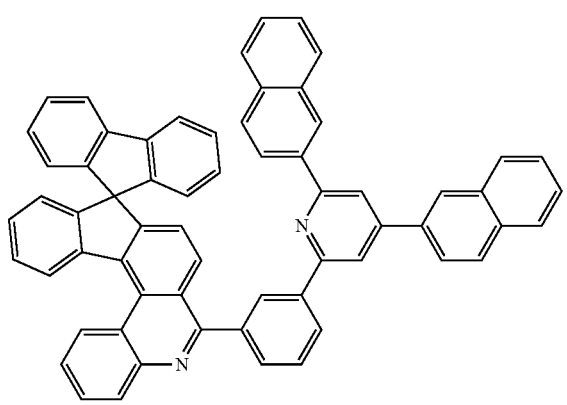
90
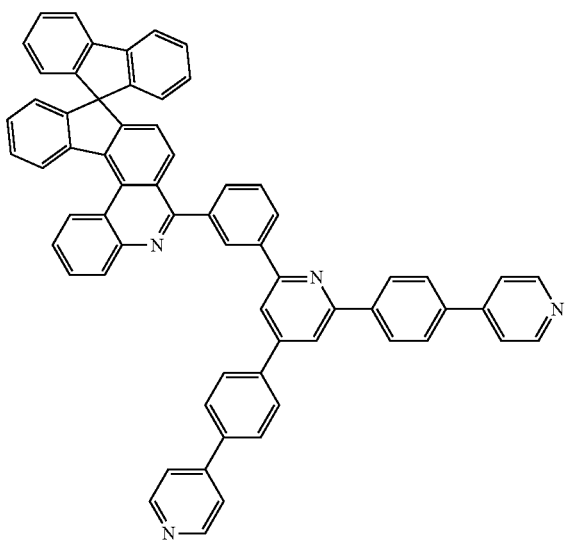
91
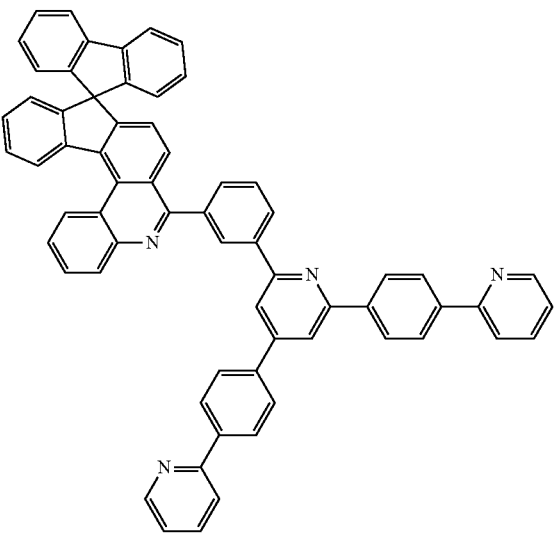
92
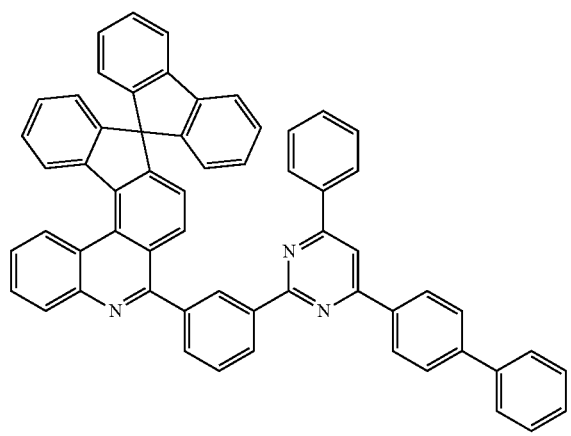
93

94
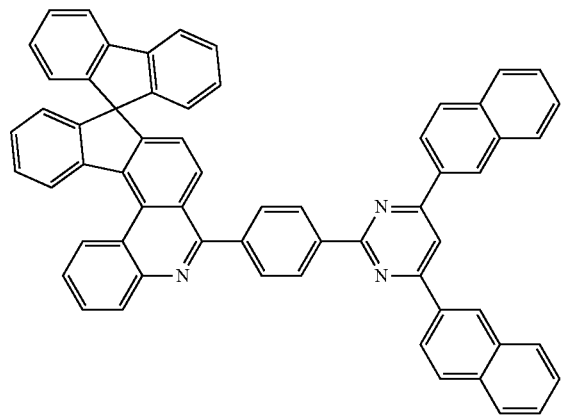
95
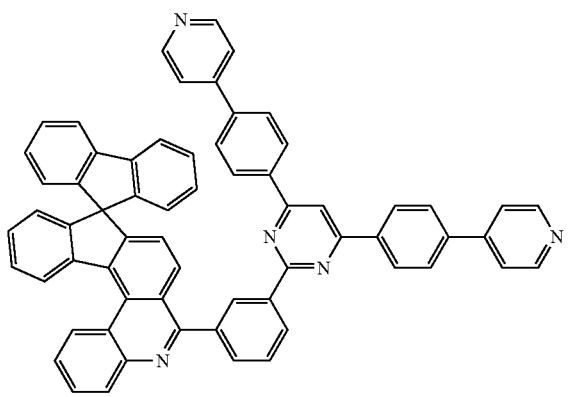
96
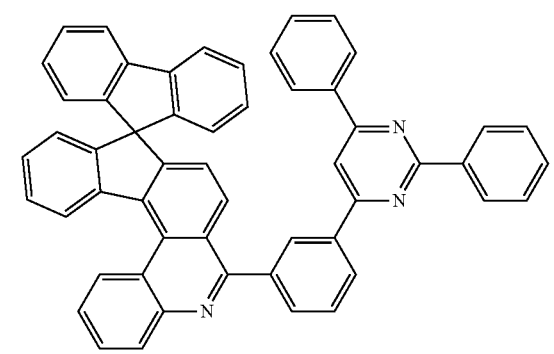
97
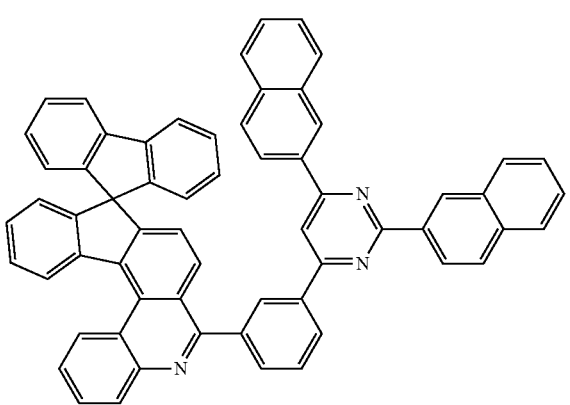
98
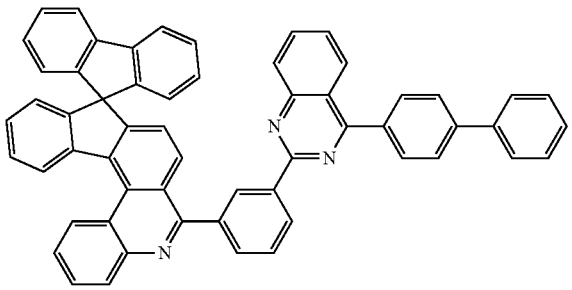
99
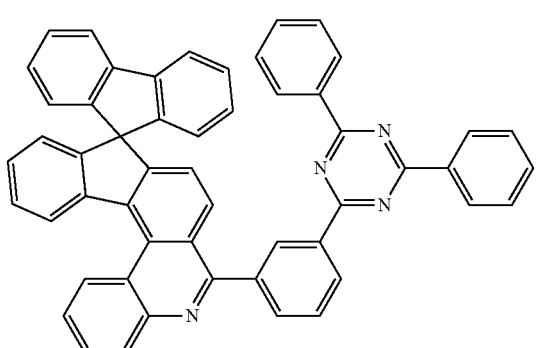
100
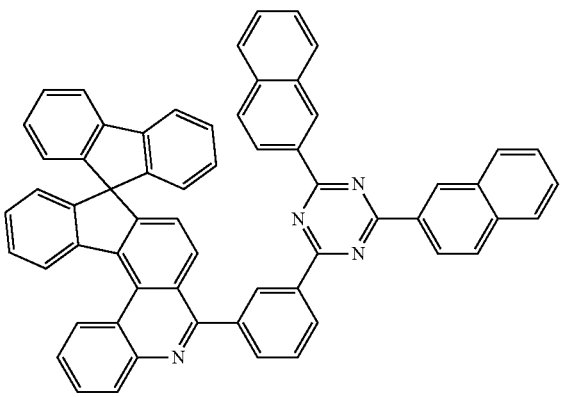
101
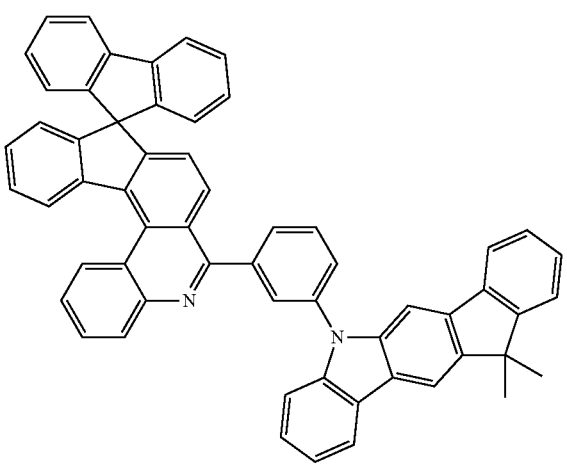

102
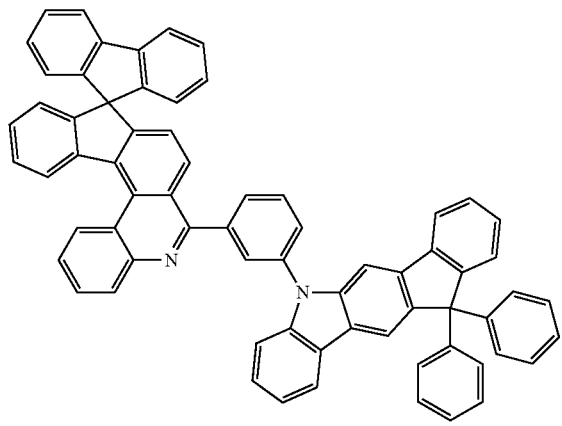
103
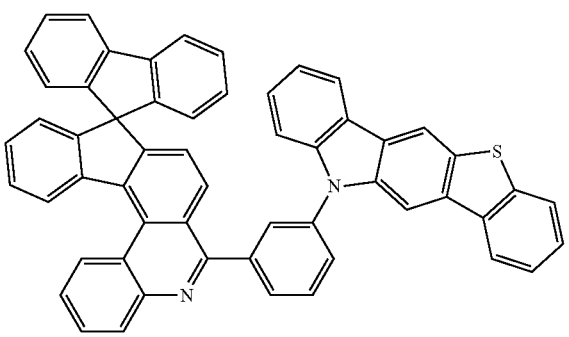
104
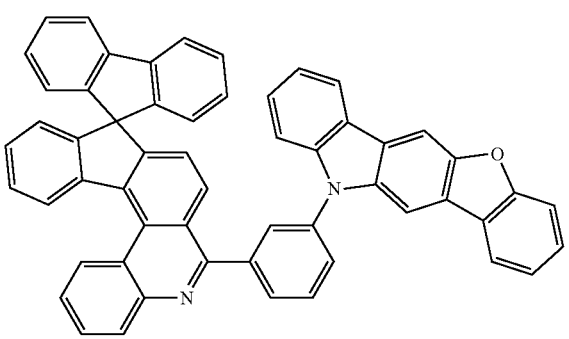
105
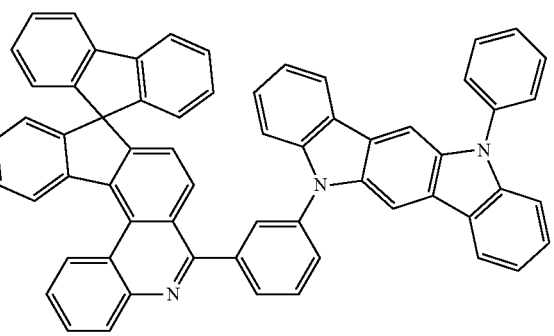
106
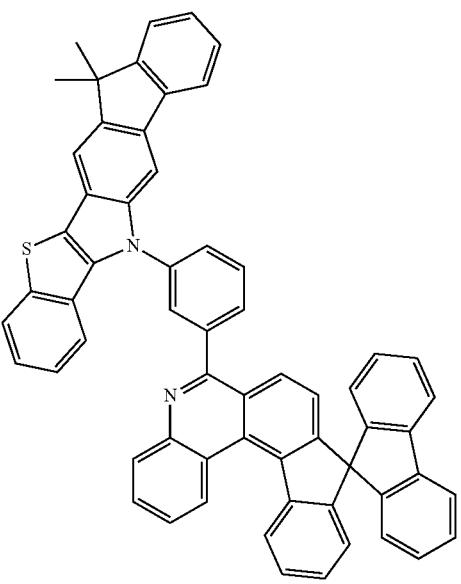
107
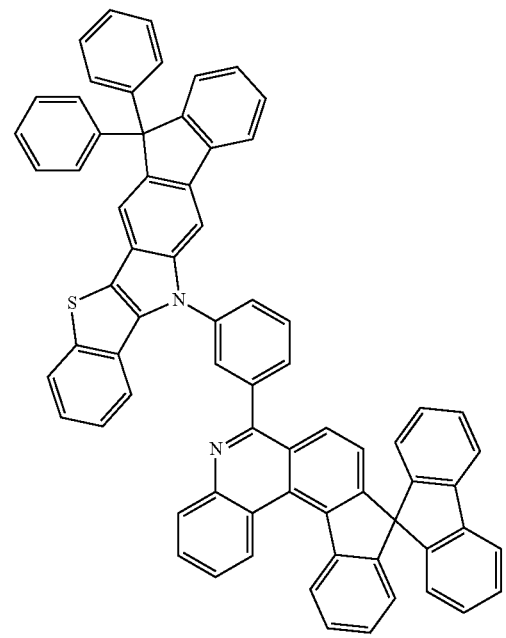

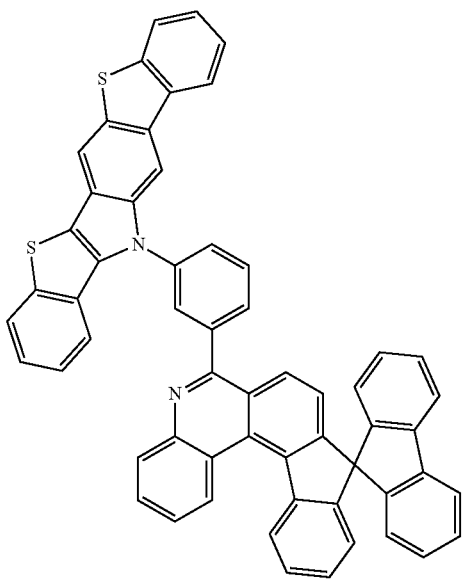
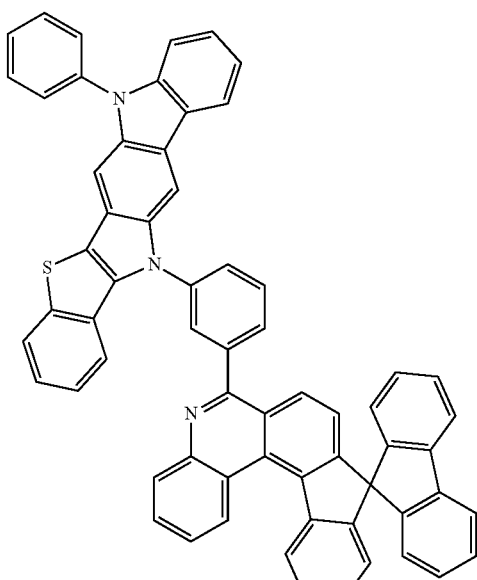
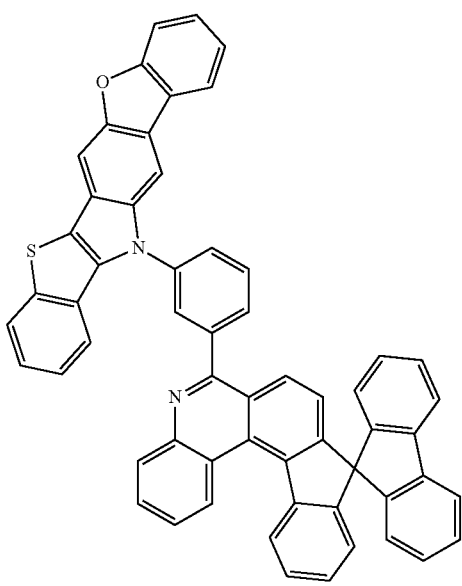
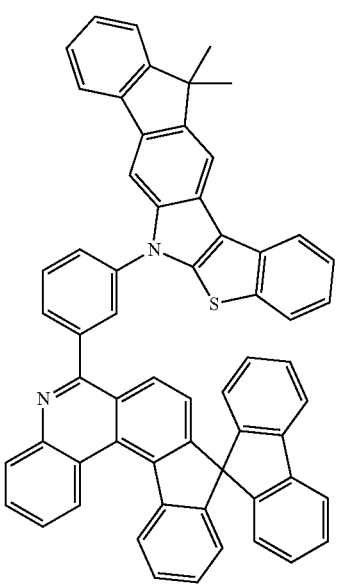

112
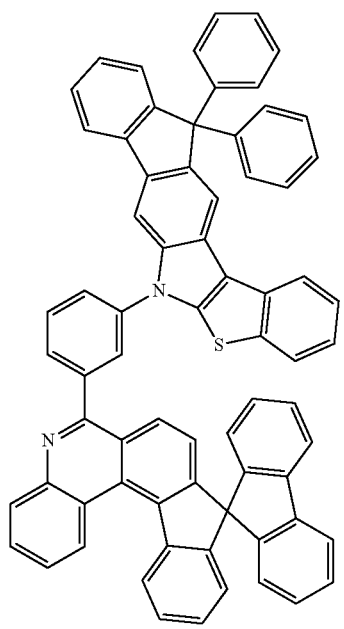
113
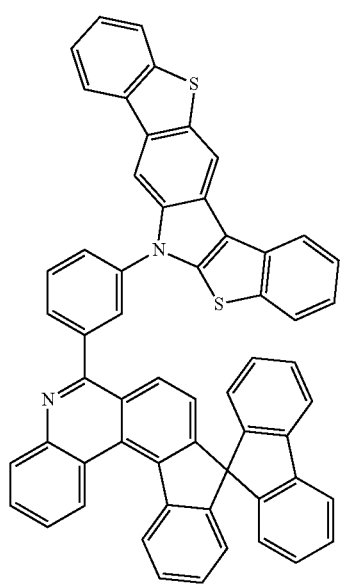
114
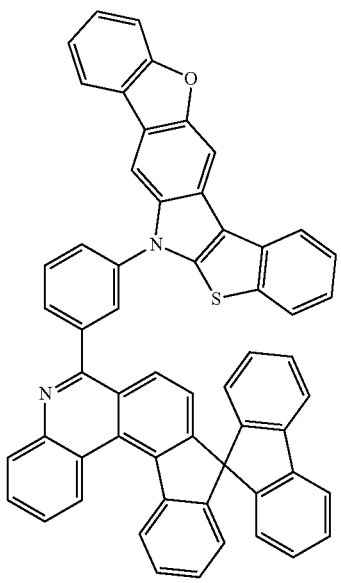
115
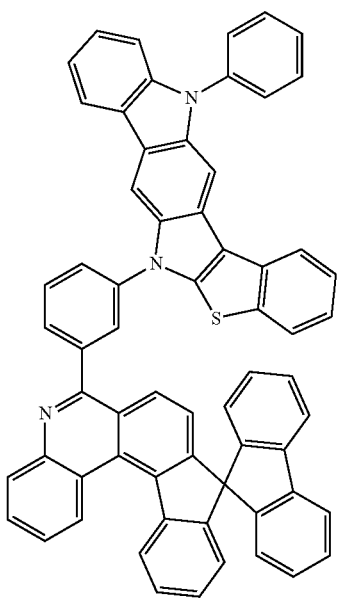

116
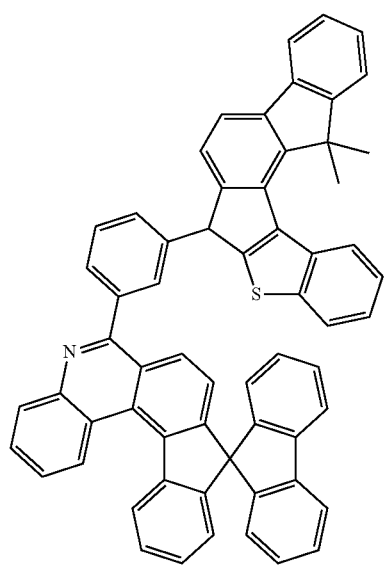
117
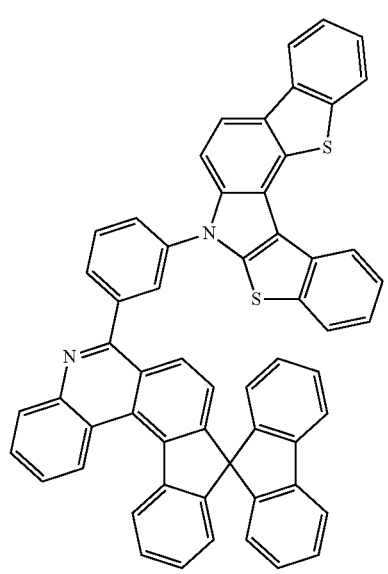
118
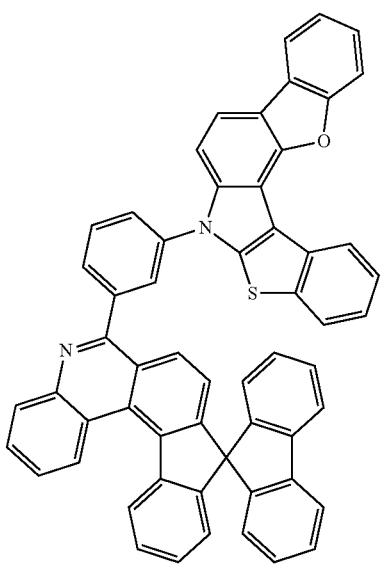
119
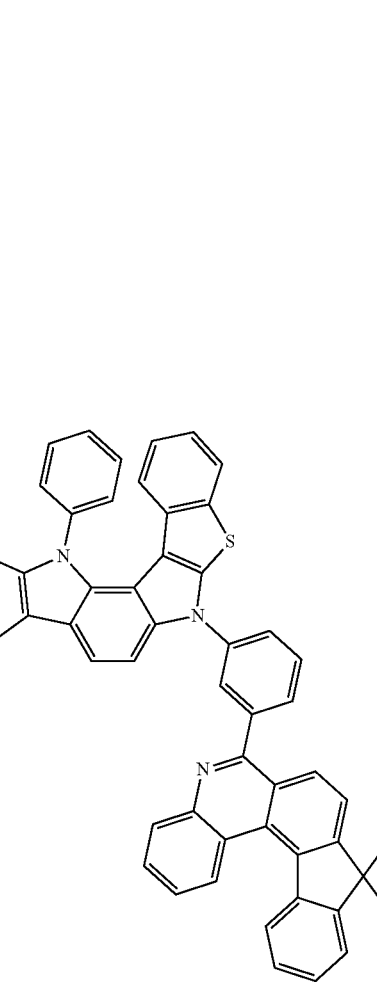

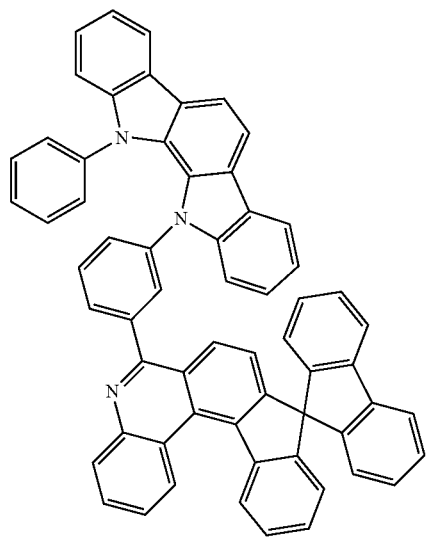
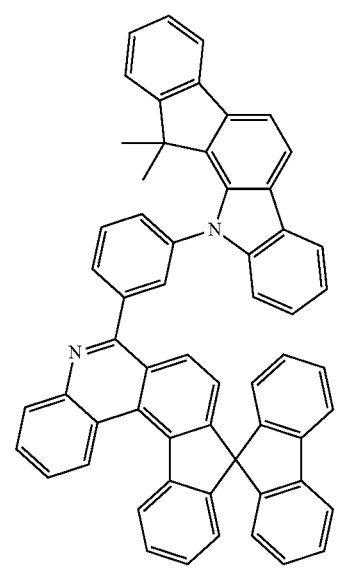
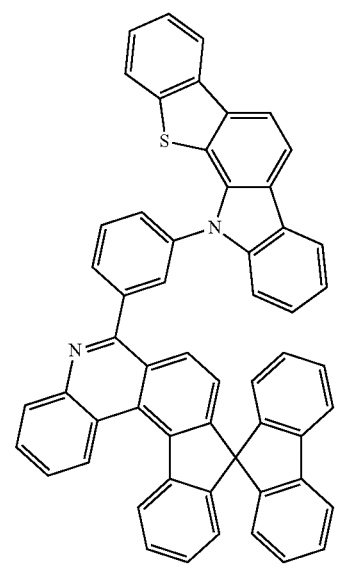
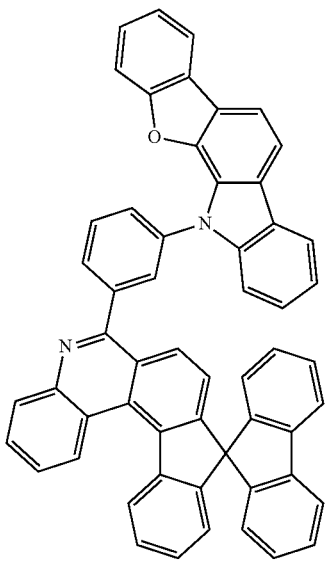
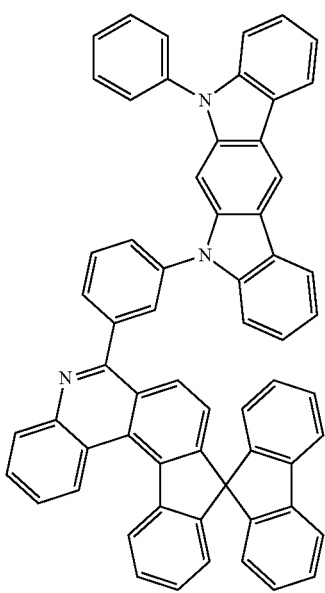

125
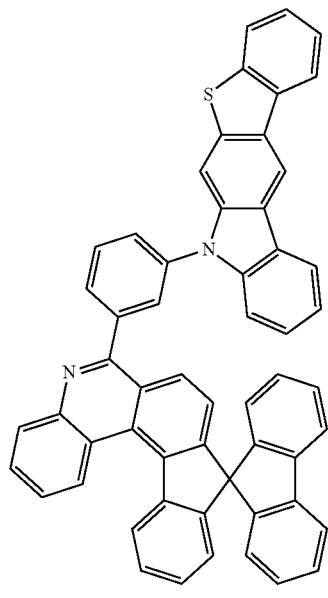
126
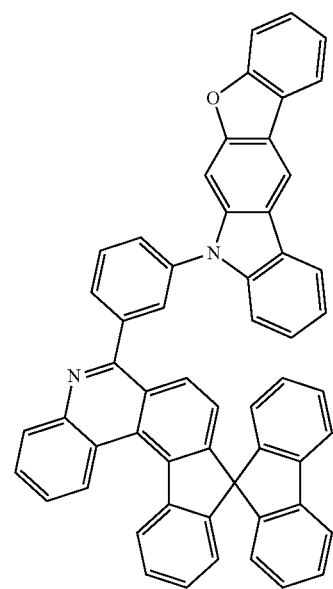
127
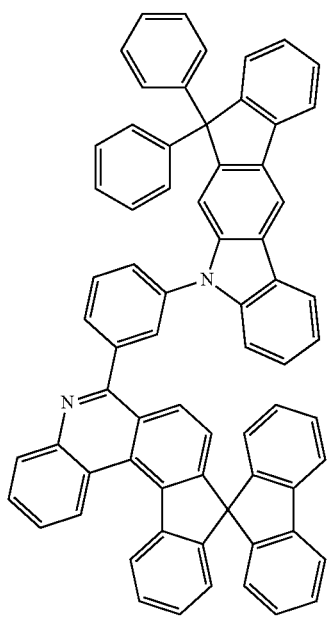
128
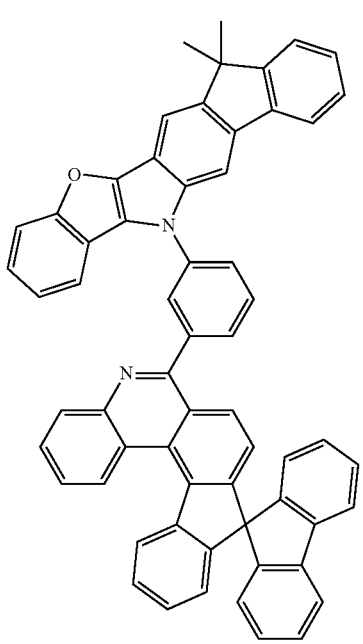

129
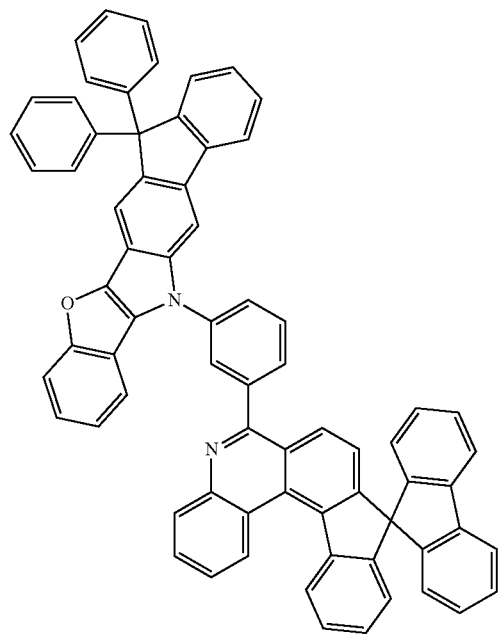
130
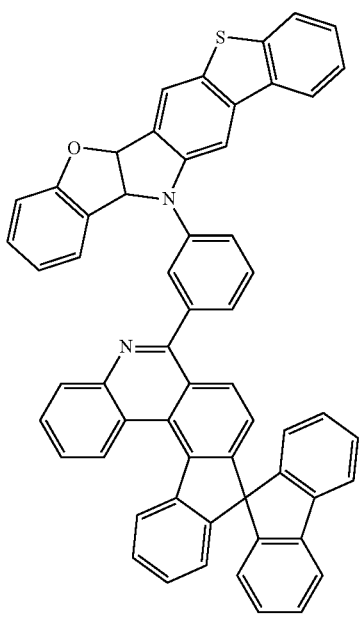
131
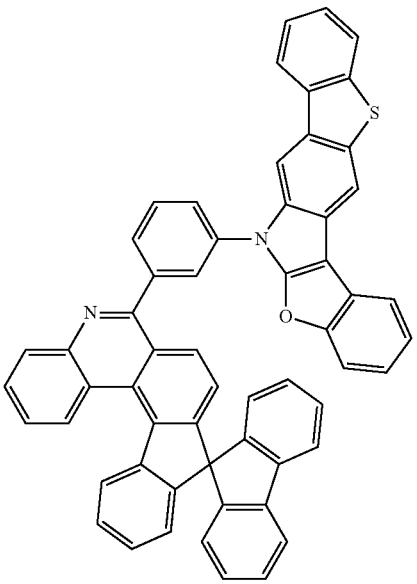
132
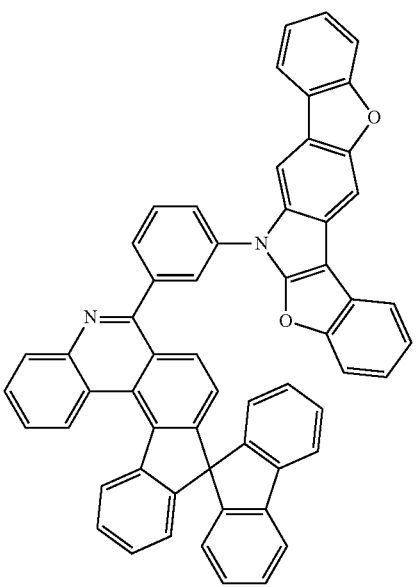

133
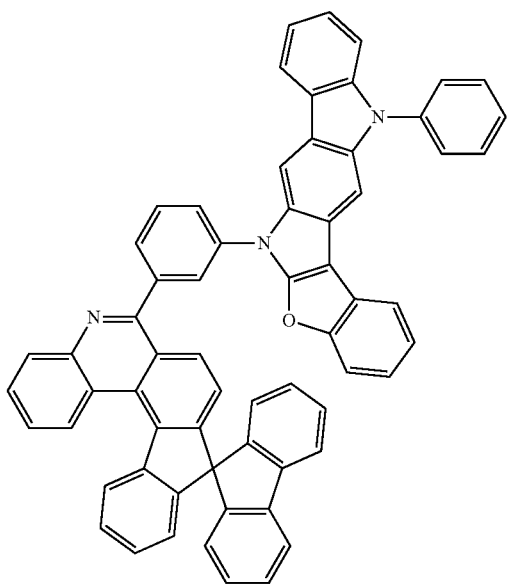
134
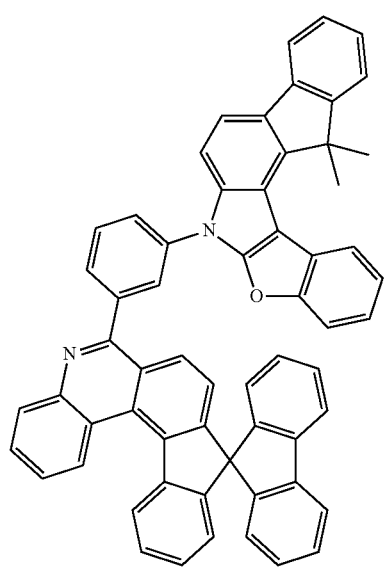
135
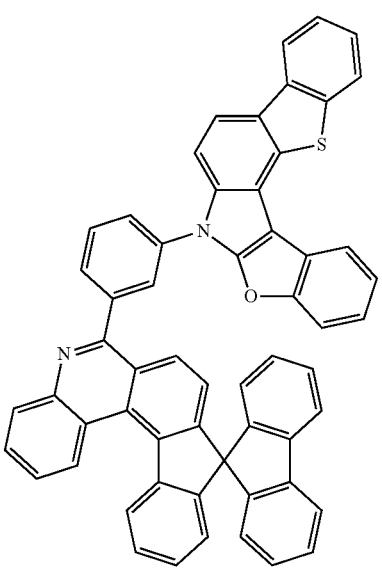
167
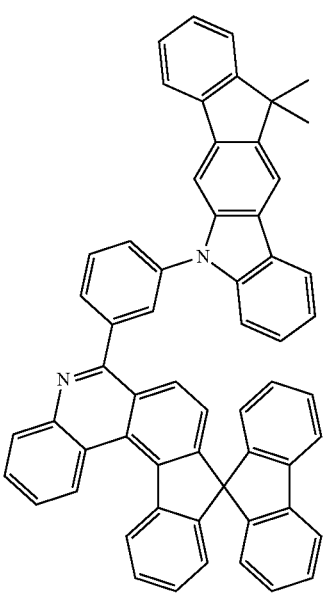

-continued
167
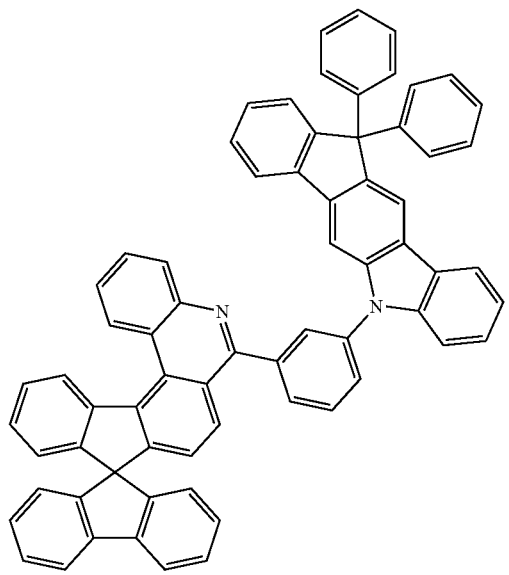
139
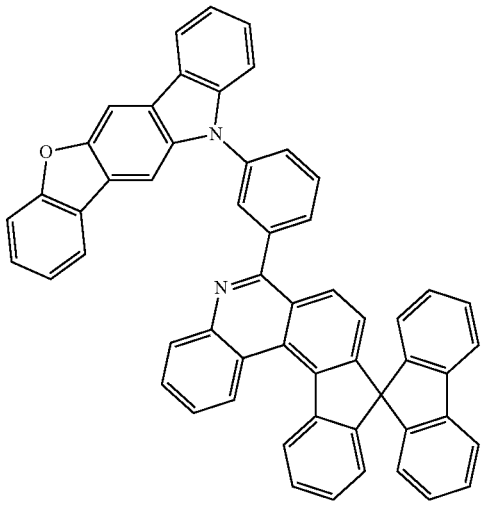
140
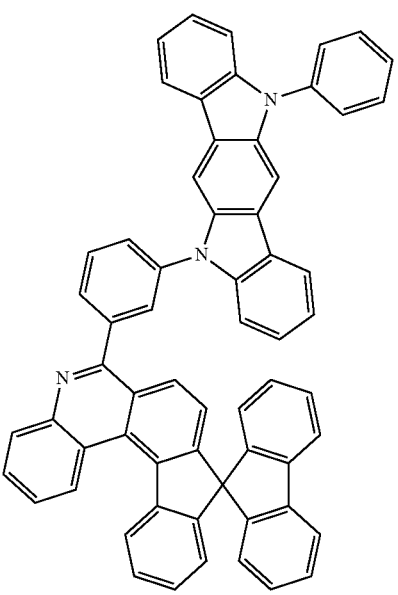
138
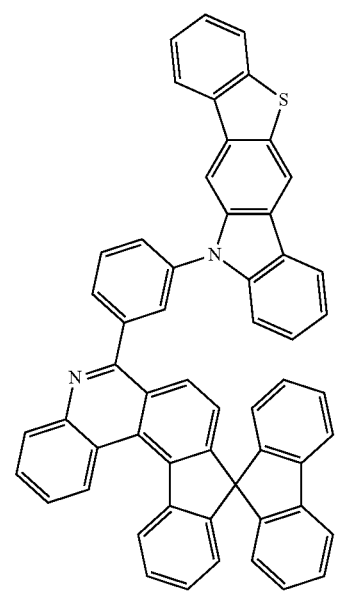
141
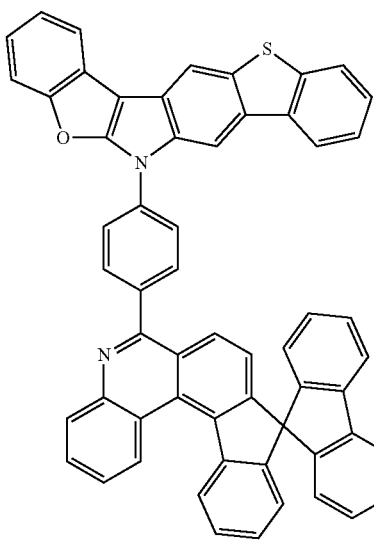

142
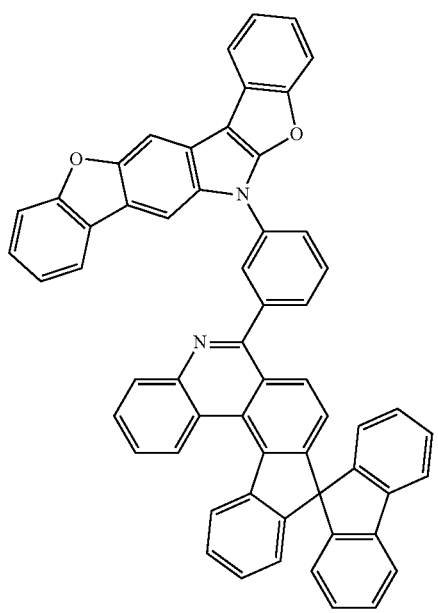
143
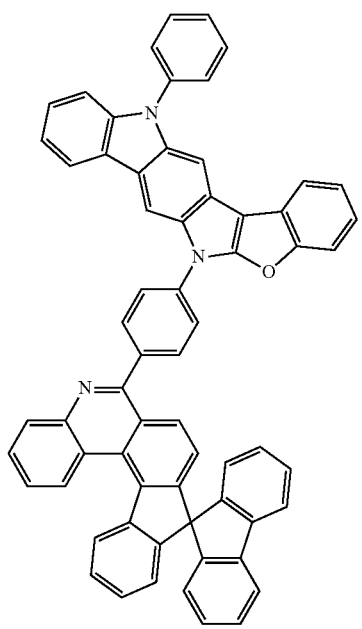
144
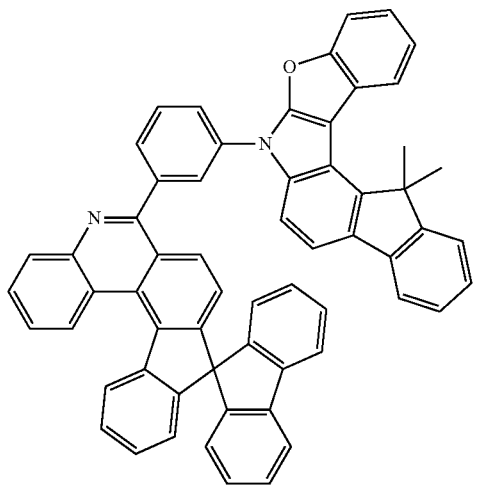
145
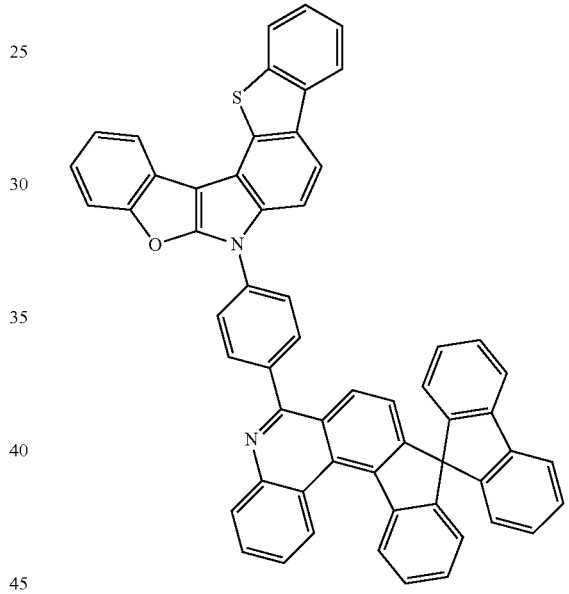
146
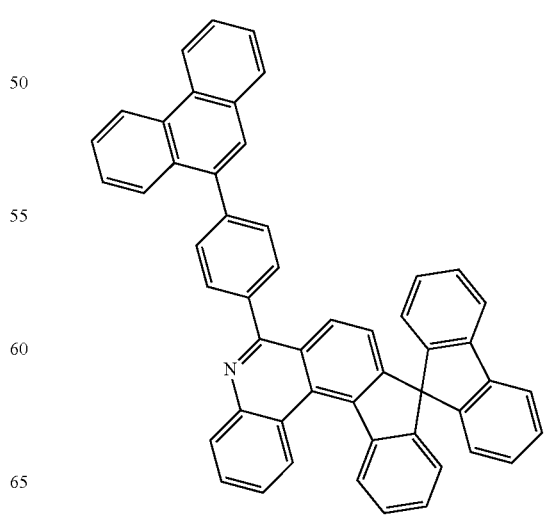

147
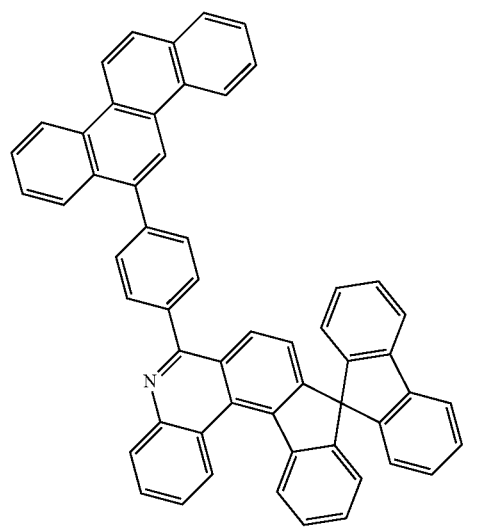
148
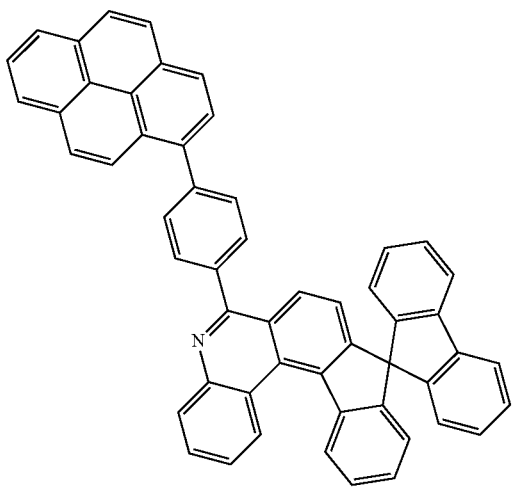
149
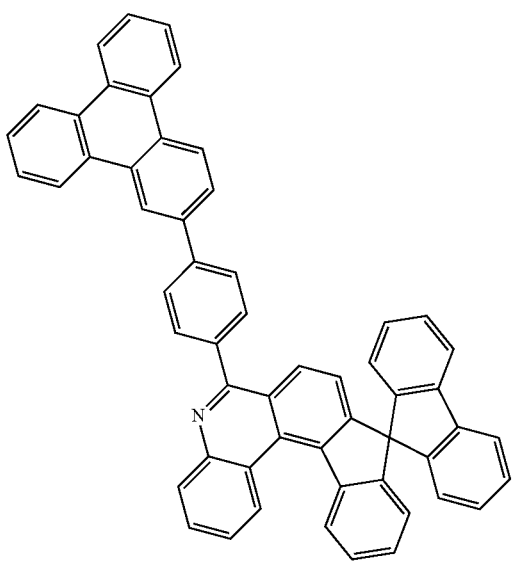
150
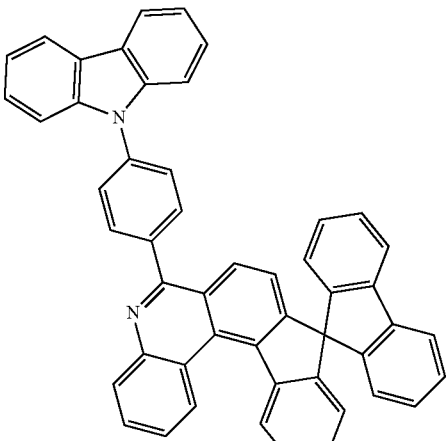
151
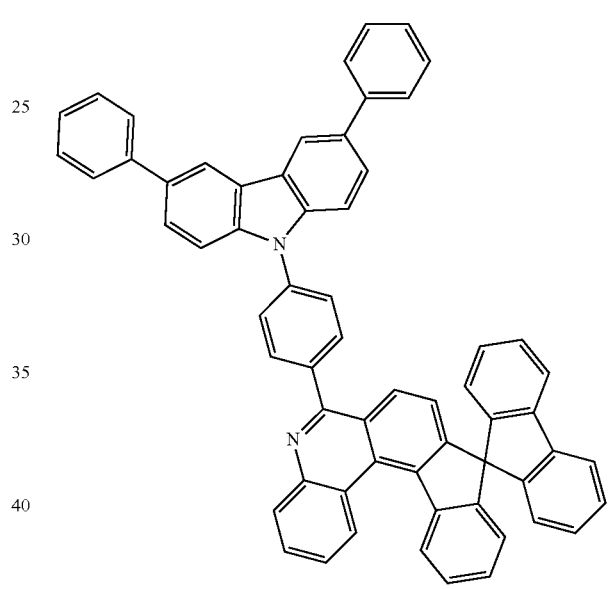
152
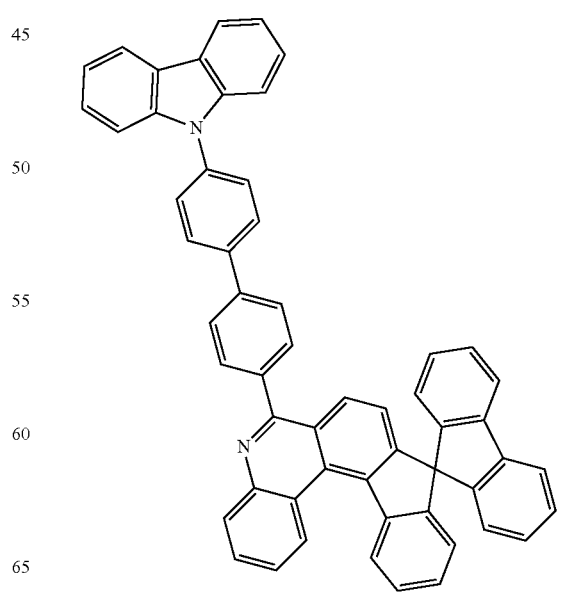

153
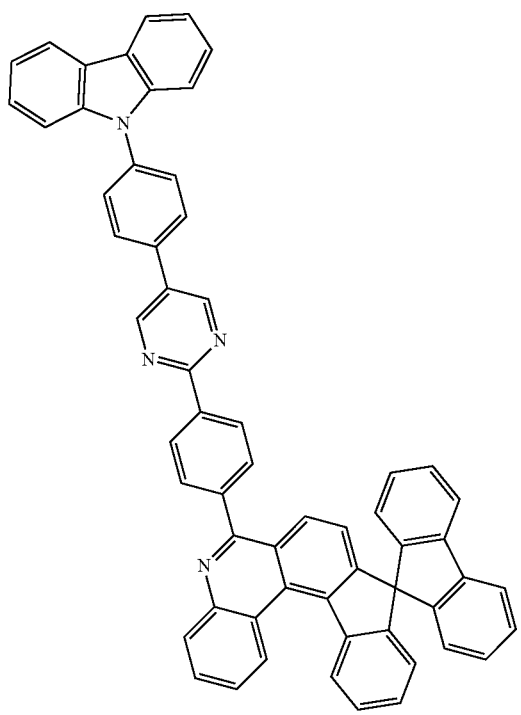
154
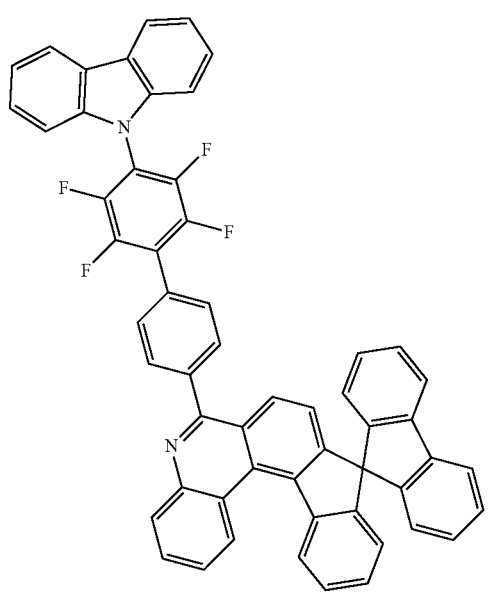
155
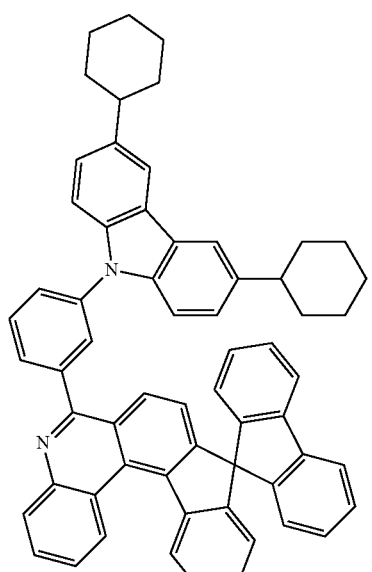
156
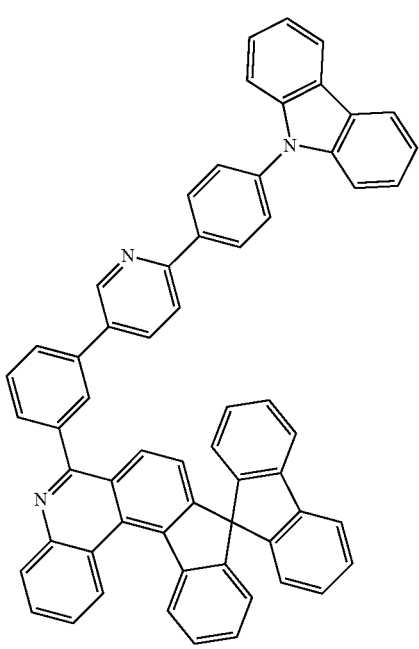

157
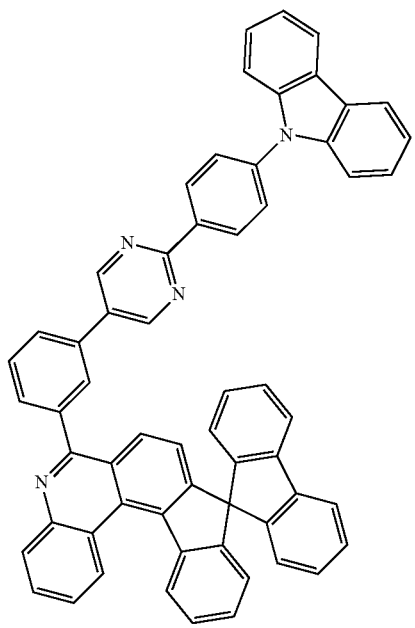
158
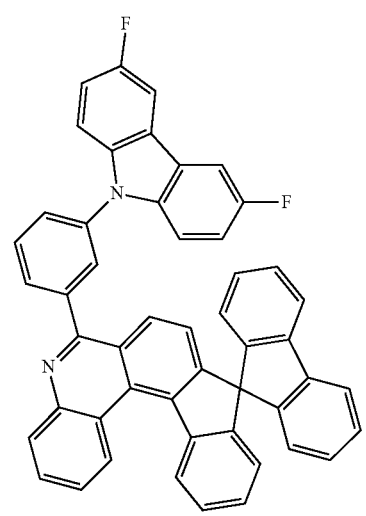
159
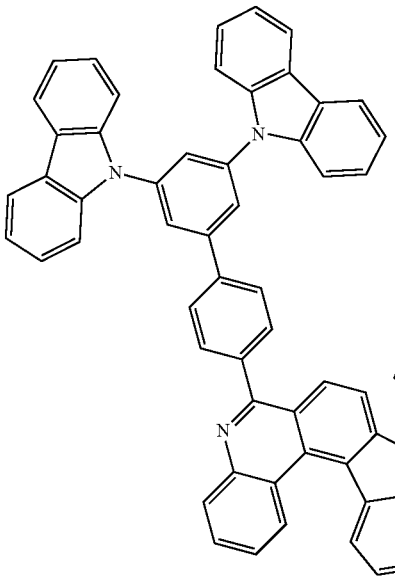
160
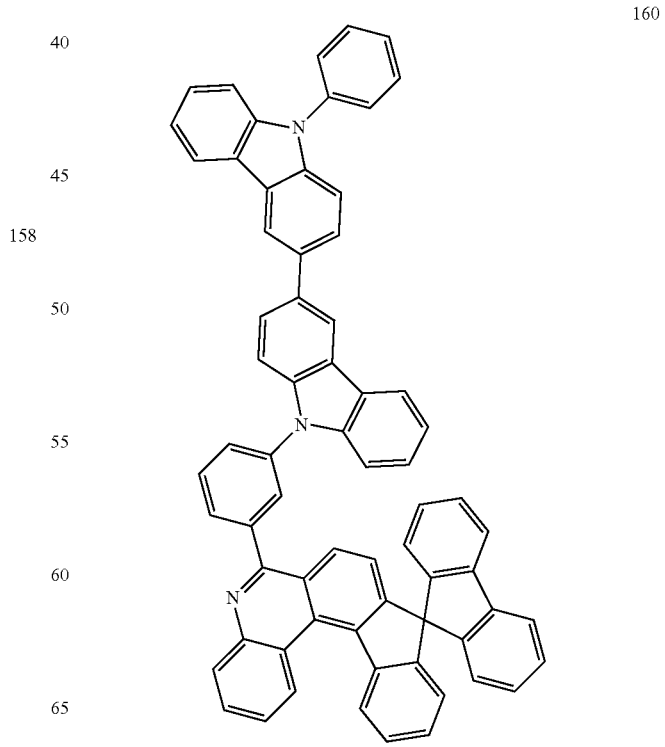

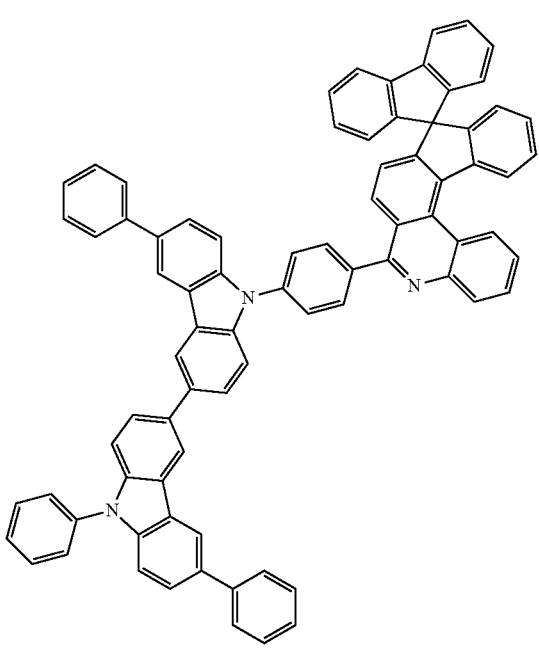
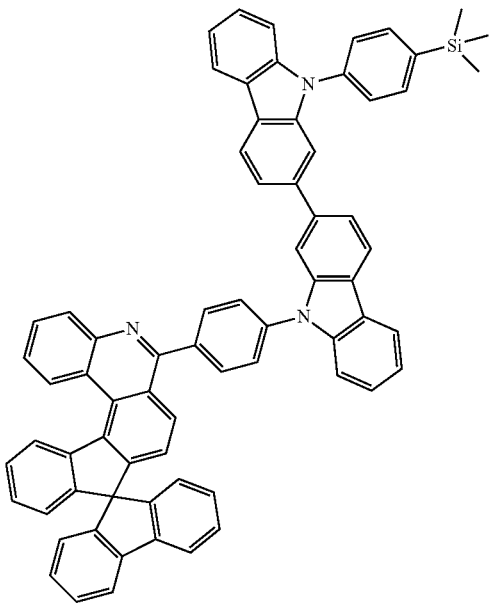
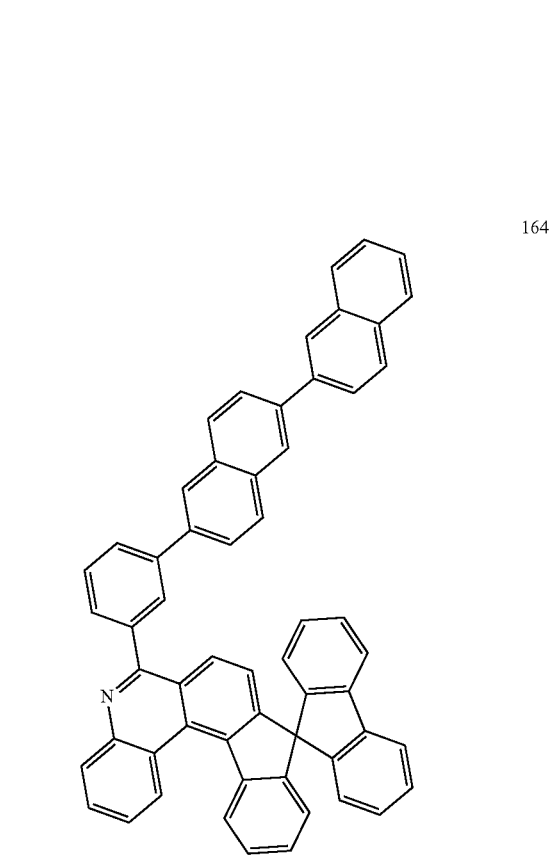

165
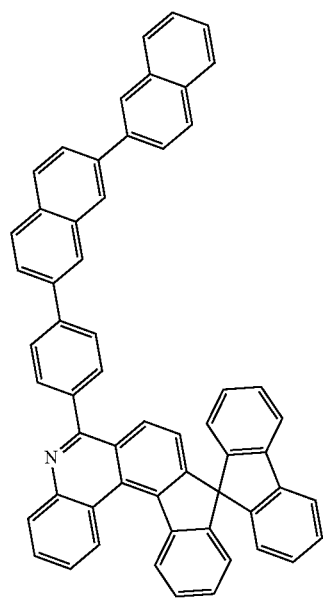
166
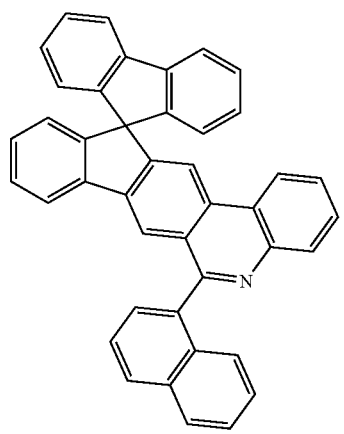
167
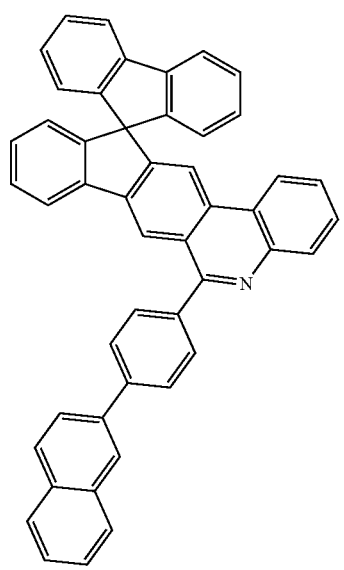
168
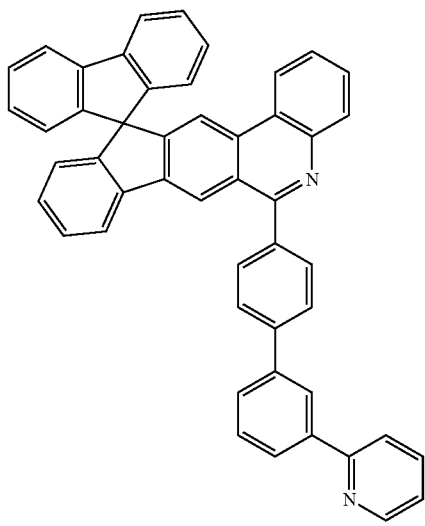
169
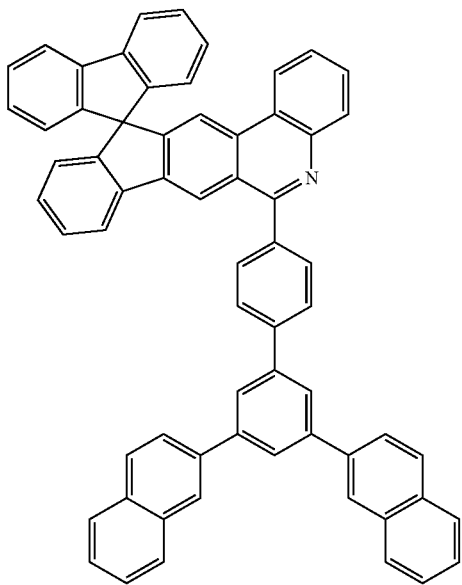

71
-continued
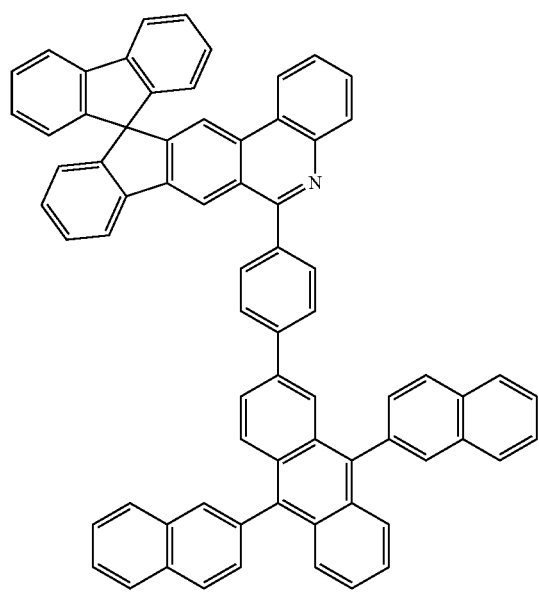
170
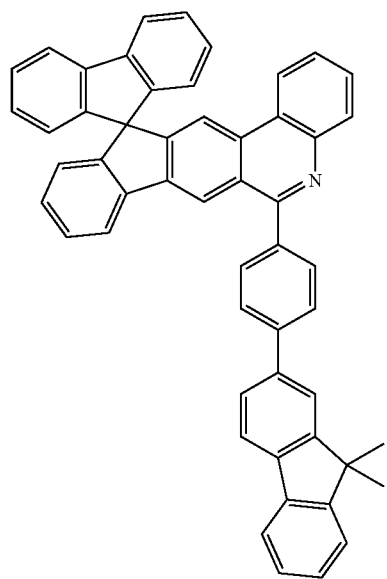
171
72
-continued
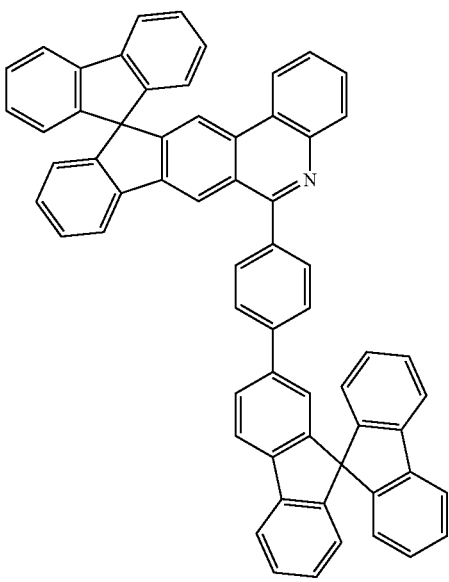
172
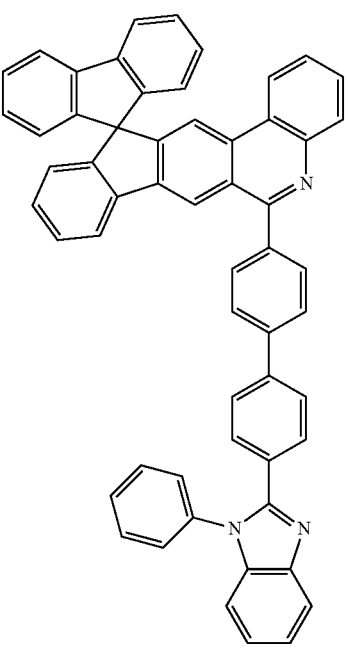
173

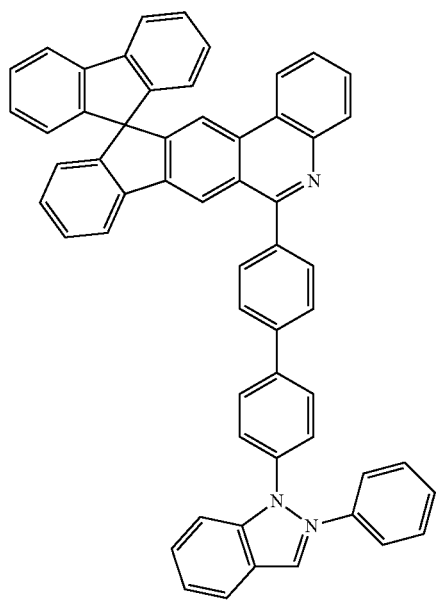
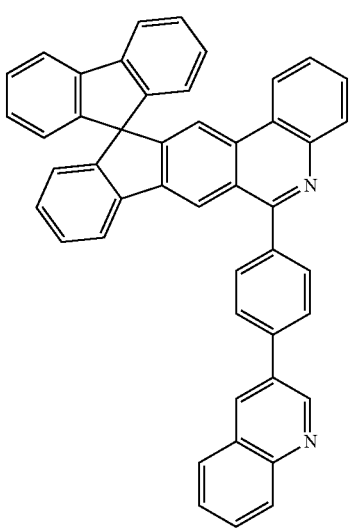

179
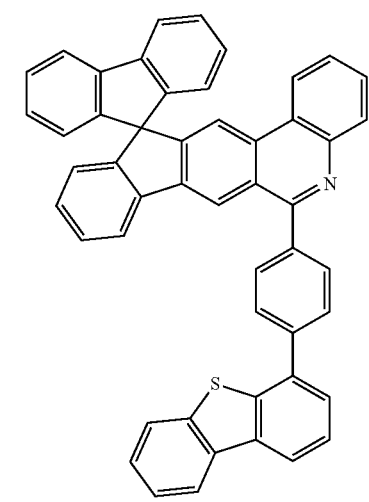
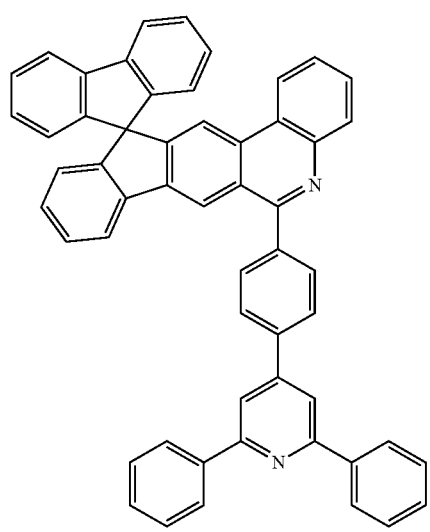
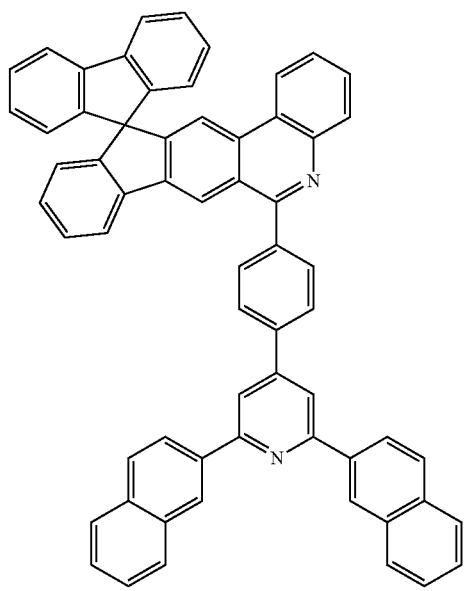
182
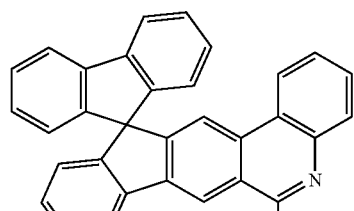
183
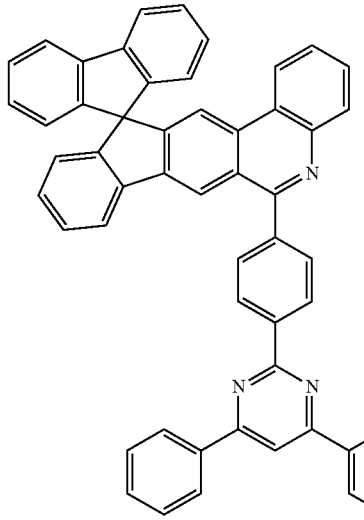

184
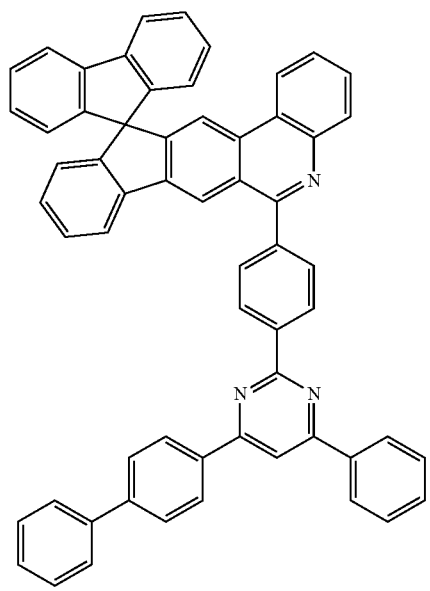
185
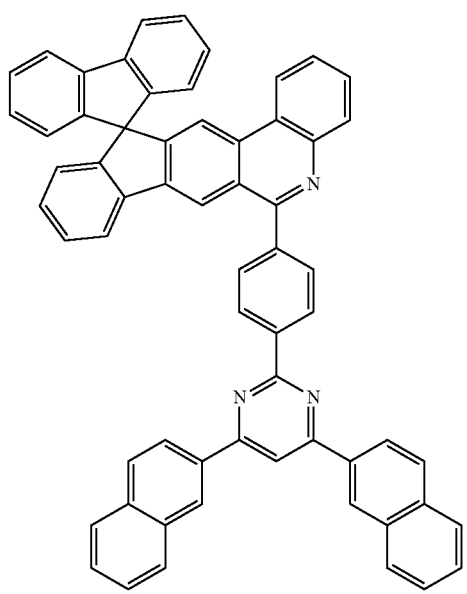
186
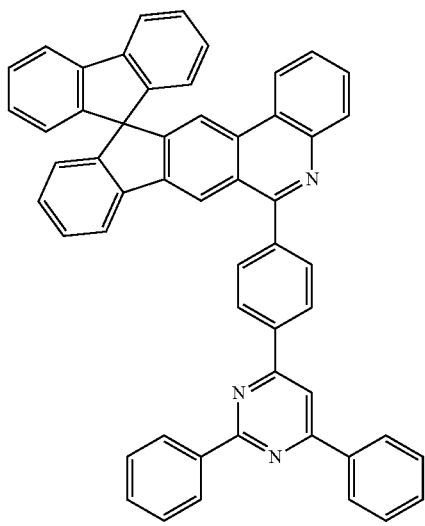
187
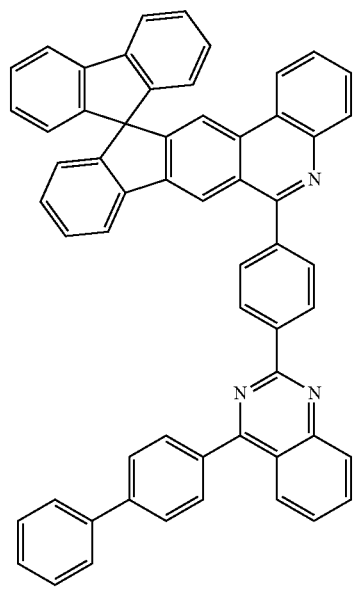
188

189
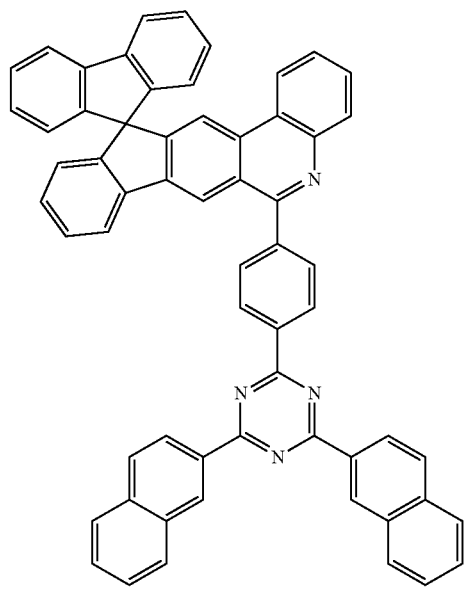
190
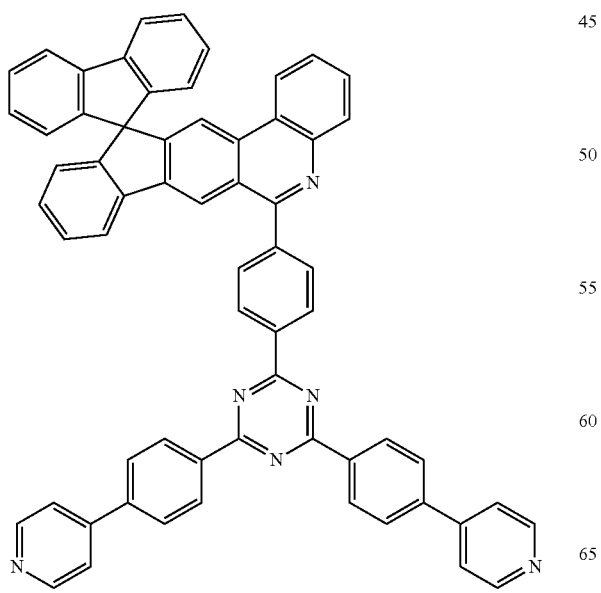
191
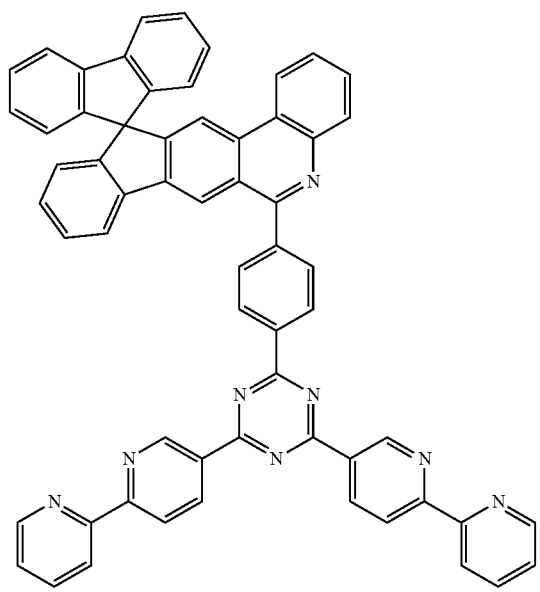
192
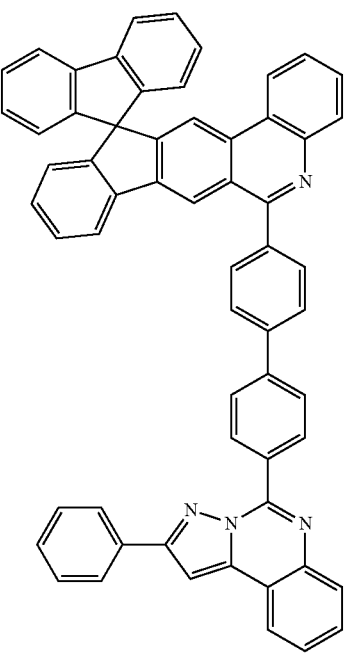

193
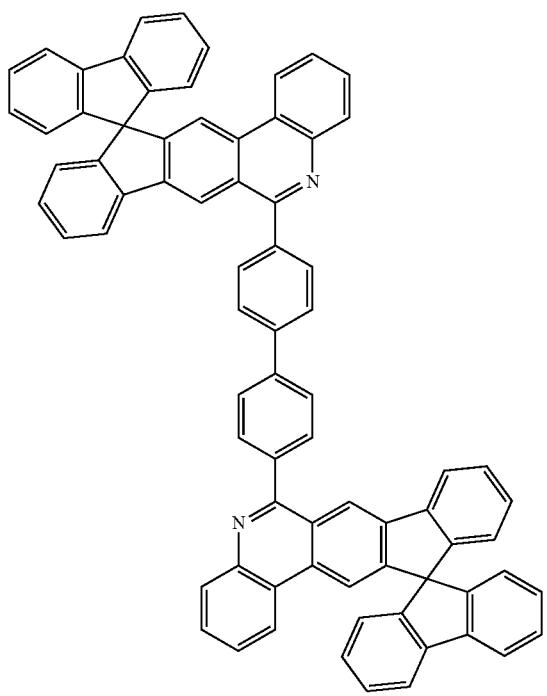
194
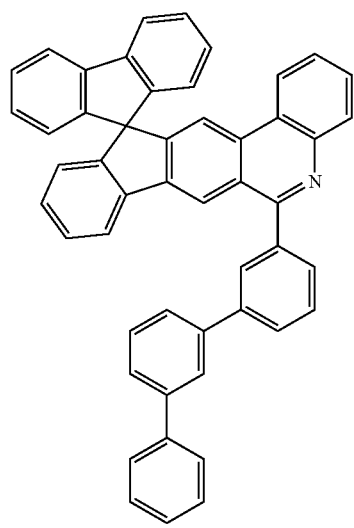
195
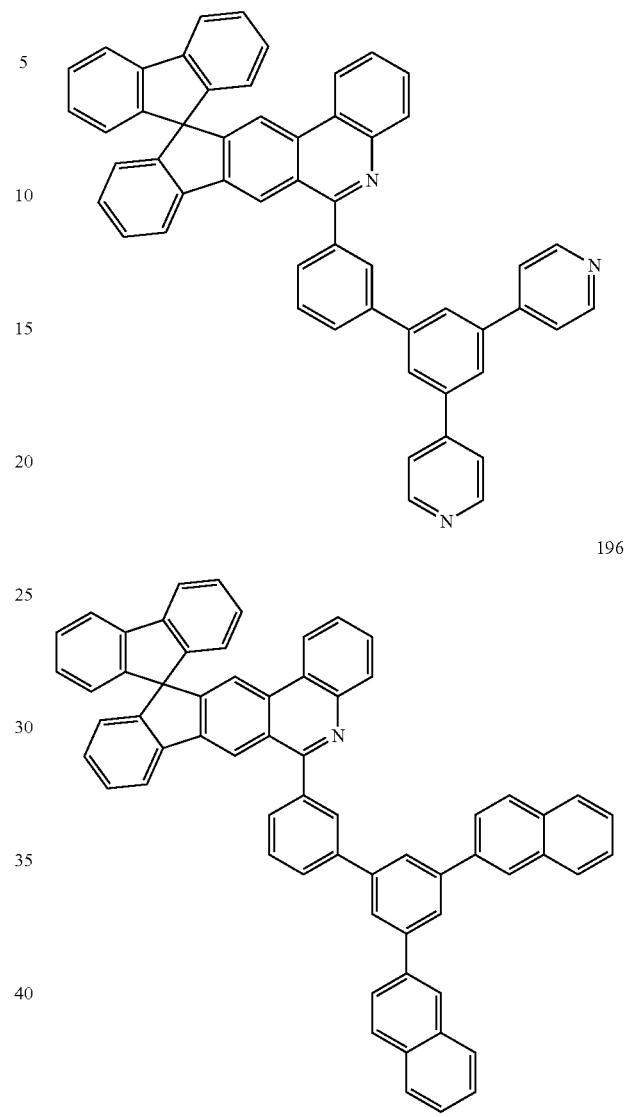
196
197
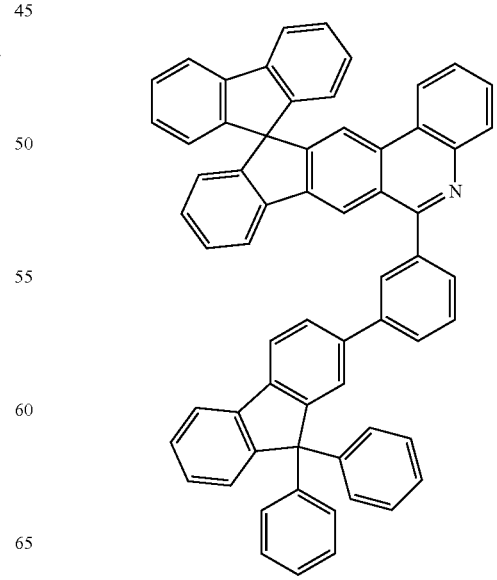

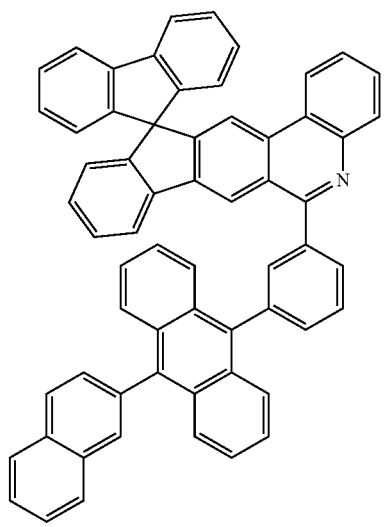
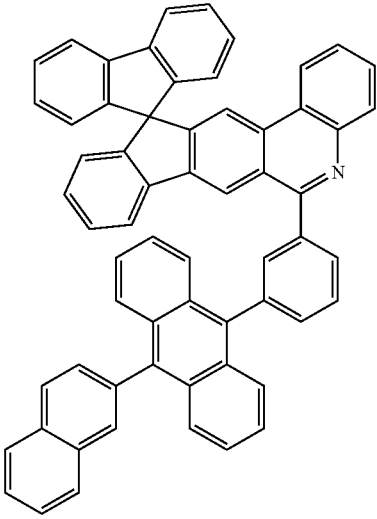
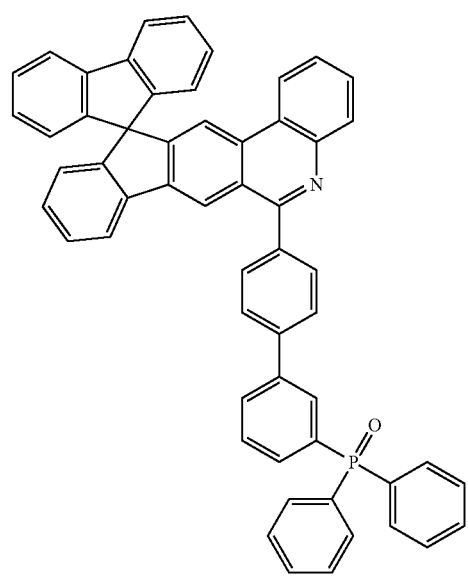
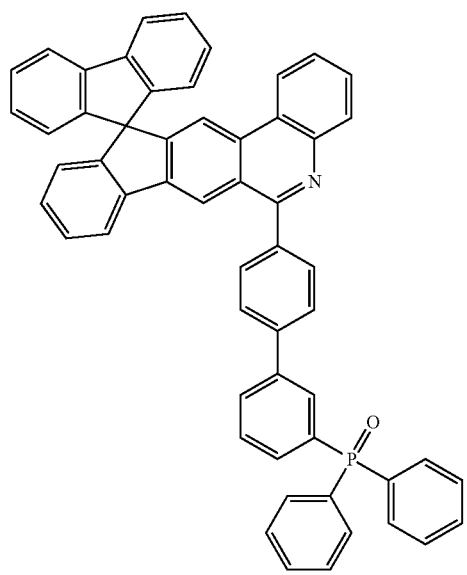
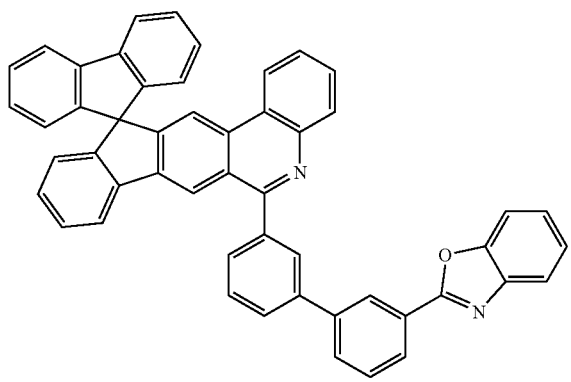
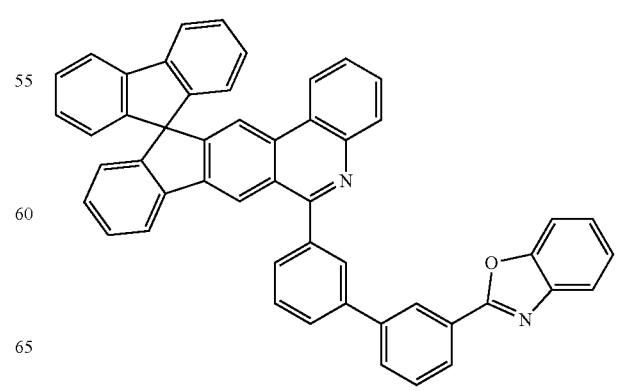

201
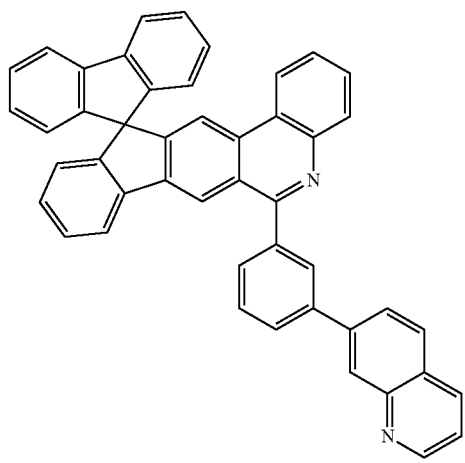
202
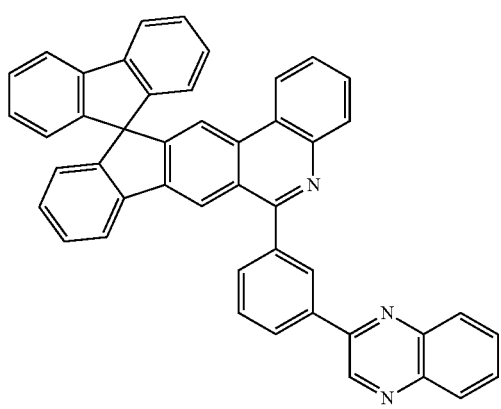
203
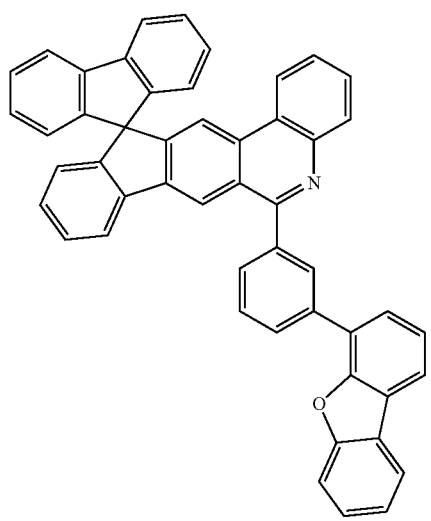
204
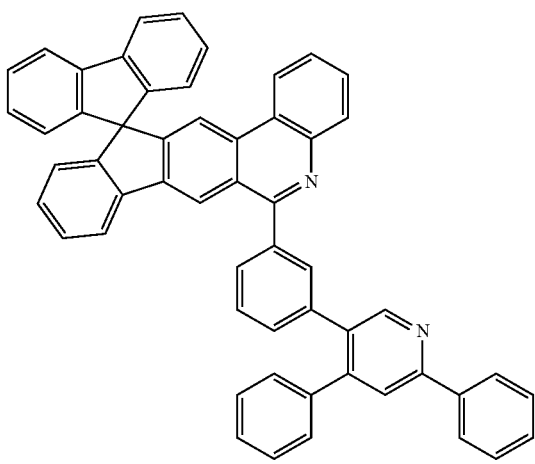
205
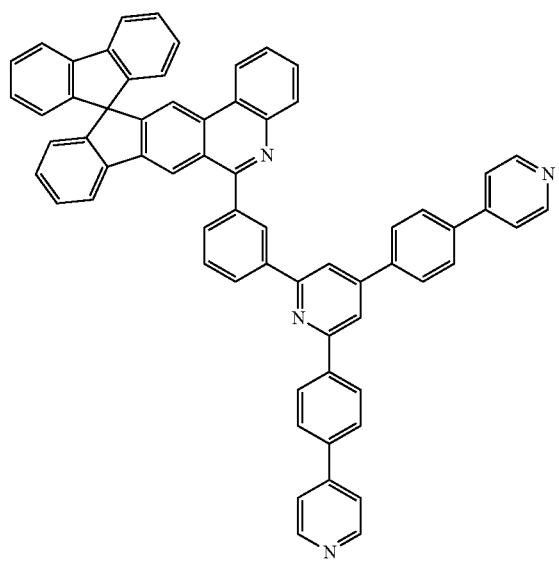
206
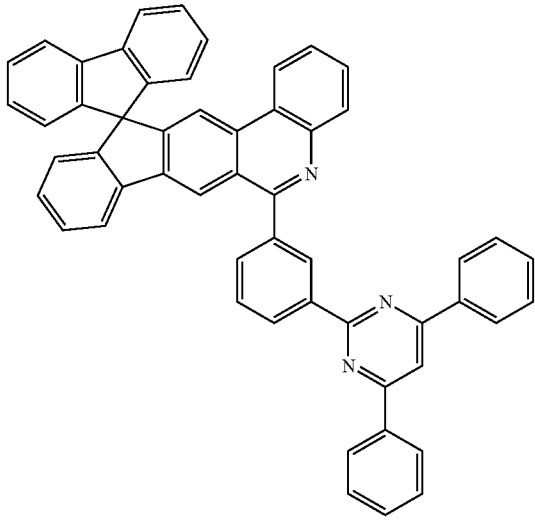

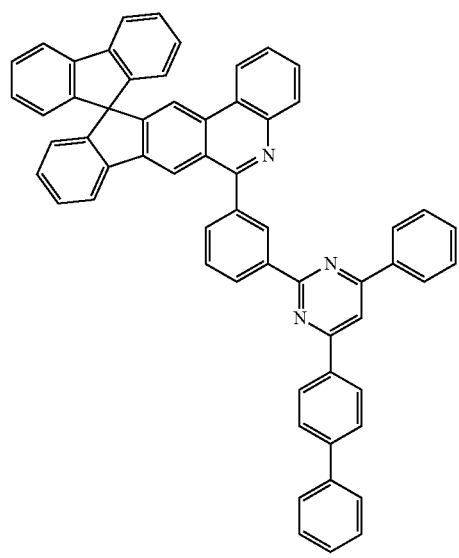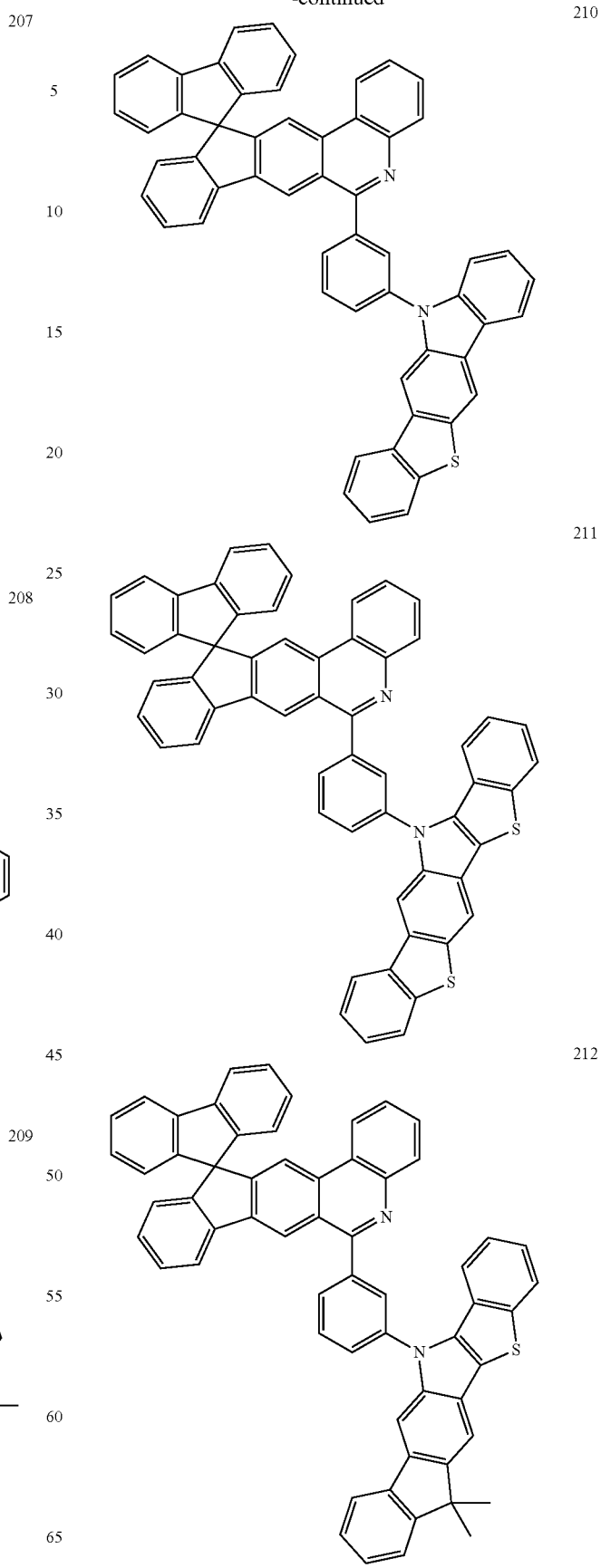

213
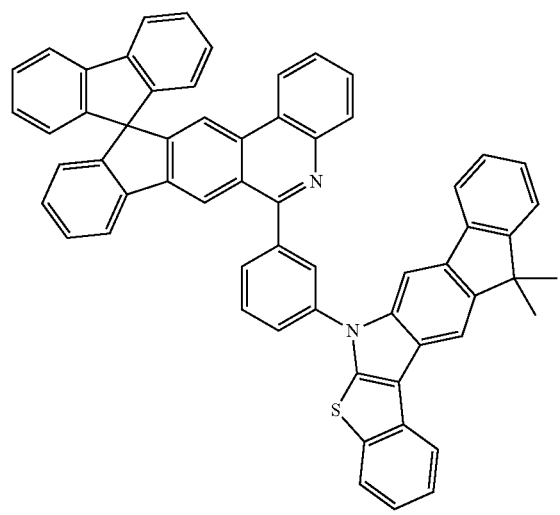
216
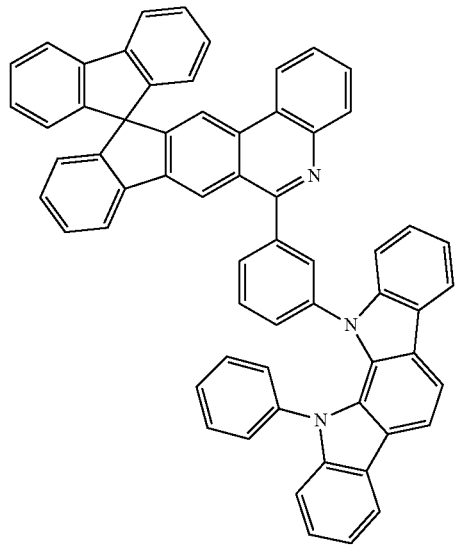
214
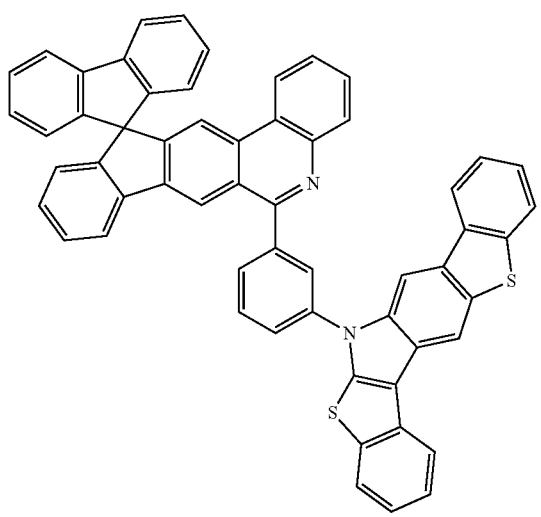
217
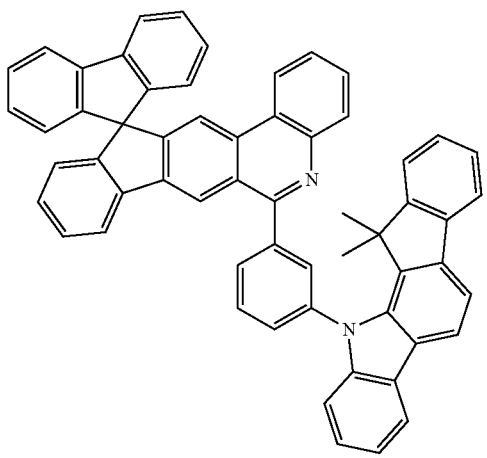
215
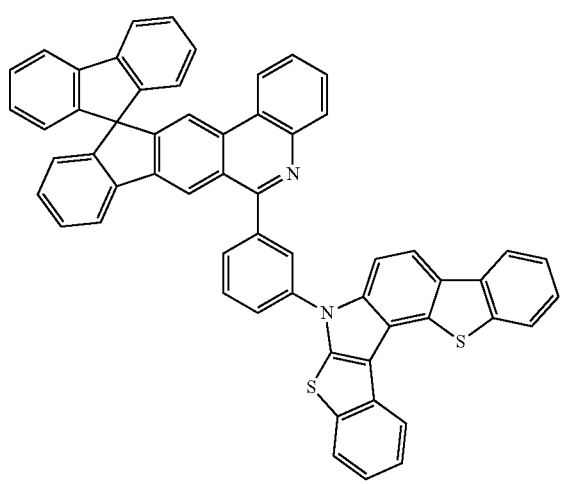
218
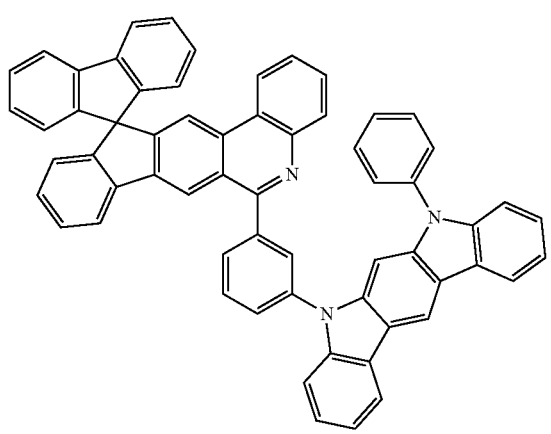

219
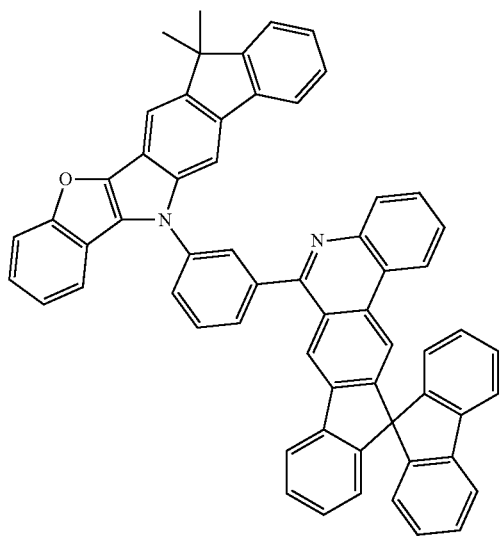
220
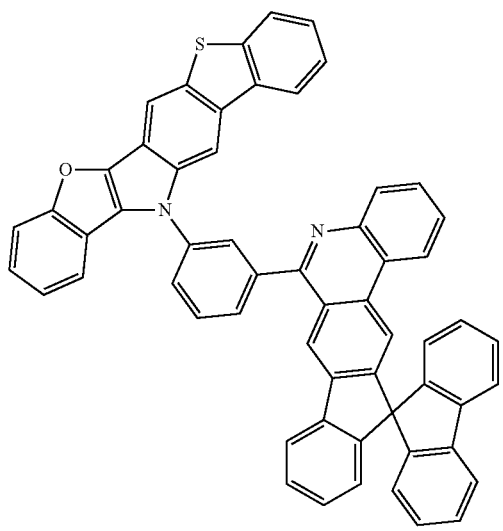
221
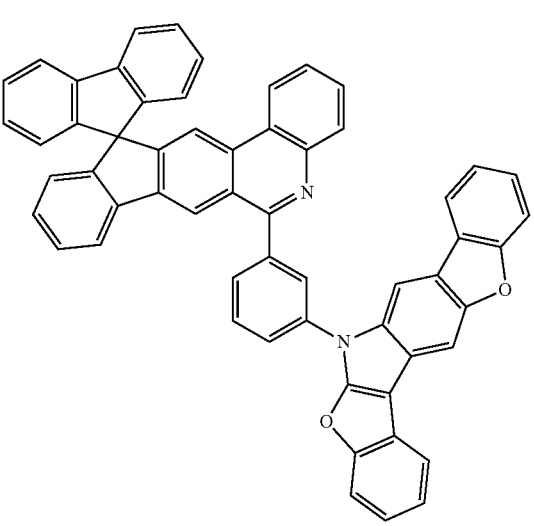
222
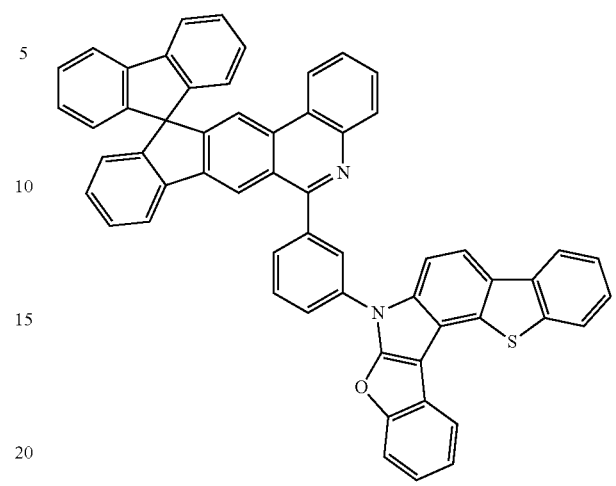
223
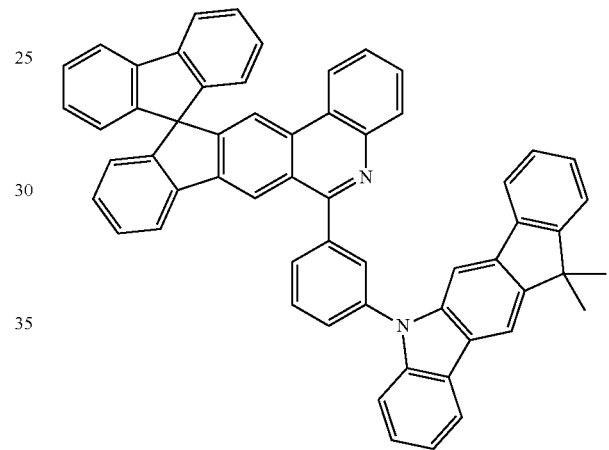
224
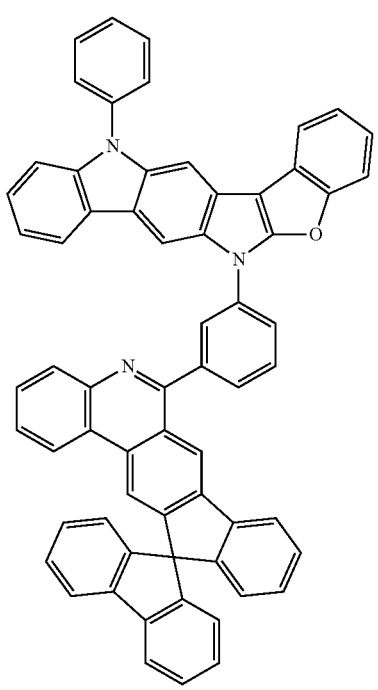

225
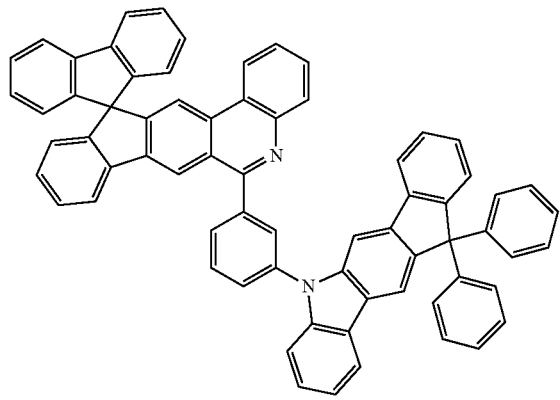
226
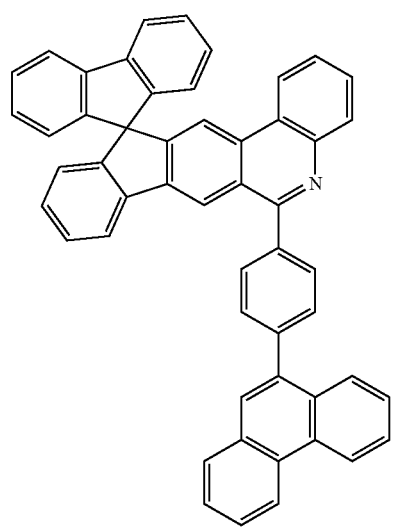
227
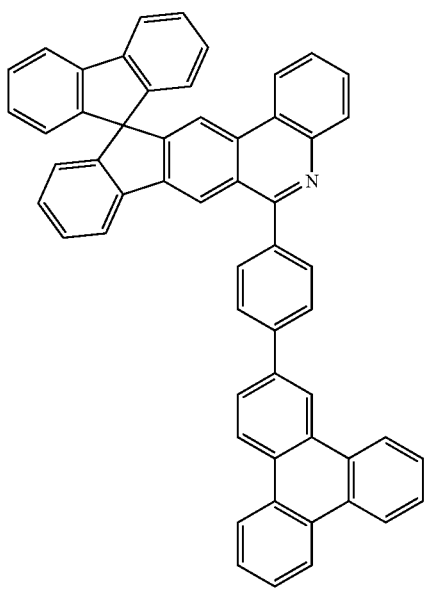
228
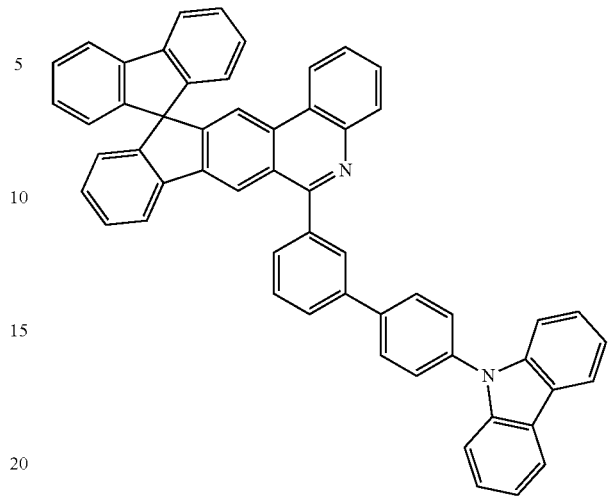
229
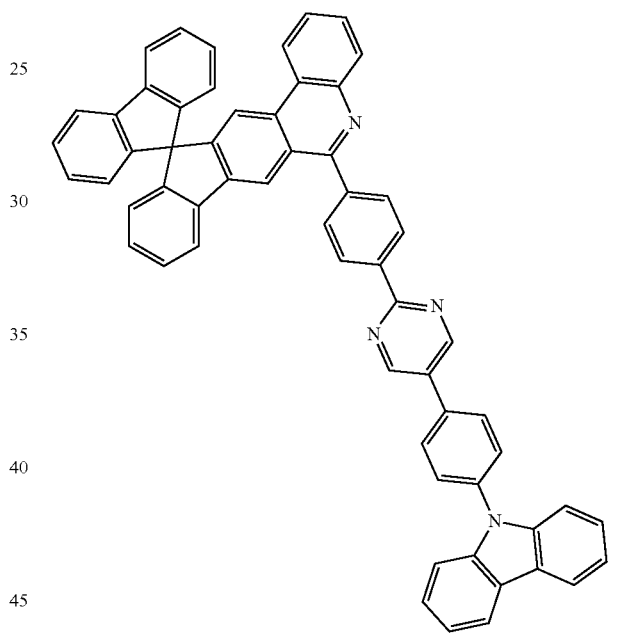
230
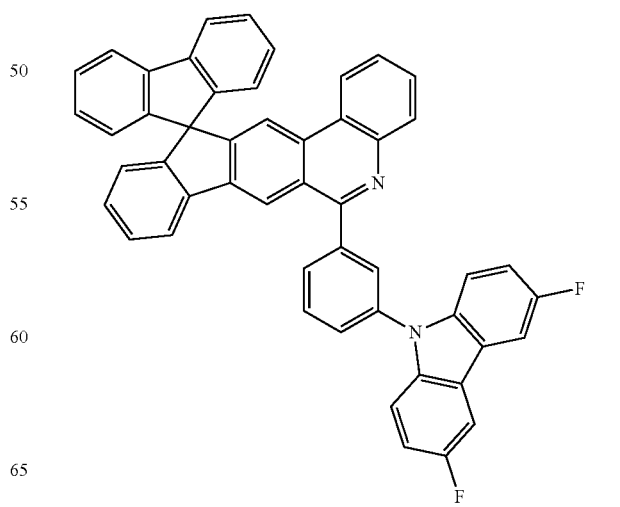

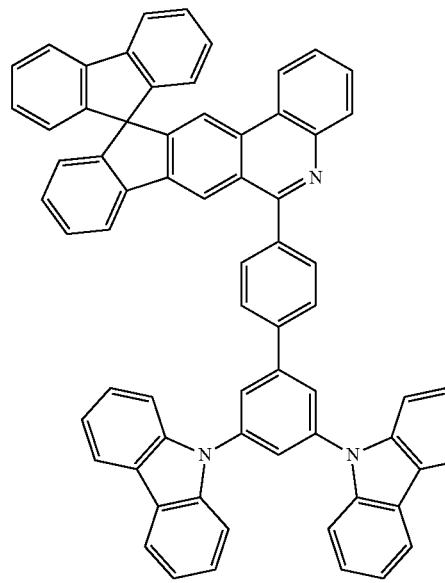
231
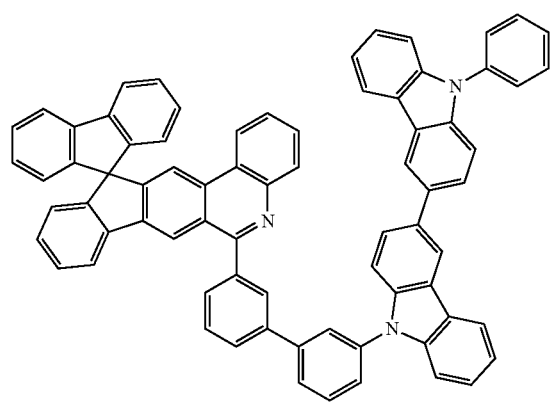
232
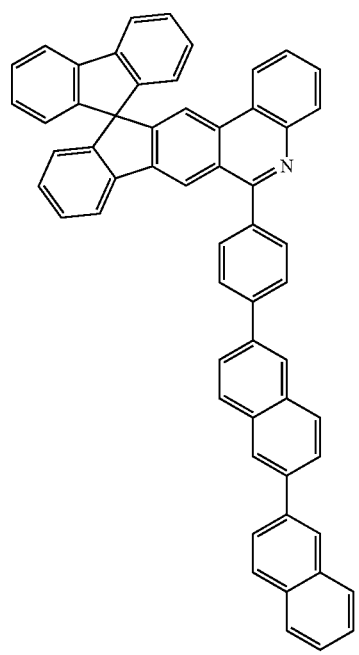
233
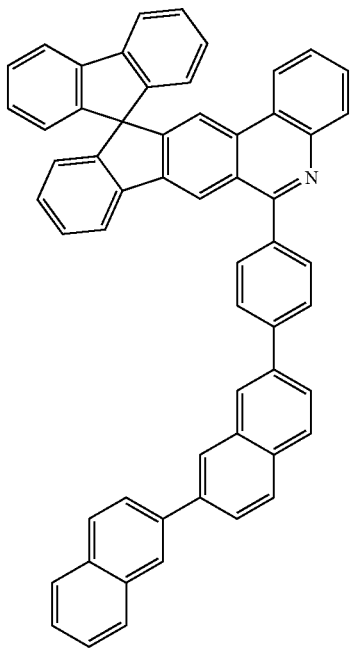
234
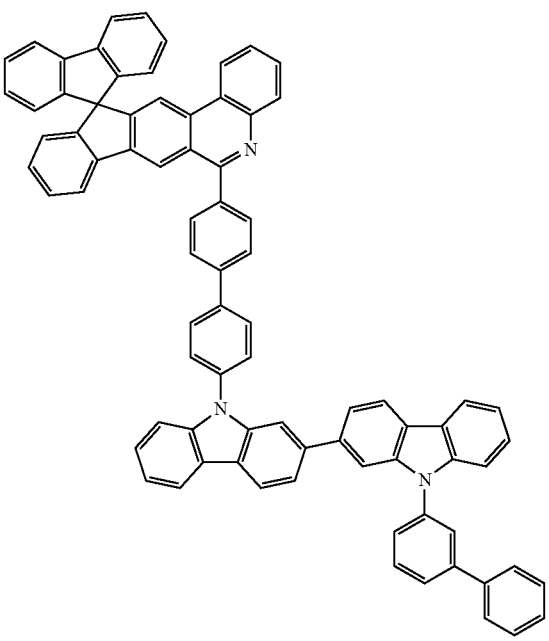
235

236
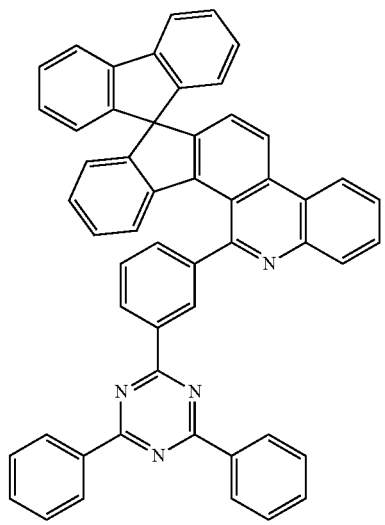
237
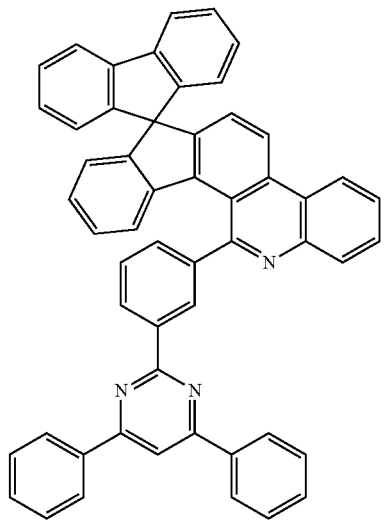
238
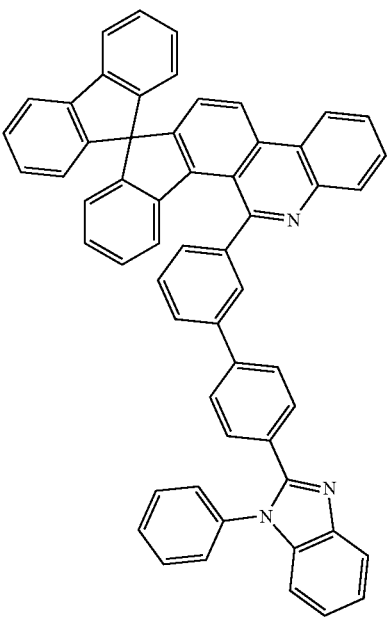
239
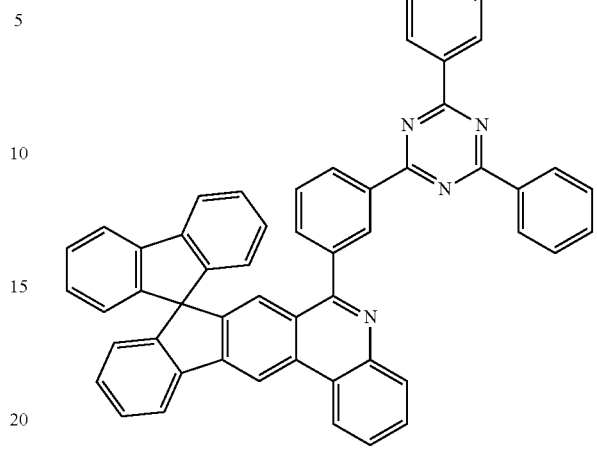
240
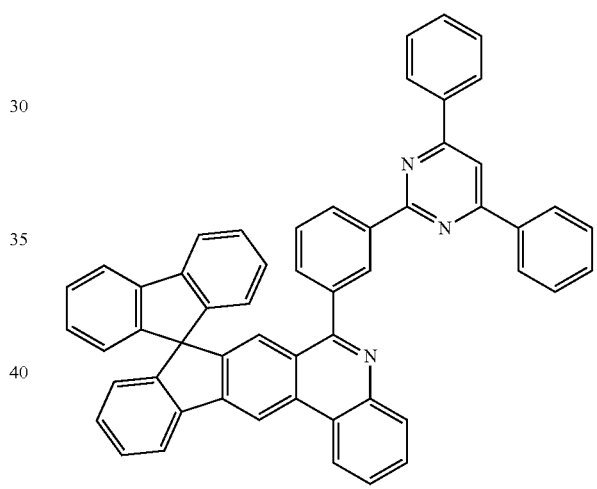
241
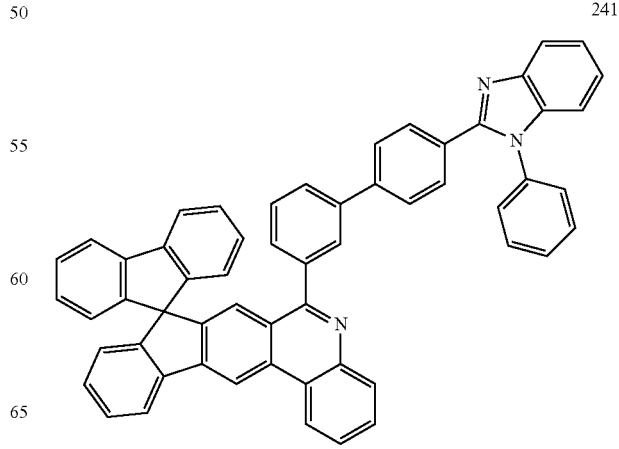

244
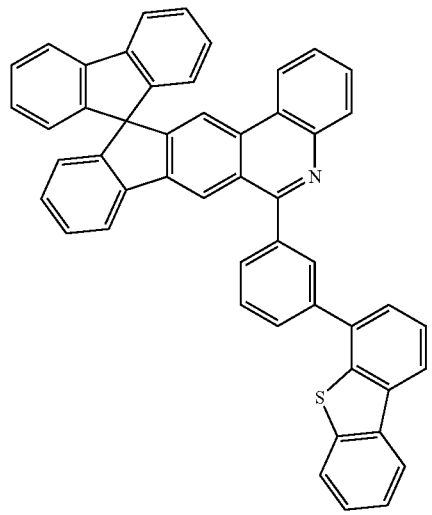
245
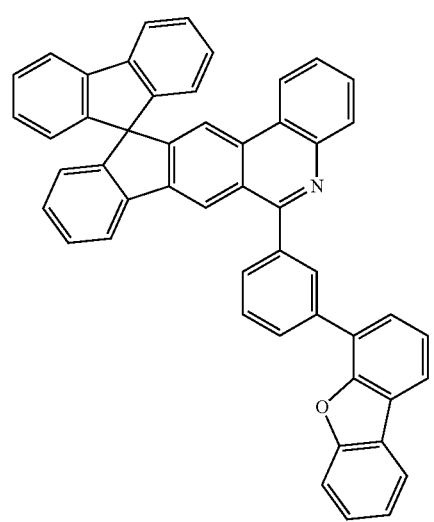
246
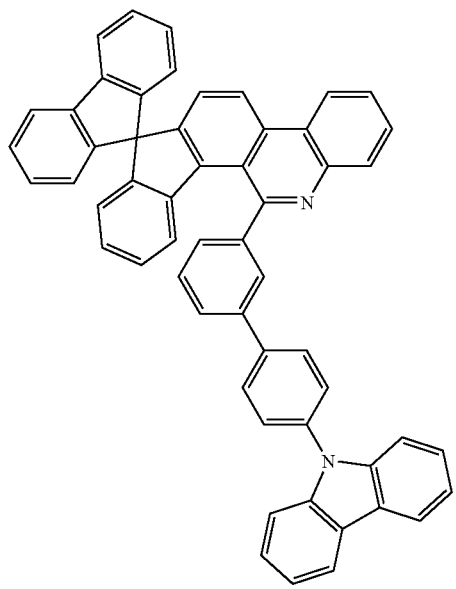
247
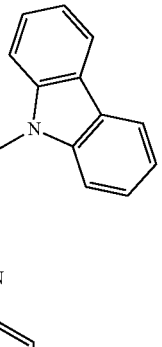
249
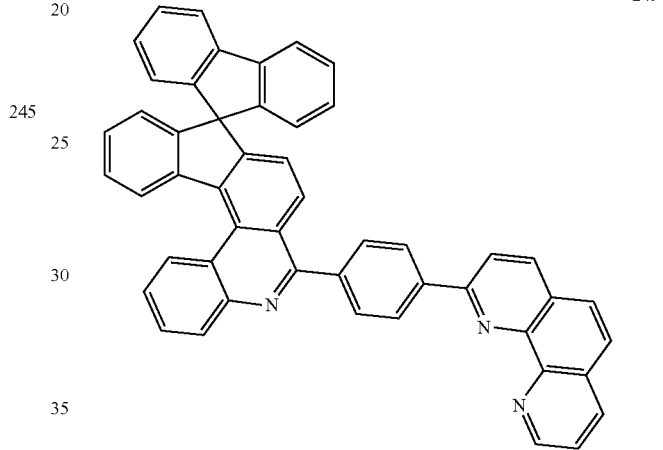
250
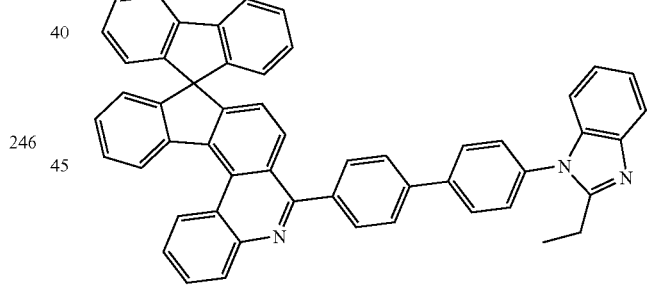
251
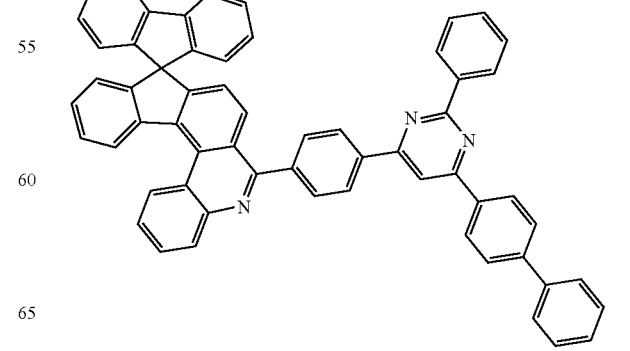

| 101 -continued | 102 -continued |
|---|---|
| 252 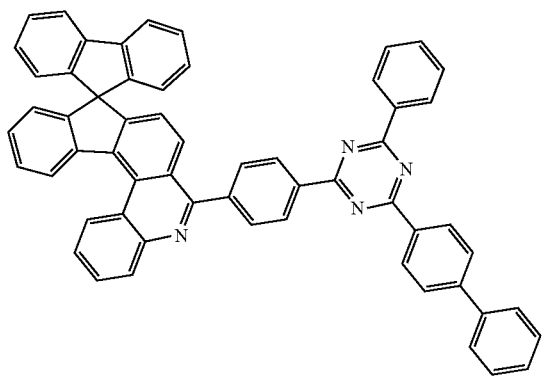 | 256 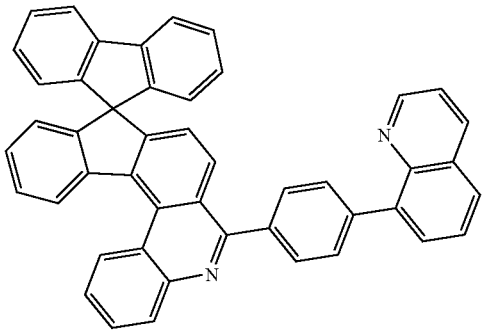 |
| 253 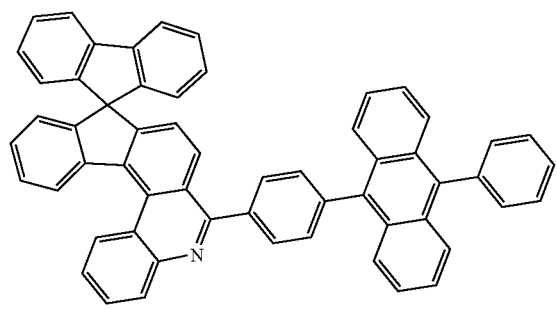 | 257 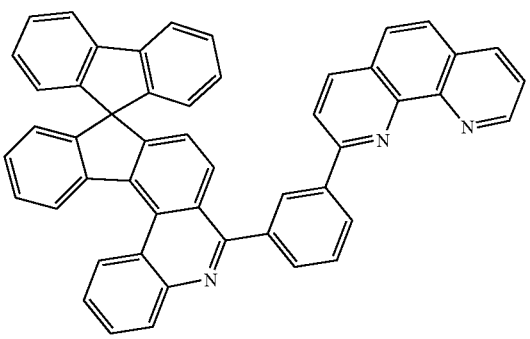 |
| 254 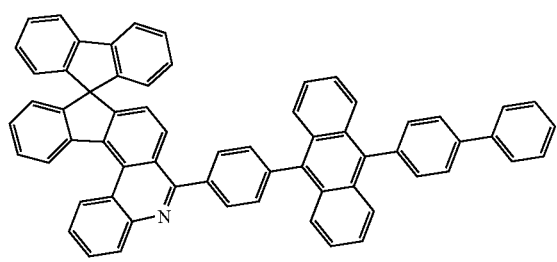 | 258 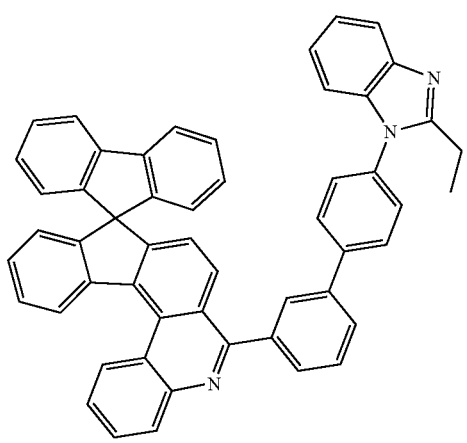 |
| 255 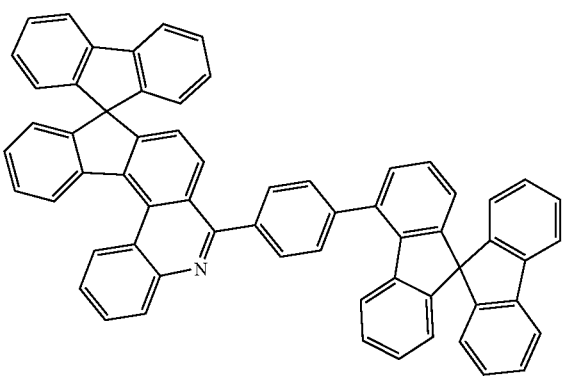 | 259 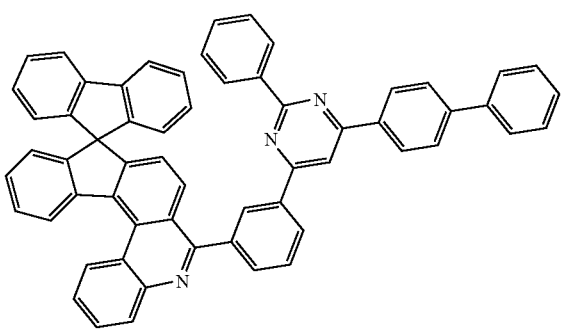 |

103
-continued
260
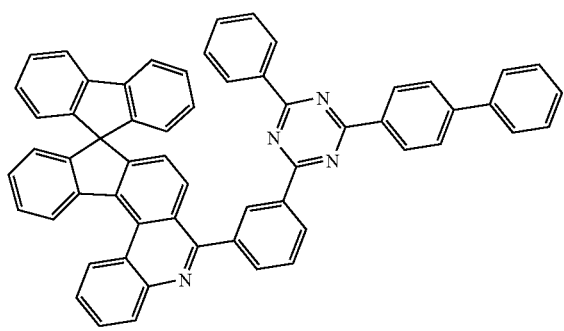
261
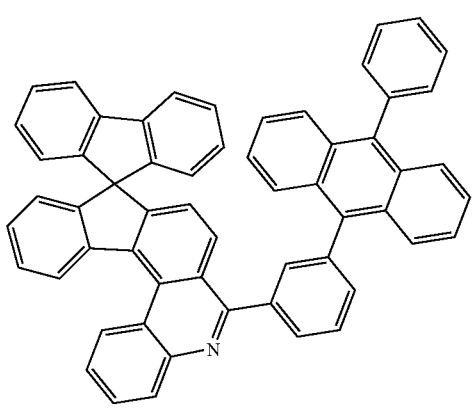
262
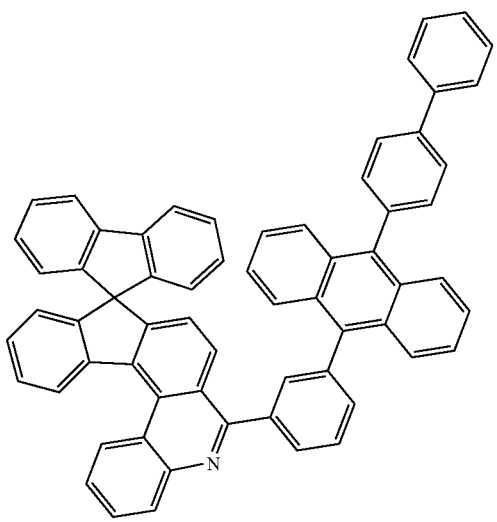
104
-continued
263
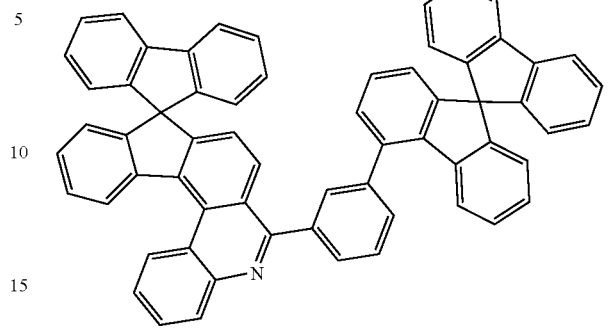
264
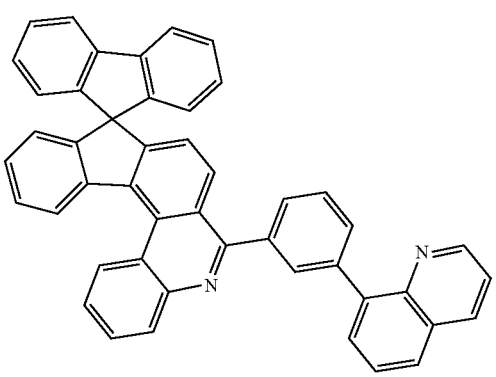
265
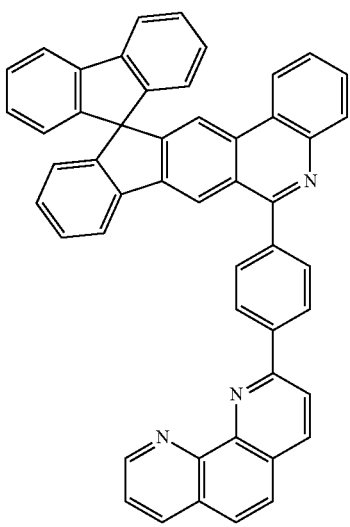

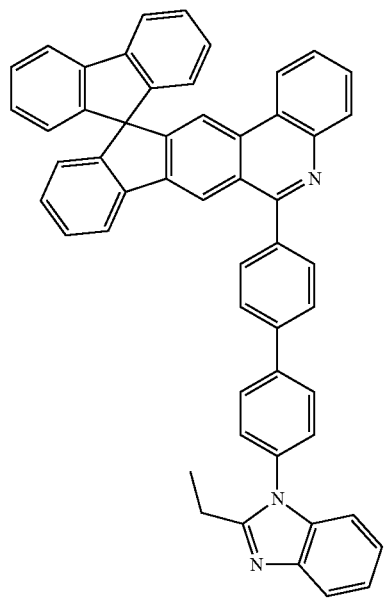
266
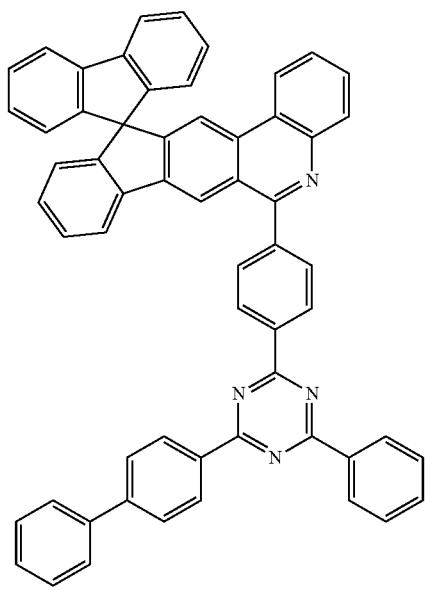
268
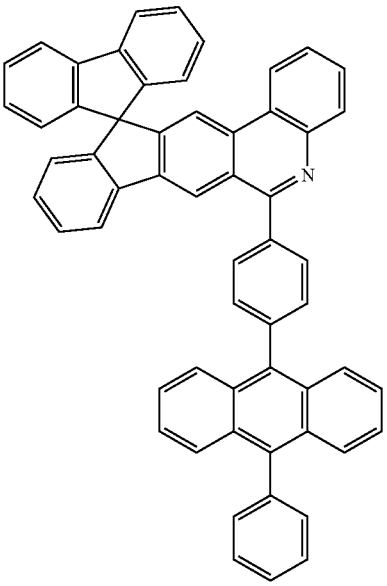
267
269

107
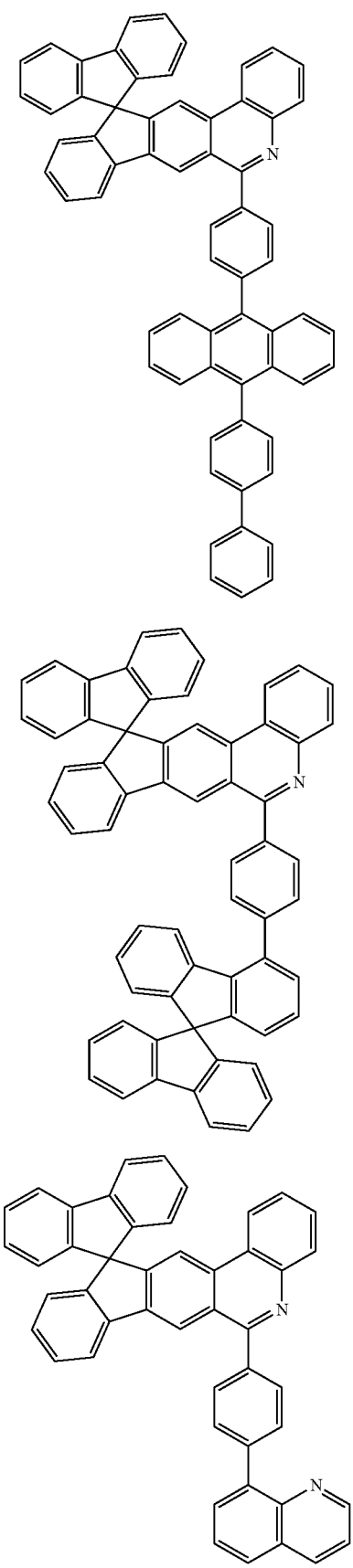
270
271
272
108
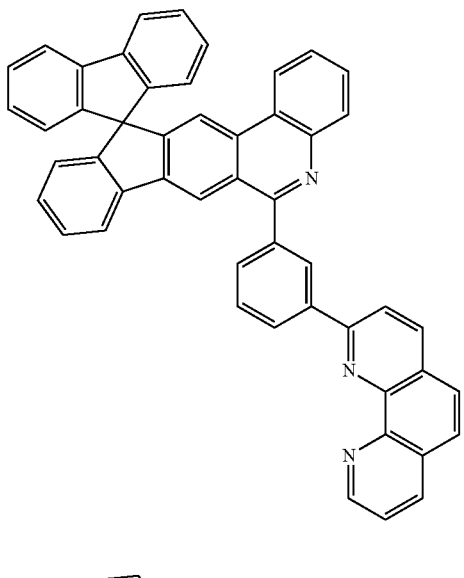
273
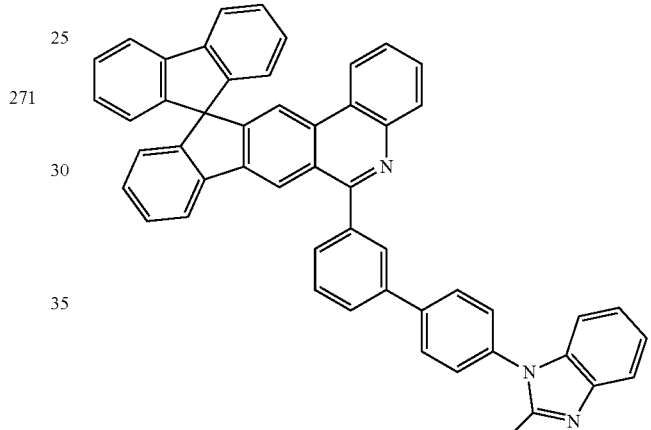
274
275
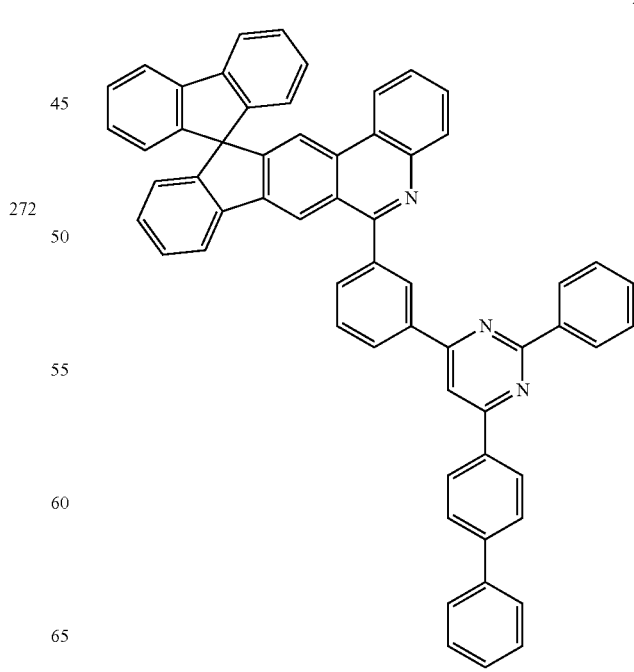

276
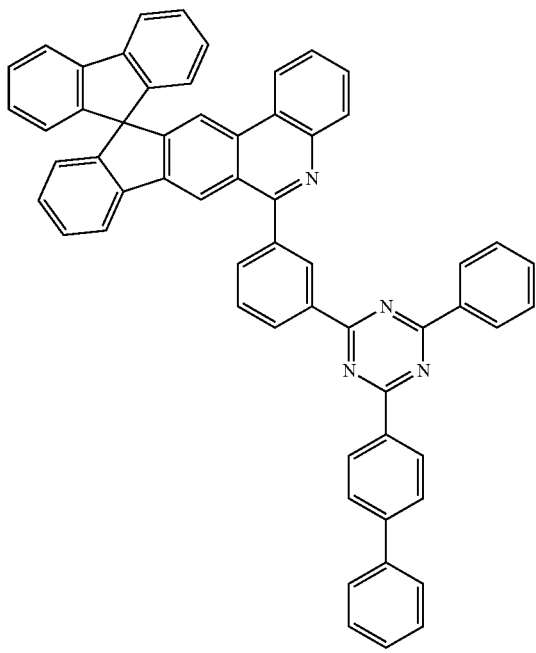
277
279
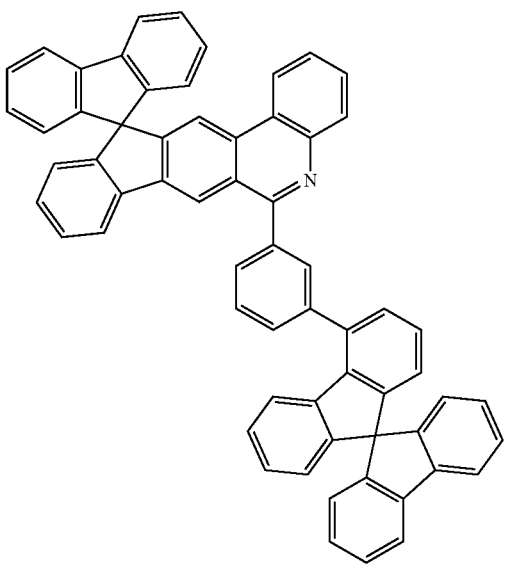
280
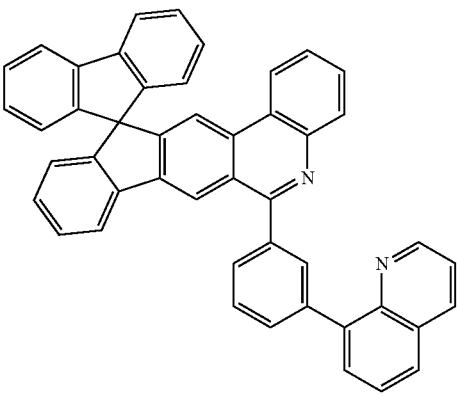
278
281
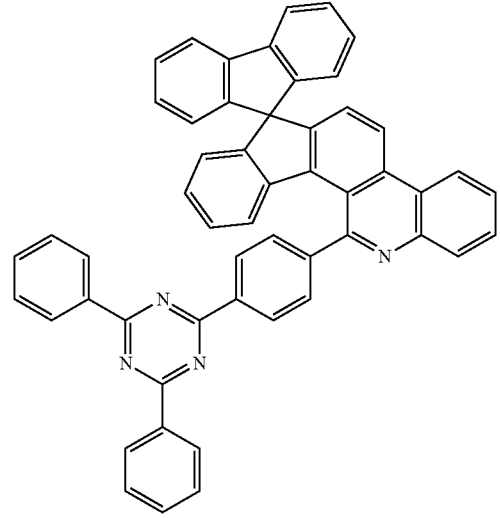

282
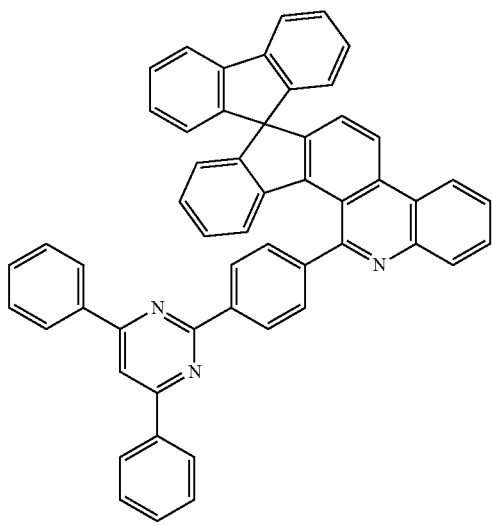
283
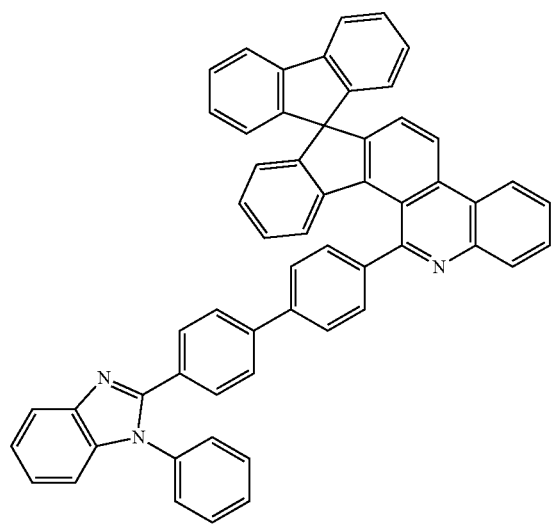
284
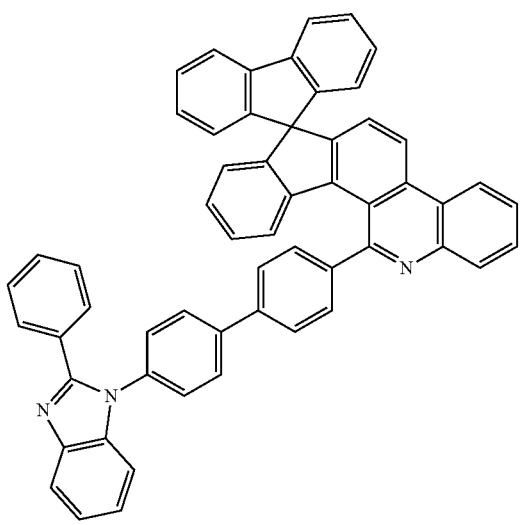
285
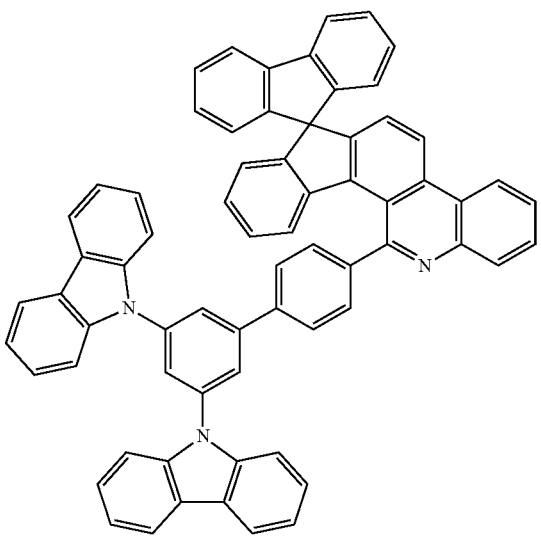
286
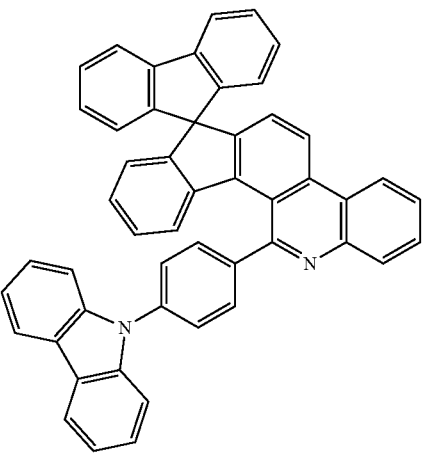
287
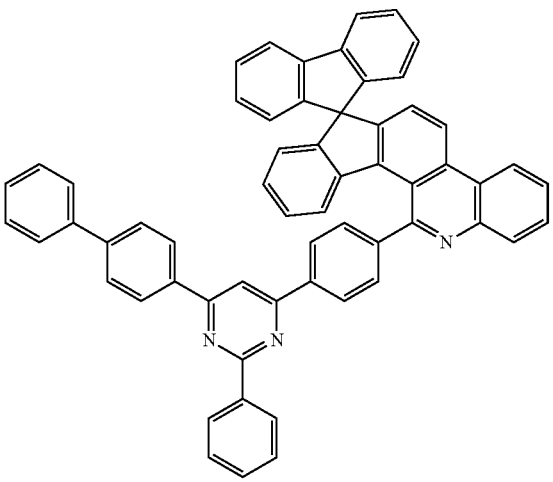

288
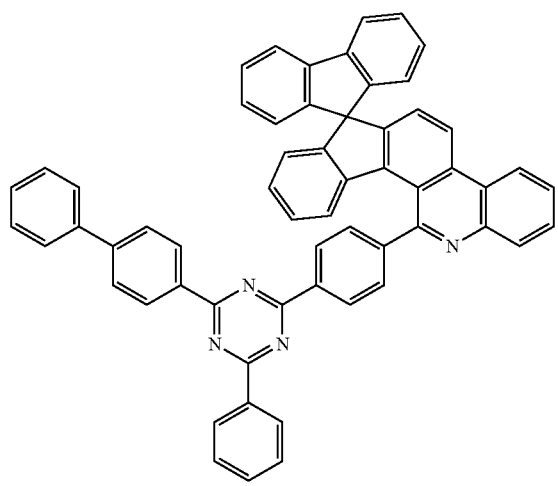
289
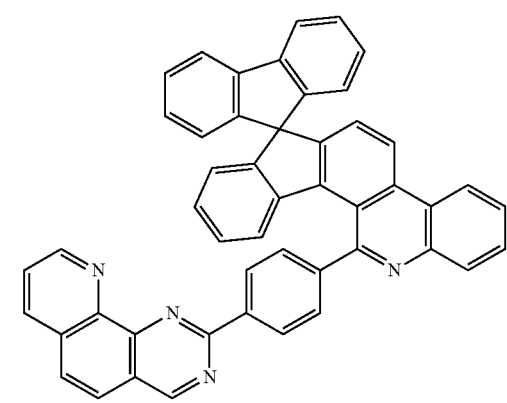
290
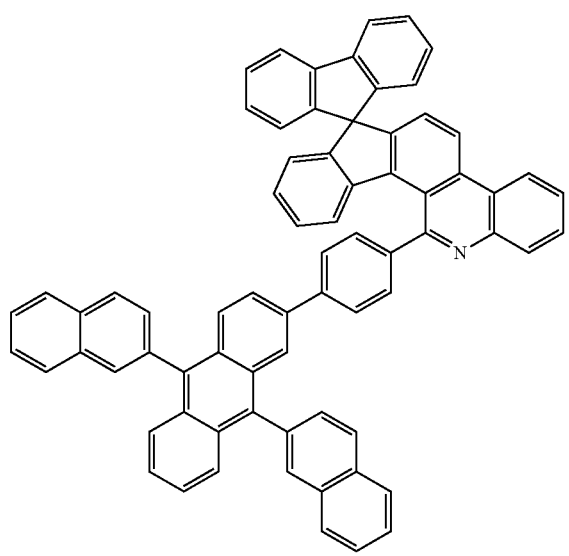
291
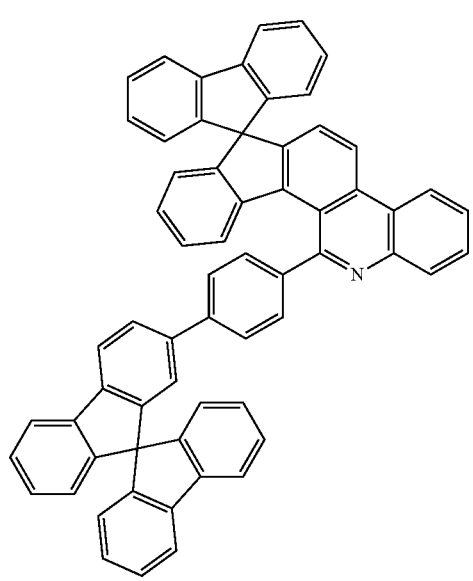
292
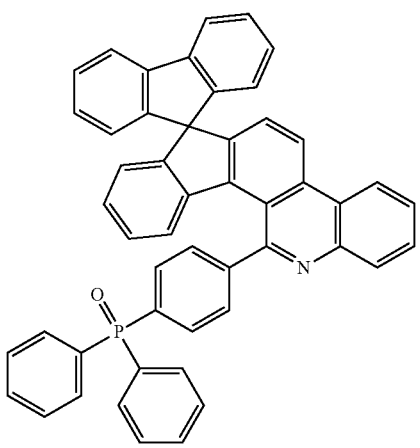
293
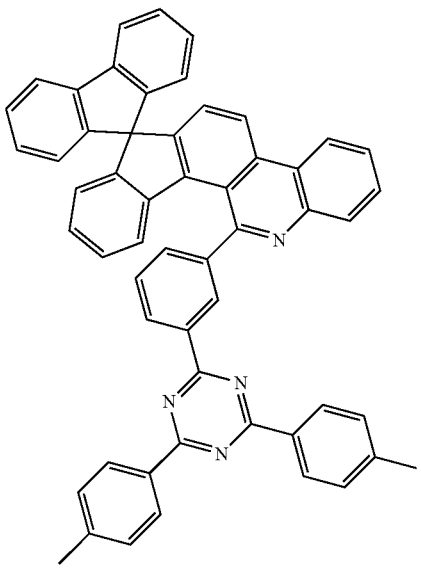

294
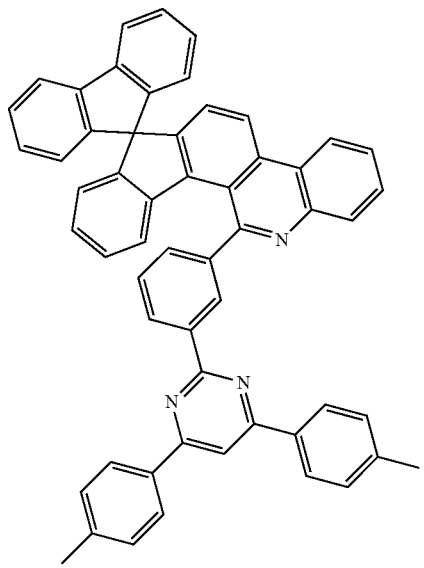
295
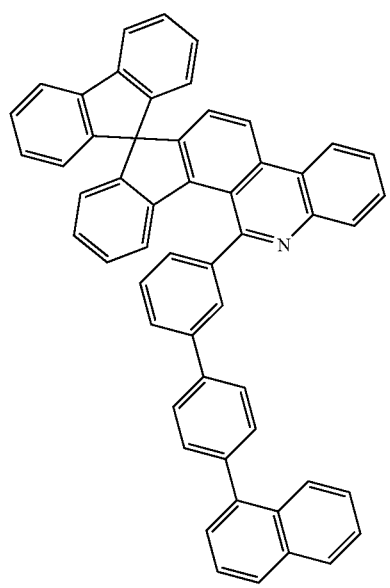
296
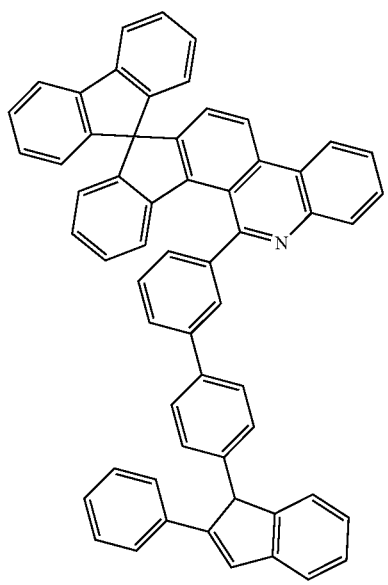
297
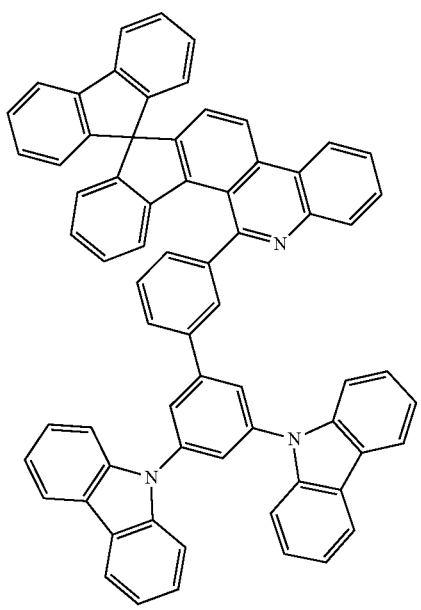
298
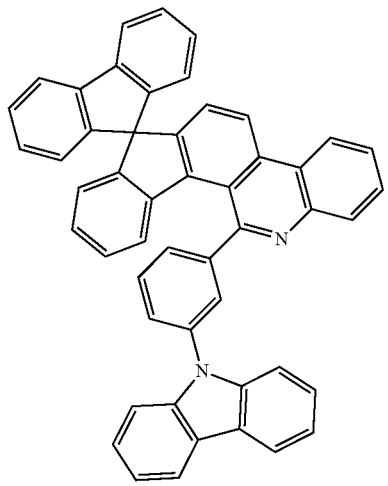

117
-continued
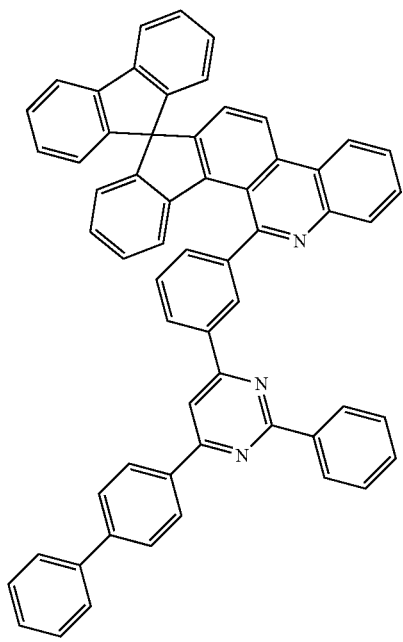
299
118
-continued
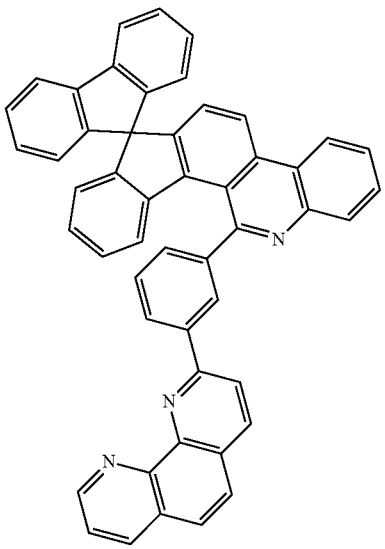
301
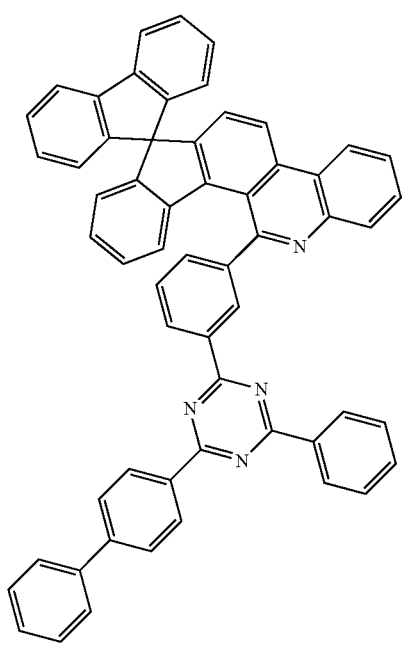
300
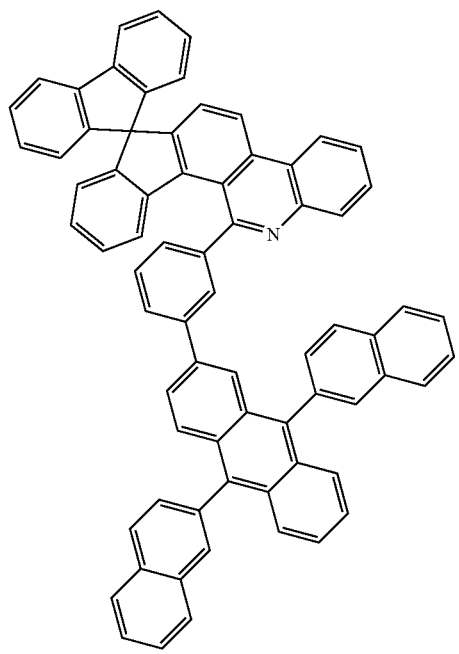
302

-continued
119
303
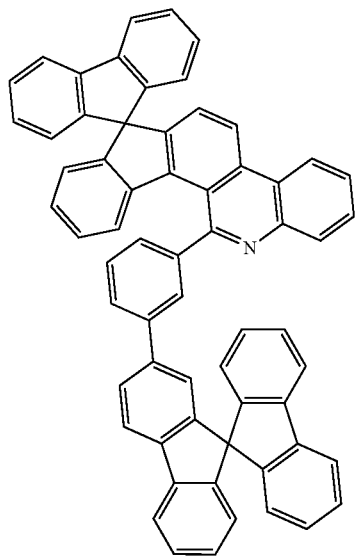
304
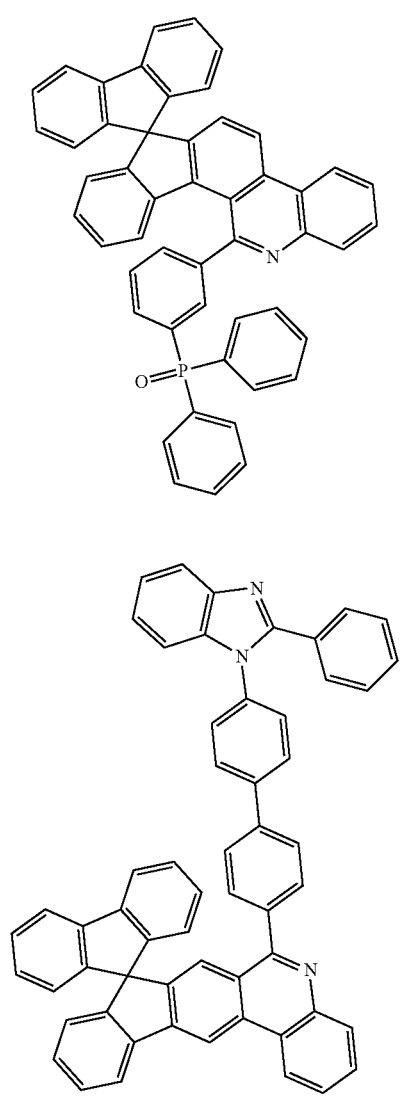
305
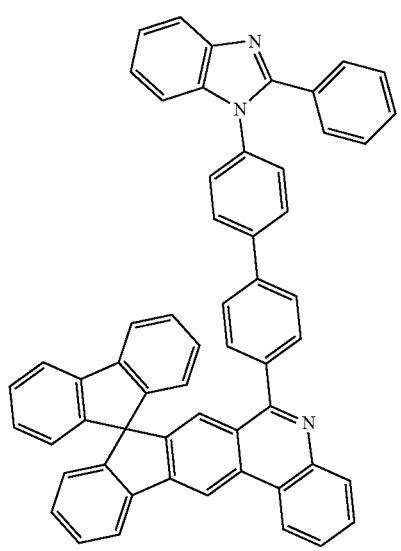
-continued
120
306
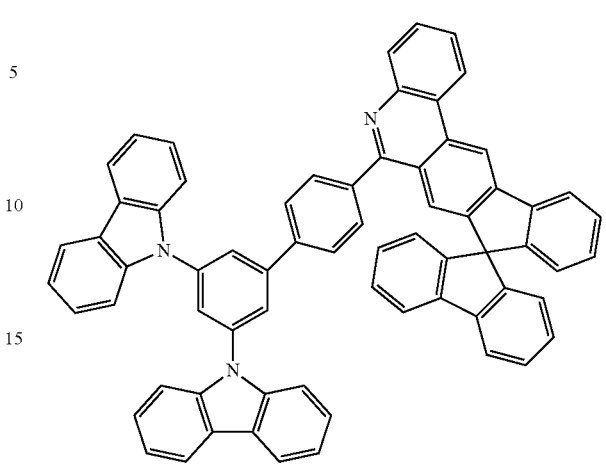
307
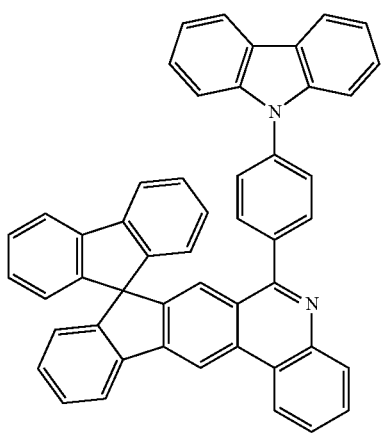
308
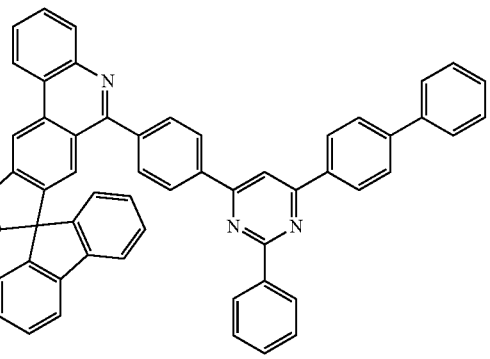

-continued
309
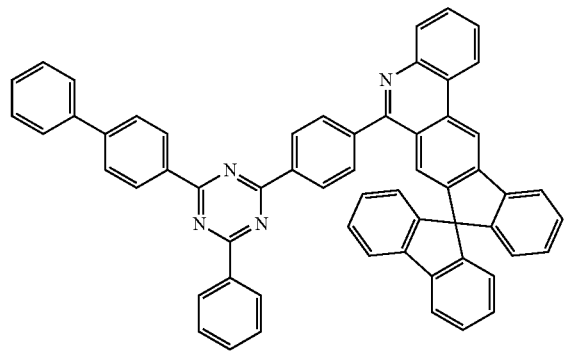
310
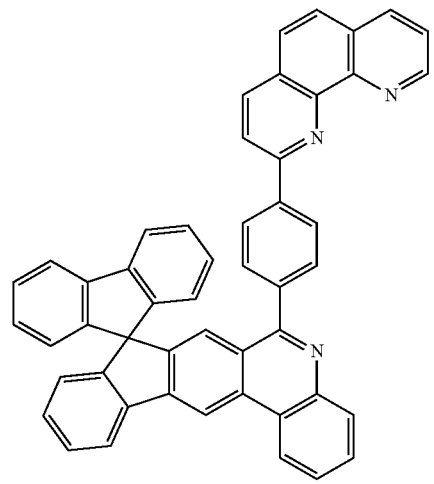
311
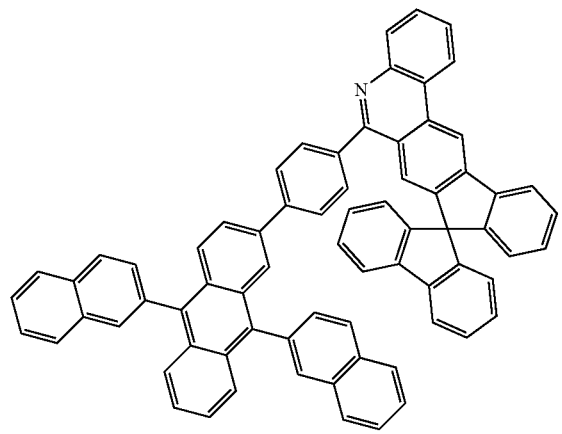
-continued
312
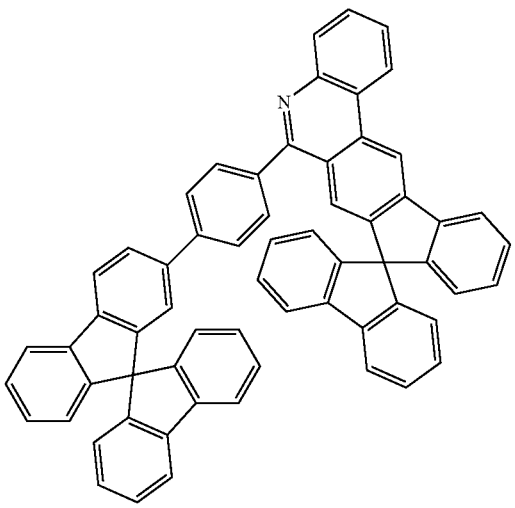
313
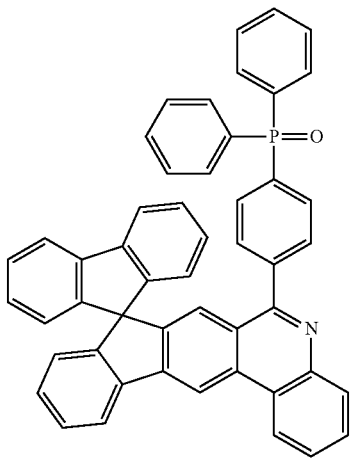
314
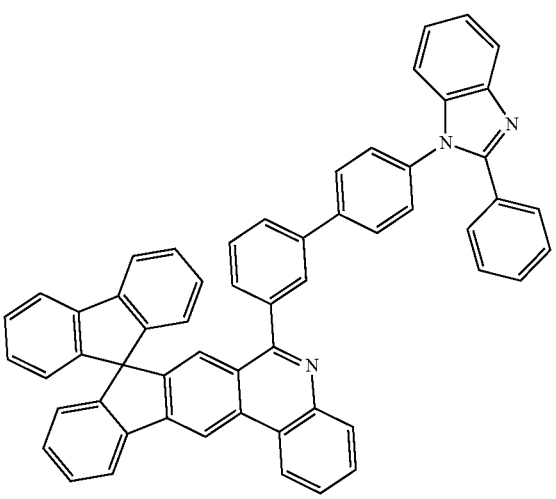

315
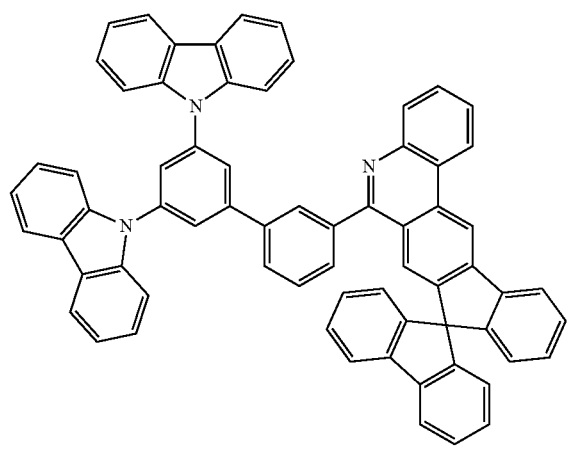
316
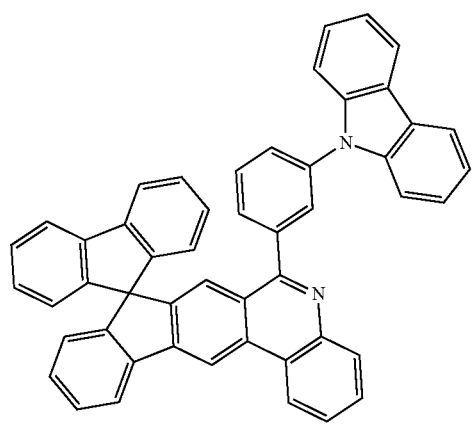
317
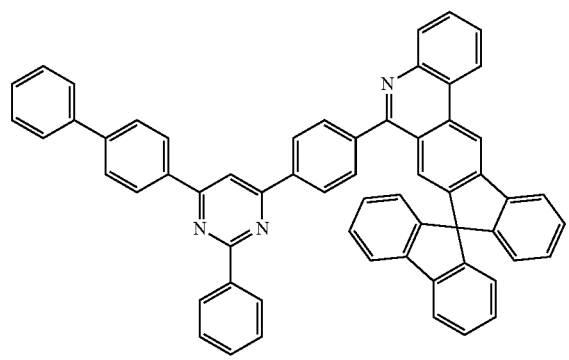
318
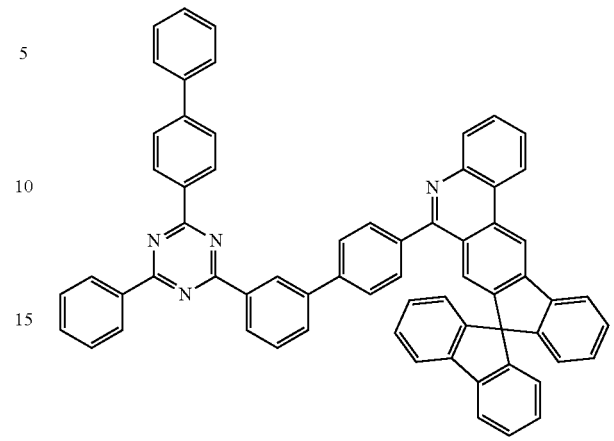
319
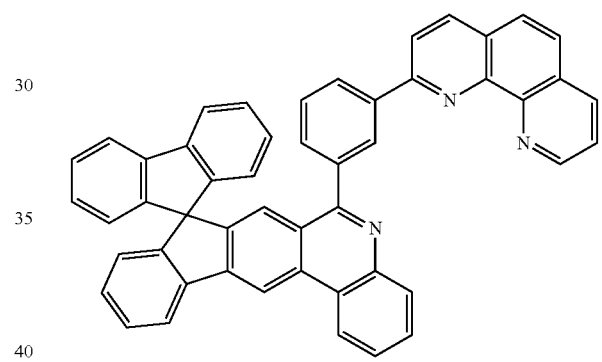
320
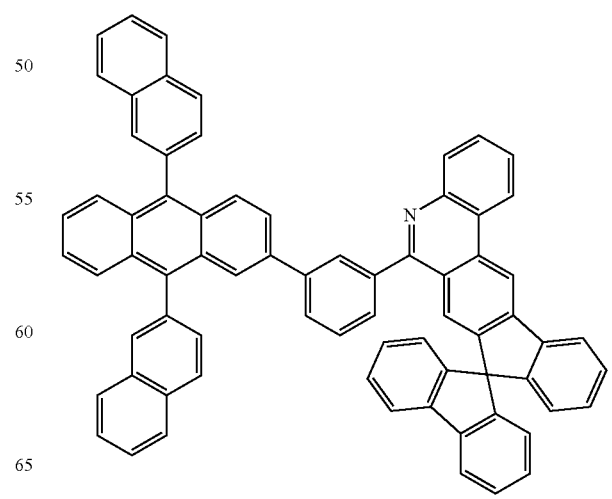

-continued
321
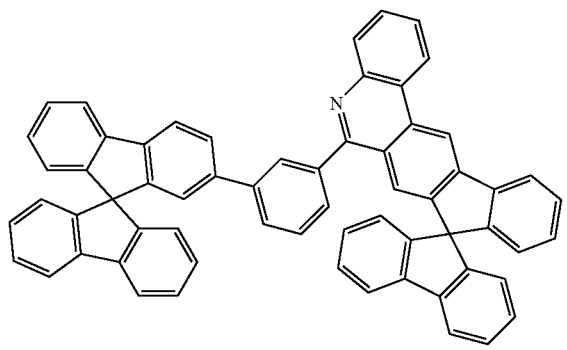
322
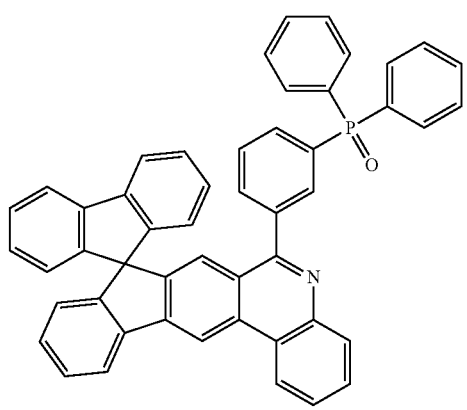
323
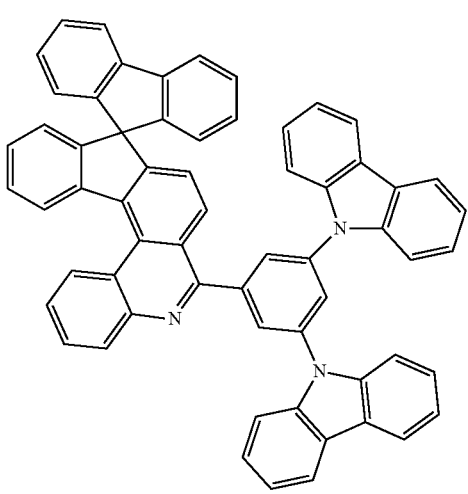
-continued
324
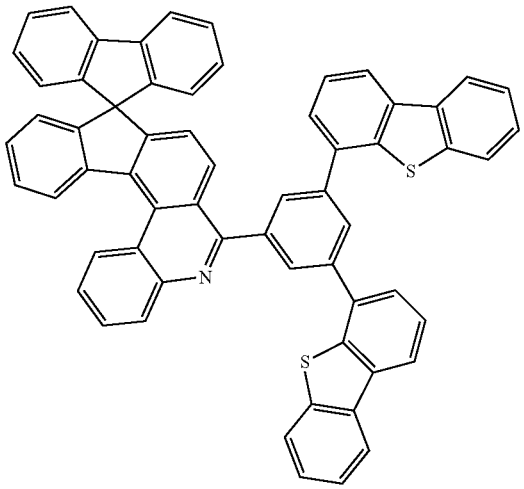
325
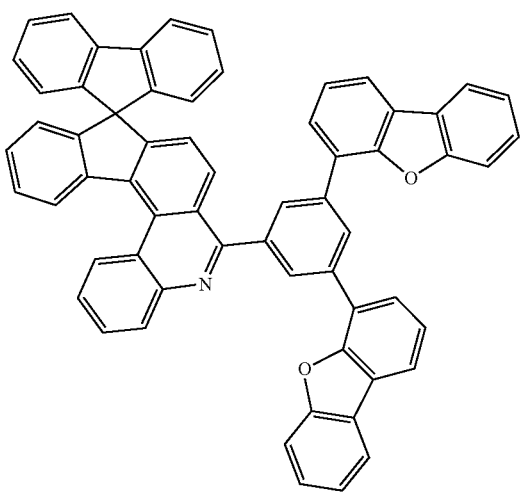
326
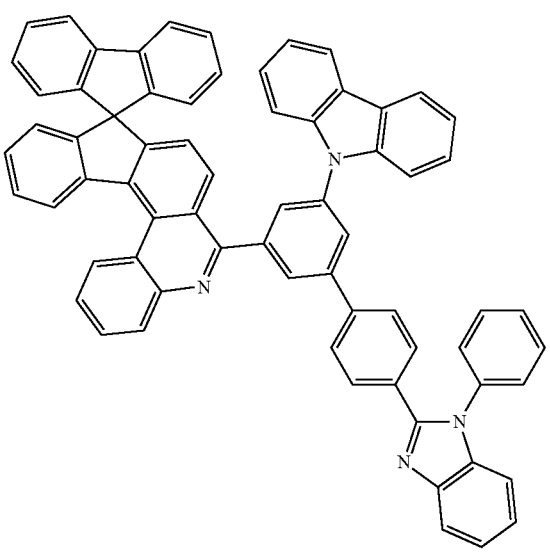

327
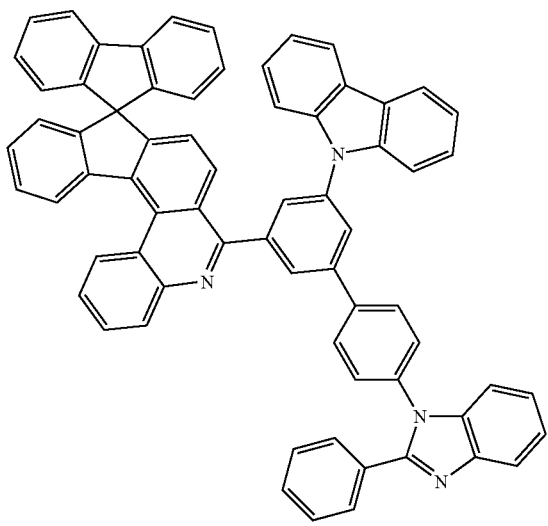
328
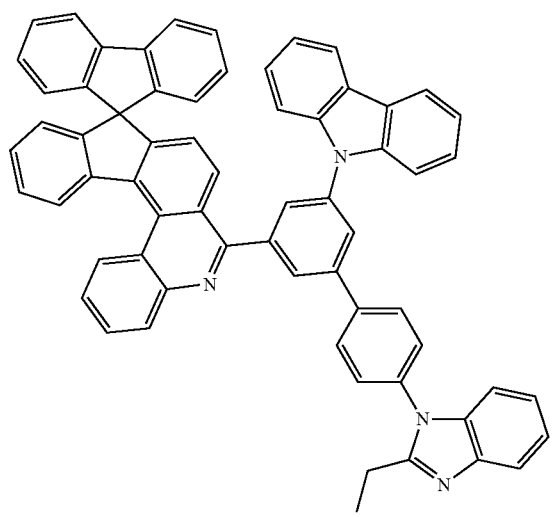
329
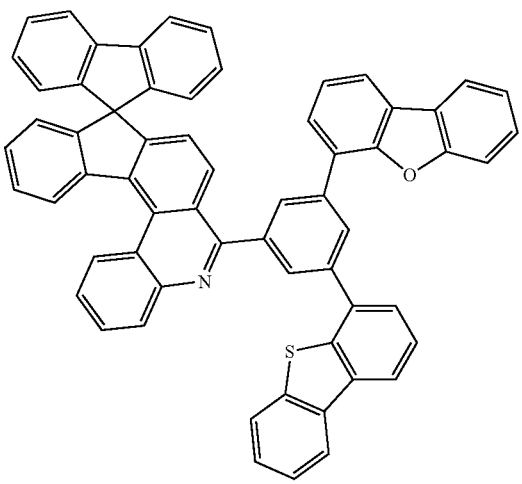
330
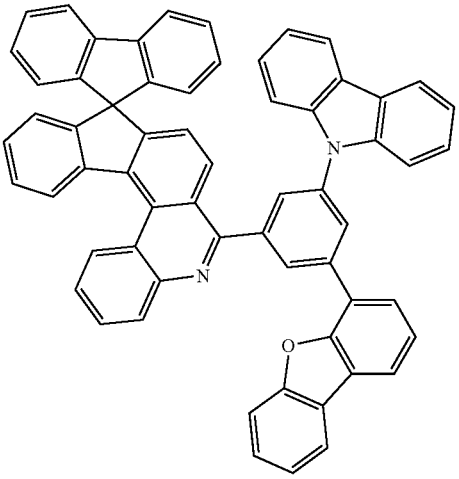
331
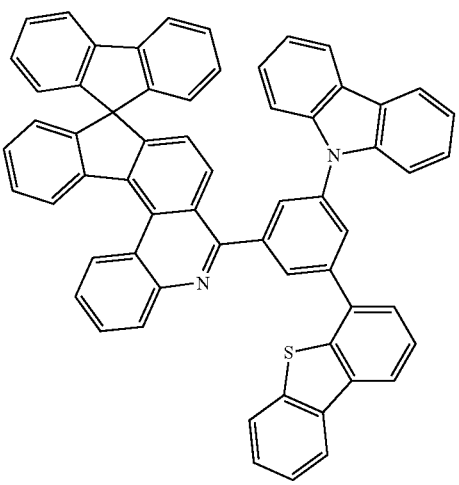
332
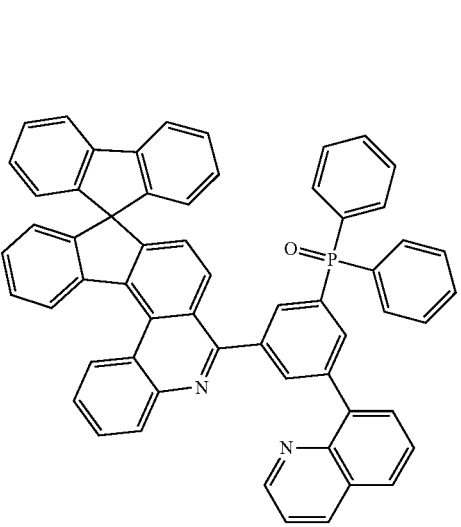

333
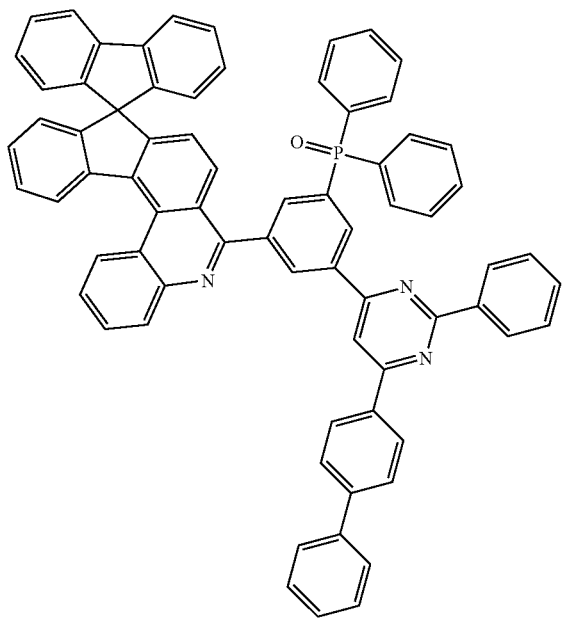
334
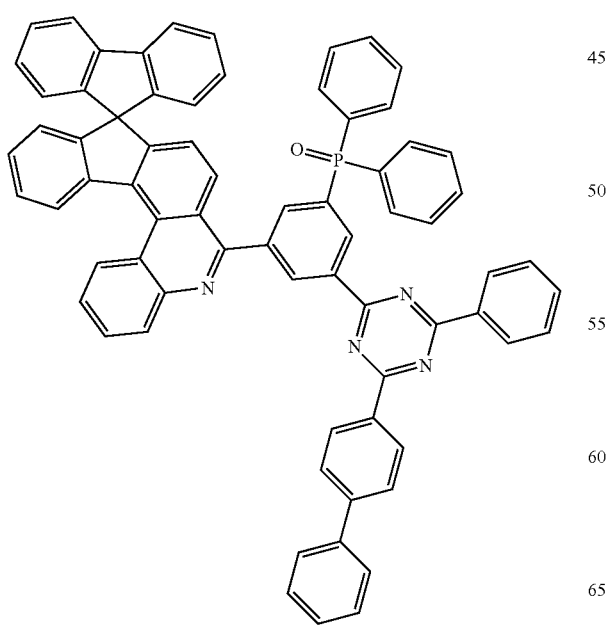
335
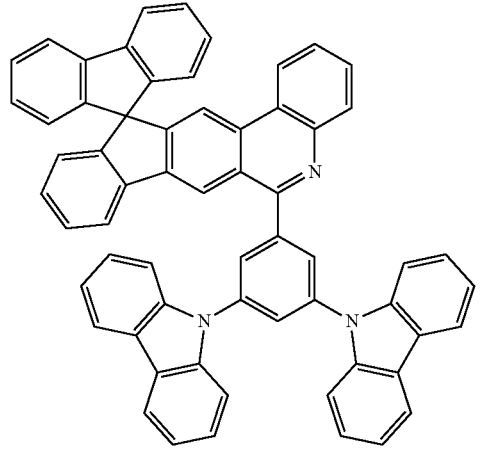
336
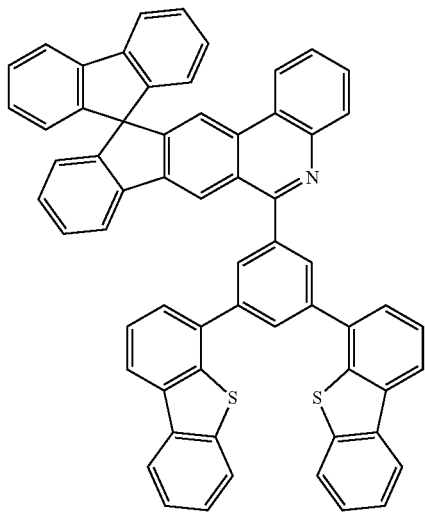
337
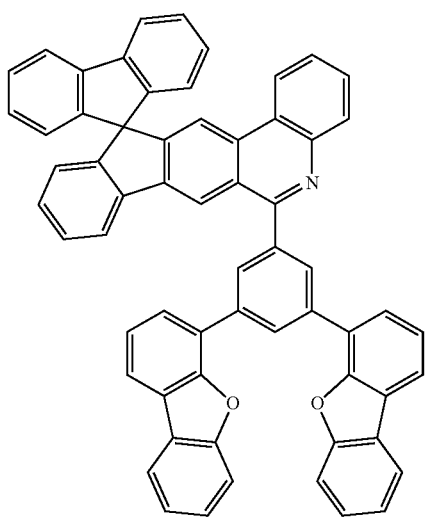

338
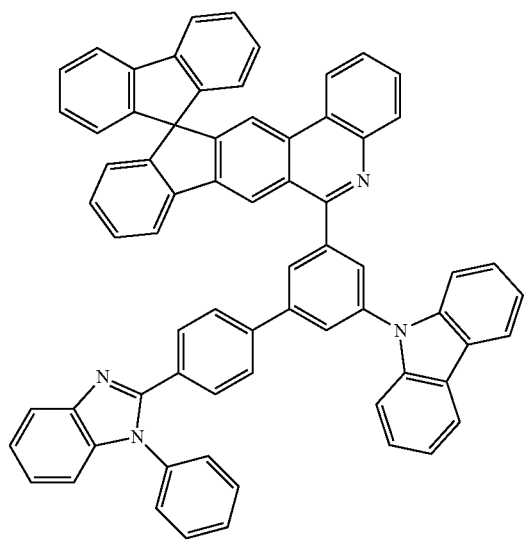
339
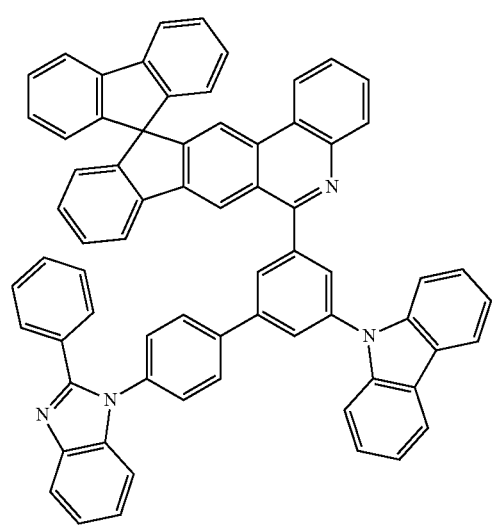
340
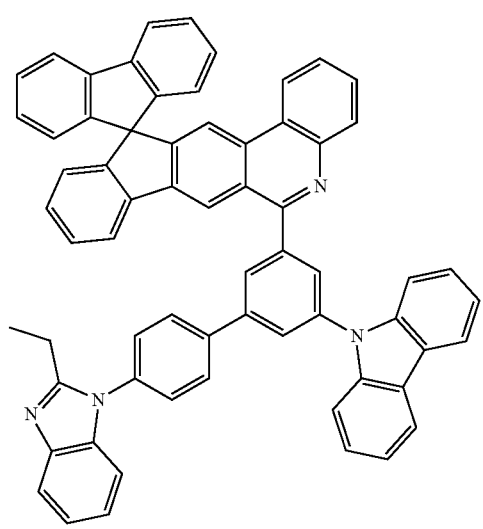
341
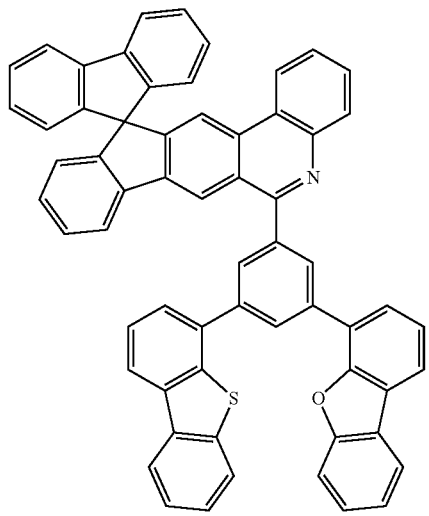
342
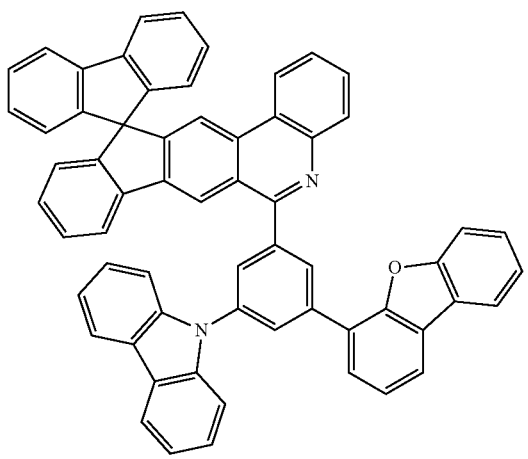
343
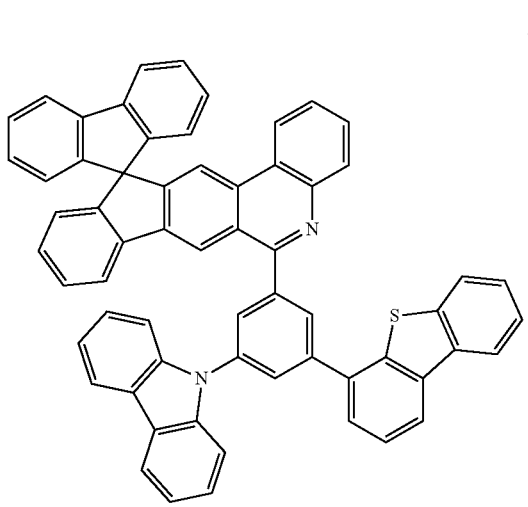

133
-continued
344
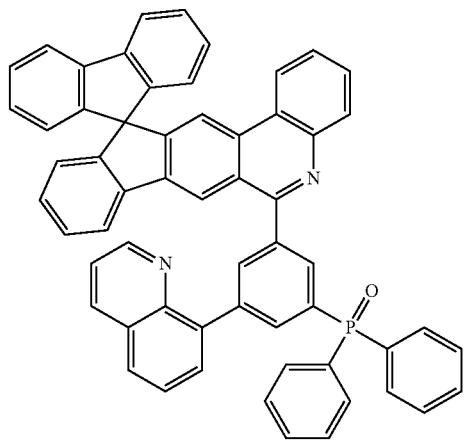
345
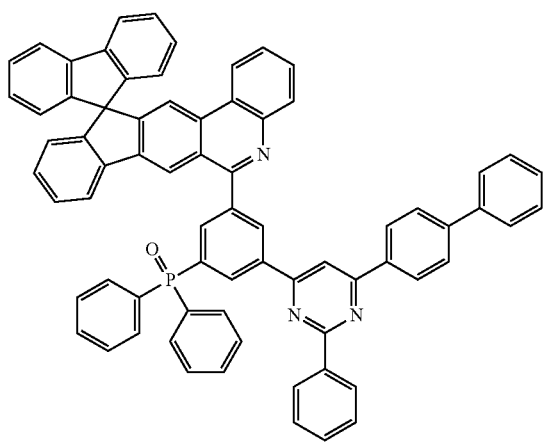
346
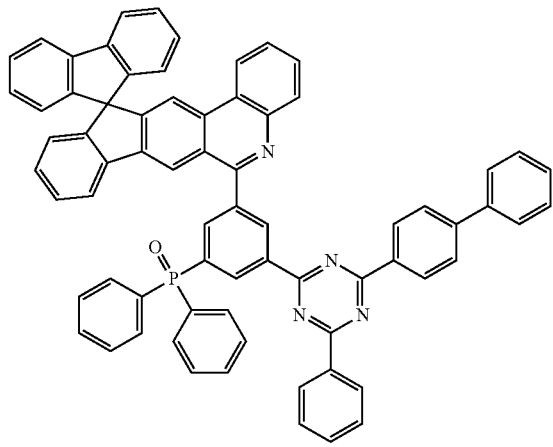
134
-continued
347
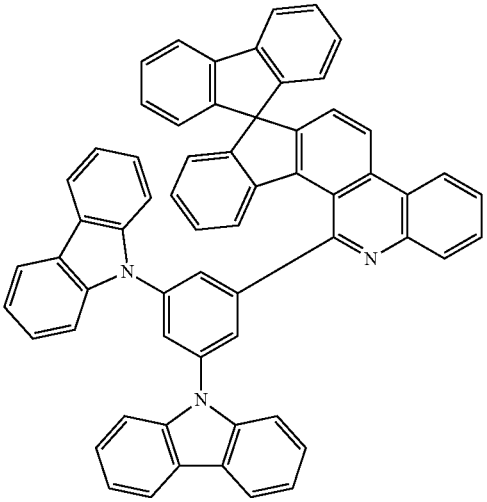
348
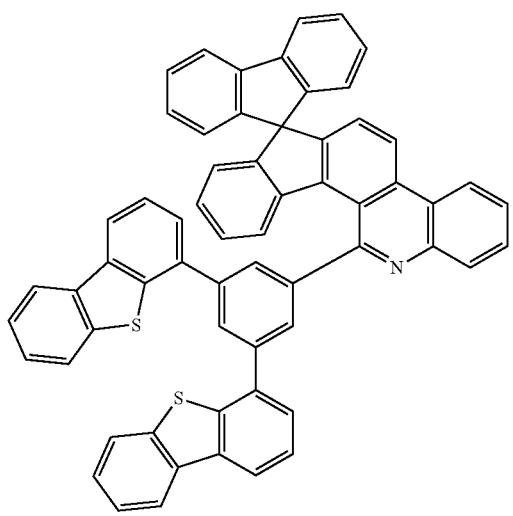
349
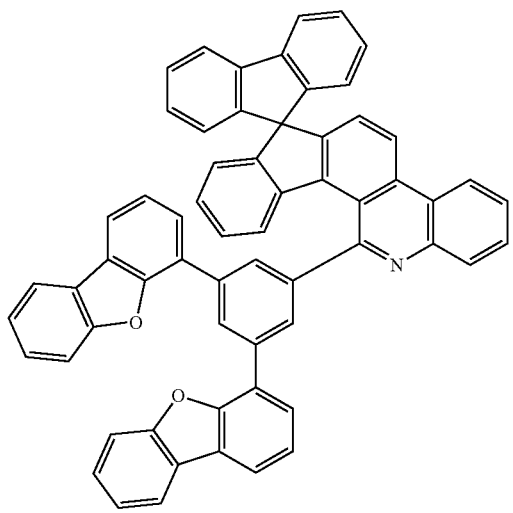

350
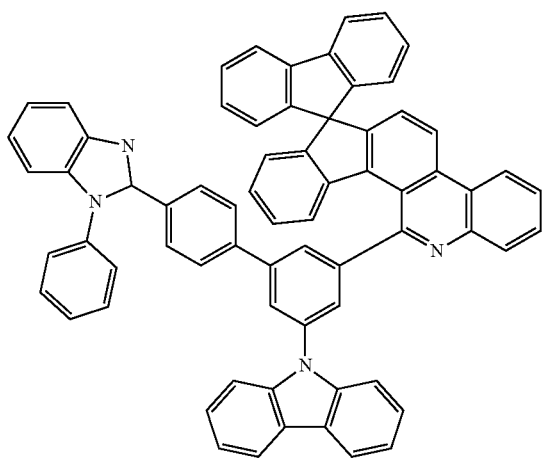
351
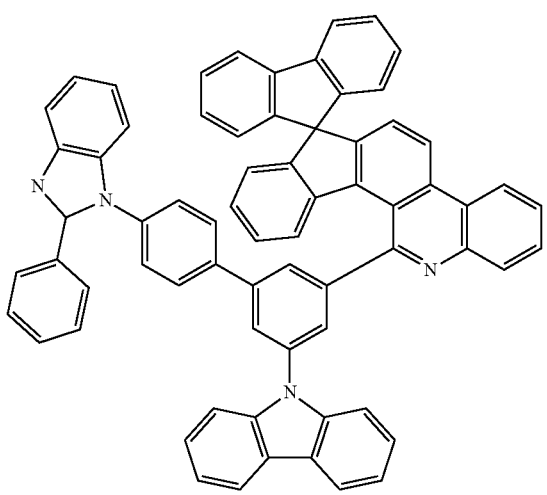
352
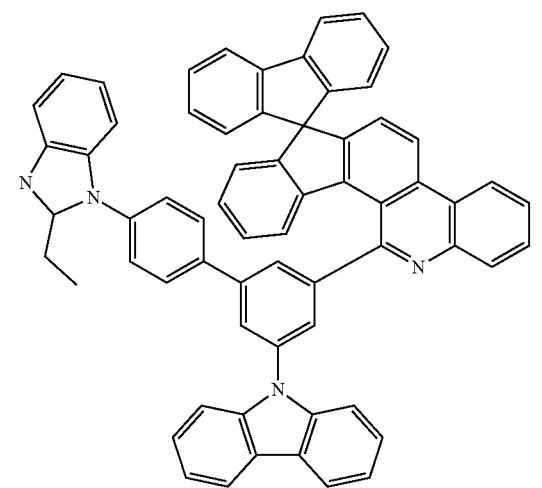
353
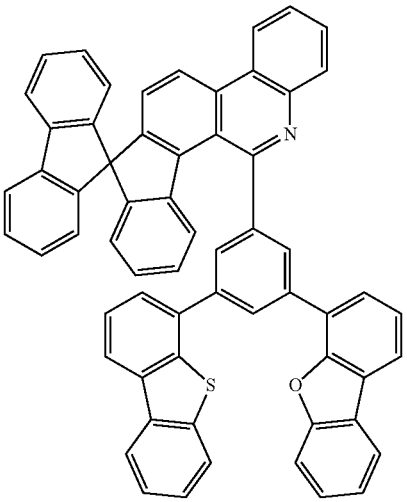
354
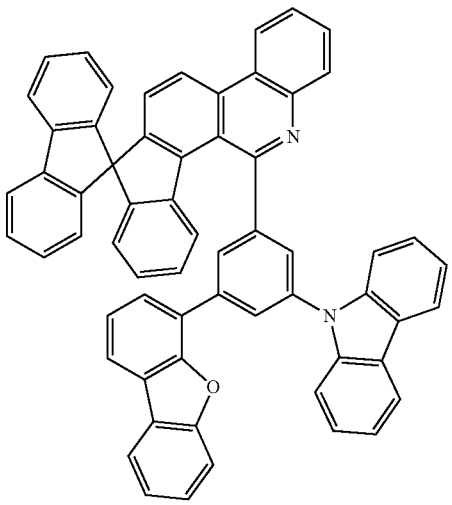
355
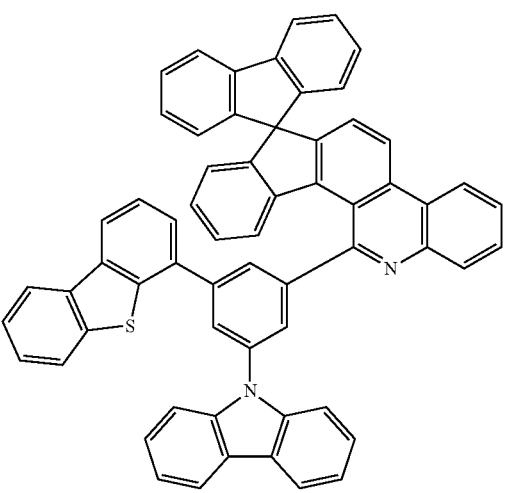

356
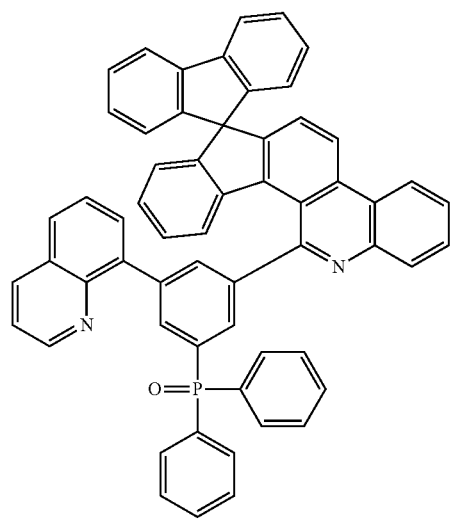
357
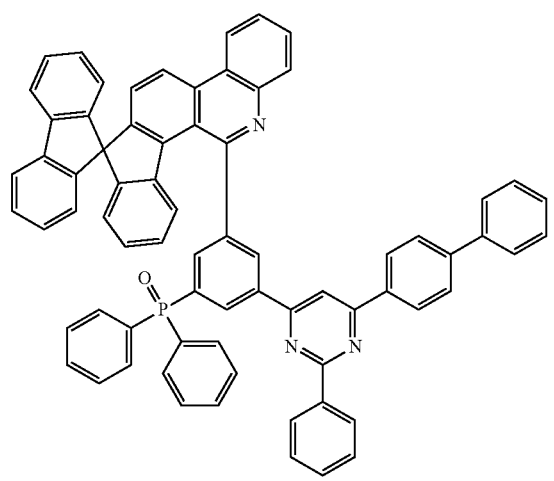
358
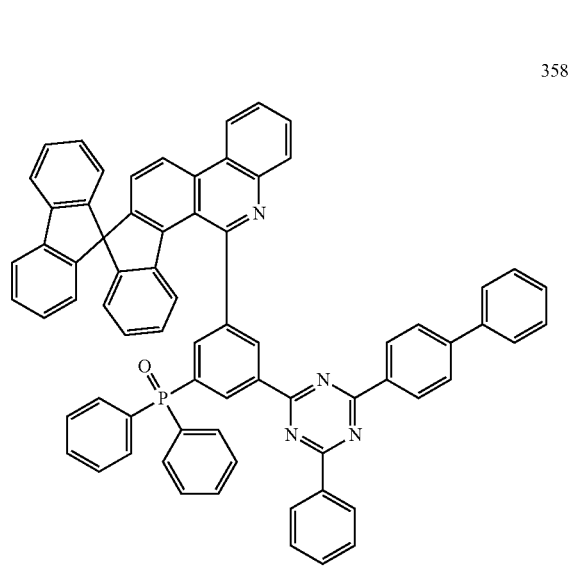
359
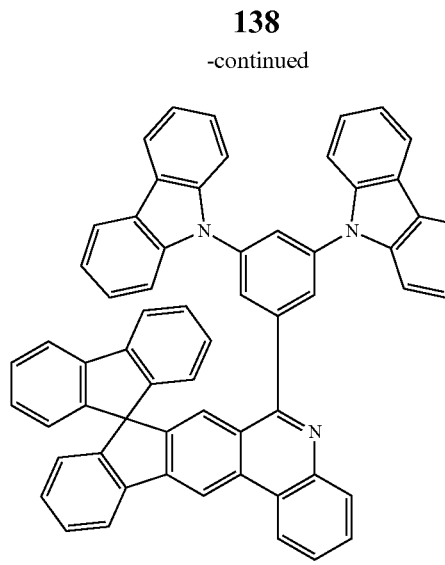
360
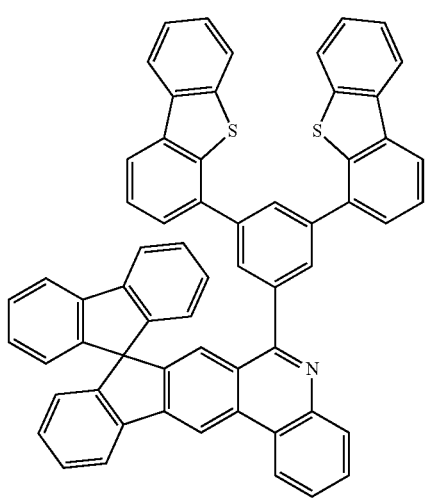
361
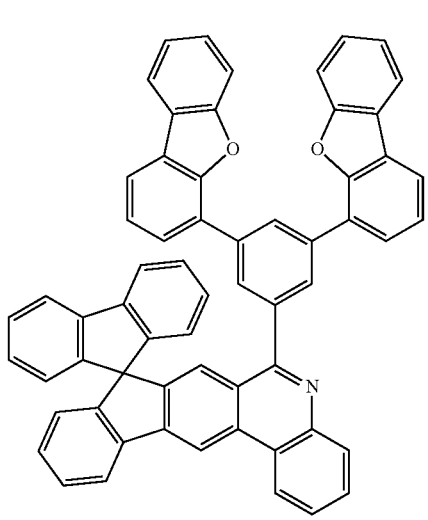

362
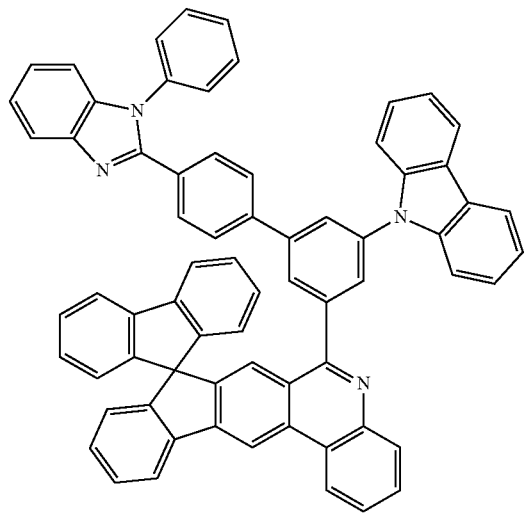
365
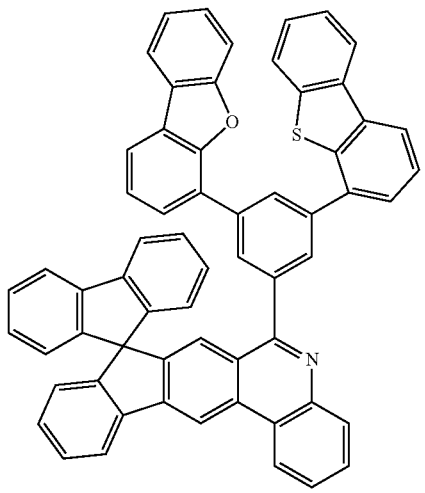
363
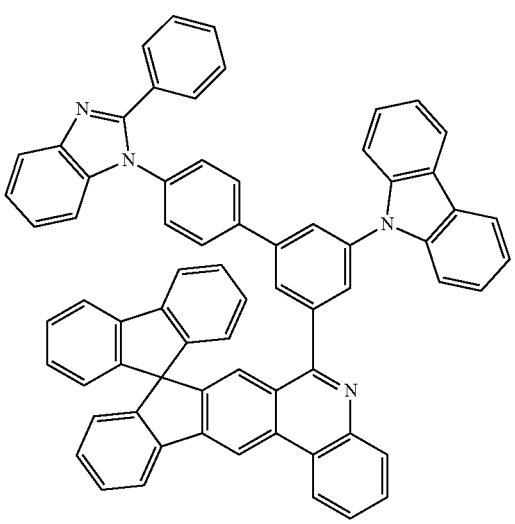
366
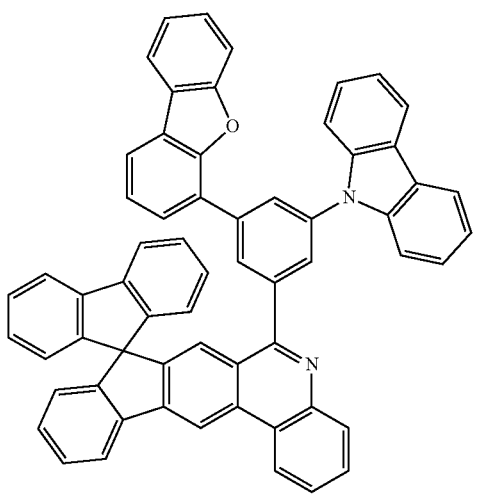
364
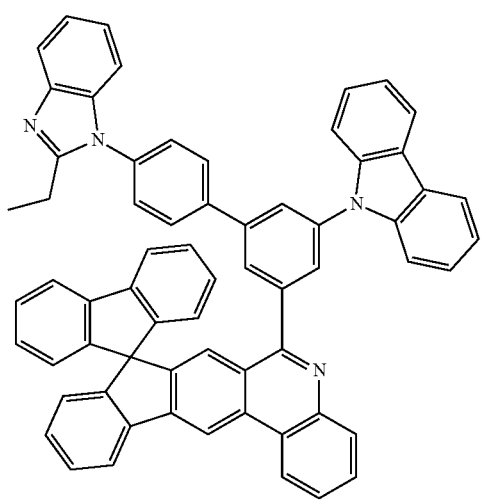
367
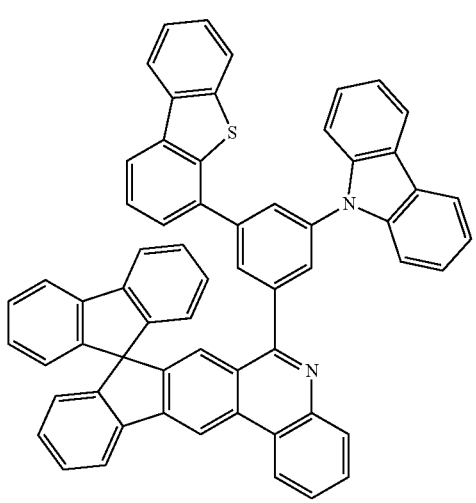

141
-continued
368
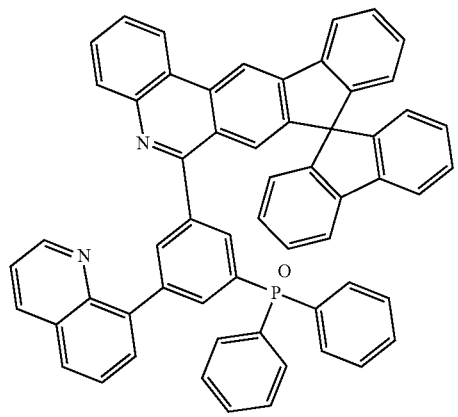
369
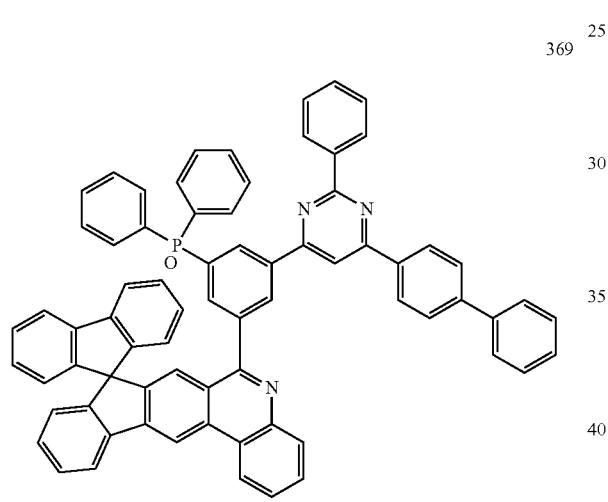
370
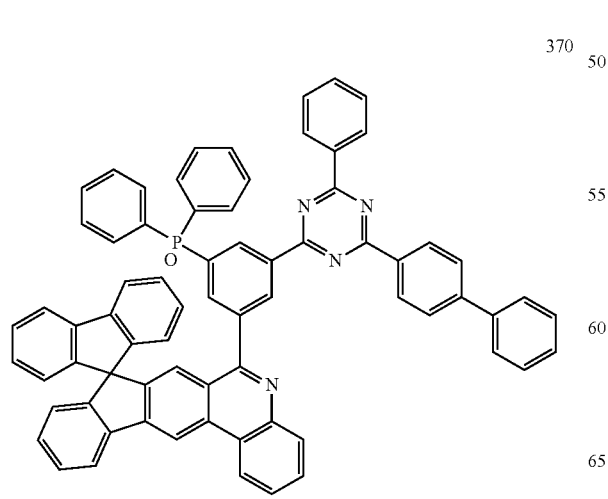
142
-continued
371
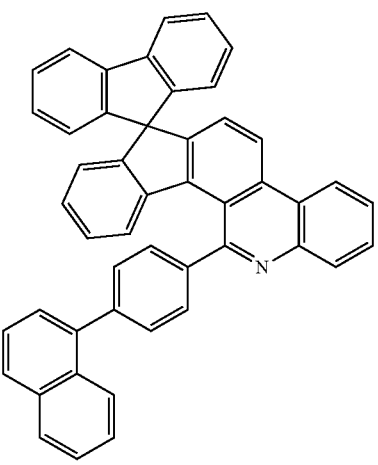
372
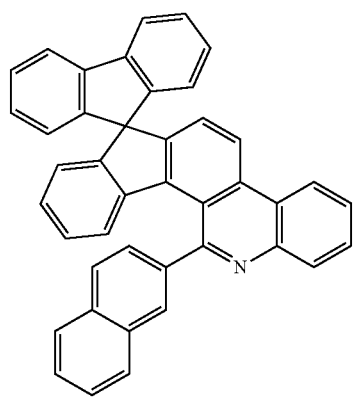
373
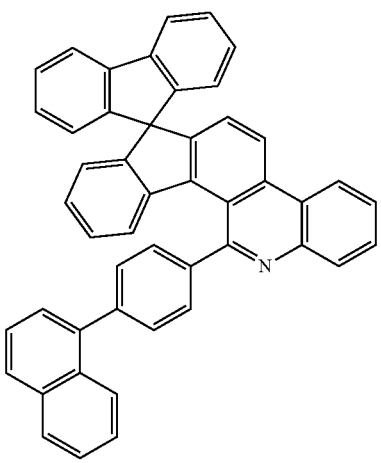

374
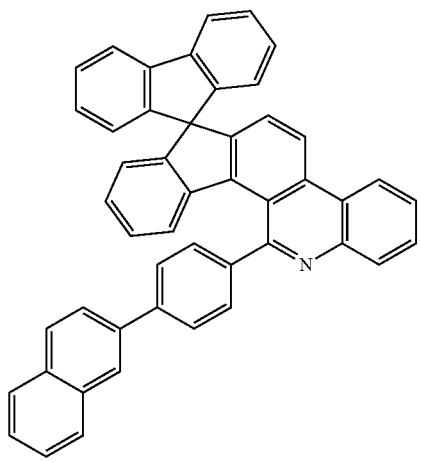
375
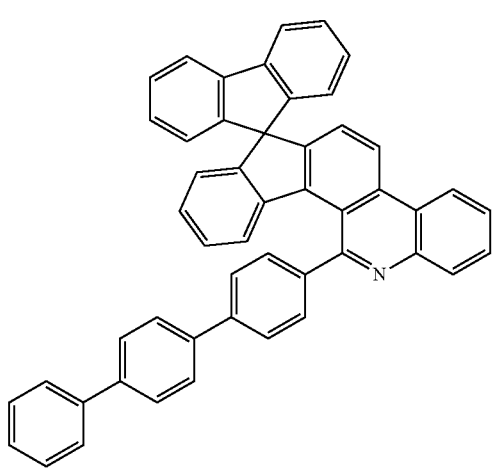
376
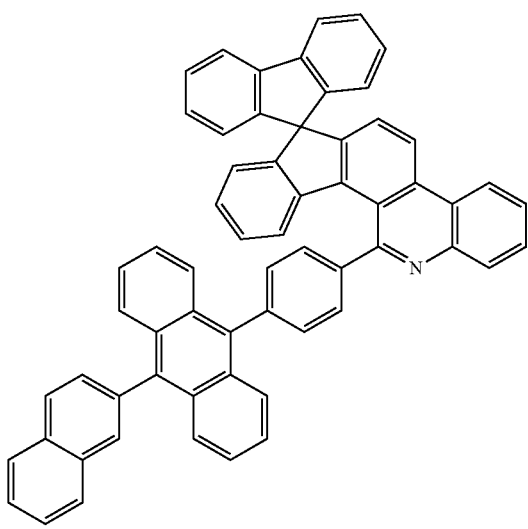
377
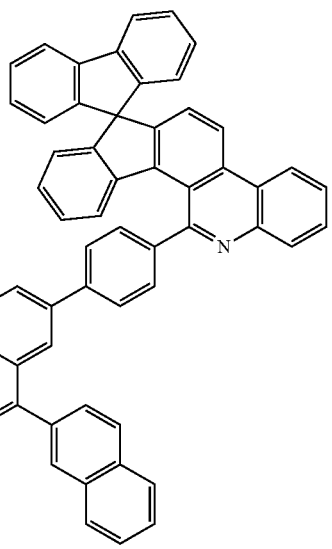
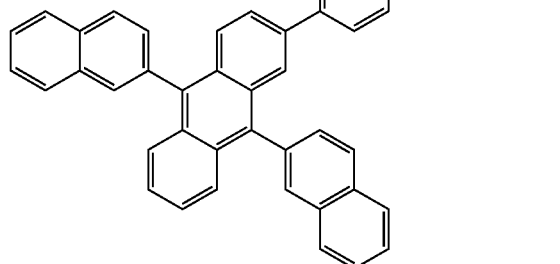
378
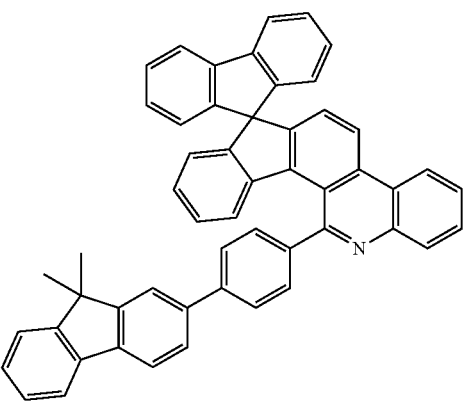
379
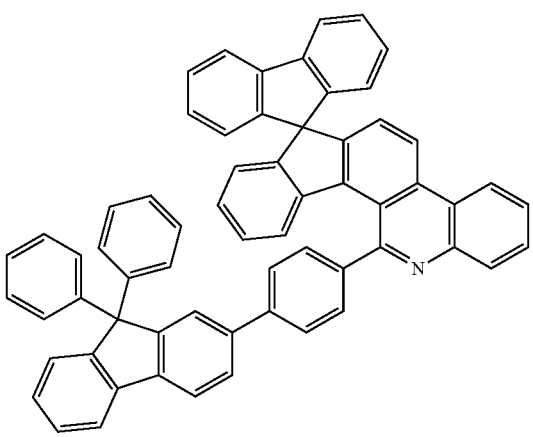

380
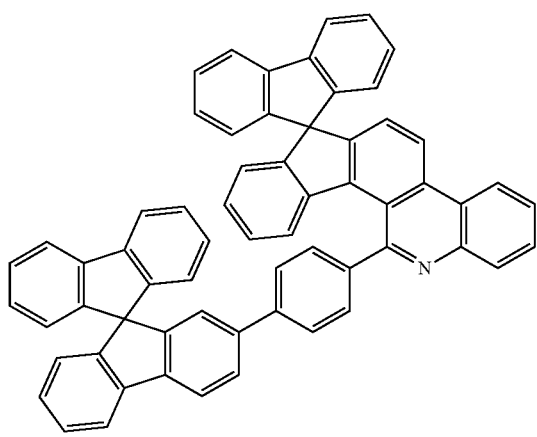
381
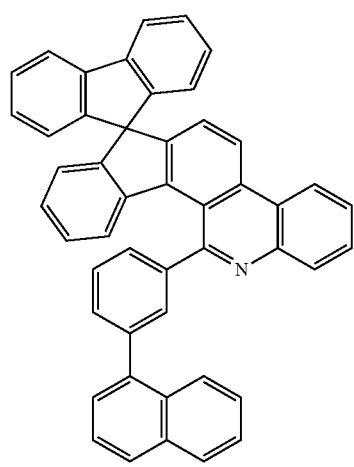
382
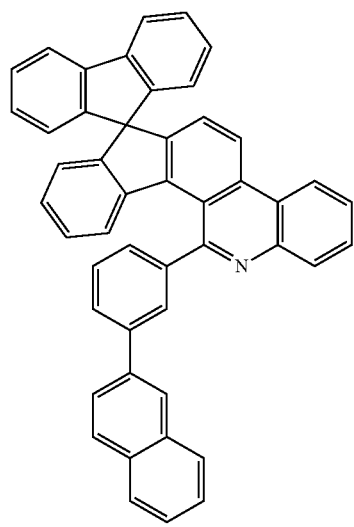
383
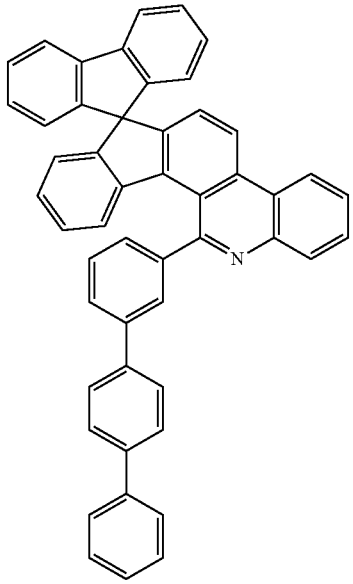
384
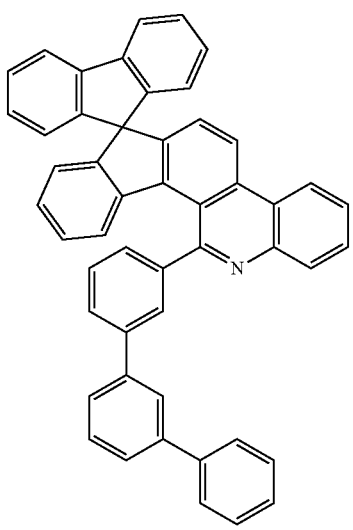
385
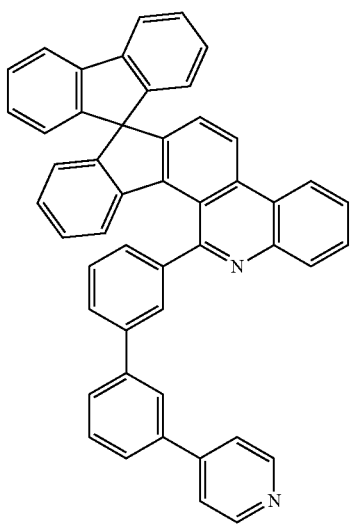

386
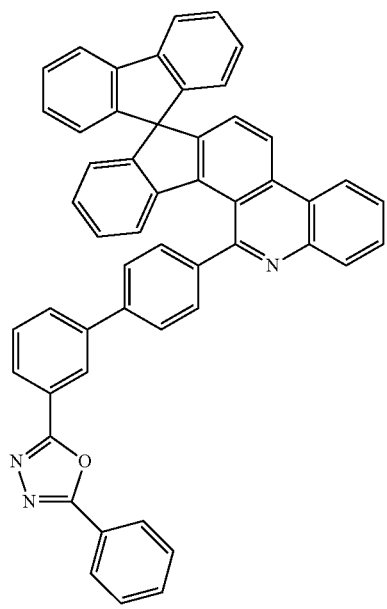
387
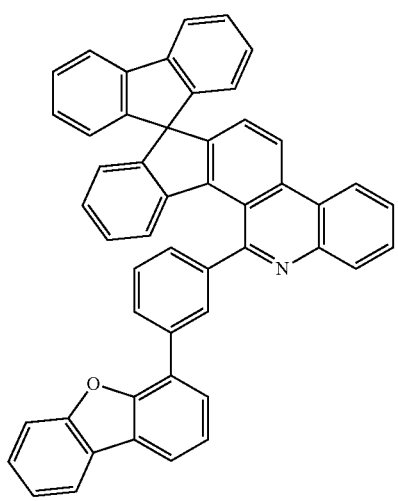
388
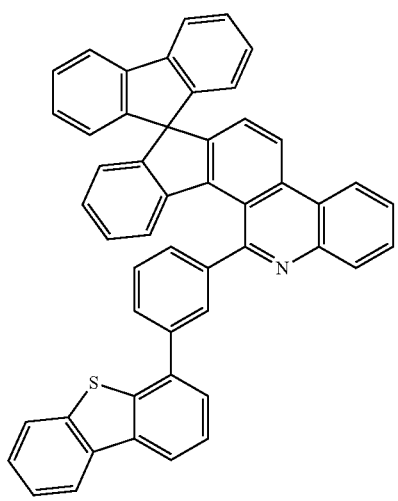
389
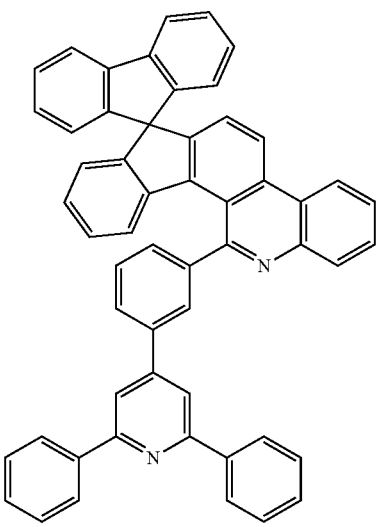
390
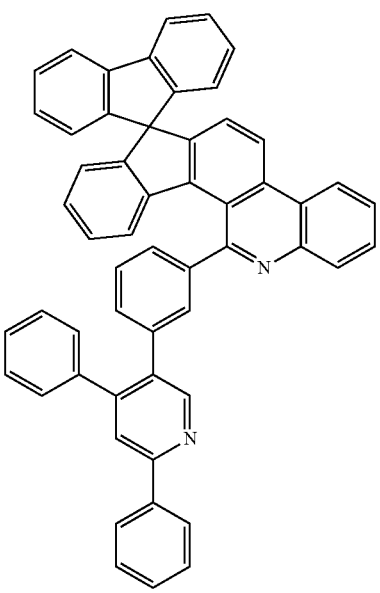
391
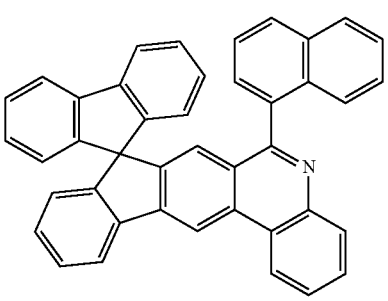

-continued
392
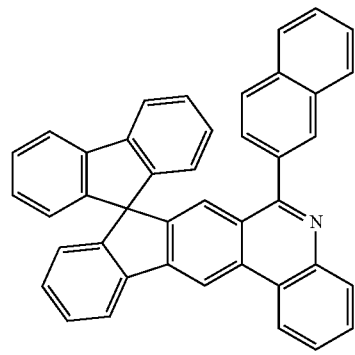
393
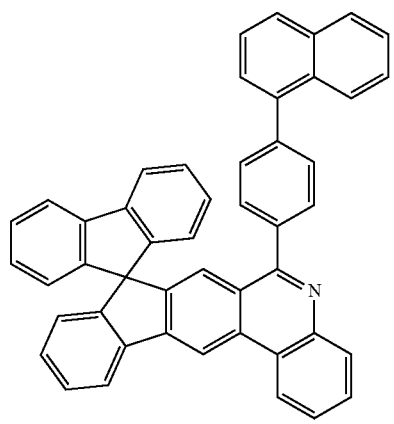
394
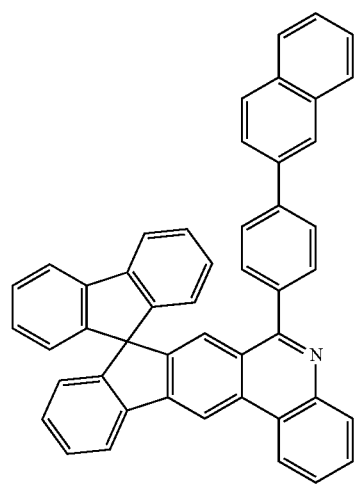
-continued
395
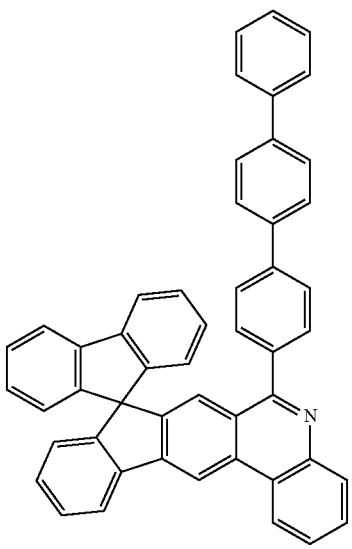
396
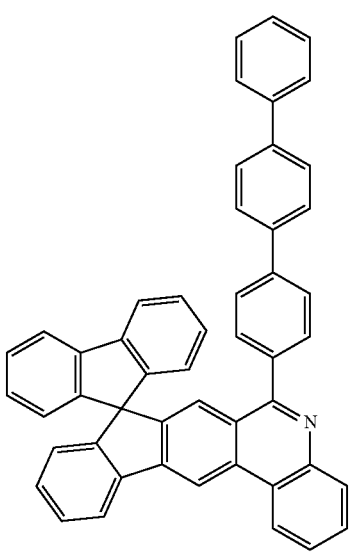
397
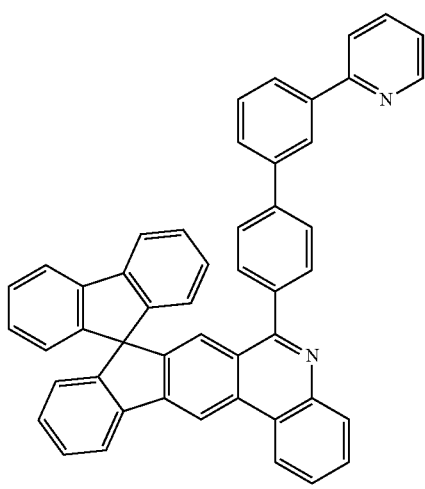

-continued
398
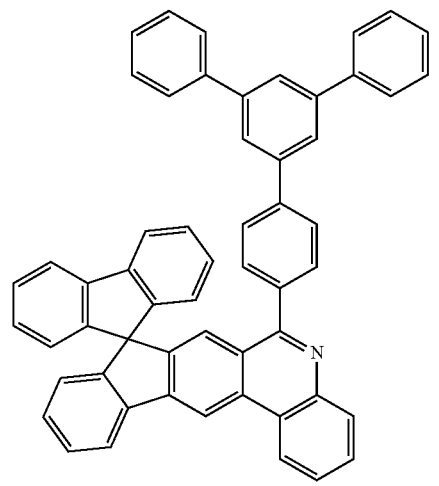
399
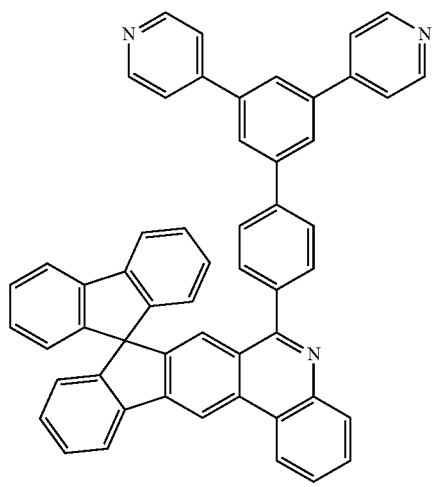
400
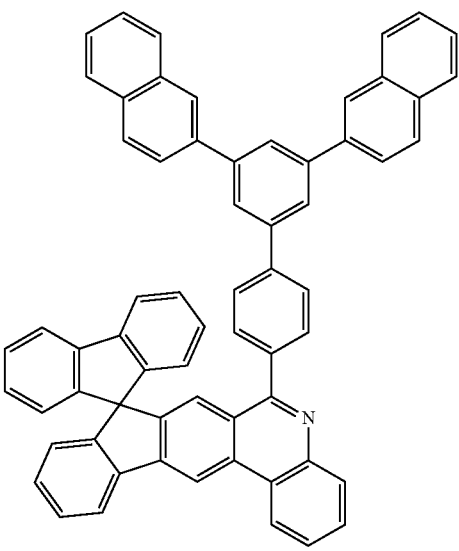
-continued
401
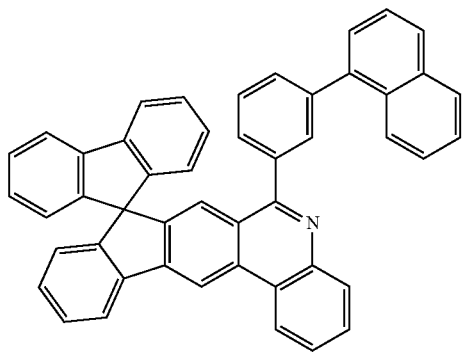
402
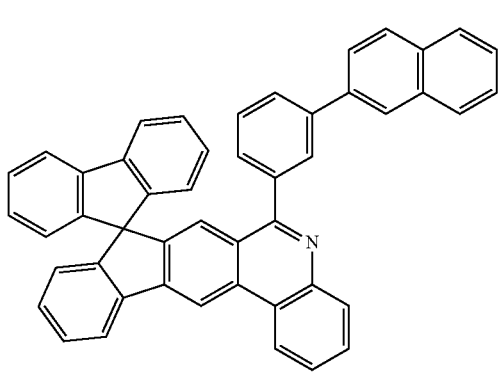
403
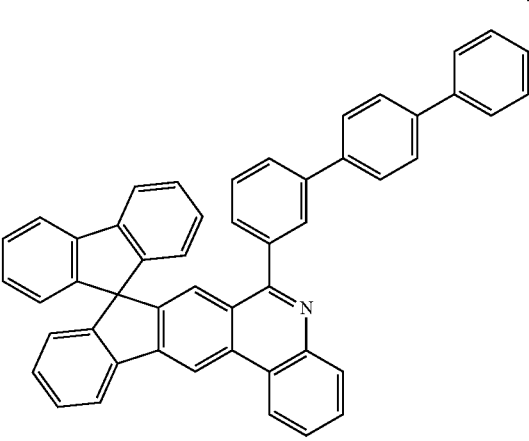
404
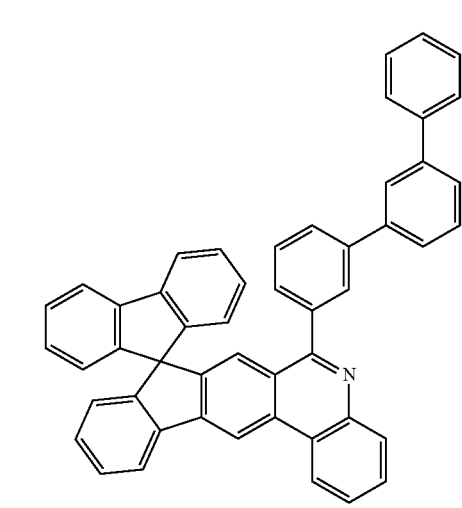

405

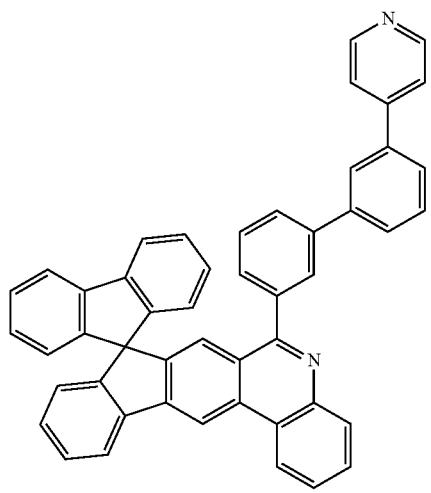

406

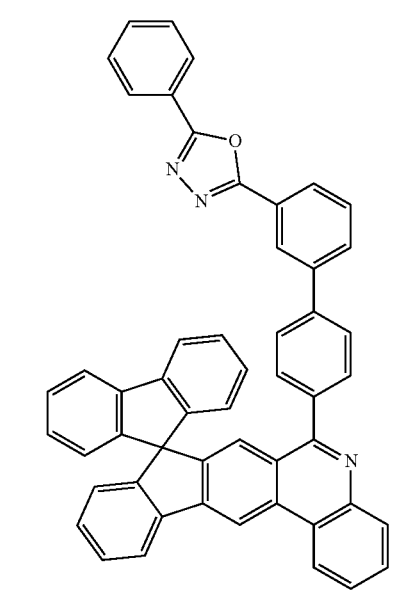

407

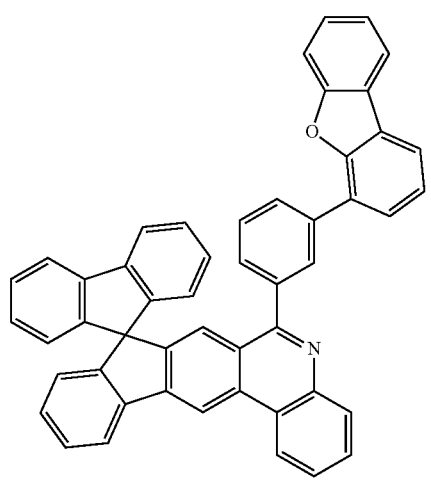

408

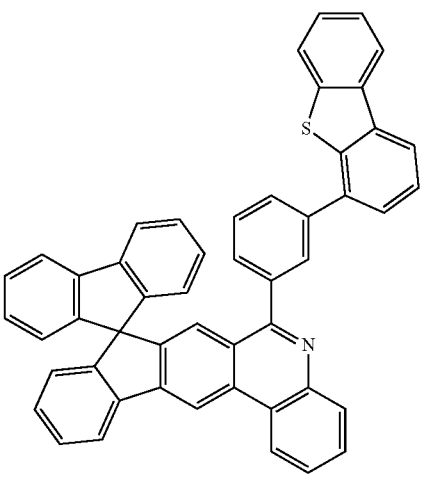

409

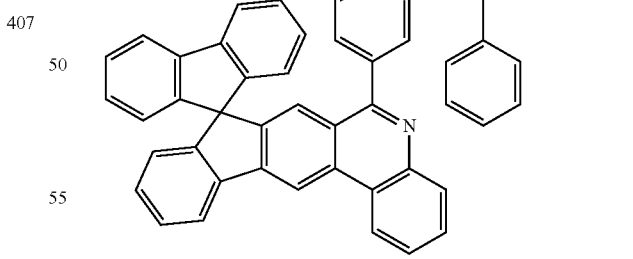

410

The above-described compounds may be prepared based on the Preparation Examples to be described below. Representative examples will be described in the Preparation Examples to be described below, but if necessary, a substituent may be added or excluded, and the position of the substituent may be changed. Further, a starting material, a reactant, reaction conditions, and the like may be changed based on the technology known in the art.

For example, in the compound of Chemical Formula 1, a core structure may be prepared as in the following Formulae 1 and 2.

Specifically, in the compound of Chemical Formula 2, a core structure may be prepared as in the following Formula 1. The substituent may be bonded by a method known in the art, and the kind and position of the substituent or the number of substituents may be changed according to the technology known in the art.

[Formula 1]

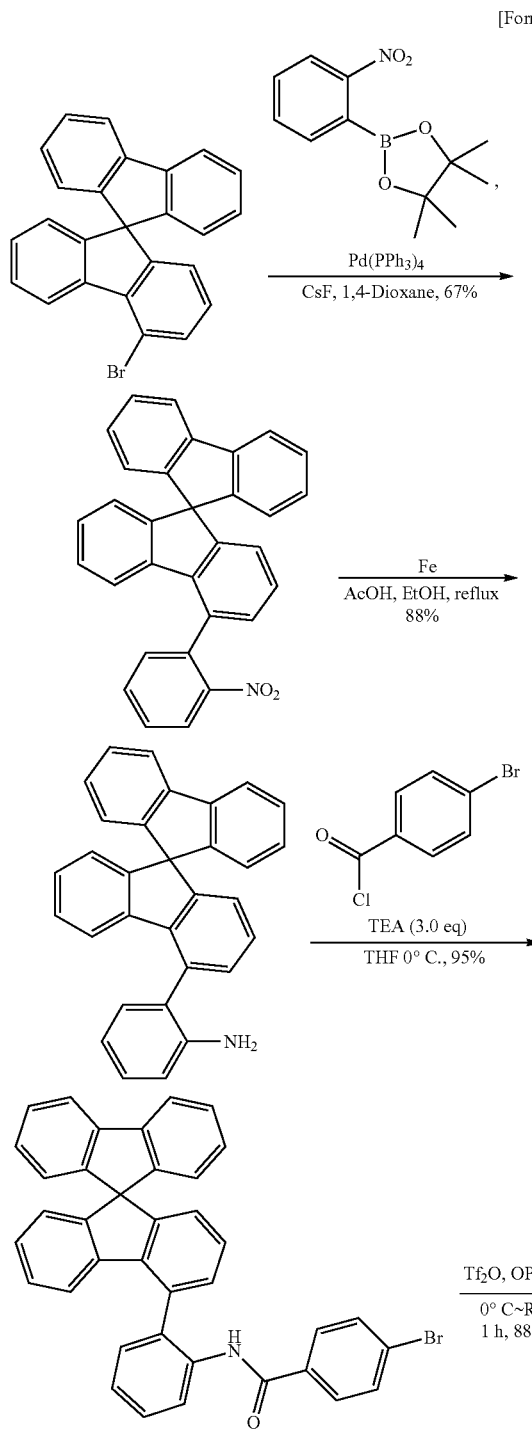

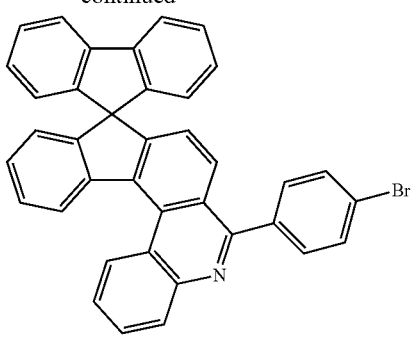

More specifically, Formula 1 is an example of the intermediate reaction for bonding a substituent to the position of $R_1$ in the core structure of Chemical Formula 2-1. Specifically, the last compound of Formula 1 is a case where $R_1$ in Chemical Formula 2-1 is a phenyl substituted with Br. Br may be changed into another substituent, if necessary, and the phenyl may also be changed into another substituent by changing a reactant benzoyl chloride.

Further, in the compound of Chemical Formula 2, a core structure may be prepared as in the following Formula 2. The substituent may be bonded by a method known in the art, and the kind and position of the substituent or the number of substituents may be changed according to the technology known in the art.

[Formula 2]

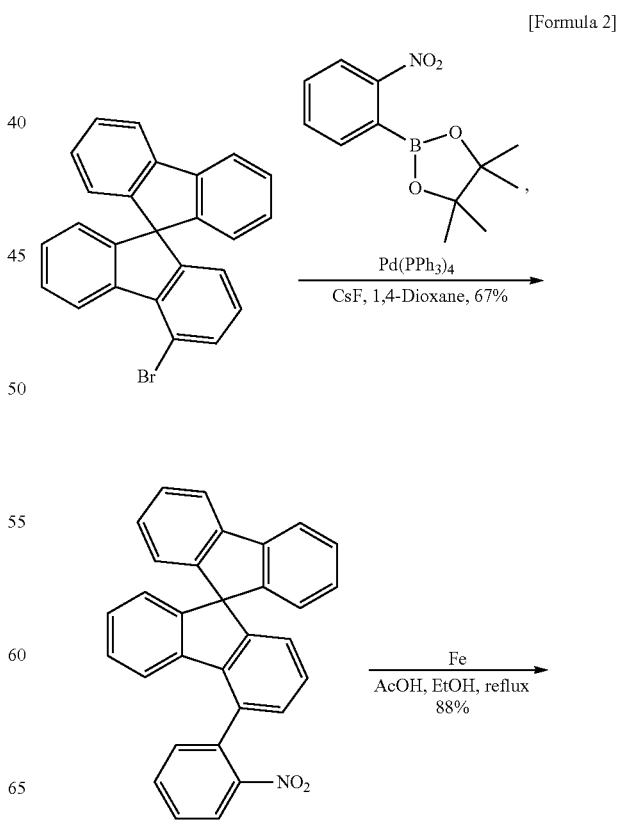

-continued

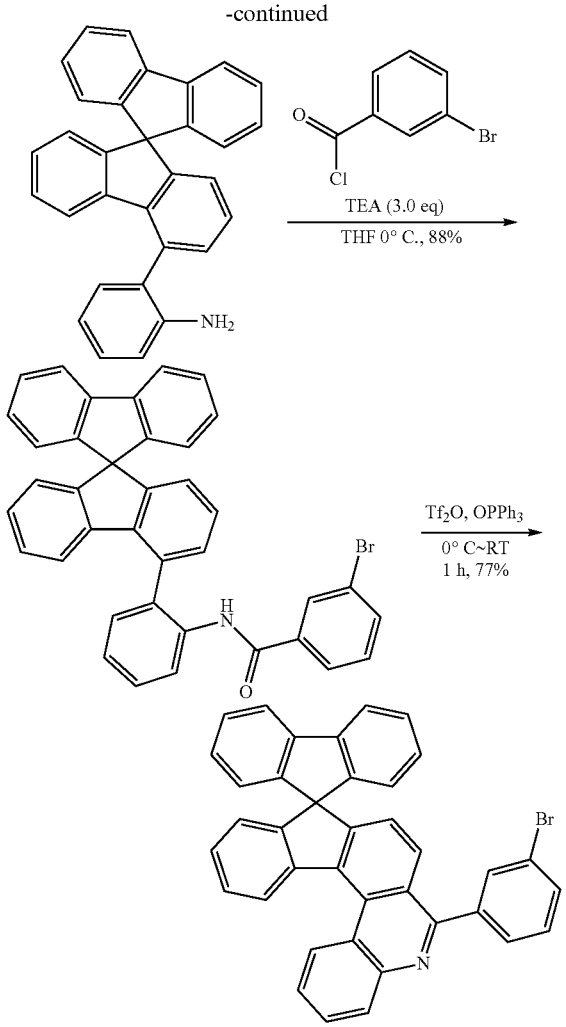

More specifically, Formula 2 is an example of the intermediate reaction for bonding a substituent to the position of $R_1$ in the core structure of Chemical Formula 2-1. Specifically, the last compound of Formula 2 is a case where $R_1$ in Chemical Formula 2-1 is a phenyl substituted with Br. Br may be changed into another substituent, if necessary, and the phenyl may also be changed into another substituent by changing a reactant benzoyl chloride.

The specific preparation method will be described in more detail in the Preparation Examples to be described below.

Another exemplary embodiment of the present application provides an organic light emitting device including the above-described compound of Chemical Formula 1. Specifically, the organic light emitting device according to the present application includes a positive electrode, a negative electrode, and one or more organic material layers provided between the positive electrode and the negative electrode, and one or more of the organic material layers include the compound of Chemical Formula 1.

FIGS. 1 to 3 exemplify the stacking sequence of the electrodes and the organic material layers of the organic light emitting device according to exemplary embodiments of the present application. However, the scope of the present application is not intended to be limited by these drawings, and the structure of the organic light emitting device known in the art may also be applied to the present application.

According to FIG. 1, an organic light emitting device in which a positive electrode 200, an organic material layer 300, and a negative electrode 400 are sequentially stacked on a substrate 100 is illustrated. However, the organic light emitting device is not limited only to such a structure, and as in FIG. 2, an organic light emitting device in which a negative electrode, an organic material layer, and a positive electrode are sequentially stacked on a substrate may also be implemented.

FIG. 3 exemplifies a case where the organic material layer is a multilayer. The organic light emitting device according to FIG. 3 includes a hole injection layer 301, a hole transporting layer 302, a light emitting layer 303, a hole blocking layer 304, an electron transporting layer 305, and an electron injection layer 306. However, the scope of the present application is not limited by the stacking structure as described above, and if necessary, the other layers except for the light emitting layer may be omitted, and another necessary functional layer may be further added.

The organic light emitting device according to the present application may be manufactured by the materials and methods known in the art, except that one or more layers of the organic material layers include the compound of Chemical Formula 1.

The compound of Chemical Formula 1 may alone constitute one or more layers of the organic material layers of the organic light emitting device. However, the compound of Chemical Formula 1 may be mixed with another material to constitute an organic material layer, if necessary.

The compound of Chemical Formula 1 may be used as a hole injection material, a hole transporting material, a light emitting material, a hole blocking material, an electron transporting material, an electron injection material, and the like in the organic light emitting device.

For example, the compound according to an exemplary embodiment of the present application may be used as a material for an electron injection layer, an electron transporting layer, or a layer, which simultaneously injects and transports electrons, in the organic light emitting device.

In addition, the compound according to an exemplary embodiment of the present application may be used as a material for the light emitting layer of the organic light emitting device. Specifically, the compound may also be used alone as a light emitting material, and as a host material or a dopant material of the light emitting layer.

Furthermore, the compound according to an exemplary embodiment of the present application may be used as a phosphorescent host material of the organic light emitting device. In this case, the compound according to an exemplary embodiment of the present application is included along with a phosphorescent dopant.

Further, the compound according to an exemplary embodiment of the present application may be used as a material for the hole blocking layer of the organic light emitting device.

In the organic light emitting device according to the present application, materials other than the compound of Chemical Formula 1 will be exemplified below, but these materials are illustrative only and are not intended to limit the scope of the present application, and may be replaced with materials publicly known in the art.

As a material for the positive electrode, materials having a relatively high work function may be used, and a transparent conductive oxide, a metal or a conductive polymer, and the like may be used.

As a material for the negative electrode, materials having a relatively low work function may be used, and a metal, a metal oxide, or a conductive polymer, and the like may be used.

As a hole injection material, a publicly-known hole injection material may also be used, and it is possible to use, for example, a phthalocyanine compound such as copper phthalocyanine disclosed in U.S. Pat. No. 4,356,429 or starburst-type amine derivatives described in the document [Advanced Material, 6, p. 677 (1994)], for example, TCTA, m-MTDATA, m-MTDAPB, polyaniline/dodecylbenzenesulfonic acid (PANI/DBSA) or poly(3,4-ethylenedioxythiophene)/poly(4-styrenesulfonate) (PEDOT/PSS), which is a soluble conductive polymer, polyaniline/camphor sulfonic acid (PANI/CSA) or polyaniline/poly(4-styrene-sulfonate) (PANI/PSS), and the like.

As the hole transporting material, a pyrazoline derivative, an arylamine-based derivative, a stilbene derivative, a triphenyldiamine derivative, and the like may be used, and a low-molecular weight or polymer material may also be used.

As the electron transporting material, it is possible to use an oxadiazole derivative, anthraquinodimethane and a derivative thereof, benzoquinone and a derivative thereof, naphthoquinone and a derivative thereof, anthraquinone and a derivative thereof, tetracyanoanthraquinodimethane and a derivative thereof, a fluorenone derivative, diphenyldicyanoethylene and a derivative thereof, a diphenoquinone derivative, a metal complex of 8-hydroxyquinoline and a derivative thereof, and the like, and a low-molecular weight material and a polymer material may also be used.

As the electron injection material, for example, LiF is typically used in the art, but the present application is not limited thereto.

As the light emitting material, a red, green, or blue light emitting material may be used, and if necessary, two or more light emitting materials may be mixed and used. Further, as the light emitting material, a fluorescent material may also be used, but a phosphorescent material may also be used. As the light emitting material, it is also possible to use alone a material which emits light by combining holes and electrons each injected from the positive electrode and the negative electrode, but materials in which both a host material and a dopant material are involved in light emission may also be used.

When the compound according to the present application is used as a phosphorescent host material, those known in the art may be used as a phosphorescent dopant material to be used together.

For example, phosphorescent dopant materials represented by LL'MX, LL'L"M, LMXX', L$_2$MX, and L$_3$M may be used, but the scope of the present application is not limited by these examples.

Here, L, L', L", X, and X' are bidendate ligands different from each other, and M is a metal forming an octahedral complex.

M may be iridium, platinum, osmium, and the like.

L is an anionic, bidendate ligand coordinated on M by sp$^2$ carbon and a heteroatom, and X may perform a function of trapping electrons or holes. Non-limiting examples of L include 2-(1-naphthyl)benzoxazole, 2-phenylbezoxazole, 2-phenylbenzothiazole, 7,8-benzoquinoline, thienylpyrizine, phenylpyridine, benzothienylpyrizine, 3-methoxy-2-phenylpyridine, thienylpyrizine, tolylpyridine, and the like. Non-limiting examples of X include acetylacetonate (acac), hexafluoroacetylacetonate, salicylidene, picolinate, 8-hydroxyquinolinate, and the like.

More specific examples thereof will be shown below, but the present application is not limited only to these examples.

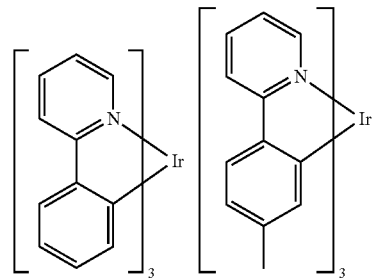

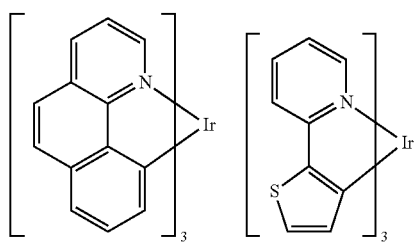

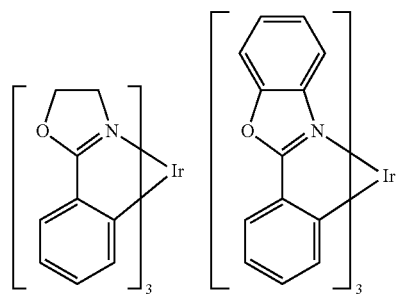

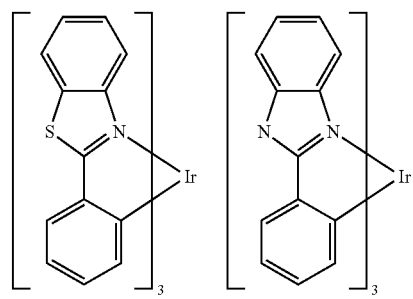

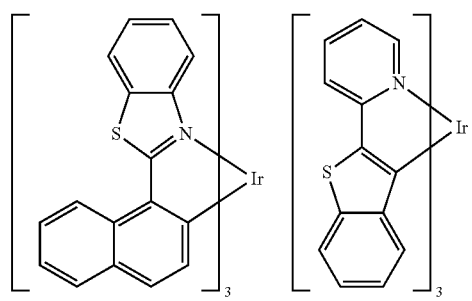

-continued

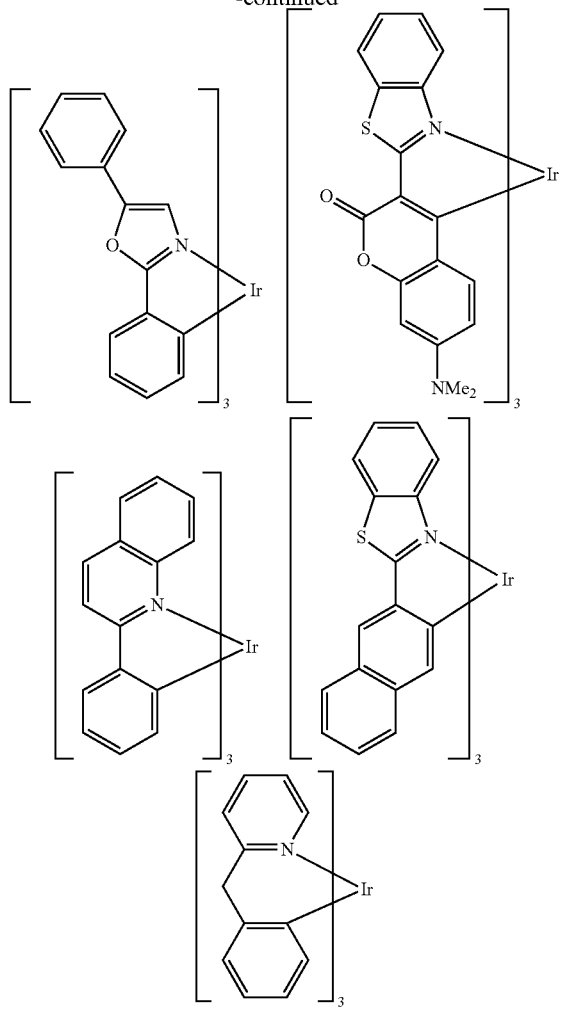

-continued

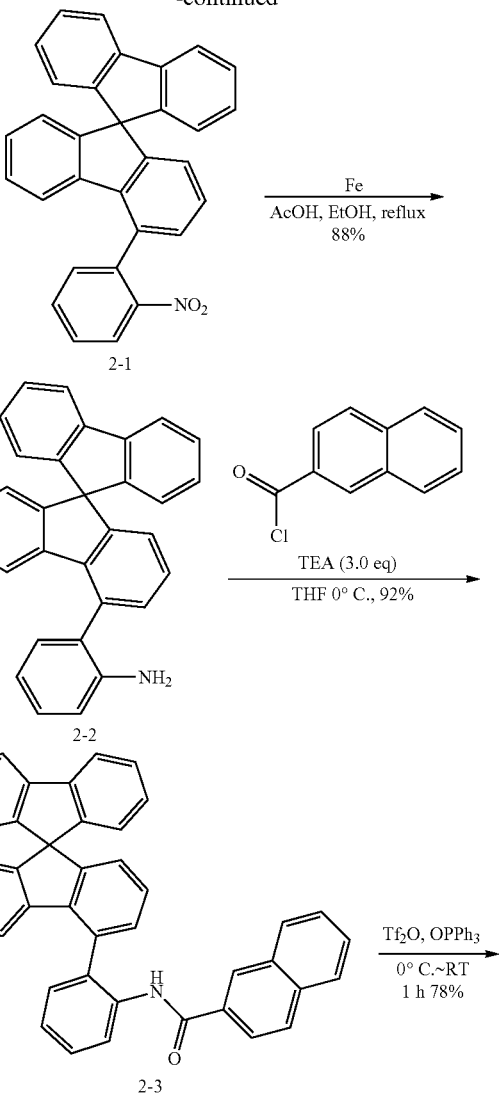

[Mode for Invention]

Hereinafter, the present application will be described in more detail through the Examples, but these are provided only for exemplifying the present application, and are not for limiting the scope of the present application.

PREPARATION EXAMPLE 1

Preparation of Compound 2

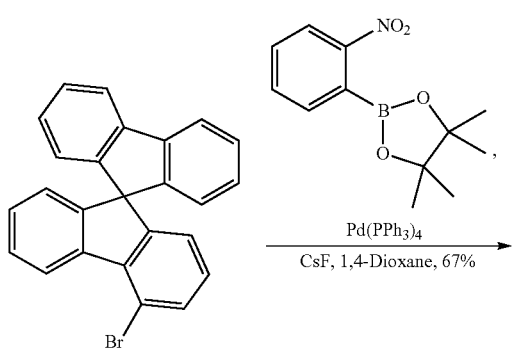

Preparation of Compound 2-1

In a one-neck round bottom flask, a 1,4-dioxane (700 ml) mixture of 3-bromospirobifluorene (40 g, 101.2 mmol), 4,4,5,5-tetramethyl-2-(2-nitrophenyl)-1,3,2-dioxaborolane (25.2 g, 101.2 mmol), Pd(PPh$_3$)$_4$ (11.6 g, 10.12 mmol), and CsF (30.7 g, 202.4 mmol) was refluxed at 110 for 1 hour. The mixture was extracted with methylene chloride (MC), and then the organic layer was dried over MgSO$_4$. The organic layer was concentrated, and then separated with column chromatography (SiO$_2$, Hexane:MC=3:1) to obtain Compound 2-1 (30 g, 67%).

Preparation of Compound 2-2

Fe (19.1 g, 342.85 mmol) was added to a mixture of Compound 2-1 (30 g, 68.57 mmol) and ethanol (EtOH) (900 ml) in a one-neck round bottom flask under nitrogen, and then the resulting mixture was stirred for 10 minutes. Acetic acid (AcOH) (90 ml) was added thereto, and then the resulting mixture was refluxed at 80° C. for 12 hours. NaHCO$_3$ was added thereto at 0° C. to neutralize the mixture, and then the organic layer extracted with EA was dried over MgSO$_4$. The organic layer was concentrated, and then separated with column chromatography (SiO$_2$, Hexane:MC=1:1) to obtain Compound 2-2 (24.6 g, 88%).

Preparation of Compound 2-3

Triethyl amine (25 ml, 181.08 mmol) was added to a mixture of Compound 2-2 (24.6 g, 60.36 mmol) and THF (400 ml) in a one-neck round bottom flask under nitrogen, and then the resulting mixture was stirred for 10 minutes. A THF (35 ml) mixture of 2-naphthyl chloride (17.25 g, 90.54 mmol) was added thereto at 0° C., and then the resulting mixture was stirred for 3 hours. The mixture was extracted with MC, and then the organic layer was dried over MgSO$_4$. The organic layer was concentrated, and then adsorbed and separated with column chromatography (SiO$_2$, Hexane:MC=1:2) to obtain solid Compound 2-3 (31.4 g, 92%).

Preparation of Compound 2

Tf$_2$O (3.16 ml, 19.3 mmol) was added to an MC (100 ml) mixture of OPPh$_3$ (11.8 g, 42.47 mmol) in a one-neck round bottom flask under nitrogen, and then the resulting mixture was stirred for 20 minutes. A mixture of Compound 2-3 (7 g, 12.87 mmol) and MC (150 ml) was added thereto at 0° C., and then the resulting mixture was slowly warmed to normal temperature, and stirred for 1 hour. From the reactant, the reaction was terminated with a saturated aqueous NaHCO$_3$ solution at 0° C., and then the organic layer extracted with MC was dried over MgSO$_4$. After being concentrated, the organic layer was adsorbed with MC, and then separated with column chromatography (SiO$_2$, Hexane:MC=1:1) to obtain solid Compound 2 (5.5 g, 78%).

PREPARATION EXAMPLE 2

Preparation of Compound 18

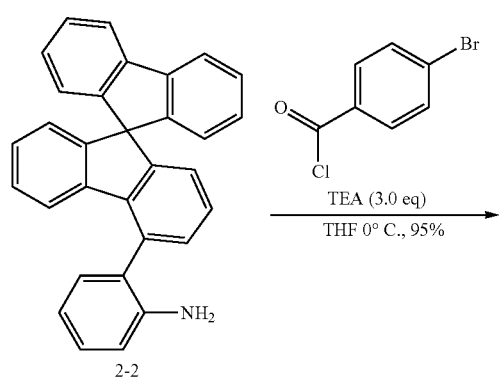

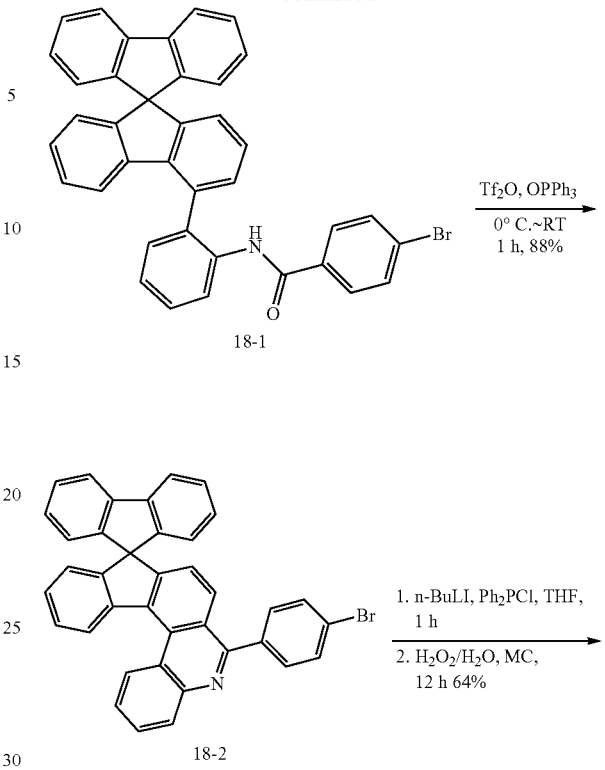

Preparation of Compound 18-1

Triethyl amine (26 ml, 191.4 mmol) was added to a mixture of Compound 2-2 (26 g, 63.8 mmol) and THF (450 ml) in a one-neck round bottom flask under nitrogen, and then the resulting mixture was stirred for 10 minutes. A THF (40 ml) mixture of 4-bromobenzoyl chloride (21 g, 95.7 mmol) was added thereto at 0° C., and then the resulting mixture was stirred for 3 hours. The mixture was extracted with MC, and then the organic layer was dried over MgSO$_4$. The organic layer was concentrated, and then adsorbed and separated with column chromatography (SiO$_2$, Hexane:MC=1:2) to obtain solid Compound 18-1 (36 g, 95%).

Preparation of Compound 18-2

Tf$_2$O (15 ml, 91.44 mmol) was added to an MC (200 ml) mixture of OPPh$_3$ (55.9 g, 201.68 mmol) in a one-neck round bottom flask under nitrogen, and then the resulting mixture was stirred for 30 minutes. An MC (180 ml) mixture of Compound 18-1 (36 g, 60.96 mmol) was added thereto at 0° C., and then the resulting mixture was slowly warmed to normal temperature, and stirred for 1 hour. From the reactant, the reaction was terminated with a saturated aqueous NaHCO$_3$ solution at 0° C., and then the organic layer extracted with MC was dried over MgSO$_4$. After being concentrated, the organic layer was adsorbed with MC, and then separated with column chromatography (SiO$_2$, Hexane:MC=1:1) to obtain solid Compound 18-2 (31 g, 88%).

Preparation of Compound 18

Compound 18-2 (10 g, 17.46 mmol) was dissolved in anhydrous THF (20 ml) in a one-neck round bottom flask under nitrogen, and then the resulting solution was cooled to −78° C. n-butyllithium (2.5 M in hexane) (9 ml, 22.69 mmol) was slowly added dropwise thereto, and then the resulting mixture was stirred for 1 hour. Chlorodiphenylphosphine (4.2 ml, 22.69 mmol) was added dropwise to the solution, and the resulting solution was stirred at room temperature for 12 hours. The reaction mixture was extracted with MC/H$_2$O, and then distilled under vacuum. The reaction mixture was dissolved in MC (200 ml), and then the resulting solution was stirred along with a 30% H$_2$O$_2$ aqueous solution (10 ml) at room temperature for 1 hour. The reaction mixture was extracted with MC/H$_2$O, and then the concentrated mixture was separated with column chromatography (SiO$_2$, MC:methanol=25:1) to obtain solid Compound 18 (7.8 g, 64%).

PREPARATION EXAMPLE 3

Preparation of Compound 28

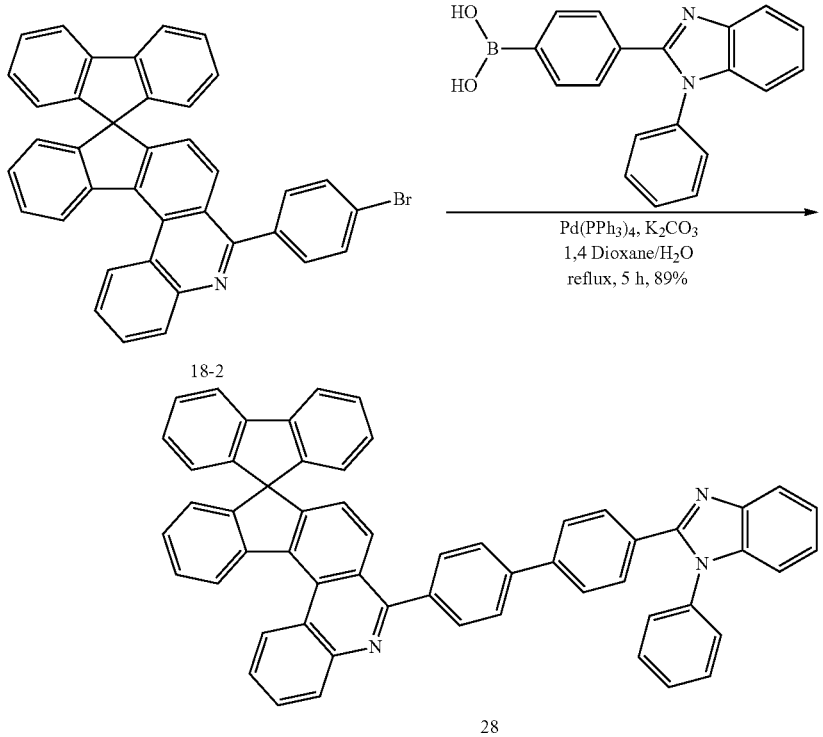

Preparation of Compound 28

A 1,4-doxane/H$_2$O (150 ml/30 ml) mixed solution of Compound 18-2 (8 g, 13.97 mmol), (4-(1-phenyl-1H-benzo[d]imidazol-2-yl)phenyl)boronic acid (4.38 g, 13.97 mmol), K$_2$CO$_3$ (3.86 g, 27.34 mmol), and Pd(PPh$_3$)$_4$ (1.6 g, 1.39 mmol) was refluxed and stirred in a two-neck round bottom flask under nitrogen for 5 hours. The reaction mixture cooled to room temperature was extracted with MC/H$_2$O and dried over MgSO$_4$, and then filtered. The reaction mixture was concentrated, and then separated with column chromatography (SiO$_2$, Hexane:MC=3:1) to obtain solid Compound 28 (9.6 g, 89%).

PREPARATION EXAMPLE 4

Preparation of Compound 37

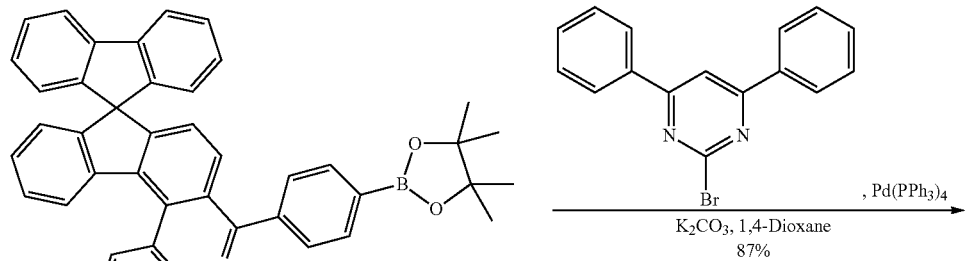

41-1

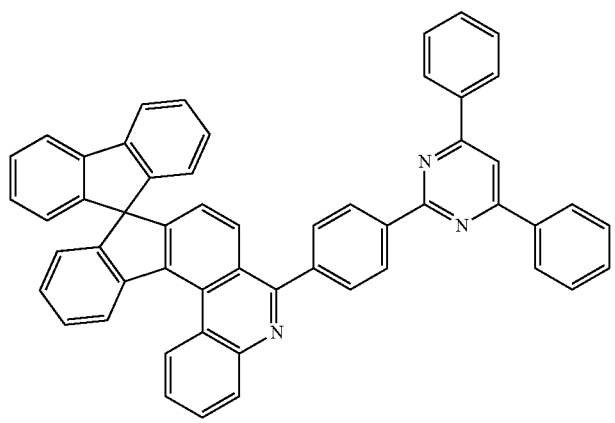

37

Preparation of Compound 37

A mixture of Compound 41-1 (8 g, 12.91 mmol), 2-bromo-4,6-diphenylpyrimidine (4.82 g, 15.49 mmol), Pd(PPh$_3$)$_4$ (1.49 g, 1.29 mmol), K$_2$CO$_3$ (3.56 g, 25.82 mmol), and 1,4-dioxane (150 ml)/H$_2$O (30 ml) was stirred at 120° C. in a one-neck round bottom flask for 4 hours. The reactant at 120° C. was filtered, and then washed with 1,4-dioxane at 120° C. and with methanol to obtain Compound 37 (4.8 g) in the form of cotton wool, and the filtrate was separated with column chromatography (SiO$_2$, Hexane: MC=3:1) to obtain powdery Compound 37 (3.4 g) (8.2 g, 87%).

PREPARATION EXAMPLE 5

Preparation of Compound 41

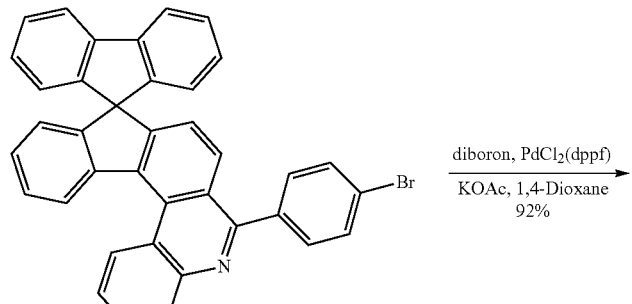

18-2

-continued

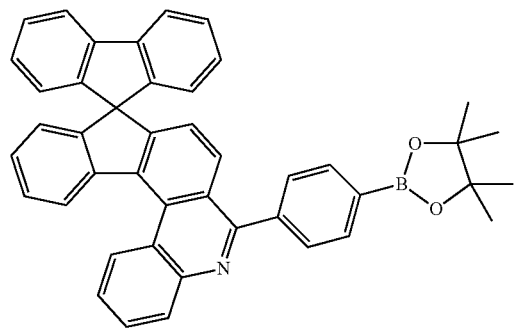 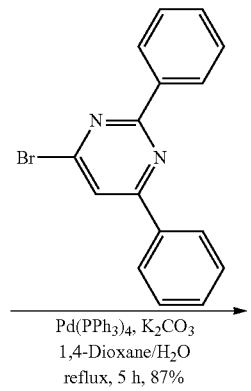

41-1

Pd(PPh3)4, K2CO3
1,4-Dioxane/H2O
reflux, 5 h, 87%

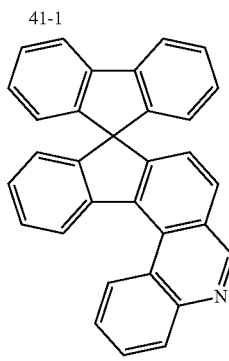

41

Preparation of Compound 41-1

A mixture of Compound 18-2 (27 g, 47.16 mmol), pinacol diboron (23.95 g, 94.32 mmol), PdCl2(dppf) (1.72 g, 2.35 mmol), KOAc (13.88 g, 141.48 mmol), and 1,4-dioxane (300 ml) was refluxed at 120° C. in a one-neck round bottom flask under nitrogen for 5 hours. The mixture was extracted with MC, and then the organic layer was dried over MgSO4. The organic layer was concentrated, and then separated with column chromatography (SiO2, Hexane:MC=5:1) to obtain solid Compound 41-1 (27 g, 92%).

Preparation of Compound 41

A mixture of Compound 41-1 (8 g, 12.91 mmol), 2-bromo-4,6-diphenylpyrimidine (4.82 g, 15.49 mmol), Pd(PPh3)4 (1.49 g, 1.29 mmol), K2CO3 (3.56 g, 25.82 mmol), and 1,4-dioxane (150 ml)/H2O (30 ml) was stirred at 120° C. in a one-neck round bottom flask for 4 hours. The reactant was filtered in a state of 120° C., and then washed with 1,4-dioxane at 120° C. and with methanol to obtain Compound 41 (4.8 g) in the form of cotton wool, and the filtrate was separated with column chromatography (SiO2, Hexane:MC=3:1) to obtain powdery Compound 41 (3.4 g) (8.2 g, 87%).

PREPARATION EXAMPLE 6

Preparation of Compound 43

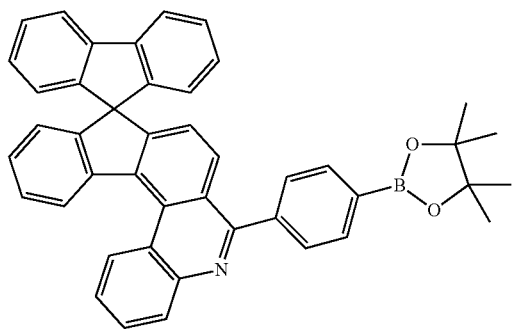 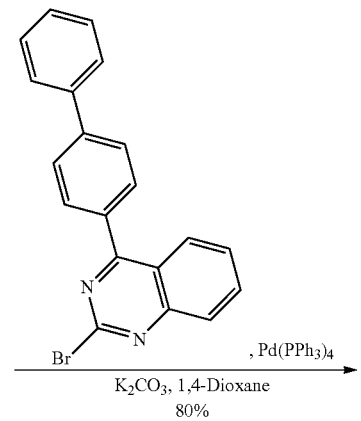

, Pd(PPh3)4
K2CO3, 1,4-Dioxane
80%

41-1

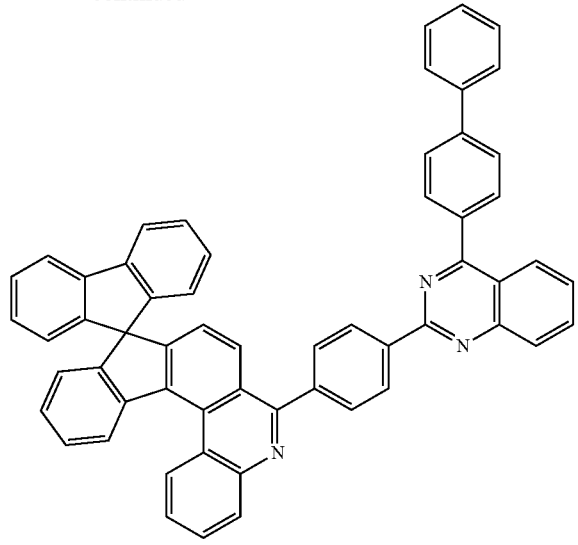

43

Preparation of Compound 43

A mixture of Compound 41-1 (9 g, 14.52 mmol), 4-([1,1'-biphenyl]-4-yl)-2-bromoquinazoline (6.27 g, 17.42 mmol), Pd(PPh$_3$)$_4$ (1.67 g, 1.452 mmol), K$_2$CO$_3$ (4 g, 29 mmol), 1,4-dioxane (180 ml), and H$_2$O (40 ml) was stirred at 120° C. in a one-neck round bottom flask for 4 hours. The reactant at 120° C. was filtered, and then washed with 1,4-dioxane at 120° C., and with methanol and hexane. The solid was dissolved in MC, adsorbed, and then separated with column chromatography (SiO$_2$, Hexane:MC=1:3) to obtain solid Compound 43 (9 g, 80%).

PREPARATION EXAMPLE 7

Preparation of Compound 44

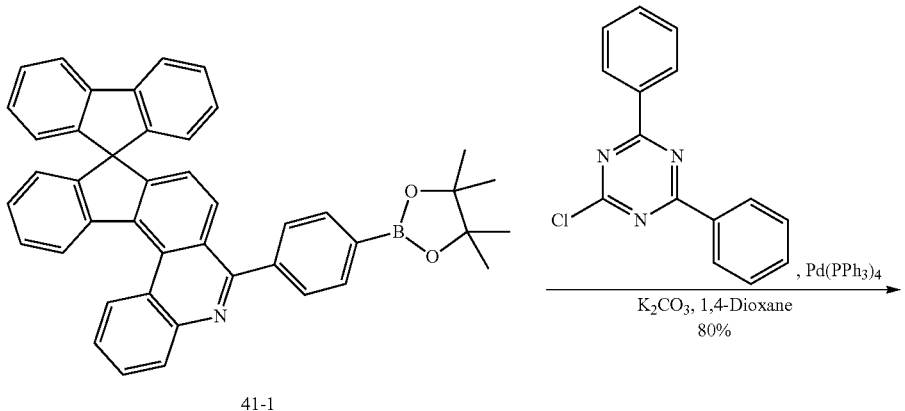

41-1

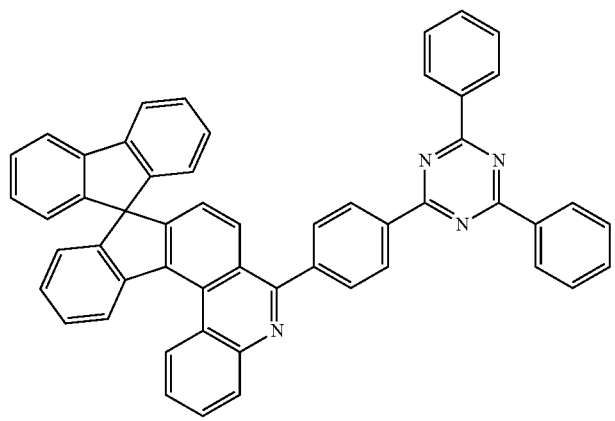

44

Preparation of Compound 44

A mixture of Compound 41-1 (9 g, 14.52 mmol), 2-chloro-4,6-diphenyl-1,3,5-triazine (4.27 g, 15.97 mmol), Pd(PPh$_3$)$_4$ (1.67 g, 1.45 mmol), K$_2$CO$_3$ (4 g, 29.04 mmol), and 1,4-dioxane (150 ml)/H$_2$O (30 ml) was stirred at 120° C. in a one-neck round bottom flask for 4 hours. The reactant at 120° C. was filtered, and then washed with 1,4-dioxane at 120° C. and with methanol to obtain Compound 44 (8.4 g, 80%).

PREPARATION EXAMPLE 8

Preparation of Compound 76

Preparation of Compound 76-1

A mixture of Compound 77-2 (45 g, 78.6 mmol), pinacol diboron (40 g, 157.2 mmol), PdCl$_2$ (dppf) (2.87 g, 3.93 mmol), KOAc (23 g, 235.8 mmol), and 1,4-dioxane (500 ml) was refluxed at 120° C. in a one-neck round bottom flask under nitrogen for 5 hours. The mixture was extracted with MC, and then the organic layer was dried over MgSO$_4$. The organic layer was concentrated, and then separated with column chromatography (SiO$_2$, Hexane:MC=3:1) to obtain solid Compound 76-1. (45 g, 92%)

Preparation of Compound 76

A mixture of Compound 76-1 (10 g, 16.14 mmol), 2-(4-bromophenyl)benzo[d]thiazole (7.4 g, 19.36 mmol),

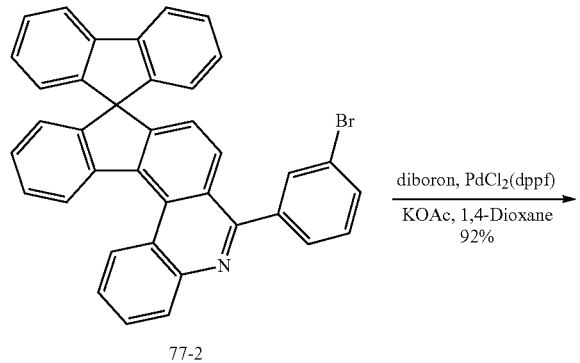

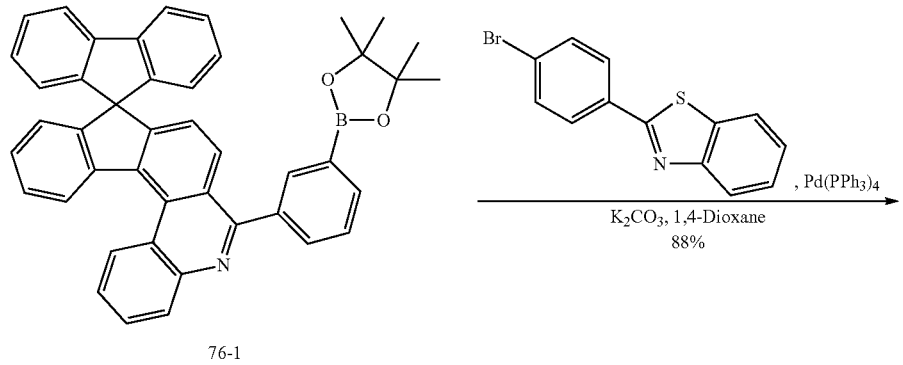

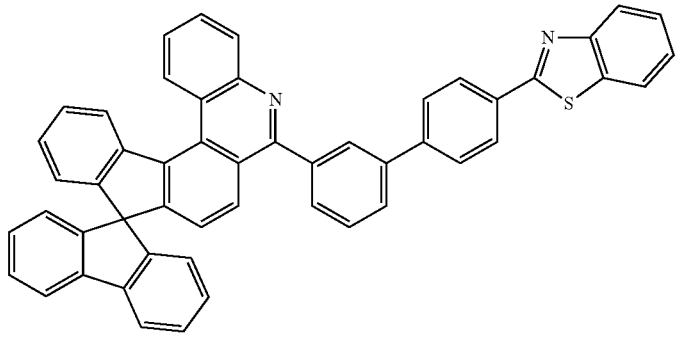

Pd(PPh₃)₄ (1.86 g, 1.614 mmol), K₂CO₃ (4.46 g, 32.28 mmol), and 1,4-dioxane (150 ml)/H₂O (30 ml) was stirred at 120° C. in a one-neck round bottom flask for 4 hours. The mixture was extracted with MC, and then the organic layer was dried over MgSO₄. The organic layer was concentrated, and then separated with column chromatography (SiO₂, Hexane:MC=1:3) to obtain solid Compound 76 (10 g, 88%).

PREPARATION EXAMPLE 9

Preparation of Compound 77

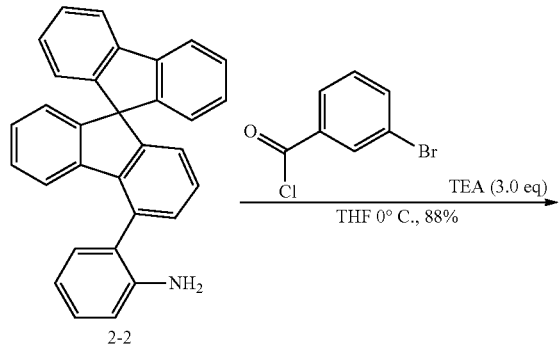

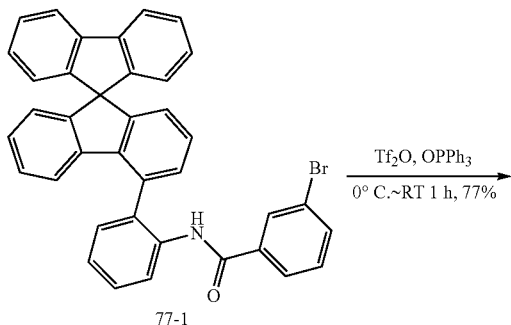

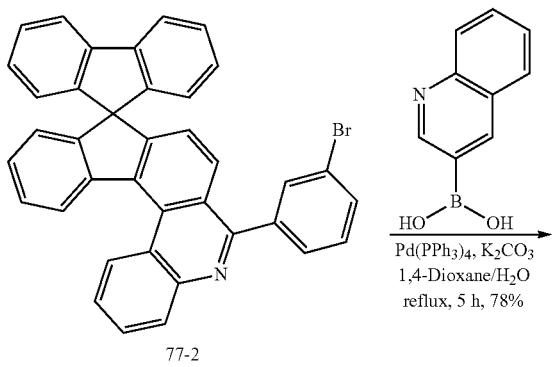

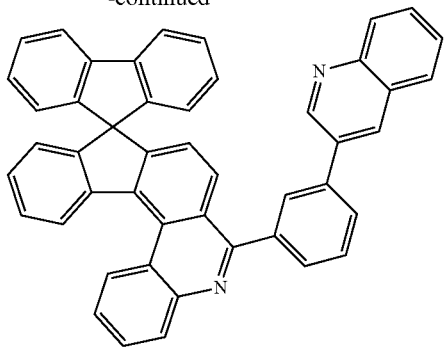

Preparation of Compound 77-1

Triethyl amine (26 ml, 191.4 mmol) was added to a mixture of Compound 2-2 (26 g, 63.8 mmol) and THF (450 ml) in a one-neck round bottom flask under nitrogen, and then the resulting mixture was stirred for 10 minutes. A THF (40 ml) mixture of 3-bromobenzoyl chloride (21 g, 95.7 mmol) was added thereto at 0° C., and then the resulting mixture was stirred for 3 hours. The mixture was extracted with MC, and then the organic layer was dried over MgSO₄. The organic layer was concentrated, and then adsorbed and separated with column chromatography (SiO₂, Hexane:MC=1:2) to obtain solid Compound 77-1 (33.4 g, 88%).

Preparation of Compound 77-2

Tf₂O (13.9 ml, 84.84 mmol) was added to an MC (200 ml) mixture of OPPh₃ (51.94 g, 186.64 mmol) in a one-neck round bottom flask under nitrogen, and then the resulting mixture was stirred for 30 minutes. An MC (170 ml) mixture of Compound 77-1 (33.4 g, 56.56 mmol) was added thereto at 0° C., and then the resulting mixture was slowly warmed to normal temperature, and stirred for 1 hour. From the reactant, the reaction was terminated with a saturated aqueous NaHCO₃ solution at 0° C., and then the organic layer extracted with MC was dried over MgSO₄. After being concentrated, the organic layer was adsorbed with MC, and then separated with column chromatography (SiO₂, Hexane:MC=1:1) to obtain solid Compound 77-2 (25 g, 77%).

Preparation of Compound 77

A 1,4-dioxane/H₂O (150 ml/30 ml) mixed solution of Compound 77-2 (8 g, 13.97 mmol), quinolin-3-ylboronic acid (2.41 g, 13.97 mmol), K₂CO₃ (3.86 g, 27.34 mmol), and Pd(PPh₃)₄ (1.6 g, 1.39 mmol) was refluxed and stirred in a two-neck round bottom flask under nitrogen for 5 hours. The reaction mixture cooled to room temperature was extracted with MC/H₂O and dried over MgSO₄, and then filtered. The mixture was concentrated, and then separated with column chromatography (SiO₂, Hexane:MC=3:1) to obtain solid Compound 77 (6.5 g, 78%).

PREPARATION EXAMPLE 10

Preparation of Compound 98

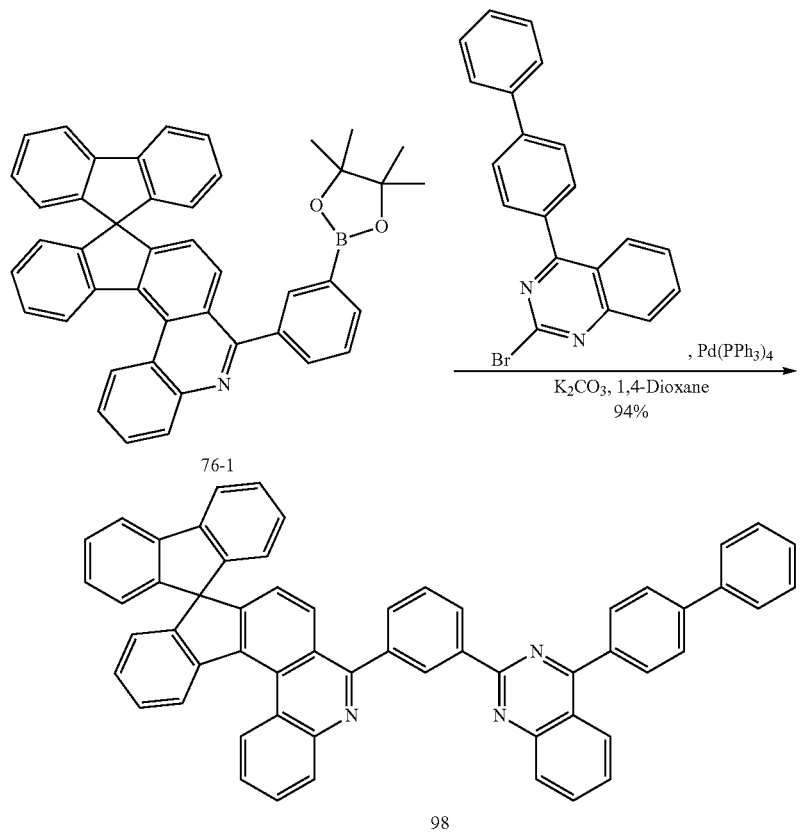 [SMILES: CC1(C)OB(c2cccc(-c3nc4ccccc4c4c5c(ccc34)C3(c4ccccc4-c4ccccc43)c3ccccc3-5)c2)OC1(C)C ; Brc1nc(-c2ccc(-c3ccccc3)cc2)c2ccccc2n1 ; c1ccc(-c2ccc(-c3nc(-c4cccc(-c5nc6ccccc6c6c7c(ccc56)C5(c6ccccc6-c6ccccc65)c5ccccc5-7)c4)nc4ccccc34)cc2)cc1]

Preparation of Compound 98

A mixture of Compound 76-1 (10 g, 16.40 mmol), 4-([1,1'-biphenyl]-4-yl)-2-bromoquinazoline (7 g, 19.68 mmol), Pd(PPh$_3$)$_4$ (1.89 g, 1.64 mmol), K$_2$CO$_3$ (4.5 g, 32.8 mmol), and 1,4-dioxane (200 ml)/H$_2$O (50 ml) was stirred at 120° C. in a one-neck round bottom flask for 4 hours. The mixture was extracted with MC, and then the organic layer was dried over MgSO$_4$. The organic layer was concentrated, and then separated with column chromatography (SiO$_2$, Hexane: MC=1:3) to obtain solid Compound 98 (12 g, 94%).

PREPARATION EXAMPLE 11

Preparation of Compound 101

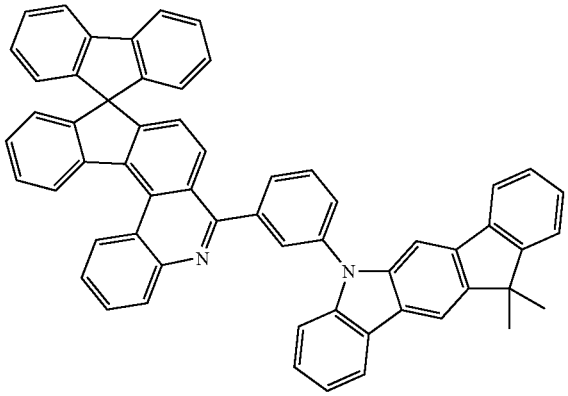

-continued

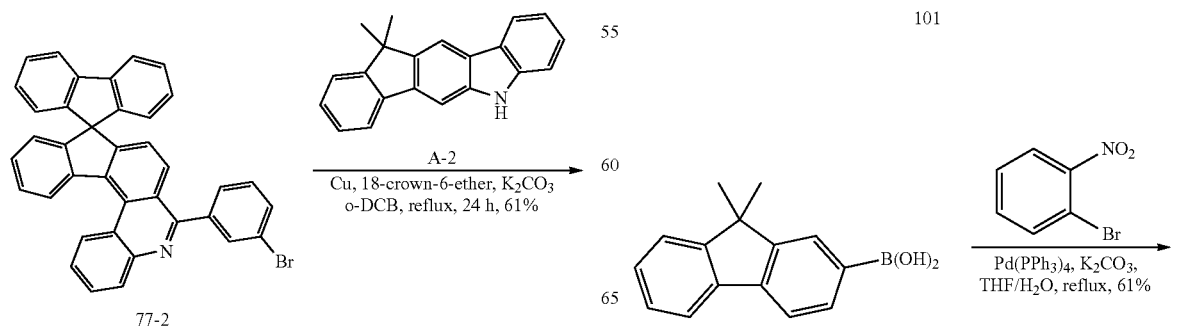

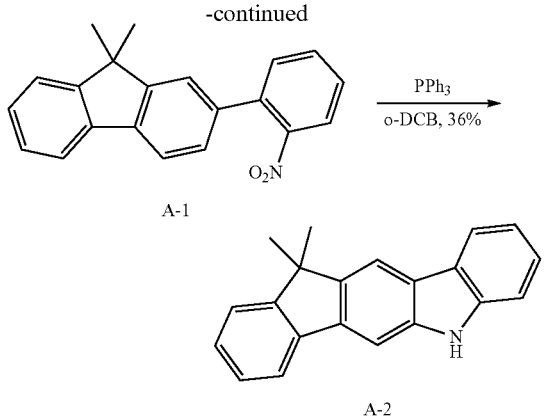

Preparation of Compound A-1

A THF (250 ml)/H₂O (50 ml) mixture of (9,9-dimethyl-9H-fluoren-2-yl)boronic acid (25.9 g, 0.108 mol), 1-bromo-2-nitrobenzene (20 g, 0.099 mol), Pd(PPh₃)₄ (5.7 g, 4.95 mmol), and K₂CO₃ (27.3 g, 0.198 mol) was refluxed and stirred in a one-neck round bottom flask for 24 hours. The aqueous layer was removed, and then the organic layer was dried over MgSO₄. The organic layer was concentrated, and then separated with column chromatography (SiO₂, Hexane:MC=2:1) to obtain yellow solid Compound A-1 (21 g, 61%).

Preparation of Compound A-2

An o-DCB (300 ml) mixture of Compound A-1 (20 g, 0.0634 mmol) and PPh₃ (49.8 g, 0.190 mol) was refluxed and stirred in a one-neck round bottom flask under nitrogen for 18 hours. o-DCB was distilled under vacuum and removed, and then the resulting product was separated with column chromatography (SiO₂, Hexane:MC=3:1) to obtain white solid Compound A-2 (6.6 g, 36%).

Preparation of Compound 101

An o-DCB (200 ml) mixture of Compound 77-2 (9 g, 15.72 mmol), Compound A-2 (4.45 g, 15.72 mmol), Cu (1 g, 15.72 mol), 18-crown-6-ether (511 mg, 1.57 mmol), and K₂CO₃ (4.43 g, 31.44 mmol) was refluxed and stirred in a one-neck round bottom flask under nitrogen for 24 hours. o-DCB was distilled under vacuum and removed, and then the resulting product was separated with column chromatography (SiO₂, Hexane:MC=1:2) to obtain solid Compound 101 (7.5 g, 61%).

PREPARATION EXAMPLE 12

Preparation of Compound 120

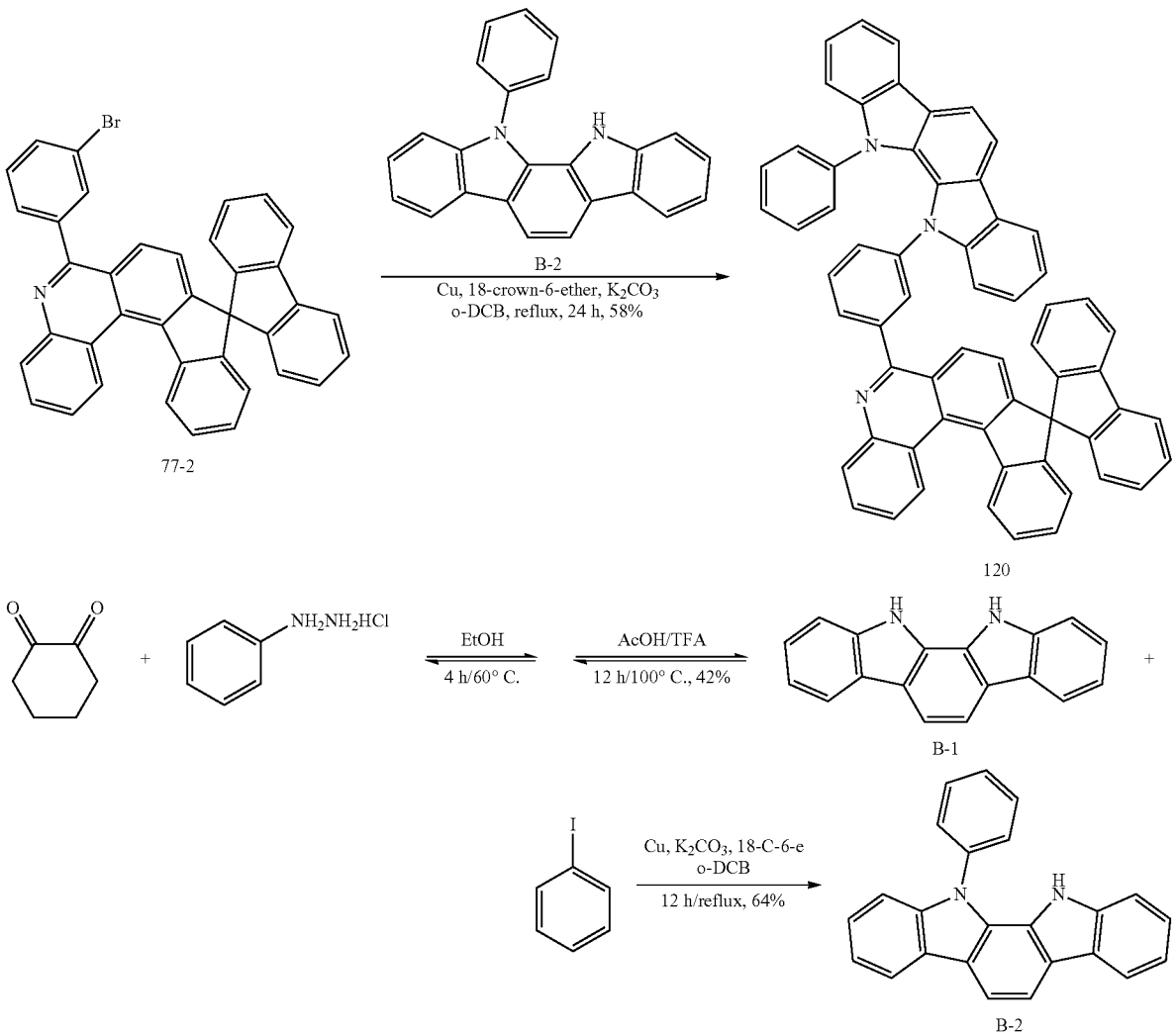

Preparation of Compound B-1

Sulfuric acid (1.4 mL, 0.0374 mol) was slowly added dropwise to an ethanol (1,000 ml) mixture of 1,2-dicyclohexanone (30.0 g, 0.374 mol) and phenylhydrazine hydrochloride (77.37 g, 0.749 mol) in a one-neck round bottom flask under nitrogen, and then the resulting mixture was stirred at 60° C. for 4 hours. The solution cooled to room temperature was filtered to obtain a yellow brown solid (69 g, 93%).

Trifluoroacetic acid (46.5 mL, 0.6 mol) was put into a mixture of the solid (68.9 g, 0.25 mol) and acetic acid (700 ml) in a one-neck round bottom flask, and the resulting mixture was stirred at 100° C. for 12 hours. The solution cooled to room temperature was washed with acetic acid and hexane and filtered to obtain ivory solid B-1 (27.3 g, 42%).

Preparation of Compound B-2

An o-DCB (20 ml) mixture of Compound B-1 (2.1 g, 0.0082 mol), iodobenzene (2.5 g, 0.013 mol), Cu (0.312 g, 0.0049 mol), 18-crown-6-ether (0.433 g, 0.0016 mol), and $K_2CO_3$ (3.397 g, 0.0246 mol) was refluxed and stirred in a two-neck round bottom flask under nitrogen for 12 hours. The solution cooled to room temperature was extracted with $MC/H_2O$ and concentrated, and separated with column chromatography ($SiO_2$, Hexane:Ethyl acetate=10:1) to obtain white solid Compound B-2 (1.76 g, 64%).

Preparation of Compound 120

An o-DCB (200 ml) mixture of Compound 77-2 (9 g, 15.72 mmol), Compound B-2 (5.22 g, 15.72 mmol), Cu (1 g, 15.72 mol), 18-crown-6-ether (511 mg, 1.57 mmol), and $K_2CO_3$ (4.43 g, 31.44 mmol) was refluxed and stirred in a one-neck round bottom flask under nitrogen for 24 hours. o-DCB was distilled under vacuum and removed, and then the resulting product was separated with column chromatography ($SiO_2$, Hexane:MC=1:2) to obtain solid Compound 120 (7.4 g, 58%).

PREPARATION EXAMPLE 13

Preparation of Compound 146

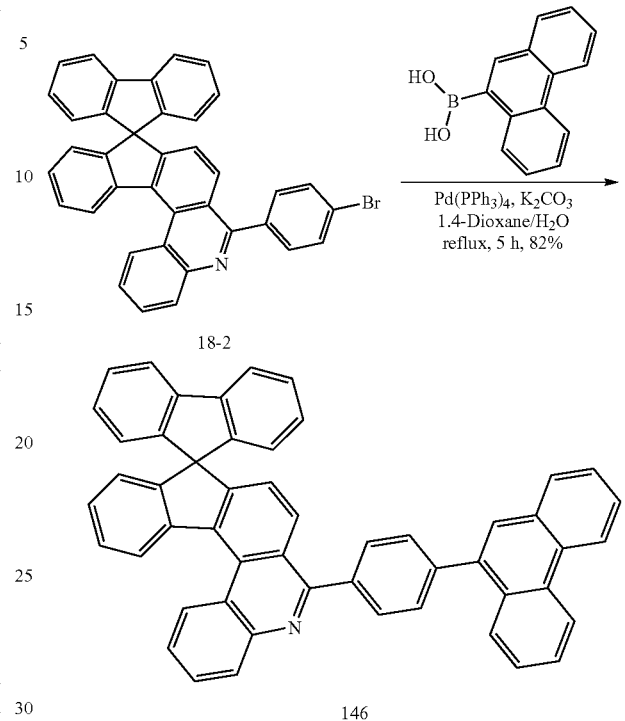

Preparation of Compound 146

A 1,4-dioxane/$H_2O$ (150 ml/30 ml) mixed solution of Compound 18-2 (8 g, 13.97 mmol), phenanthrenyl-9-boronic acid (3.1 g, 13.97 mmol), $K_2CO_3$ (3.86 g, 27.34 mmol), and $Pd(PPh_3)_4$ (1.6 g, 1.39 mmol) was refluxed and stirred in a two-neck round bottom flask under nitrogen for 5 hours. The reaction mixture cooled to room temperature was extracted with $MC/H_2O$ and dried over $MgSO_4$, and then filtered. The mixture was concentrated, and then separated with column chromatography ($SiO_2$, Hexane:MC=1:1) to obtain solid Compound 146 (7.7 g, 82%).

PREPARATION EXAMPLE 14

Preparation of Compound 159

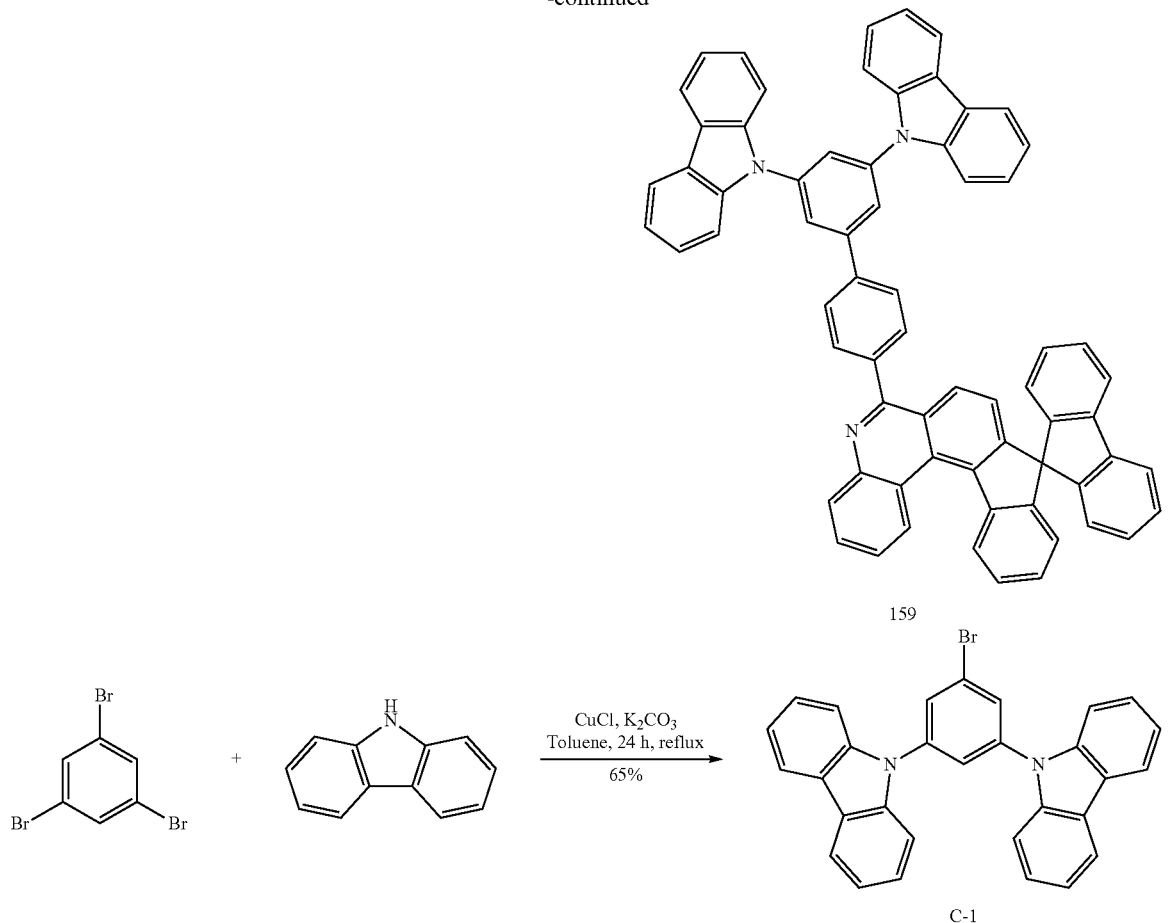

159

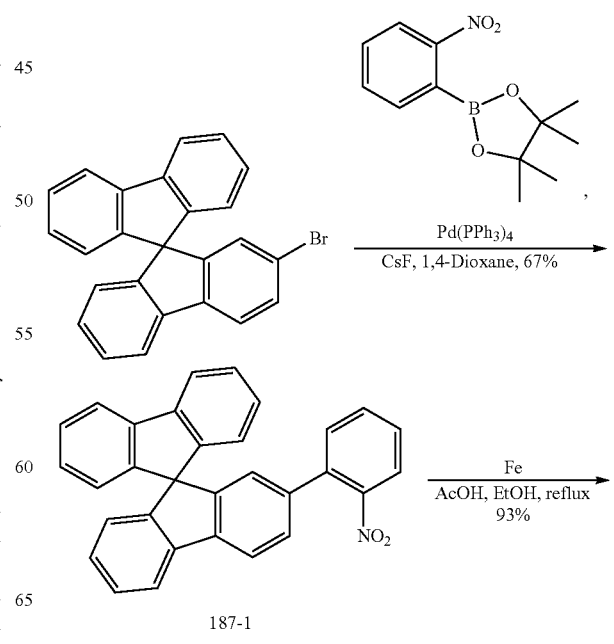

C-1

Preparation of Compound C-1

A toluene (400 ml) mixture of 1,3,5-tribromo benzene (10.0 g, 0.031 mol), 9H-carbazole (10.37 g, 0.062 mol), CuCl (0.3 g, 3.1 mmol), and $K_2CO_3$ (8.56 g, 0.062 mol) was refluxed and stirred in a two-neck round bottom flask under nitrogen for 24 hours. The reaction mixture cooled to room temperature was extracted with $MC/H_2O$ and dried over $MgSO_4$, and then filtered. The reaction mixture was concentrated, and then separated with column chromatography ($SiO_2$, Hexane:MC=1:1) to obtain white solid Compound C-1 (9.75 g, 65%).

Preparation of Compound 159

A 1,4-dioxane/$H_2O$ (150 ml/30 ml) mixed solution of Compound 41-1 (8.6 g, 13.88 mmol), Compound C-1 (6.8 g, 13.88 mmol), $K_2CO_3$ (3.86 g, 27.34 mmol), and $Pd(PPh_3)_4$ (1.6 g, 1.39 mmol) was refluxed and stirred in a two-neck round bottom flask under nitrogen for 12 hours. The reaction mixture cooled to room temperature was extracted with $MC/H_2O$ and dried over $MgSO_4$, and then filtered. The reaction mixture was concentrated, and then separated with column chromatography ($SiO_2$, Hexane:MC=1:3) to obtain solid Compound 159 (8.9 g, 71%).

PREPARATION EXAMPLE 15

Preparation of Compound 187

187-1

-continued

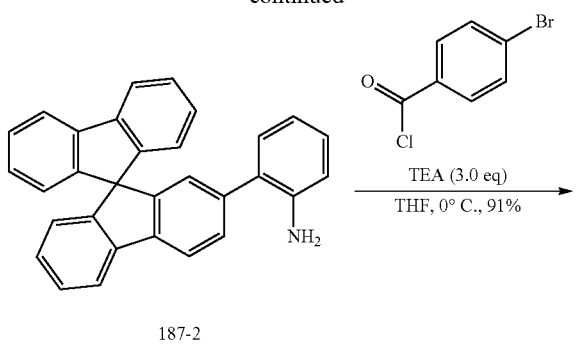

187-2

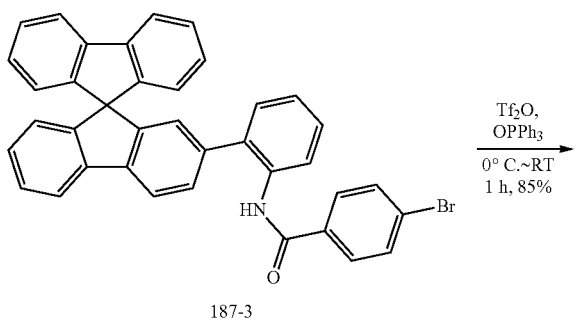

187-3

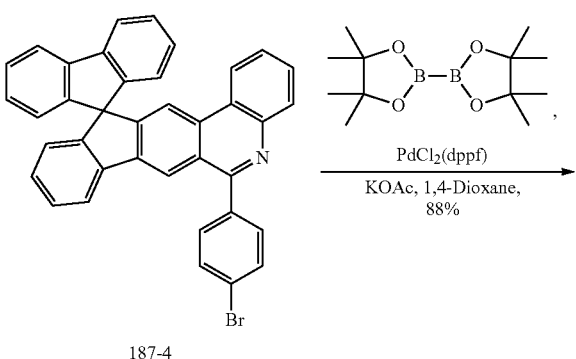

187-4

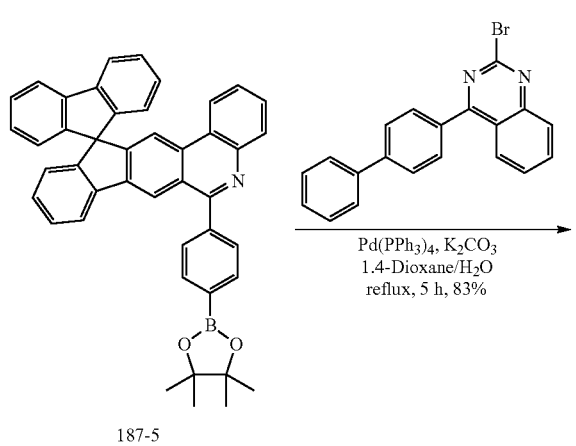

187-5

-continued

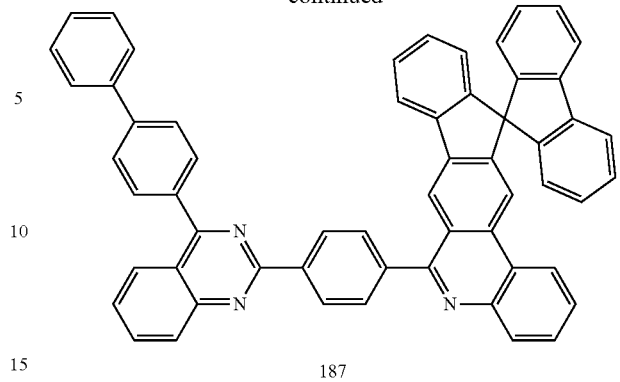

187

Preparation of Compound 187-1

In a one-neck round bottom flask, a 1,4-dioxane (700 ml) mixture of 2-bromo-9,9'-spirobi[fluorene] (40 g, 101.2 mmol), 4,4,5,5-tetramethyl-2-(2-nitrophenyl)-1,3,2-dioxaborolane (25.2 g, 101.2 mmol), Pd(PPh$_3$)$_4$ (11.6 g, 10.12 mmol), and CsF (30.7 g, 202.4 mmol) was refluxed at 110° C. for 1 hour. The mixture was extracted with MC, and then the organic layer was dried over MgSO$_4$. The organic layer was concentrated, and then separated with column chromatography (SiO$_2$, Hexane:MC=3:1) to obtain Compound 187-1 (30 g, 67%).

Preparation of Compound 187-2

Fe (19.1 g, 342.85 mmol) was added to a mixture of Compound 187-1 (30 g, 68.57 mmol) and ethanol (EtOH) (900 ml) in a one-neck round bottom flask under nitrogen, and then the resulting mixture was stirred for 10 minutes. Acetic acid (AcOH) (90 ml) was added thereto, and then the resulting mixture was refluxed at 80° C. for 12 hours. NaHCO$_3$ was added thereto at 0° C. to neutralize the mixture, and then the organic layer extracted with EA was dried over MgSO$_4$. The organic layer was concentrated, and then separated with column chromatography (SiO$_2$, Hexane: MC=1:1) to obtain Compound 187-2 (26 g, 93%).

Preparation of Compound 187-3

Triethyl amine (26 ml, 191.4 mmol) was added to a mixture of Compound 187-2 (26 g, 63.8 mmol) and THF (450 ml) in a one-neck round bottom flask under nitrogen, and then the resulting mixture was stirred for 10 minutes. A mixture of 4-bromobenzoyl chloride (21 g, 95.7 mmol) and THF (40 ml) was added thereto at 0° C., and then the resulting mixture was stirred for 3 hours. The mixture was extracted with MC, and then the organic layer was dried over MgSO$_4$. The organic layer was concentrated, and then adsorbed and separated with column chromatography (SiO$_2$, Hexane:MC=1:2) to obtain solid Compound 187-3 (34.3 g, 91%).

Preparation of Compound 187-4

Tf$_2$O (14.2 ml, 87 mmol) was added to an MC (200 ml) mixture of OPPh$_3$ (53.26 g, 191.4 mmol) in a one-neck round bottom flask under nitrogen, and then the resulting mixture was stirred for 30 minutes. An MC (180 ml) mixture of Compound 187-3 (34.3 g, 58 mmol) was added thereto at 0° C., and then the resulting mixture was slowly warmed to normal temperature, and stirred for 1 hour. From the reactant, the reaction was terminated with a saturated aqueous NaHCO₃ solution at 0° C., and then the organic layer extracted with MC was dried over MgSO₄. After being concentrated, the organic layer was adsorbed with MC, and then separated with column chromatography (SiO₂, Hexane:MC=1:1) to obtain solid Compound 187-4 (28.2 g, 85%).

Preparation of Compound 187-5

A 1,4-dioxane (250 ml) mixture of Compound 187-4 (21 g, 45.81 mmol), pinacol diboron (23.26 g, 91.62 mmol), PdCl₂(dppf) (1.67 g, 2.29 mmol), and KOAc (13.4 g, 137.43 mmol) was refluxed at 120° C. in a one-neck round bottom flask under nitrogen for 5 hours. The mixture was extracted with MC, and then the organic layer was dried over MgSO₄. After concentration, an MC/methanol precipitate was collected from the solid material, and again dissolved in MC, silica gel was added thereto, and the resulting mixture was stirred and then silica gel-filtered to obtain yellow solid Material 187-5 (20.4 g, 88%).

Preparation of Compound 187

A 1,4-dioxane/H₂O (150 ml/30 ml) mixed solution of Compound 187-5 (8 g, 13.97 mmol), 4-([1,1'-biphenyl]-4-yl)-2-bromoquinazoline (4.38 g, 13.97 mmol), K₂CO₃ (5.04 g, 27.34 mmol), and Pd(PPh₃)₄ (1.6 g, 1.39 mmol) was refluxed and stirred in a two-neck round bottom flask under nitrogen for 5 hours. The reactant at 110° C. was hot-filtered, washed with H₂O and methanol, and then dried to obtain Compound 187 (9 g, 83%).

PREPARATION EXAMPLE 16

Preparation of Compound 233

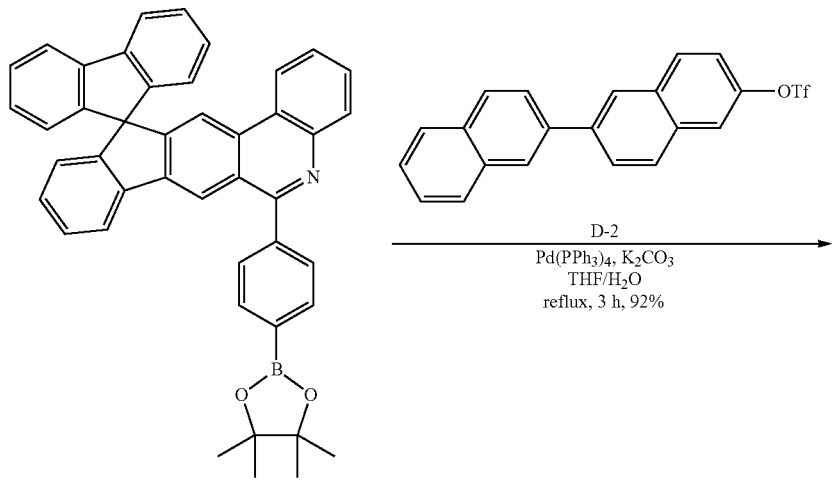

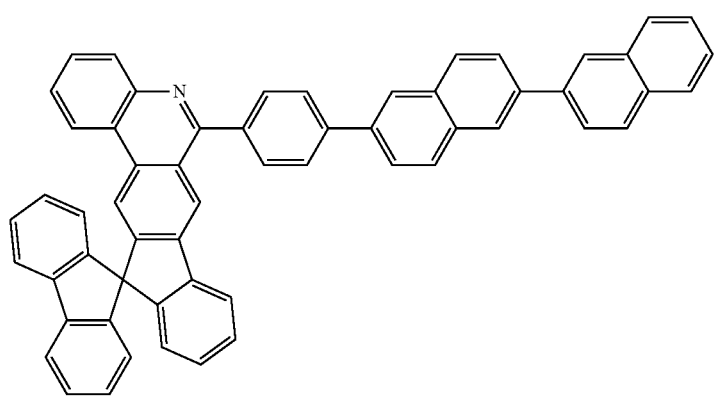

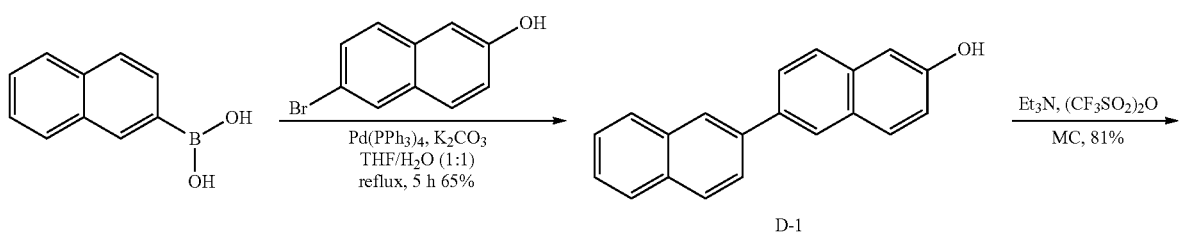

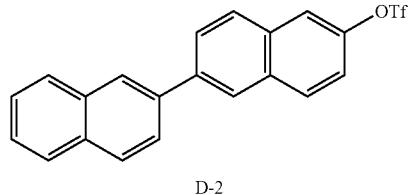

D-2

Preparation of Compound D-1

A THF/H$_2$O (100 ml/100 ml) mixed solution of naphthalen-2-ylboronic acid (10 g, 58.1 mmol), 6-bromonaphthalen-2-ol (10.8 g, 48.4 mmol), K$_2$CO$_3$ (16 g, 116.2 mmol), and Pd(PPh$_3$)$_4$ (1.12 g, 2 mol %) was refluxed and stirred in a one-neck round bottom flask under nitrogen for 5 hours. The mixed solution was cooled to normal temperature, the aqueous layer was removed, and the resulting solution was dried over MgSO$_4$. A precipitate was collected from the concentrate with Hex/MC, and then hot-filtered with hexane to obtain filtered Compound D-1 (8.5 g, 65%).

Preparation of Compound D-2

After Compound D-1 (7.2 g, 26.7 mmol) was dissolved in MC in a one-neck round bottom flask under nitrogen, Et$_3$N (7.47 ml, 53.6 mmol) was added dropwise thereto, and then the resulting mixture was stirred for 10 minutes. (CF$_3$SO$_2$)$_2$O (6.76 ml, 40.2 mmol) was slowly added thereto at 0° C., and then the resulting mixture was stirred at room temperature for 1 hour. The reaction was terminated with a saturated NaHCO$_3$ solution, the aqueous layer was removed, and then the resulting solution was dried over MgSO$_4$. The concentrate was recrystallized with hexane to obtain Compound D-2 (8.69 g, 81%).

Preparation of Compound 233

A THF/H$_2$O (150 ml/30 ml) mixed solution of Compound 187-5 (8 g, 12.91 mmol), Compound D-2 (5.19 g, 12.91 mmol), K$_2$CO$_3$ (3.56 g, 25.82 mmol), and Pd(PPh$_3$)$_4$ (1.49 g, 1.91 mmol) was refluxed and stirred in a two-neck round bottom flask under nitrogen for 6 hours. The reactant at 110° C. was hot-filtered, washed with H$_2$O and methanol, and then dried to obtain Compound 233 (8.9 g, 92%).

PREPARATION EXAMPLE 17

Preparation of Compound 237

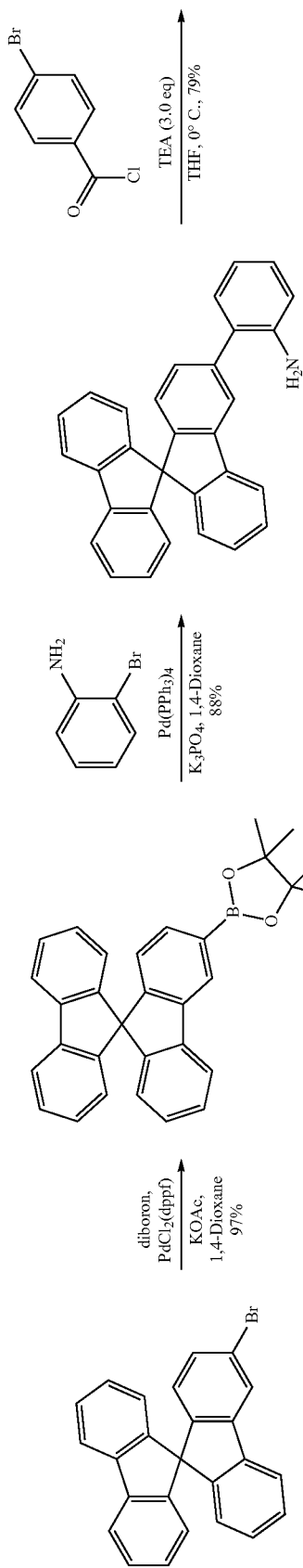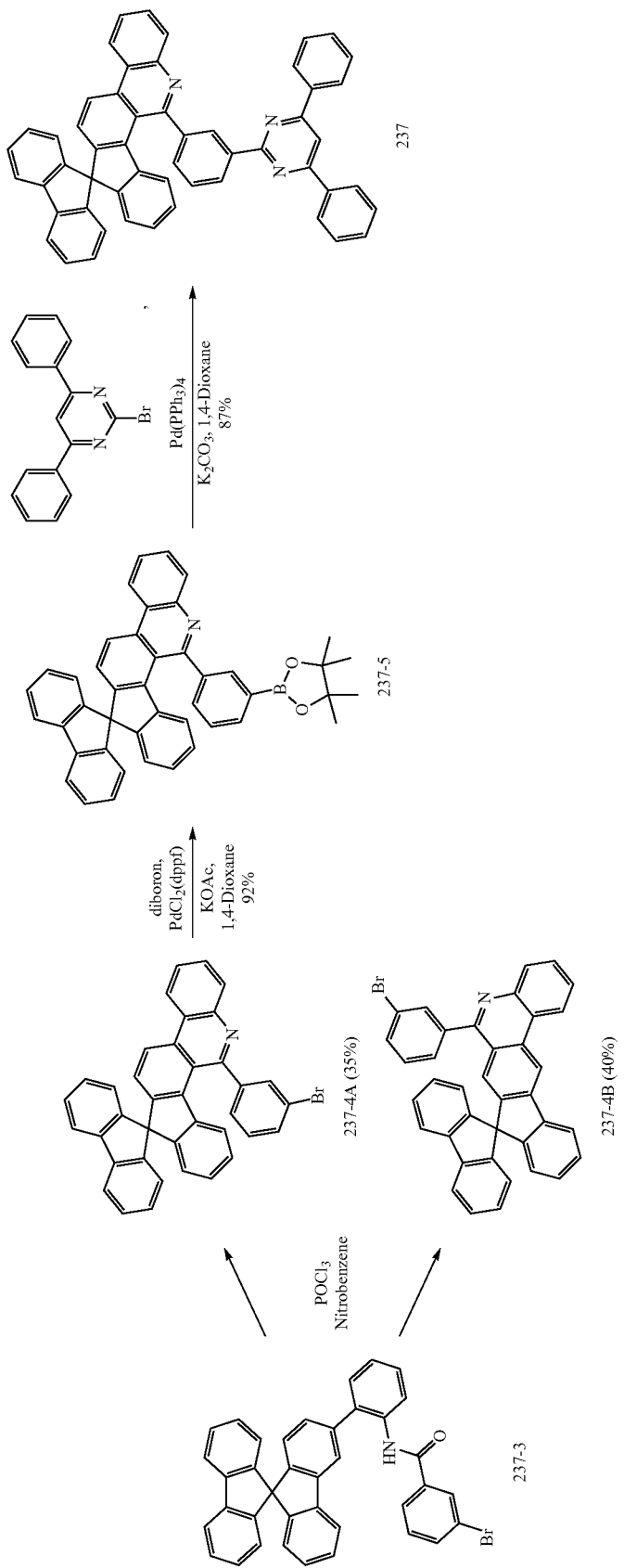

Preparation of Compound 237-1

A mixture of 3-bromo-9,9'-spirobi[fluorene] (50 g, 126.48 mmol), pinacol diboron (64.2 g, 252.97 mmol), PdCl$_2$(dppf) (4.62 g, 6.32 mmol), KOAc (37.2 g, 379.4 mmol), and 1,4-dioxane (700 ml) was refluxed at 120° C. in a one-neck round bottom flask under nitrogen for 4 hours. The mixture was extracted with MC, and then the organic layer was dried over MgSO$_4$. After being concentrated, the organic layer was dissolved in MC, and the resulting solution was filtered with silica gel and separated with column chromatography (SiO$_2$, Hexane:MC=3:1) to obtain Compound 273-1 (54.5 g, 97%)

Preparation of Compound 237-2

A mixture of Compound 237-1 (54.5 g, 123.2 mmol), 2-bromoaniline (21.2 g, 123.2 mmol), Pd(PPh$_3$)$_4$ (7.1 g, 6.16 mmol), and K$_3$PO$_4$ (78.4 g, 369.6 mmol), and 1,4-dioxane (800 ml)/H$_2$O (200 ml) was refluxed at 110° C. in a one-neck round bottom flask for 12 hours. The mixture was extracted with MC, and then the organic layer was dried over MgSO$_4$. The organic layer was concentrated, and then filtered with silica gel and separated with column chromatography (SiO$_2$, Hexane:MC=1:1) to obtain Compound 237-2 (44.69 g, 88%).

Preparation of Compound 237-3

Triethyl amine (45.6 ml, 328.98 mmol) was added to a mixture of Compound 237-2 (44.69 g, 109.66 mmol) and THF (500 ml) in a one-neck round bottom flask under nitrogen, and then the resulting mixture was stirred for 10 minutes. A THF (50 ml) mixture of 4-bromobenzoyl chloride (36 g, 164.49 mmol) was added thereto at 0° C., and then the resulting mixture was stirred for 3 hours. The mixture was extracted with MC, and then the organic layer was dried over MgSO$_4$. The organic layer was concentrated, and then adsorbed and separated with column chromatography (SiO$_2$, Hexane:MC=1:3) to obtain solid Compound 237-3 (51.52 g, 79%).

Preparation of Compound 237-4 (A, B)

POCl$_3$ (4 ml, 43.62 mmol) was added to a nitrobenzene (700 ml) mixture of Compound 273-3 (51.52 g, 87.24 mmol) in a one-neck round bottom flask under nitrogen, and then the resulting mixture was stirred at 150° C. for 4 hours. From the reactant, the reaction was terminated with a saturated aqueous NaHCO$_3$ solution at 0° C., and then the organic layer extracted with MC was dried over MgSO$_4$. The organic layer was concentrated, and then separated with column chromatography (SiO$_2$, Hexane:MC=3:1) to obtain solid Compounds 237-4A and 237-4B. Compound 237-4A (17.5 g, 35%) and Compound 237-4B (20 g, 40%)

Preparation of Compound 237-5

A mixture of Compound 237-4(A) (27 g, 47.16 mmol), pinacol diboron (23.95 g, 94.32 mmol), PdCl$_2$(dppf) (1.72 g, 2.35 mmol), KOAc (13.88 g, 141.48 mmol), and 1,4-dioxane (300 ml) was refluxed at 120° C. in a one-neck round bottom flask under nitrogen for 5 hours. The mixture was extracted with MC, and then the organic layer was dried over MgSO$_4$. The mixture was concentrated, and then separated with column chromatography (SiO$_2$, Hexane:MC=5:1) to obtain solid Compound 237-5 (27 g, 92%).

Preparation of Compound 237

A mixture of Compound 237-5 (8 g, 12.91 mmol), 2-bromo-4,6-diphenylpyrimidine (4.82 g, 15.49 mmol), Pd(PPh$_3$)$_4$ (1.49 g, 1.29 mmol), K$_2$CO$_3$ (3.56 g, 25.82 mmol), and 1,4-dioxane (150 ml)/H$_2$O (30 ml) was stirred at 120° C. in a one-neck round bottom flask for 4 hours. The reactant was filtered at 110° C., and then washed with 1,4-dioxane at 110° C. and with methanol to obtain Compound 237 (4.8 g) in the form of cotton wool, and the filtrate was separated with column chromatography (SiO$_2$, Hexane: MC=3:1) to obtain powdery Compound 237 (8.2 g, 87%).

PREPARATION EXAMPLE 18

Preparation of Compound 239

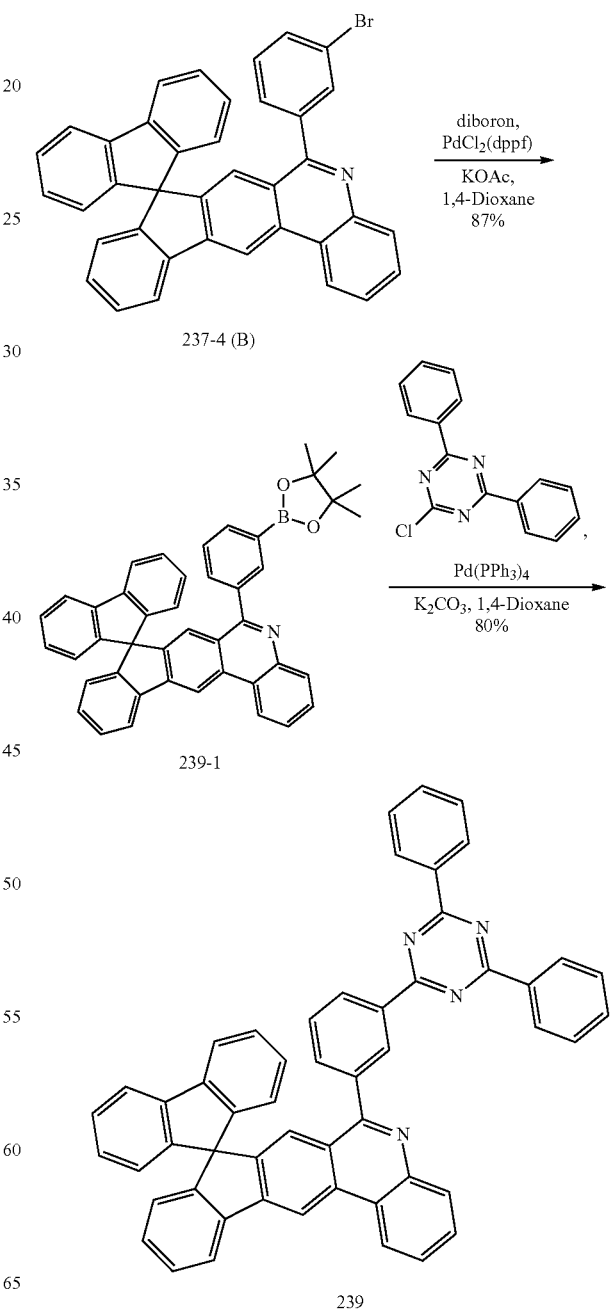

Preparation of Compound 239-1

A mixture of Compound 237-4(B) (27 g, 47.16 mmol), pinacol diboron (23.95 g, 94.32 mmol), PdCl$_2$(dppf) (1.72 g, 2.35 mmol), KOAc (13.88 g, 141.48 mmol), and 1,4-dioxane (250 ml) was refluxed at 120° C. in a one-neck round bottom flask under nitrogen for 5 hours. The mixture was extracted with MC, and then the organic layer was dried over MgSO$_4$. The organic layer was concentrated, and then separated with column chromatography (SiO$_2$, Hexane:MC=6:1) to obtain solid Compound 239-1 (25.5 g, 87%).

Preparation of Compound 239

A mixture of Compound 239-1 (9 g, 14.52 mmol), 2-chloro-4,6-diphenyl-1,3,5-triazine (4.27 g, 15.97 mmol), Pd(PPh$_3$)$_4$ (1.67 g, 1.45 mmol), K$_2$CO$_3$ (4 g, 27.4 mmol), and 1,4-dioxane (150 ml)/H$_2$O (30 ml) was stirred at 120° C. in a one-neck round bottom flask for 4 hours. The reactant at 120° C. was filtered, and then washed with 1,4-dioxane at 110° C. and with methanol to obtain Compound 239 (8.4 g, 80%)

PREPARATION EXAMPLE 19

Preparation of Compound 242

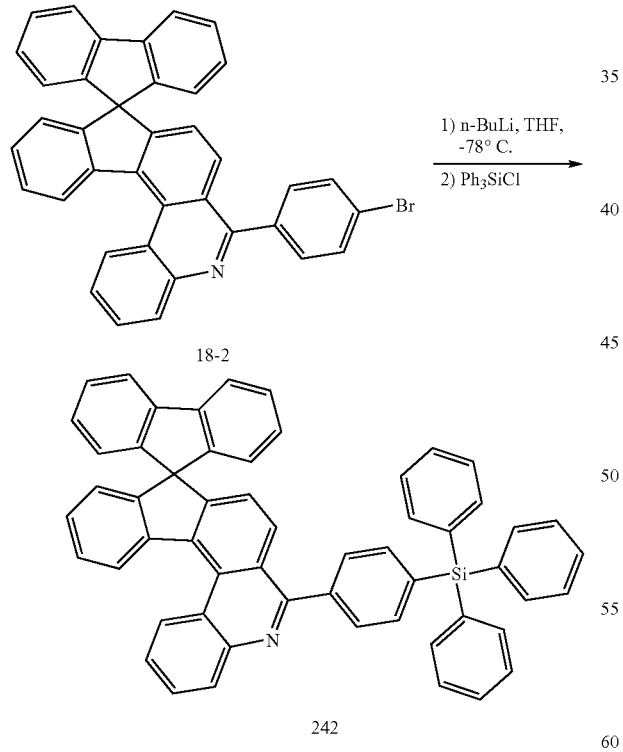

Preparation of Compound 242

0.83 mL (2.1 mmol) of 2.5 M n-BuLi was added dropwise to a mixed solution containing 1 g (1.7 mmol) of Compound 18-2 and 20 mL of THF at −78° C., and the resulting mixture was stirred for 30 minutes. 507 mg (1.7 mmol) of chlorotriphenylsilane was added dropwise to the reaction mixture, and the resulting mixture was stirred at room temperature for 2 hours. After the reaction was completed, distilled water and MC were added thereto at room temperature and the mixture was extracted, the organic layer was dried over MgSO$_4$, and then the solvent was removed by a rotary evaporator. The reactant was purified with column chromatography (MC:Hex=1:3), and recrystallized with methanol to obtain target Compound 242 (942 mg, 72%).

PREPARATION EXAMPLE 20

Preparation of Compound 245

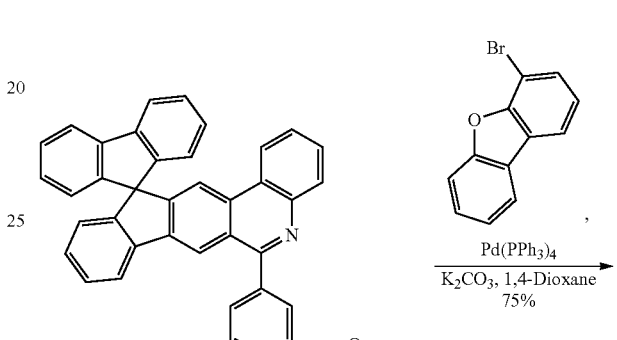

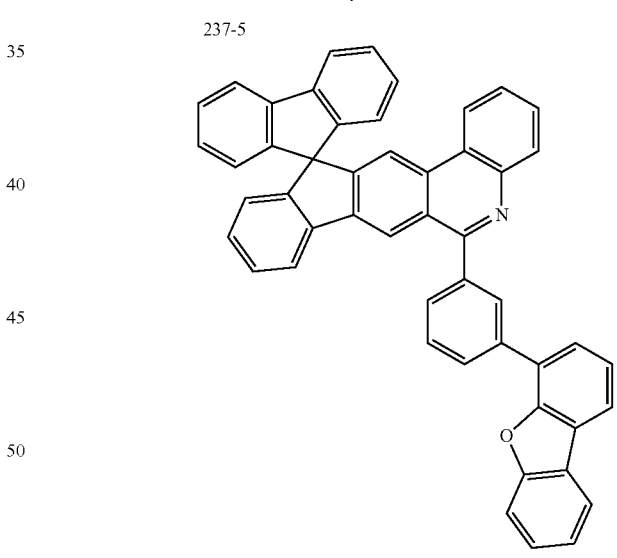

Preparation of Compound 245

A mixture of Compound 237-5 (9 g, 14.52 mmol), 4-bromodibenzo[b,d]furan (3.5 g, 14.52 mmol), Pd(PPh$_3$)$_4$ (1.67 g, 1.45 mmol), K$_2$CO$_3$ (4 g, 27.04 mmol), and 1,4-dioxane (150 ml)/H$_2$O (30 ml) was stirred at 120° C. in a one-neck round bottom flask for 4 hours. The reactant at 120° C. was filtered, and then washed with 1,4-dioxane at 110° C. and with methanol to obtain Compound 245 (7.2 g, 75%).

PREPARATION EXAMPLE 21

Preparation of Compound 248

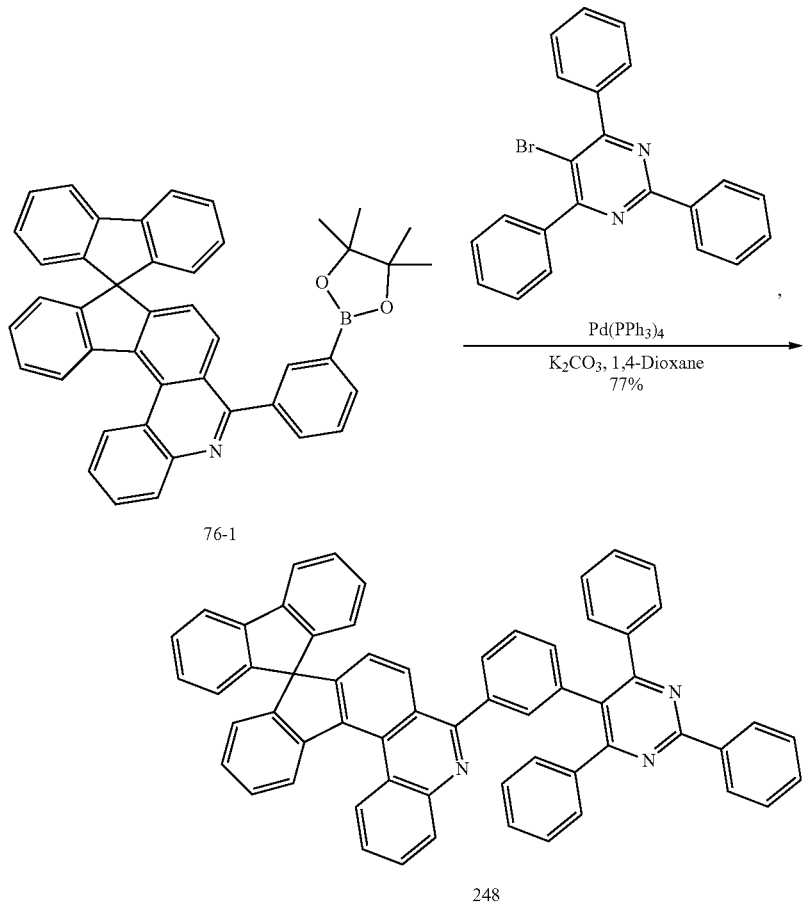

Preparation of Compound 248

A mixture of Compound 76-1 (10 g, 16.14 mmol), 5-bromo-2,4,6-triphenylpyrimidine (7.4 g, 19.36 mmol), Pd(PPh$_3$)$_4$ (1.86 g, 1.614 mmol), and K$_2$CO$_3$ (4.46 g, 32.28 mmol), and 1,4-dioxane (150 ml)/H$_2$O (30 ml) was stirred at 120° C. in a one-neck round bottom flask for 4 hours. The mixture was extracted with MC, and then the organic layer was dried over MgSO$_4$. The organic layer was concentrated, and then separated with column chromatography (SiO$_2$, hexane:MC=1:3) to obtain solid Compound 248 (10 g, 77%).

PREPARATION EXAMPLE 22

Preparation of Compound 255

A preparation was performed in the same manner as in the preparation of Compound 28 in Preparation Example 3, except that the compound 9,9'-spirobi[fluoren]-5-ylboronic acid was used instead of (4-(1-phenyl-1H-benzo[d]imidazol-2-yl)phenyl)boronic acid, thereby obtaining Target Compound 255 (10.1 g, 71%).

PREPARATION EXAMPLE 23

Preparation of Compound 263

A preparation was performed in the same manner as in the preparation of Compound 76 in Preparation Example 8, except that the compound 4-bromo-9,9'-spirobi[fluorene] was used instead of 2-(4-bromophenyl)benzo[d]thiazole, thereby obtaining Target Compound 263 (9.8 g, 75%)

PREPARATION EXAMPLE 24

Preparation of Compound 266

A preparation was performed in the same manner as in the preparation of Compound 187 in Preparation Example 15, except that the compound 1-(4-bromophenyl)-2-ethyl-1H-benzo[d]imidazole was used instead of 4-([1,1'-biphenyl]-4-yl)-2-bromoquinazoline, thereby obtaining Target Compound 266 (8.4 g, 73%)

PREPARATION EXAMPLE 25

Preparation of Compound 267

A preparation was performed in the same manner as in the preparation of Compound 187 in Preparation Example 15, except that the compound 4-([1,1'-biphenyl]-4-yl)-6-chloro-2-phenylpyrimidine was used instead of 4-([1,1'-biphenyl]-4-yl)-2-bromoquinazoline, thereby obtaining Target Compound 267 (9.2 g, 71%)

PREPARATION EXAMPLE 26

Preparation of Compound 268

A preparation was performed in the same manner as in the preparation of Compound 187 in Preparation Example 15, except that the compound 2-([1,1'-biphenyl]-4-yl)-4-chloro-6-phenyl-1,3,5-triazine was used instead of 4-([1,1'-biphenyl]-4-yl)-2-bromoquinazoline, thereby obtaining Target Compound 268 (9.4 g, 72%).

PREPARATION EXAMPLE 27

Preparation of Compound 274

A preparation was performed in the same manner as in the preparation of Compound 266 in Preparation Example 24, except that the compound 3-bromobenzoyl chloride was used instead of 4-bromobenzoyl chloride, thereby obtaining Target Compound 274 (8.9 g, 77%).

PREPARATION EXAMPLE 28

Preparation of Compound 275

A preparation was performed in the same manner as in the preparation of Compound 267 in Preparation Example 25, except that the compound 3-bromobenzoyl chloride was used instead of 4-bromobenzoyl chloride, thereby obtaining Target Compound 275 (9.0 g, 69%).

PREPARATION EXAMPLE 29

Preparation of Compound 276

A preparation was performed in the same manner as in the preparation of Compound 268 in Preparation Example 26, except that the compound 3-bromobenzoyl chloride was used instead of 4-bromobenzoyl chloride, thereby obtaining Target Compound 276 (9.4 g, 77%).

PREPARATION EXAMPLE 30

Preparation of Compound 278

A preparation was performed in the same manner as in the preparation of Compound 226 in Preparation Example 24, except that the compound 9-([1,1'-biphenyl]-4-yl)-10-bromoanthracene was used instead of 1-(4-bromophenyl)-2-ethyl-1H-benzo[d]imidazole, thereby obtaining Target Compound 278 (10.4 g, 78%).

PREPARATION EXAMPLE 31

Preparation of Compound 283

A preparation was performed in the same manner as in the preparation of Compound 237 in Preparation Example 17, except that the compounds 3-bromobenzoyl chloride and 2-(4-bromophenyl)-1-phenyl-1H-benzo[d]imidazole were used instead of 4-bromobenzoyl chloride and 2-bromo-4,6-diphenylpyrimidine, thereby obtaining Target Compound 283 (8.9 g, 72%).

PREPARATION EXAMPLE 32

Preparation of Compound 287

A preparation was performed in the same manner as in the preparation of Compound 287 in Preparation Example 31, except that the compound 4-([1,1'-biphenyl]-4-yl)-6-chloro-2-phenylpyrimidine was used instead of 2-(4-bromophenyl)-1-phenyl-1H-benzo[d]imidazole, thereby obtaining Target Compound 287 (9.7 g, 75%).

PREPARATION EXAMPLE 33

Preparation of Compound 290

A preparation was performed in the same manner as in the preparation of Compound 287 in Preparation Example 31, except that the compound 2-bromo-9,10-di(naphthalen-2-yl)anthracene was used instead of 2-(4-bromophenyl)-1-phenyl-1H-benzo[d]imidazole, thereby obtaining Target Compound 290 (10.1 g, 69%).

PREPARATION EXAMPLE 34

Preparation of Compound 296

A preparation was performed in the same manner as in the preparation of Compound 237 in Preparation Example 17, except that the compound 1-(4-bromophenyl)-2-phenyl-1H-benzo[d]imidazole was used instead of 2-bromo-4,6-diphenylpyrimidine, thereby obtaining Target Compound 296 (10.6 g, 86%).

PREPARATION EXAMPLE 35

Preparation of Compound 298

A preparation was performed in the same manner as in the preparation of Compound 101 in Preparation Example 11, except that Compound 237-4A and 9H-carbazole were used instead of Compounds 77-2 and A-2, thereby obtaining Target Compound 298 (7.3 g, 68%).

PREPARATION EXAMPLE 36

Preparation of Compound 304

A preparation was performed in the same manner as in the preparation of Compound 18 in Preparation Example 2, except that Compound 237-4A was used instead of Compound 18-2, thereby obtaining Target Compound 304 (7.6 g, 62%).

PREPARATION EXAMPLE 37

Preparation of Compound 292

A preparation was performed in the same manner as in the preparation of Compound 304 in Preparation Example 36, except that the compound 4-bromobenzoyl chloride was used instead of 3-bromobenzoyl chloride, thereby obtaining Target Compound 292 (5.9 g, 48%).

PREPARATION EXAMPLE 38

Preparation of Compound 307

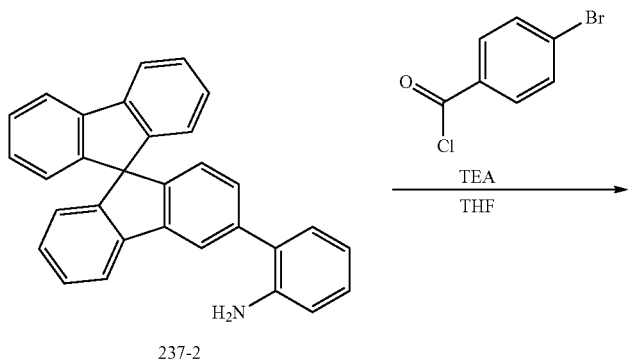

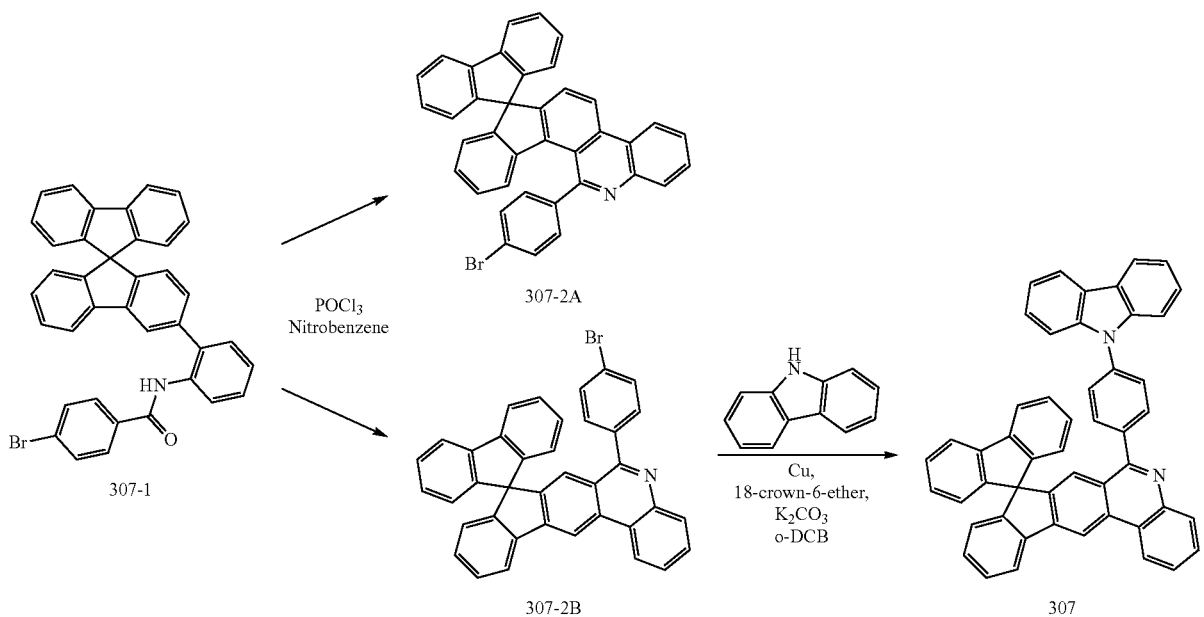

Preparation of Compound 307-1

A preparation was performed in the same manner as in the preparation of Compound 237-3 in Preparation Example 17, except that the compound 4-bromobenzoyl chloride was used instead of 3-bromobenzoyl chloride, thereby obtaining Target Compound 307-1 (48.3 g, 74%).

Preparation of Compound 307-2B

A preparation was performed in the same manner as in the preparation of Compound 237-4(B) in Preparation Example 17, except that Compound 307-1 was used instead of Compound 237-3, thereby obtaining Target Compound 307-2B (18 g, 36%).

Preparation of Compound 307

A preparation was performed in the same manner as in the preparation of Compound 101 in Preparation Example 11, except that Compound 307-2B and 9H-carbazole were used instead of Compounds 77-2 and A-2, thereby obtaining Target Compound 307 (8.1 g, 75%).

PREPARATION EXAMPLE 39

Preparation of Compound 305

A preparation was performed in the same manner as in the preparation of Compound 296 in Preparation Example 34, except that Compound 307-2B was used instead of Compound 237-4A, thereby obtaining Target Compound 305 (8.9 g, 73%).

PREPARATION EXAMPLE 40

Preparation of Compound 311

A preparation was performed in the same manner as in the preparation of Compound 305 in Preparation Example 39, except that the compound 2-bromo-9,10-di(naphthalen-2-yl)anthracene was used instead of 1-(4-bromophenyl)-2-phenyl-1H-benzo[d]imidazole, thereby obtaining Target Compound 311 (10.9 g, 73%).

PREPARATION EXAMPLE 41

Preparation of Compound 316

A preparation was performed in the same manner as in the preparation of Compound 298 in Preparation Example 35, except that Compound 307-4B was used instead of Compound 237-4A, thereby obtaining Target Compound 316 (7.8 g, 67%).

PREPARATION EXAMPLE 42

Preparation of Compound 322

A preparation was performed in the same manner as in the preparation of Compound 18 in Preparation Example 2, except that Compound 307-4B was used instead of Compound 18-2, thereby obtaining Target Compound 322 (6.8 g, 59%).

PREPARATION EXAMPLE 43

Preparation of Compound 323

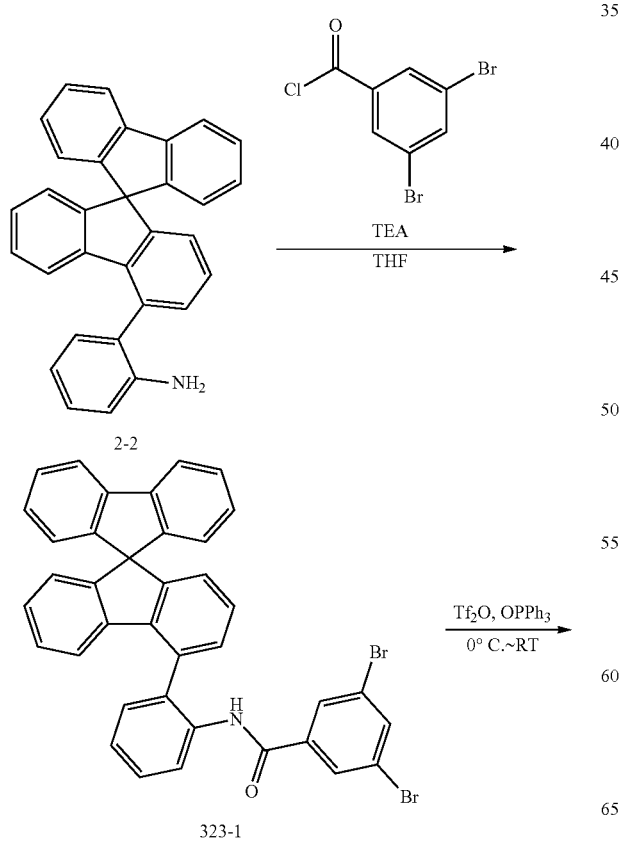

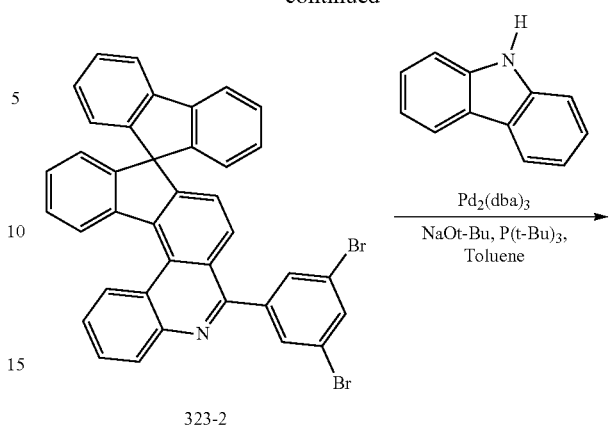

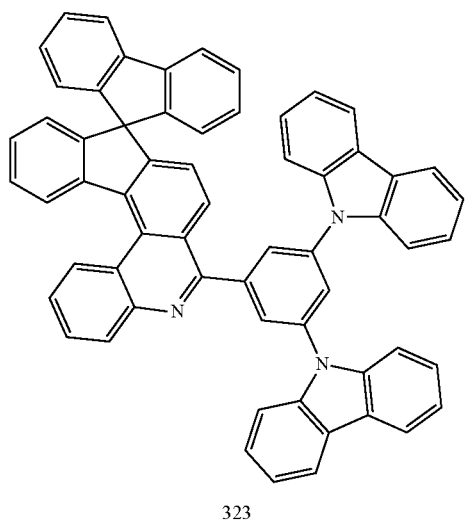 [SMILES: c1ccc2c(c1)-c1ccccc1C21c2ccccc2-c2c1ccc1c(-c3cc(-n4c5ccccc5c5ccccc54)cc(-n4c5ccccc5c5ccccc54)c3)nc3ccccc3c21]

Preparation of Compound 323-1

A preparation was performed in the same manner as in the preparation of Compound 77-2 in Preparation Example 9, except that the compound 3,5-dibromobenzoyl chloride was used instead of 3-bromobenzoyl chloride, thereby obtaining Target Compound 323-2 (43 g, 88%).

Preparation of Compound 323

A toluene (600 ml) mixed solution of Compound 323-2 (38.2 g, 58.6 mmol), 9H-carbazole (24.6 g, 147.3 mmol), Pd(dba)$_3$ (10.7 g, 11.76 mmol), NaOt-Bu (22.6 g, 235.2 mmol), and P(t-Bu)$_3$ (20 ml, 35.2 mmol) was refluxed and stirred in a two-neck round bottom flask under nitrogen for 3 hours. The reactant at 110° C. was hot-filtered, washed with H$_2$O and

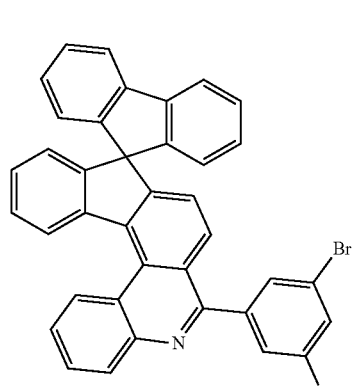
323-2
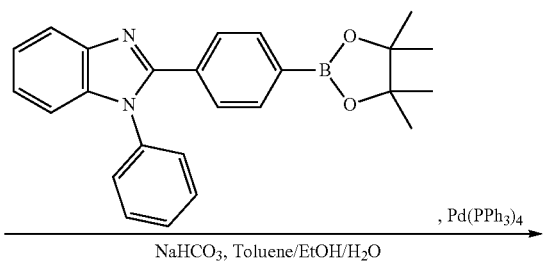
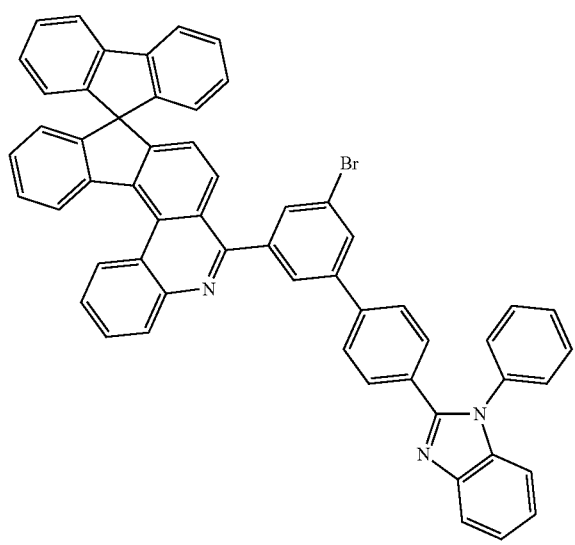
326-1
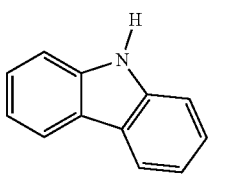
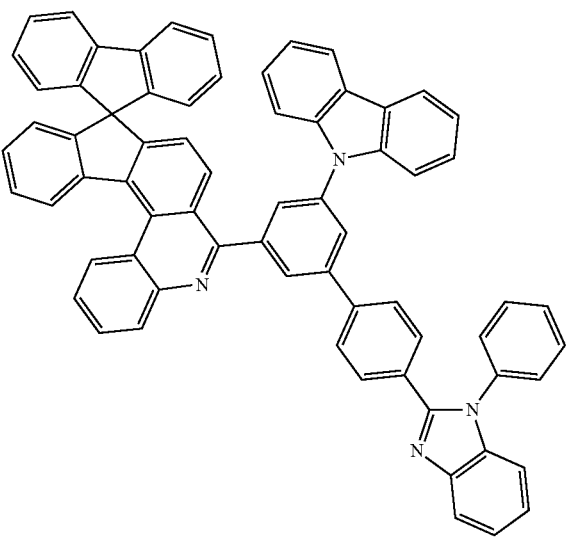
326
methanol, and then dried to obtain Compound 323 (29 g, 60%).

PREPARATION EXAMPLE 44

Preparation of Compound 326

Preparation of Compound 326-1

A toluene/EtOH/H$_2$O (600 ml/120 ml/120 ml) mixture of Compound 323-2 (54.6 g, 83.8 mmol), 1-phenyl-2-(4-(4,4,5,5-tetramethyl-1,3,2-dioxaborolan-2-yl)phenyl)-1H-benzo[d]imidazole (36.6 g, 92.3 mmol), Pd(PPh$_3$)$_4$ (9.69 g, 8.39 mmol), and NaHCO$_3$ (14.1 g, 167.9 mmol) was refluxed at 110° C. in a one-neck round bottom flask for 6 hours.

The mixture was extracted with MC, and then the organic layer was dried over MgSO$_4$. The organic layer was concentrated, and then separated with column chromatography (SiO$_2$, MC:EA=4:1) to obtain Compound 326-1 (49 g, 69%).

Preparation of Compound 326

A toluene (300 ml) mixed solution of Compound 326-1 (37.5 g, 43.6 mmol), 9H-carbazole (8.6 g, 51.92 mmol), Pd(dba)$_3$ (3.9 g, 4.32 mmol), NaOt-Bu (8.3 g, 86.4 mmol), and P(t-Bu)$_3$ (15 ml, 12.98 mmol) was refluxed and stirred in a two-neck round bottom flask under nitrogen for 5 hours. The mixture was extracted with MC, and then the organic layer was dried over MgSO$_4$. After being concentrated, the organic layer was separated with column chromatography (SiO$_2$, MC:EA=4:1), and then stirred with EA and then filtered to obtain Compound 326 (32 g, 79%).

PREPARATION EXAMPLE 45

Preparation of Compound 333

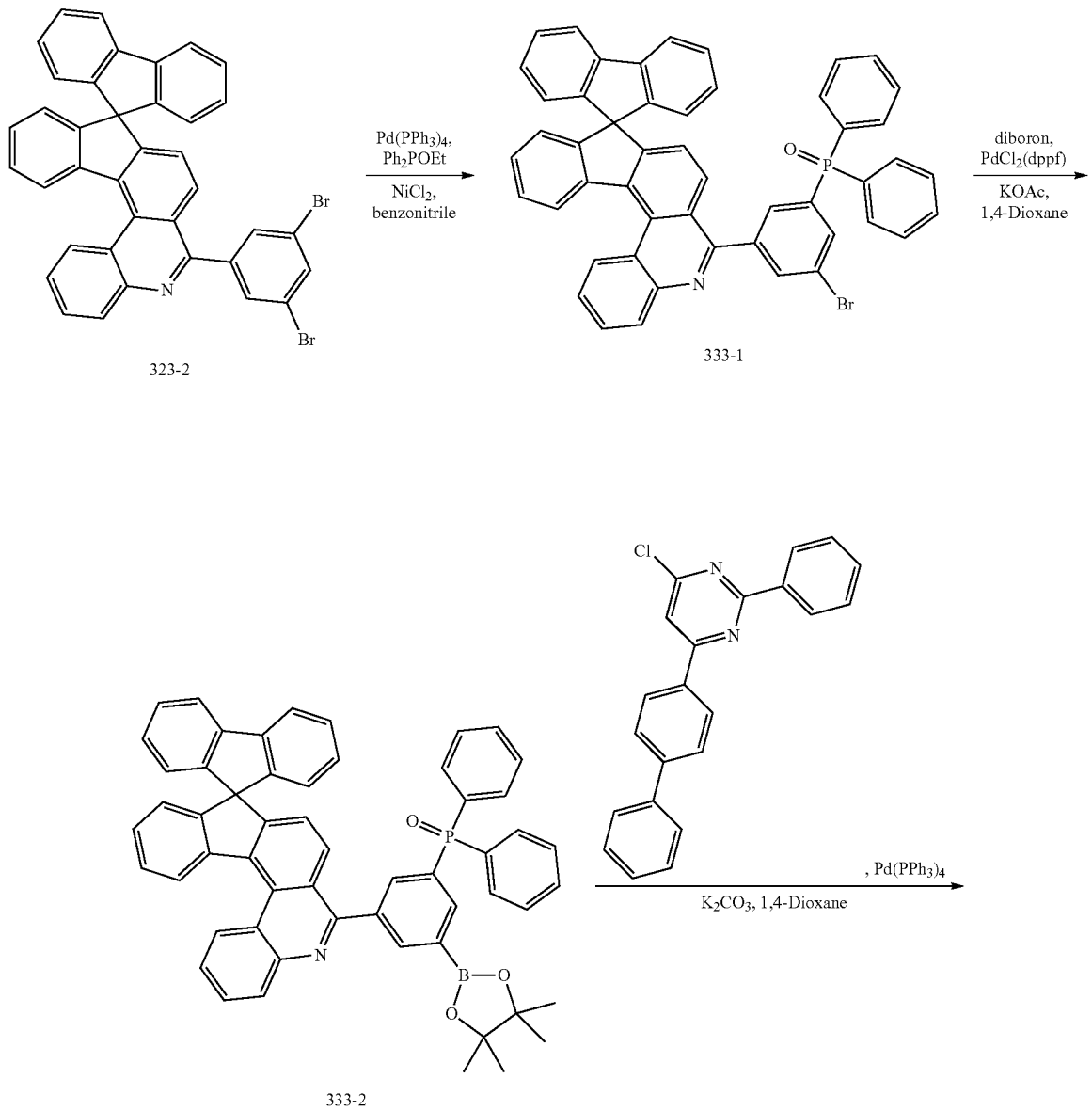

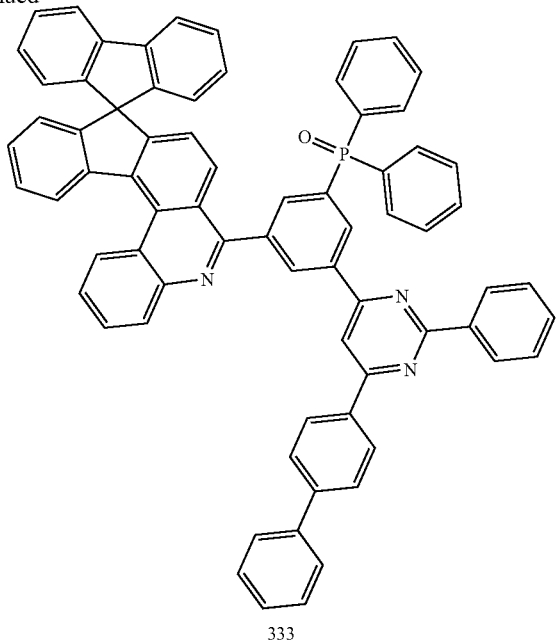

333

Preparation of Compound 333-1

A benzonitrile (1,200 ml) mixture of Compound 323-2 (83 g, 127.4 mmol) and $NiCl_2$ (9 g, 76.68 mmol) was refluxed at 180° C. in a one-neck round bottom flask for 1 hour, and then $Ph_2POEt$ (27 ml, 127.8 mmol) was added thereto at 180° C. After being stirred for 6 hours, the mixture was filtered in a hot state of 150° C., concentrated and then separated with column chromatography ($SiO_2$, MC:EA=4:1) to obtain Compound 333-1 (54 g, 54%).

Preparation of Compound 333-2

A mixture of Compound 333-1 (20 g, 25.88 mmol), pinacol diboron (13.1 g, 51.7 mmol), $PdCl_2(dppf)$ (943 mg, 1.29 mmol), KOAc (7.59 g, 77.4 mmol), and 1,4-dioxane (200 ml) was refluxed at 120° C. in a one-neck round bottom flask under nitrogen for 5 hours. The mixture was extracted with MC, and then the organic layer was dried over $MgSO_4$. The organic layer was concentrated, and then separated with column chromatography ($SiO_2$, MC:EA=2:1) to obtain solid Compound 333-2 (19 g, 90%).

Preparation of Compound 333

A mixture of Compound 333-2 (10 g, 12.2 mmol), 4-([1,1'-biphenyl]-4-yl)-6-chloro-2-phenylpyrimidine (4.6 g, 13.42 mmol), $Pd(PPh_3)_4$ (704 mg, 0.61 mmol), $K_2CO_3$ (3.37 g, 24.4 mmol), and 1,4-dioxane (200 ml)/$H_2O$ (50 ml) was stirred at 120° C. in a one-neck round bottom flask for 6 hours. The reactant was filtered at 110° C., and then washed with 1,4-dioxane at 110° C. and with methanol to obtain Compound 333 (9.3 g, 76%).

PREPARATION EXAMPLE 46

Preparation of Compound 335

A preparation was performed in the same manner as in the preparation of Compound 323 in Preparation Example 43, except that Compound 187-2 was used instead of Compound 2-2, thereby obtaining Target Compound 335 (8.9 g, 70%).

PREPARATION EXAMPLE 47

Preparation of Compound 338

A preparation was performed in the same manner as in the preparation of Compound 326 in Preparation Example 44, except that Compound 187-2 was used instead of Compound 2-2, thereby obtaining Target Compound 338 (9.2 g, 83%).

PREPARATION EXAMPLE 48

Preparation of Compound 345

A preparation was performed in the same manner as in the preparation of Compound 333 in Preparation Example 45, except that Compound 187-2 was used instead of Compound 2-2, thereby obtaining Target Compound 345 (9.1 g, 74%).

PREPARATION EXAMPLE 49

Preparation of Compound 347

A preparation was performed in the same manner as in the preparation of Compound 323 in Preparation Example 43, except that Compound 237-2 was used instead of Compound 2-2, thereby obtaining Target Compound 347 (8.9 g, 74%).

PREPARATION EXAMPLE 50

Preparation of Compound 350

A preparation was performed in the same manner as in the preparation of Compound 326 in Preparation Example 44, except that Compound 237-2 was used instead of Compound 2-2, thereby obtaining Target Compound 350 (9.8 g, 88%).

PREPARATION EXAMPLE 51

Preparation of Compound 356

A preparation was performed in the same manner as in the preparation of Compound 333 in Preparation Example 45, except that Compound 237-2 and 8-bromoquinoline were used instead of Compound 2-2 and 4-([1,1'-biphenyl]-4-yl)-6-chloro-2-phenylpyrimidine, thereby obtaining Target Compound 356 (8.6 g, 86%).

PREPARATION EXAMPLE 52

Preparation of Compound 362

A preparation was performed in the same manner as in the preparation of Compound 326 in Preparation Example 44, except that Compound 237-2 was used instead of Compound 2-2, thereby obtaining Target Compound 362 (98 g, 89%).

PREPARATION EXAMPLE 53

Preparation of Compound 370

A preparation was performed in the same manner as in the preparation of Compound 333 in Preparation Example 45, except that Compound 237-2 and 2-([1,1'-biphenyl]-4-yl)-4-chloro-6-phenyl-1,3,5-triazine were used instead of Compound 2-2 and 4-([1,1'-biphenyl]-4-yl)-6-chloro-2-phenylpyrimidine, thereby obtaining Target Compound 370 (10.3 g, 84%).

PREPARATION EXAMPLE 54

Preparation of Compound 5

A preparation was performed in the same manner as in the preparation of Compound 28 in Preparation Example 3, except that the compound [1,1'-biphenyl]-4-ylboronic acid was used instead of (4-(1-phenyl-1H-benzo[d]imidazol-2-yl)phenyl)boronic acid, thereby obtaining Target Compound 5 (8.3 g, 76%).

PREPARATION EXAMPLE 55

Preparation of Compound 15

A preparation was performed in the same manner as in the preparation of Compound 28 in Preparation Example 3, except that the compound 9,9'-spirobi[fluoren]-2-ylboronic acid was used instead of (4-(1-phenyl-1H-benzo[d]imidazol-2-yl)phenyl)boronic acid, thereby obtaining Target Compound (12.3 g, 80%).

PREPARATION EXAMPLE 56

Preparation of Compound 253

A preparation was performed in the same manner as in the preparation of Compound 28 in Preparation Example 3, except that the compound (10-phenylanthracen-9-yl)boronic acid was used instead of (4-(1-phenyl-1H-benzo[d]imidazol-2-yl)phenyl)boronic acid, thereby obtaining Target Compound 15 (7.4 g, 79%).

PREPARATION EXAMPLE 57

Preparation of Compound 261

A preparation was performed in the same manner as in the preparation of Compound 76 in Preparation Example 8, except that the compound 9-bromo-10-phenylanthracene was used instead of 2-(4-bromophenyl)benzo[d]thiazole, thereby obtaining Target Compound 261 (5.3 g, 74%).

PREPARATION EXAMPLE 58

Preparation of Compound 167

A preparation was performed in the same manner as in the preparation of Compound 187 in Preparation Example 15, except that the compound 2-bromonaphthalene was used instead of 4-([1,1'-biphenyl]-4-yl)-2-bromoquinazoline, thereby obtaining Target Compound 167 (4.3 g, 77%).

PREPARATION EXAMPLE 59

Preparation of Compound 169

A preparation was performed in the same manner as in the preparation of Compound 187 in Preparation Example 15, except that the compound 2,2'-(5-bromo-1,3-phenylene)dinaphthalene was used instead of 4-([1,1'-biphenyl]-4-yl)-2-bromoquinazoline, thereby obtaining Target Compound 169 (5.3 g, 84%).

PREPARATION EXAMPLE 60

Preparation of Compound 194

A preparation was performed in the same manner as in the preparation of Compound 266 in Preparation Example 24, except that the compounds 3-bromobenzoyl chloride and 3-bromo-1,1'-biphenyl were used instead of 4-bromobenzoyl chloride and 4-([1,1'-biphenyl]-4-yl)-2-bromoquinazoline, thereby obtaining Target Compound 194 (6.4 g, 82%).

PREPARATION EXAMPLE 61

Preparation of Compound 227

A preparation was performed in the same manner as in the preparation of Compound 187 in Preparation Example 15, except that the compound 2-bromotriphenylene was used instead of 4-([1,1'-biphenyl]-4-yl)-2-bromoquinazoline, thereby obtaining Target Compound 227 (6.2 g, 78%).

PREPARATION EXAMPLE 62

Preparation of Compound 372

A preparation was performed in the same manner as in the preparation of Compound 2 in Preparation Example 1, except that the compound 3-bromo-9,9'-spirobi[fluorene] was used instead of 4-bromo-9,9'-spirobi[fluorene], thereby obtaining Target Compound 327 (4.9 g, 68%).

PREPARATION EXAMPLE 63

Preparation of Compound 375

A preparation was performed in the same manner as in the preparation of Compound 5 in Preparation Example 54,

213 except that the compound 3-bromo-9,9'-spirobi[fluorene] was used instead of 4-bromo-9,9'-spirobi[fluorene], thereby obtain Target Compound 375 (6.1 g, 83%).

PREPARATION EXAMPLE 64

Preparation of Compound 380

A preparation was performed in the same manner as in the preparation of Compound 15 in Preparation Example 55, except that the compound 3-bromo-9,9'-spirobi[fluorene] was used instead of 4-bromo-9,9'-spirobi[fluorene], thereby obtaining Target Compound 380 (4.9 g, 79%).

PREPARATION EXAMPLE 65

Preparation of Compound 383

A preparation was performed in the same manner as in the preparation of Compound 237 in Preparation Example 17, except that the compound 3-bromo-1,1'-biphenyl was used instead of 2-bromo-4,6-diphenylpyrimidine, thereby obtaining Target Compound 383 (6.6 g, 87%).

PREPARATION EXAMPLE 66

Preparation of Compound 388

A preparation was performed in the same manner as in the preparation of Compound 237 in Preparation Example 17, except that the compound 4-bromodibenzo[b,d]thiophene was used instead of 2-bromo-4,6-diphenylpyrimidine, thereby obtaining Target Compound 383 (6.4 g, 86%).

PREPARATION EXAMPLE 67

Preparation of Compound 393

A preparation was performed in the same manner as in the preparation of Compound 237 in Preparation Example 17, except that Compound 307-4B and naphthalen-1-ylboronic acid were used instead of Compound 237-4A and 2-bromo-4,6-diphenylpyrimidine, thereby obtaining Target Compound 393 (7.2 g, 71%).

PREPARATION EXAMPLE 68

Preparation of Compound 398

A preparation was performed in the same manner as in the preparation of Compound 237 in Preparation Example 17, except that Compound 307-4B and (1',6'-dihydro-[1,1':3',1''-terphenyl]-5'-yl)boronic acid were used instead of Compound 237-4A and 2-bromo-4,6-diphenylpyrimidine, thereby obtaining Target Compound 398 (8.4 g, 73%).

PREPARATION EXAMPLE 69

Preparation of Compound 403

A preparation was performed in the same manner as in the preparation of Compound 239 in Preparation Example 18, except that the compound 4-bromo-1,1'-biphenyl was used instead of chloro-4,6-diphenyl-1,3,5-triazine, thereby obtaining Target Compound 403 (8.5 g, 80%).

PREPARATION EXAMPLE 70

Preparation of Compound 404

A preparation was performed in the same manner as in the preparation of Compound 239 in Preparation Example 18, except that the compound 3-bromo-1,1'-biphenyl was used instead of chloro-4,6-diphenyl-1,3,5-triazine, thereby obtaining Target Compound 404 (3.4 g, 75%).

PREPARATION EXAMPLE 71

Preparation of Compound 407

A preparation was performed in the same manner as in the preparation of Compound 239 in Preparation Example 18, except that the compound 4-bromodibenzo[b,d]furan was used instead of chloro-4,6-diphenyl-1,3,5-triazine, thereby obtaining Target Compound 407 (6.1 g, 78%).

Compounds were prepared in the same manner as in the Preparation Examples, and the synthesis confirmation results thereof are shown in Tables 1 and 2. Table 1 is about the measurement values of $^1$H NMR(CDCl$_3$, 200 MHz), and Table 2 is about the measurement values of field desorption mass spectrometry (FD-MS).

TABLE 1

| Compound | $^1$H NMR (CDCl$_3$, 200 MHz) |
|---|---|
| 2 | 8.55 (1H, s), 8.38 (1H, d), 8.09~7.95 (6H, m), 7.82~7.75 (4H, m), 7.61~7.59 (4H, m), 7.44~7.35 (4H, m), 7.24~7.16 (5H, m) |
| 18 | 8.30 (2H, d), 8.09~8.06 (2H, td), 7.98 (1H, d), 7.78~7.75 (10H, m), 7.61~7.60 (2H, m), 7.45~7.35 (10H, m), 7.61~7.60 (2H, m), 7.45~7.35 (9H, m), 7.24~7.16 (5H, m) |
| 28 | 8.81 (2H, d), 8.56 (1H, m), 8.09~8.06 (2H, td), 7.98 (1H, d), 7.88~7.55 (8H, m), 7.59~7.16 (21H, m) |
| 37 | 8.81(2H, d), 8.23 (1H, s), 8.09~8.06 (2H, t), 7.98 (1H, d), 7.88~7.75 (10H, m), 7.60~7.41 (12H, m), 7.24~7.16 (5H, m) |
| 41 | 8.81 (2H, d), 8.33~8.23 (4H, m), 8.09~8.06 (2H, td), 7.98 (1H, d), 7.82~7.75 (6H, m), 7.60~7.41 (11H, m), 7.24~7.16 (5H, m) |
| 43 | 8.81 (2H, d), 8.30 (2H, d), 8.16 (1H, d), 8.06 (1H, d), 7.98~7.97 (2H, m), 7.88~7.78 (10H, m), 7.60~7.28 (16H, m), 7.12 (1H, t) |
| 44 | 8.81 (2H, d), 8.28 (4H, d), 8.09~8.06 (2H, t), 7.98 (1H, d), 7.88~7.75 (6H, m), 7.60~7.41 (12H, m), 7.24~7.16 (5H, m) |
| 76 | 8.26~8.18 (3H, m), 8.06~7.97 (4H, m), 7.87~7.78 (6H, m), 7.60~7.41 (7H, m), 7.38~7.25 (9H, m), 7.12 (1H, t) |
| 77 | 8.75 (1H, s), 8.26~8.21 (3H, m), 8.09~7.98 (5H, m), 7.82~7.75 (5H, m), 7.60~7.54 (5H, m), 7.44~7.35 (4H, m), 7.24~7.16 (5H, m) |
| 98 | 8.30~8.21 (6H, m), 8.06 (1H, d), 7.98~7.97 (2H, m), 7.87~7.78 (8H, m), 7.60~7.33 (14H, m), 7.27~7.25 (3H, m), 7.12 (1H, t) |
| 101 | 8.85 (1H, s), 8.60 (1H, s), 8.30 (1H, m), 8.12~8.06 (4H, q) 7.98 (1H, d), 7.82~7.75 (4H, m), 7.61~7.16 (20H, m), 1.72 (6H, s) |
| 120 | 8.60~8.55 (3H, m), 8.30 (1H, m), 8.12~7.94 (6H, m), 7.82~7.75 (4H, m), 7.60~7.16 (23H, m) |
| 146 | 8.93 (2H, d), 8.81 (2H, d), 8.12~7.75 (14H, m), 7.61~7.60 (2H, m), 7.44~7.16 (11H, m) |
| 159 | 8.81 (2H, d), 8.55 (2H, d), 8.12~7.75 (15H, m), 7.63~7.16 (22H, m) |
| 187 | 8.81 (2H, d), 8.30 (2H, d), 8.16~7.98 (5H, m), 7.85~7.75 (9H, m), 7.61~7.41 (12H, m), 7.24~7.16 (5H, m) |
| 233 | 8.81 (2H, d), 8.09~7.88 (11H, m), 7.78~7.73 (6H, m), 7.60~7.56 (8H, m), 7.44 (1H, t), 7.35 (2H, m), 7.24~7.16 (5H, m) |
| 237 | 8.30~8.21 (4h, M), 8.09~8.06 (2H, m), 7.98 (1H, d), 7.79~7.75 (7H, m), 7.66~7.41 (14H, m), 7.24~7.16 (5H, m) |

TABLE 1-continued

| Compound | $^1$H NMR (CDCl$_3$, 200 MHz) |
|---|---|
| 239 | 8.30~8.27 (7H, m), 8.09~8.06 (2H, td), 7.98 (1H, d), 7.86 (1H, s), 7.78~7.75 (3H, m), 7.60~7.41 (12H, m), 7.24~7.16 (5H, m) |
| 242 | 8.40 (2H, d), 8.09~8.06 (2H, td), 7.98 (1H, d), 7.82~7.75 (4H, m), 7.60~7.47 (22H, m), 7.24~7.16 (5H, m) |
| 245 | 8.26~8.21 (2H, m), 8.09~8.06 (2H, td), 8.03 (1H, s), 7.98 (1H, d), 7.89~7.54 (12H, m), 7.44~7.16 (11H, m) |
| 248 | 8.28~8.21 (4H, m), 8.06 (1H, d), 7.98~7.91 (2H, m), 7.87~7.78 (8H, m), 7.60~7.38 (18H, m), 7.28~7.25 (3H, m), 7.12 (1H, t) |
| 255 | δ = 8.81(2H, d), 8.09~8.06(2H, t), 7.98(1H, d), 7.87~7.75(7H, m), 7.60~7.16(25H, m) |
| 263 | δ = 8.26~8.21(2H, m), 8.09~8.06(2H, t), 7.98(1H, d), 7.82~7.75(7H, m), 7.60~7.16(5H, m) |
| 266 | δ = 8.81(2H, d), 8.56(1H, m), 8.09~7.98(4H, m), 7.79~7.59(13H, m), 7.61~7.44(3H, m), 7.24~7.16(7H, m), 2.85(2H, q), 1.25(3H, t) |
| 267 | δ = 8.81 (2H, d), 8.33~8.23 (7H, m), 8.09~7.98 (4H, m), 7.85~7.75 (5H, m), 7.61~7.41 (14H, m), 7.24~7.16 (5H, m) |
| 268 | δ = 8.81 (2H, d), 8.28 (2H, d), 8.09~7.98 (4H, m), 7.88~7.75 (7H, m), 7.61~7.41 (14H, m), 7.25~7.16 (7H, m) |
| 274 | δ = 8.56 (1H, m), 8.26~8.21 (2H, m), 7.56~7.44 (3H, m), 7.24~7.16 (7H, m), 2.85 (2H, q), 1.25 (3H, t) |
| 275 | δ = 8.30~8.21 (7H, m), 8.09~7.98 (4H, m), 7.85~7.75 (6H, m), 7.60~7.41 (15H, m), 7.24~7.16 (5H, m) |
| 276 | δ = 8.30~8.26 (5H, m), 8.09~7.89 (4H, m), 7.85~7.75 (5H, m), 7.61~7.41 (15H, m), 7.25~7.16 (7H, m) |
| 278 | δ = 8.26~8.21 (2H, m), 8.09~7.91 (8H, m), 7.78~7.75 (3H, m), 7.61~7.39 (17H, m), 7.25~7.16 (9H, m) |
| 283 | δ = 8.81 (2H, d), 8.56 (1H, m), 8.09~8.06 (2H, t), 7.98 (1H, d), 7.78~7.16 (29H, m) |
| 287 | δ = 8.81 (2H, d), 8.33~8.23 (7H, m), 8.09~8.06 (2H, t), 7.98 (1H, d), 7.85~7.78 (5H, m), 7.60~7.41 (15H, m), 7.24~7.16 (5H, m) |
| 290 | δ = 8.81 (2H, d), 8.06~7.91 (15H, m), 7.78~7.59 (15H, m), 7.49~7.39 (6H, m), 7.24~7.16 (5H, m) |
| 292 | δ = 8.30 (2H, d), 8.09~8.06 (2H, t), 7.98 (1H, d), 7.78~7.75 (9H, m), 7.66~7.60 (3H, m), 7.49~7.45 (8H, m), 7.35 (2H, m), 7.24~7.16 (5H, m) |
| 296 | δ = 8.53 (1H, m), 8.28~8.21 (4H, m), 8.09~8.06 (3H, m), 7.78~7.41 (20H, m), 7.24~7.16 (7H, m) |
| 298 | δ = 8.60~8.55 (2H, m), 8.30 (1H, d), 8.12~7.98 (5H, m), 7.78~7.16 (22H, m) |
| 304 | δ = 8.30 (1H, d), 8.17 (1H, s), 8.09~8.06 (2H, t), 7.98 (1H, d), 7.79~7.75 (8H, m), 7.66~7.45 (12H, m), 7.35 (2H, m), 7.24~7.16 (7H, m) |
| 305 | δ = 8.81 (2H, d), 8.56 (1H, m), 8.28 (2H, d), 8.09~7.98 (3H, m), 7.88~7.41 (20H, m), 7.24~7.16 (7H, m) |
| 307 | δ = 8.55 (1H, d), 8.30 (2H, d), 8.12~7.98 (5H, m), 7.89 (1H, s), 7.78~7.16 (20H, m) |
| 311 | δ = 8.81 (2H, d), 8.09~7.91 (16H, m), 7.78~7.73 (6H, m), 7.61~7.59 (9H, m), 7.44~7.39 (5H, m), 7.24~7.16 (5H, m) |
| 316 | δ = 8.60~8.55 (2H, m), 8.30 (1H, m), 8.12~7.94 (5H, m), 7.87 (1H, s), 7.78~7.75 (4H, m), 7.60~7.16 (17H, m) |
| 322 | δ = 8.30 (1H, m), 8.17 (1H, s), 8.09~8.06 (2H, t), 7.98 (1H, d), 7.87 (1H, s), 7.78~7.75 (9H, m), 7.60~7.44 (10H, m), 7.356 (2H, m), 7.24~7.16 (5H, m) |
| 323 | δ = 8.60~8.55 (4H, m), 8.12~7.94 (7H, m), 7.82~7.75 (4H, m), 7.60~7.16 (22H, m) |
| 326 | δ = 8.56~8.55 (3H, m), 8.39 (1H, s), 8.12~8.06 (4H, q), 7.98~7.94 (2H, q), 7.85~7.75 (6H, m), 7.63~7.16 (26H, m) |
| 333 | δ = 8.39 (1H, s), 8.30~8.28 (5H, m), 8.13~8.06 (3H, q), 7.98 (1H, d), 7.85~7.75 (10H, m), 7.68 (1H, s), 7.60~7.41 (20H, m), 7.24~7.16 (5H, m) |
| 335 | δ = 8.60 (2H, s), 8.55 (2H, d), 8.12~7.94 (8H, m), 7.78~7.75 (3H, m), 7.63~7.16 (22H, m) |
| 338 | δ = 8.56~8.55 (3H, m), 8.39 (1H, s), 8.12~7.94 (7H, m), 7.85~7.75 (5H, m), 7.63~7.16 (26H, m) |
| 345 | δ = 8.39 (1H, s), 8.30~8.23 (5H, m), 8.09~7.98 (5H, m), 7.85~7.75 (10H, m), 7.60~7.41 (20H, m), 7.24~7.16 (5H, m) |
| 347 | δ = 8.60~8.55 (4H, m), 8.12~7.94 (7H, m), 7.78~7.16 (26H, m) |
| 350 | δ = 8.56~8.55 (3H, m), 8.39 (1H, s), 8.12~8.06 (4H, q), 7.98~7.94 (2H, q), 7.78~7.16 (32H, m) |
| 356 | δ = 8.83 (1H, d), 8.39~8.38 (2H, m), 8.21 (1H, d), 8.13~7.98 (5H, m), 7.78~7.58 (13H, m), 7.61~7.45 (10H, m), 7.19~7.16 (5H, m) |
| 359 | δ = 8.60~8.55 (5H, m), 8.12~7.87 (8H, m), 7.78~7.75 (4H, m), 7.60~7.16 (21H, m) |
| 362 | δ = 8.56~8.55 (3H, m), 8.39 (1H, s), 8.12~8.06 (4H, q), 7.98~7.94 (2H, q), 7.87~7.75 (7H, m), 7.60~7.16 (25H, m) |
| 370 | δ = 8.39 (1H, s), 8.28 (2H, d), 8.13~8.06 (3H, q), 7.98 (1H, d), 7.87~7.75 (12H, m), 7.60~7.41 (19H, m), 7.256~7.16 (7H, m) |
| 5 | δ = 8.81 (2H, d), 8.09~8.06 (2H, t), 7.98 (1H, d), 7.88~7.75 (5H, m), 7.52~7.35 (10H, m), 7.25~7.16 (10H, m) |
| 15 | δ = 8.81 (2H, d), 8.09~8.06 (2H, t), 7.93~7.75 (12H, m), 7.63~7.53 (4H, m), 7.44~9.16 (17H, m) |
| 253 | δ = 8.81 (2H, d), 8.09~8.06 (2H, m), 7.98~7.91 (5H, m), 7.82~7.75 (3H, m), 7.60~7.16 (22H, m) |
| 261 | δ = 8.81 (2H, m), 8.09~7.98 (3H, m), 7.78~7.75 (5H, m), 7.60~7.16 (26H, m) |
| 167 | δ = 8.81 (2H, d), 8.09~7.88 (9H, m), 7.78~7.73 (4H, m), 7.60~7.59 (6H, m), 7.56~7.44 (3H, m), 7.24~7.16 (5H, m) |
| 169 | δ = 8.81 (2H, d), 8.06~7.88 (12H, m), 7.78~7.66 (17H, m), 7.44 (1H, t), 7.61~7.56(2H, d), 7.24~7.16 (5H, m) |
| 194 | δ = 8.26~8.21 (2H, m), 8.09~7.98 (4H, m), 7.78~7.75 (4H, m), 7.60~7.41 (16H, m), 7.24~7.16 (5H, m) |
| 227 | δ = 9.15 (1H, s), 8.93 (2H, d), 8.81 (2H, d), 8.12~7.75 (17H, m), 7.60~7.56 (3H, m), 7.44~7.35 (3H, m), 7.24~7.16 (5H, m) |
| 372 | δ = 8.85 (1H, s), 8.09 (1H, d), 8.06~7.98 (6H, m), 7.78~7.66 (8H, m), 7.61~7.35 (4H, m), 7.24~7.16 (5H, m) |
| 375 | δ = 8.81 (1H, d), 8.09~8.06 (2H, t), 7.98 (1H, d), 7.88 (2H, t), 7.78~7.75 (3H, m), 7.65~7.41 (12H, m), 7.25~7.16 (9H, m) |
| 380 | δ = 8.81 (2H, d), 8.09~8.06 (2H, t), 7.98~7.86 (5H, m), 7.78 (27H, m) |
| 383 | δ = 8.26~8.21 (2H, m), 8.09~8.06 (2H, t), 7.98 (1H, d), 7.78~7.75(3H, m), 7.60~7.41 (14H, m), 7.25~7.16 (9H, m) |
| 388 | δ = 8.45~8.41 (2H, m), 8.26~8.20 (3H, m), 8.06~7.98 (4H, m), 7.78~7.52 (15H,), 7.24~7.16 (5H, m) |
| 393 | δ = 8.81 (2H, d), 8.55 (1H, d), 8.42 (1H, d), 8.09~8.04 (5H, m), 7.87 (1H, s), 7.78~7.75 (4H, m), 7.61~7.35 (5H, m), 7.44~7.16 (18H, m) |
| 398 | δ = 8.81 (1H, d), 8.09~8.06 (2H, t), 7.98 (1H, d), 7.88~7.87 (3H, d), 7.60~7.41 (18H, m), 7.24~7.16 (5H, m) |
| 403 | δ = 8.26~8.21 (2H, m), 8.09~8.06 (2H, t), 7.98 (1H, d), 7.87 (1H, d), 7.87 (1H, s), 7.78~7.75 (4H, m), 7.60~7.41 (12H, m), 7.25~7.16 (9H, m) |
| 404 | δ = 8.26~8.21 (2H, m), 8.09~8.06 (2H, t), 7.98 (1H, d), 7.87 (1H, s), 7.78~7.70 (5H, m), 7.60~7.41 (15H, m), 7.24~7.16 (5H, m) |
| 407 | 8.26~8.21 (2H, m), 8.09~8.06 (2H, t), 7.98 (1H, d), 7.89~7.60(13H, m), 7.44~7.16 (11H, m) |

TABLE 2

| Compound | FD-Mass |
|---|---|
| 1 | m/z = 540.20(C42H25N = 543.65) |
| 2 | m/z = 543.20(C42H25N = 543.65) |
| 3 | m/z = 619.23(C48H29N = 619.75) |
| 4 | m/z = 619.23(C48H29N = 619.75) |
| 5 | m/z = 645.25(C50H31N = 245.79) |
| 6 | m/z = 646.24(C49H30N2 = 646.78) |

TABLE 2-continued

| Compound | FD-Mass | Compound | FD-Mass |
|---|---|---|---|
| 7 | m/z = 646.24(C49H30N2 = 646.78) | 8 | m/z = 721.28(C56H35N = 721.88) |
| 9 | m/z = 723.86(C54H33N3 = 723.86) | 10 | m/z = 821.31(C64H39N = 821.31) |
| 11 | m/z = 795.29(C62H37N = 795.96) | 12 | m/z = 921.34(C72H43N = 922.12) |
| 13 | m/z = 685.28(C53H35N = 685.85) | 14 | m/z = 809.31(C63H39N = 809.99) |
| 15 | m/z = 807.29(C63H37N = 807.29) | 16 | m/z = 6575.20(C50H29NS = 675.84) |
| 17 | m/z = 761.28(C57H35N3 = 761.91) | 18 | m/z = 693.22(C50H32NOP = 693.77) |
| 19 | m/z = 769.25(C56H36NOP = 769.86) | 20 | m/z = 686.24(C51H30N2O = 686.80) |
| 21 | m/z = 702.21(C51H30N2S = 702.86) | 22 | m/z = 620.23(C47H28N2 = 620.74) |
| 23 | m/z = 620.23(C47H28N2 = 620.74) | 24 | m/z = 621.22(C46H27N3 = 621.73) |
| 25 | m/z = 621.22(C46H27N3 = 621.73) | 26 | m/z = 713.25(C52H31N3O = 713.82) |
| 27 | m/z = 659.22(C50H29NO = 659.77) | 28 | m/z = 761.28(C57H35N3 = 761.91) |
| 29 | m/z = 722.27(C55H34N2 = 722.87) | 30 | m/z = 722.27(C55H34N2 = 722.87) |
| 31 | m/z = 822.30(C63H38N2 = 822.99) | 32 | m/z = 876.33(C65H40N4 = 877.04) |
| 33 | m/z = 876.33(C65H40N4 = 877.04) | 34 | m/z = 822.30(C63H38N2 = 822.99) |
| 35 | m/z = 876.33(C65H40N4 = 877.04) | 36 | m/z = 876.33(C65H40N4 = 877.04) |
| 37 | m/z = 723.27(C54H33N3 = 723.86) | 38 | m/z = 799.30(C60H37N3 = 799.96) |
| 39 | m/z = 823.30(C62H37N3 = 823.98) | 40 | m/z = 877.32(C64H39N5 = 878.32) |
| 41 | m/z = 723.27(C54H33N3 = 723.86) | 42 | m/z = 823.30(C62H37N3 = 823.98) |
| 43 | m/z = 773.28(C58H35N3 = 773.92) | 44 | m/z = 724.26(C53H32N4 = 724.85) |
| 45 | m/z = 824.29(C61H36N4 = 824.97) | 46 | m/z = 876.33(C65H40N4 = 877.04) |
| 47 | m/z = 726.25(C51H30N6 = 726.82) | 48 | m/z = 726.25(C51H30N6 = 726.82) |
| 49 | m/z = 878.32(C63H38N6 = 879.02) | 50 | m/z = 880.31(C61H36N8 = 880.99) |
| 51 | m/z = 880.31(C61H36N8 = 880.99) | 52 | m/z = 880.31(C61H36N8 = 880.99) |
| 53 | m/z = 880.31(C61H36N8 = 880.99) | 54 | m/z = 812.29(C60H36N4 = 812.95) |
| 55 | m/z = 870.30(C67H38N2 = 871.03) | 56 | m/z = 619.23(C48H29N = 619.75) |
| 57 | m/z = 619.23(C48H29N = 619.75) | 58 | m/z = 645.25(C50H31N = 645.79) |
| 59 | m/z = 645.25(C50H31N = 645.79) | 60 | m/z = 646.24(C49H30N2 = 646.78) |
| 61 | m/z = 648.25(C49H30N2 = 646.78) | 62 | m/z = 646.24(C49H30N2 = 646.78) |
| 63 | m/z = 721.28(C56H35N = 721.88) | 64 | m/z = 723.27(C54H33N3 = 723.86) |
| 65 | m/z = 821.31(C64H39N = 822.00) | 66 | m/z = 795.29(C62H37N = 795.96) |
| 67 | m/z = 921.34(C72H43N = 922.12) | 68 | m/z = 685.28(C53H35N = 685.85) |
| 69 | m/z = 809.31(C63H39N = 809.99) | 70 | m/z = 807.29(C63H37N = 807.97) |
| 71 | m/z = 763.29(C57H35N3 = 761.91) | 72 | m/z = 685.25(C51H31N3 = 685.81) |
| 73 | m/z = 693.22(C50H32NOP = 693.77) | 74 | m/z = 769.25(C56H36NOP = 769.86) |
| 75 | m/z = 686.24(C51H30N2O = 686.80) | 76 | m/z = 702.21(C51H30N2 = 702.86) |
| 77 | m/z = 620.23(C47H28N2 = 620.74) | 78 | m/z = 620.23(C47H28N2 = 620.74) |
| 79 | m/z = 621.22(C46H27N3 = 621.73) | 80 | m/z = 621.22(C46H27N3 = 621.73) |
| 81 | m/z = 713.25(C52H31N3O = 713.82) | 82 | m/z = 659.22(C50H29NO = 659.77) |
| 83 | m/z = 675.20(C50H29NS = 675.84) | 84 | m/z = 722.27(C55H34N2 = 722.87) |

TABLE 2-continued

| Compound | FD-Mass | Compound | FD-Mass |
|---|---|---|---|
| 85 | m/z = 722.27(C55H34N2 = 722.87) | 86 | m/z = 822.30(C63H38N2 = 822.99) |
| 87 | m/z = 876.33(C65H40N4 = 877.04) | 88 | m/z = 876.33(C65H40N4 = 877.04) |
| 89 | m/z = 822.30(C63H38N2 = 822.99) | 90 | m/z = 876.33(C65H40N4 = 877.04) |
| 91 | m/z = 876.33(C65H40N4 = 877.04) | 92 | m/z = 723.27(C54H33N3 = 723.86) |
| 93 | m/z = 799.30(C60H37N3 = 799.96) | 94 | m/z = 823.30(C62H37N3 = 823.98) |
| 95 | m/z = 877.32(C64H39N5 = 878.03) | 96 | m/z = 723.27(C54H33N3 = 723.86) |
| 97 | m/z = 823.30(C62H37N3 = 823.98) | 98 | m/z = 773.28(C58H35N3 = 773.92) |
| 99 | m/z = 724.26(C53H32N4 = 724.85) | 100 | m/z = 824.29(C61H36N4 = 824.97) |
| 101 | m/z = 774.30(C59H38N2 = 774.95) | 102 | m/z = 898.33(C69H42N2 = 899.09) |
| 103 | m/z = 764.23(C56H32NS = 764.93) | 104 | m/z = 748.25(C56H32N2 = 748.87) |
| 105 | m/z = 823.30(C62H37N3 = 823.98) | 106 | m/z = 832.29(C61H40N2 = 834.) |
| 107 | m/z = 954.31(C71H42N2S = 955.17) | 108 | m/z = 820.20(C58H32N2S2 = 821.02) |
| 109 | m/z = 804.22(C58H32N2OS = 804.95) | 110 | m/z = 879.27(C64H37N3S = 880.06) |
| 111 | m/z = 832.29(C61H40N2S = 833.05) | 112 | m/z = 954.31(C71H42N2S = 955.17) |
| 113 | m/z = 820.20(C58H32N2S2 = 821.02) | 114 | m/z = 804.22(C58H32N2OS = 804.95) |
| 115 | m/z = 879.27(C64H37N3S = 880.06) | 116 | m/z = 829.28(C62H39NS = 830.04) |
| 117 | m/z = 820.20(C58H32N2S2 = 821.02) | 118 | m/z = 804.22(C58H32N2OS = 804.95) |
| 119 | m/z = 879.27(C64H37N3 = 880.06) | 120 | m/z = 823.30(C62H37N3 = 823.98) |
| 121 | m/z = 774.30(C59H38N2 = 774.95) | 122 | m/z = 764.23(C56H32N2S = 764.93) |
| 123 | m/z = 748.25(C56H32N2O = 748.87) | 124 | m/z = 823.30(C62H37N3 = 823.98) |
| 125 | m/z = 764.23(C56H32N2S = 764.93) | 126 | m/z = 748.25(C56H32N2O = 748.87) |
| 127 | m/z = 898.33(C69H42N2 = 899.09) | 128 | m/z = 814.30(C61H38N2O = 814.97) |
| 129 | m/z = 938.33(C71H42N2O = 939.11) | 130 | m/z = 804.22(C58H32N2OS = 804.95) |
| 131 | m/z = 804.22(C58H32N2OS = 804.95) | 132 | m/z = 788.25(C58H32N2O2 = 788.89) |
| 133 | m/z = 869.29(C64H37N3O = 864.00) | 134 | m/z = 814.30(C61H38N2O = 814.97) |
| 135 | m/z = 804.32(C58H32N2OS = 804.95) | 136 | m/z = 744.30(C59H38N2 = 774.95) |
| 137 | m/z = 898.33(C69H42N2 = 899.09) | 138 | m/z = 764.23(C56H32N2S = 764.93) |
| 139 | m/z = 748.25(C56H32N2O = 748.87) | 140 | m/z = 823.30(C62H37N3 = 923.98) |
| 141 | m/z = 804.22(C58H32N2OS = 804.95) | 142 | m/z = 788.25(C58H32N2O2 = 788.89) |
| 143 | m/z = 863.29(C64H37N3O = 864.00) | 144 | m/z = 814.30(C61H38N2O = 814.97) |
| 145 | m/z = 804.22(C58H32N2OS = 804.95) | 146 | m/z = 669.25(C52H31N = 669.81) |
| 147 | m/z = 719.26(C56H33N = 719.87) | 148 | m/z = 693.25(C54H31N = 693.83) |
| 149 | m/z = 719.26(C56H33N = 719.87) | 150 | m/z = 658.24(C50H30N2 = 658.79) |
| 151 | m/z = 810.30(C62H38N2 = 810.98) | 152 | m/z = 734.27(C56H34N2 = 734.88) |
| 153 | m/z = 812.29(C60H36N4 = 812.95) | 154 | m/z = 806.23(C56H30N2F4 = 806.84) |
| 155 | m/z = 822.40(C62H50N2 = 823.07) | 156 | m/z = 811.30(C61H37N3 = 811.97) |
| 157 | m/z = 812.29(C60H36N4 = 812.95) | 158 | m/z = 694.22(C50H28N2F2 = 694.77) |
| 159 | m/z = 899.33(C68H41N3 = 900.07) | 160 | m/z = 899.33(C68H41N3 = 900.07) |
| 161 | m/z = 1051.39(C80H49N3 = 1052.27) | 162 | m/z = 1051.39(C80H49N3 = 1052.27) |

TABLE 2-continued

| Compound | FD-Mass | Compound | FD-Mass |
|---|---|---|---|
| 163 | m/z = 971.37(C71H49N3Si = 972.25) | 164 | m/z = 745.28(C58H35N = 745.91) |
| 165 | m/z = 745.28(C58H35N = 745.91) | 166 | m/z = 543.20(C42H25N = 543.65) |
| 167 | m/z = 619.23(C48H29N = 619.75) | 168 | m/z = 646.24(C49H30N2 = 646.78) |
| 169 | m/z = 821.31(C64H39N = 822.00) | 170 | m/z = 921.34(C72H43N = 922.12) |
| 171 | m/z = 685.28(C53H35N = 685.85) | 172 | m/z = 807.29(C63H37N = 807.97) |
| 173 | m/z = 761.28(C57H35N3 = 761.91) | 174 | m/z = 761.28(C57H35N3 = 761.91) |
| 175 | m/z = 693.22(C50H32NOP = 693.77) | 176 | m/z = 702.21(C51H30N2S = 702.86) |
| 177 | m/z = 620.23(C47H28N2 = 620.74) | 178 | m/z = 713.25(C52H31N3O = 713.82) |
| 179 | m/z = 675.20(C50H29NS = 675.84) | 180 | m/z = 722.27(C55H34N2 = 722.87) |
| 181 | m/z = 822.30(C63H38N2 = 922.99) | 182 | m/z = 876.33(C65H40N4 = 877.04) |
| 183 | m/z = 723.27(C54H33N3 = 723.86) | 184 | m/z = 799.30(C60H37N3 = 799.96) |
| 185 | m/z = 823.30(C62H37N3 = 823.98) | 186 | m/z = 723.27(C54H33N3 = 723.86) |
| 187 | m/z = 773.28(C58H35N3 = 773.92) | 188 | m/z = 724.26(C53H32N4 = 724.85) |
| 189 | m/z = 824.29(C61H36N4 = 824.97) | 190 | m/z = 878.32(C63H38N6 = 879.02) |
| 191 | m/z = 880.31(C61H36N8 = 880.99) | 192 | m/z = 812.29(C60H36N4 = 812.95) |
| 193 | m/z = 984.35(C76H44N2 = 985.18) | 194 | m/z = 645.25(C50H31N = 645.79) |
| 195 | m/z = 723.27(C54H33N3 = 723.86) | 196 | m/z = 821.31(C64H39N = 822.00) |
| 197 | m/z = 809.31(C63H39N = 809.99) | 198 | m/z = 795.29(C62H37N = 795.96) |
| 199 | m/z = 769.25(C56H36NOP = 769.86) | 200 | m/z = 686.24(C51H30N2 = 686.80) |
| 201 | m/z = 620.23(C47H28N2 = 620.74) | 202 | m/z = 621.22(C46H27N3 = 621.73) |
| 203 | m/z = 659.22(C50H29NO = 659.77) | 204 | m/z = 722.27(C55H34N2 = 722.87) |
| 205 | m/z = 876.33(C65H40N4 = 877.04) | 206 | m/z = 723.27(C54H33N3 = 723.86) |
| 207 | m/z = 799.30(C60H37N3 = 799.96) | 208 | m/z = 723.27(C54H33N3 = 723.86) |
| 209 | m/z = 774.30(C59H38N2 = 774.95) | 210 | m/z = 764.23(C56H32N2S = 764.93) |
| 211 | m/z = 820.20(C58H32N2S2 = 821.02) | 212 | m/z = 830.28(C61H38N2S = 831.03) |
| 213 | m/z = 830.28(C61H38N2S = 831.03) | 214 | m/z = 820.20(C58H32N2S2 = 821.02) |
| 215 | m/z = 820.20(C58H32N2S2 = 821.02) | 216 | m/z = 823.30(C62H37N3 = 823.98) |
| 217 | m/z = 774.30(C59H38N2 = 774.95) | 218 | m/z = 823.30(C62H37N3 = 823.98) |
| 219 | m/z = 814.30(C61H38N2O = 814.97) | 220 | m/z = 804.22(C58H32N2OS = 804.95) |
| 221 | m/z = 788.25(C58H32N2O2 = 788.89) | 222 | m/z = 804.22(C58H32N2OS = 804.95) |
| 223 | m/z = 774.30(C59H38N2 = 774.95) | 224 | m/z = 863.29(C64H37N3O = 864.00) |
| 225 | m/z = 898.33(C69H42N2 = 899.09) | 226 | m/z = 669.25(C52H31N = 669.81) |
| 227 | m/z = 719.26(C56H33N = 719.87) | 228 | m/z = 734.27(C56H34N2 = 734.88) |
| 229 | m/z = 812.29(C60H36N4 = 812.95) | 230 | m/z = 694.22(C50H28N2F2 = 694.77) |
| 231 | m/z = 899.33(C68H41N3 = 900.07) | 232 | m/z = 975.36(C74H45N3 = 976.17) |
| 233 | m/z = 745.28(C58H35N = 745.91) | 234 | m/z = 745.28(C58H35N = 745.91) |
| 235 | m/z = 1051.39(C80H49N3 = 1052.27) | 236 | m/z = 724.26(C53H32N4 = 724.85) |
| 237 | m/z = 723.27(C54H33N3 = 723.86) | 238 | m/z = 761.28(C57H35N3 = 761.92) |
| 239 | m/z = 724.26(C53H32N4 = 724.85) | 240 | m/z = 723.27(C54H33N3 = 723.86) |

TABLE 2-continued

| Compound | FD-Mass | Compound | FD-Mass |
|---|---|---|---|
| 241 | m/z = 761.28(C57H35N3 = 761.92) | 242 | m/z = 751.27(C56H37NSi = 751.99) |
| 243 | m/z = 825.29(C62H39NSi = 826.07) | 244 | m/z = 675.20(C50H29NS = 675.84) |
| 245 | m/z = 659.22(C50H29NO = 659.22) | 246 | m/z = 734.27(C56H34N2 = 734.88) |
| 247 | m/z = 658.24(C50H30N2 = 658.79) | 248 | m/z = 799.30(C60H37N3 = 799.96) |
| 249 | m/z = 674.24(C50H29N3 = 671.79) | 250 | m/z = 713.28(C53H35N3 = 713.87) |
| 251 | m/z = 799.30(C60H37N3 = 799.96) | 252 | m/z = 800.29(C59H36N4 = 800.94) |
| 253 | m/z = 745.28(C58H35N = 745.91) | 254 | m/z = 821.31(C64H39N = 822.00) |
| 255 | m/z = 807.29(C63H37N = 807.97) | 256 | m/z = 620.23(C47H28N2 = 620.74) |
| 257 | m/z = 674.24(C50H29N3 = 671.79) | 258 | m/z = 713.28(C53H35N3 = 713.87) |
| 259 | m/z = 799.30(C60H37N3 = 799.96) | 260 | m/z = 800.29(C59H36N4 = 800.94) |
| 261 | m/z = 745.28(C58H35N = 745.91) | 262 | m/z = 821.31(C64H39N = 822.00) |
| 263 | m/z = 807.29(C63H37N = 807.97) | 264 | m/z = 620.23(C47H28N2 = 620.74) |
| 265 | m/z = 674.24(C50H29N3 = 671.79) | 266 | m/z = 713.28(C53H35N3 = 713.87) |
| 267 | m/z = 799.30(C60H37N3 = 799.96) | 268 | m/z = 800.29(C59H36N4 = 800.94) |
| 269 | m/z = 745.28(C58H35N = 745.91) | 270 | m/z = 821.31(C64H39N = 822.00) |
| 271 | m/z = 807.29(C63H37N = 807.97) | 272 | m/z = 620.23(C47H28N2 = 620.74) |
| 273 | m/z = 674.24(C50H29N3 = 671.79) | 274 | m/z = 713.28(C53H35N3 = 713.87) |
| 275 | m/z = 799.30(C60H37N3 = 799.96) | 276 | m/z = 800.29(C59H36N4 = 800.94) |
| 277 | m/z = 745.28(C58H35N = 745.91) | 278 | m/z = 821.31(C64H39N = 822.00) |
| 279 | m/z = 807.29(C63H37N = 807.97) | 280 | m/z = 620.23(C47H28N2 = 620.74) |
| 281 | m/z = 724.26(C53H32N4 = 724.85) | 282 | m/z = 723.27(C54H33N3 = 723.86) |
| 283 | m/z = 761.28(C57H35N3 = 761.91) | 284 | m/z = 761.28(C57H35N3 = 761.91) |
| 285 | m/z = 899.33(C68H41N3 = 900.07) | 286 | m/z = 658.24(C50H30N2 = 658.79) |
| 287 | m/z = 799.30(C60H37N3 = 799.96) | 288 | m/z = 800.29(C59H36N4 = 800.94) |
| 289 | m/z = 674.24(C50H29N3 = 671.79) | 290 | m/z = 921.34(C72H43N = 922.12) |
| 291 | m/z = 807.29(C63H37N = 807.97) | 292 | m/z = 693.22(C50H32NOP = 693.77) |
| 293 | m/z = 752.29(C55H36N4 = 752.90) | 294 | m/z = 751.30(C56H37N3 = 751.91) |
| 295 | m/z = 695.26(C54H33N3 = 695/85) | 296 | m/z = 761.28(C57H35N3 = 761.91) |
| 297 | m/z = 899.33(C68H41N3 = 900.07) | 298 | m/z = 658.24(C50H30N2 = 658.79) |
| 299 | m/z = 799.30(C60H37N3 = 799.96) | 300 | m/z = 800.29(C59H36N4 = 800.94) |
| 301 | m/z = 674.24(C50H29N3 = 671.79) | 302 | m/z = 921.34(C72H43N = 922.12) |
| 303 | m/z = 807.29(C63H37N = 807.97) | 304 | m/z = 693.22(C50H32NOP = 693.77) |
| 305 | m/z = 761.28(C57H35N3 = 761.91) | 306 | m/z = 899.33(C68H41N3 = 900.07) |
| 307 | m/z = 658.24(C50H30N2 = 658.79) | 308 | m/z = 799.30(C60H37N3 = 799.96) |
| 309 | m/z = 800.29(C59H36N4 = 800.94) | 310 | m/z = 671.24(C50H29N3 = 671.79) |
| 311 | m/z = 921.34(C72H43N = 922.12) | 312 | m/z = 807.29(C63H37N = 807.97) |
| 313 | m/z = 693.22(C50H32NOP = 693.77) | 314 | m/z = 761.28(C57H35N3 = 761.91) |
| 315 | m/z = 899.33(C68H41N3 = 900.07) | 316 | m/z = 658.24(C50H30N2 = 658.79) |
| 317 | m/z = 799.30(C60H37N3 = 799.96) | 318 | m/z = 800.29(C59H36N4 = 800.94) |

TABLE 2-continued

| Compound | FD-Mass | Compound | FD-Mass |
|---|---|---|---|
| 319 | m/z = 671.24(C50H29N3 = 671.79) | 320 | m/z = 921.34(C72H43N = 922.12) |
| 321 | m/z = 807.29(C63H37N = 807.97) | 322 | m/z = 693.22(C50H32NOP = 693.77) |
| 323 | m/z = 823.30(C62H37N3 = 823.98) | 324 | m/z = 857.22(C62H35NS2 = 858.08) |
| 325 | m/z = 825.27(C62H35NO2 = 825.95) | 326 | m/z = 926.34(C69H42N4 = 927.10) |
| 327 | m/z = 926.34(C69H42N4 = 927.10) | 328 | m/z = 878.34(C65H42N4 = 879.06) |
| 329 | m/z = 841.24(C62H35NOS = 842.01) | 330 | m/z = 824.28(C62H36N2O = 824.96) |
| 331 | m/z = 840.26(C62H36N2S = 841.03) | 332 | m/z = 820.26(C59H37N2OP = 820.91) |
| 333 | m/z = 999.34(C72H46N3OP = 1000.13) | 334 | m/z = 1000.33(C71H45N4OP = 1001.12) |
| 335 | m/z = 823.30(C62H37N3 = 823.98) | 336 | m/z = 857.22(C62H35NS2 = 858.08) |
| 337 | m/z = 825.27(C62H35NO2 = 825.95) | 338 | m/z = 926.34(C69H42N4 = 927.10) |
| 339 | m/z = 926.34(C69H42N4 = 927.10) | 340 | m/z = 878.34(C65H42N4 = 879.06) |
| 341 | m/z = 841.24(C62H35NOS = 842.01) | 342 | m/z = 824.28(C62H36N2O = 824.96) |
| 343 | m/z = 840.26(C62H36N2S = 841.03) | 344 | m/z = 820.26(C59H37N2OP = 820.91) |
| 345 | m/z = 999.34(C72H46N3OP = 1000.13) | 346 | m/z = 1000.33(C71H45N4OP = 1001.12) |
| 347 | m/z = 823.30(C62H37N3 = 823.98) | 348 | m/z = 857.22(C62H35NS2 = 858.08) |
| 349 | m/z = 825.27(C62H35NO2 = 825.95) | 350 | m/z = 926.34(C69H42N4 = 927.10) |
| 351 | m/z = 926.34(C69H42N4 = 927.10) | 352 | m/z = 878.34(C65H42N4 = 879.06) |
| 353 | m/z = 841.24(C62H35NOS = 842.01) | 354 | m/z = 824.28(C62H36N2O = 824.96) |
| 355 | m/z = 840.26(C62H36N2S = 841.03) | 356 | m/z = 820.26(C59H37N2OP = 820.91) |
| 357 | m/z = 999.34(C72H46N3OP = 1000.13) | 358 | m/z = 1000.33(C71H45N4OP = 1001.12) |
| 359 | m/z = 823.30(C62H37N3 = 823.98) | 360 | m/z = 857.22(C62H35NS2 = 858.08) |
| 361 | m/z = 825.27(C62H35NO2 = 825.95) | 362 | m/z = 926.34(C69H42N4 = 927.10) |
| 363 | m/z = 926.34(C69H42N4 = 927.10) | 364 | m/z = 878.34(C65H42N4 = 879.06) |
| 365 | m/z = 841.24(C62H35NOS = 842.01) | 366 | m/z = 824.28(C62H36N2O = 824.96) |
| 367 | m/z = 840.26(C62H36N2S = 841.03) | 368 | m/z = 820.26(C59H37N2OP = 820.91) |
| 369 | m/z = 999.34(C72H46N3OP = 1000.13) | 370 | m/z = 1000.33(C71H45N4OP = 1001.12) |
| 371 | m/z = 540.20(C42H25N = 543.65) | 372 | m/z = 543.20(C42H25N = 543.65) |
| 373 | m/z = 619.23(C48H29N = 619.75) | 374 | m/z = 619.23(C48H29N = 619.75) |
| 375 | m/z = 645.25(C50H31N = 245.79) | 376 | m/z = 795.29(C62H37N = 795.96) |
| 377 | m/z = 921.34(C72H43N = 922.12) | 378 | m/z = 685.28(C53H35N = 685.85) |
| 379 | m/z = 809.31(C63H39N = 809.99) | 380 | m/z = 807.29(C63H37N = 807.29) |
| 381 | m/z = 619.23(C48H29N = 619.75) | 382 | m/z = 619.23(C48H29N = 619.75) |
| 383 | m/z = 645.25(C50H31N = 645.79) | 384 | m/z = 645.25(C50H31N = 645.79) |
| 385 | m/z = 646.24(C49H30N2 = 646.78) | 386 | m/z = 713.25(C52H31N3O = 713.82) |
| 387 | m/z = 659.22(C50H29NO = 659.77) | 388 | m/z = 675.20(C50H29NS = 675.84) |
| 389 | m/z = 722.27(C55H34N2 = 722.87) | 390 | m/z = 722.27(C55H34N2 = 722.87) |
| 391 | m/z = 540.20(C42H25N = 543.65) | 392 | m/z = 543.20(C42H25N = 543.65) |
| 393 | m/z = 619.23(C48H29N = 619.75) | 394 | m/z = 619.23(C48H29N = 619.75) |
| 395 | m/z = 645.25(C50H31N = 245.79) | 396 | m/z = 646.24(C49H30N2 = 646.78) |

TABLE 2-continued

| Compound | FD-Mass | Compound | FD-Mass |
|---|---|---|---|
| 397 | m/z = 646.24($C_{49}H_{30}N_2$ = 646.78) | 398 | m/z = 721.28($C_{56}H_{35}N$ = 721.88) |
| 399 | m/z = 723.86($C_{54}H_{33}N_3$ = 723.86) | 400 | m/z = 821.31($C_{64}H_{39}N$ = 821.31) |
| 401 | m/z = 619.23($C_{48}H_{29}N$ = 619.75) | 402 | m/z = 619.23($C_{48}H_{29}N$ = 619.75) |
| 403 | m/z = 645.25($C_{50}H_{31}N$ = 645.79) | 404 | m/z = 645.25($C_{50}H_{31}N$ = 645.79) |
| 405 | m/z = 646.24($C_{49}H_{30}N_2$ = 646.78) | 406 | m/z = 713.25($C_{52}H_{31}N_3O$ = 713.82) |
| 407 | m/z = 659.22($C_{50}H_{29}NO$ = 659.77) | 408 | m/z = 675.20($C_{50}H_{29}NS$ = 675.84) |
| 409 | m/z = 722.27($C_{55}H_{34}N_2$ = 722.87) | 410 | m/z = 722.27($C_{55}H_{34}N_2$ = 722.87) |

Meanwhile, FIGS. 4 to 17 illustrate measurement graphs of PL or LTPL of the compounds.

For the measurement of PL, a model name LS55 spectrometer manufactured by Perkin Elmer Inc., was used, and for the measurement of LTPL, a model name F7000 spectrometer manufactured by Hitachi, Ltd., was used, and an analysis was made at −196° C. (77 K) by using liquid nitrogen.

FIG. 4 illustrates a measurement graph of PL of Compound 37 at a wavelength of 265 nm.

FIG. 5 illustrates a measurement graph of LTPL of Compound 37 at a wavelength of 279 nm.

FIG. 6 illustrates a measurement graph of PL of Compound 43 at a wavelength of 298 nm.

FIG. 7 illustrates a measurement graph of LTPL of Compound 43 at a wavelength of 308 nm.

FIG. 8 illustrates a measurement graph of PL of Compound 44 at a wavelength of 278 nm.

FIG. 9 illustrates a measurement graph of LTPL of Compound 44 at a wavelength of 307 nm.

FIG. 10 illustrates a measurement graph of PL of Compound 76 at a wavelength of 309 nm.

FIG. 11 illustrates a measurement graph of LTPL of Compound 76 at a wavelength of 327 nm.

FIG. 12 illustrates a measurement graph of PL of Compound 98 at a wavelength of 271 nm.

FIG. 13 illustrates a measurement graph of LTPL of Compound 98 at a wavelength of 271 nm.

FIG. 14 illustrates a measurement graph of PL of Compound 248 at a wavelength of 262 nm.

FIG. 15 illustrates a measurement graph of LTPL of Compound 248 at a wavelength of 307 nm.

FIG. 16 illustrates a measurement graph of PL of Compound 267 at a wavelength of 280 nm.

FIG. 17 illustrates a measurement graph of PL of Compound 275 at a wavelength of 325 nm.

In the PL/LTPL graphs of FIGS. 4 to 17, the y-coordinate refers to intensity, and the x-coordinate refers to wavelength (unit: nm).

Manufacture of Organic Electroluminescence Device

COMPARATIVE EXAMPLE 1

Trichloroethylene, acetone, ethanol, and distilled water were sequentially used to ultrasonically wash a transparent electrode ITO thin film obtained from glass for OLED (manufactured by Samsung-Corning Co., Ltd.) for each of 5 minutes, and then the ITO thin film was placed in isopropanol, stored, and then used.

Next, the ITO substrate was installed in a vacuum deposition device. Sequentially, in a vacuum chamber, 4,4',4"-tris(N,N-(2-naphthyl)-phenylamino)triphenyl amine (2-TNATA) was vacuum deposited to a thickness of 600 Å on the ITO, thereby forming a hole injection layer.

Thereafter, a hole transporting layer was formed by depositing N,N'-bis(α-naphthyl)-N,N'-diphenyl-4,4'-diamine (NPB) under vacuum to a thickness of 300 Å on the hole injection layer.

And then, a light emitting layer having a thickness of 200 Å was deposited under vacuum on the hole transporting layer by setting a blue light emitting host material H1 and a blue light emitting dopant material D1 at a ratio of 95:5.

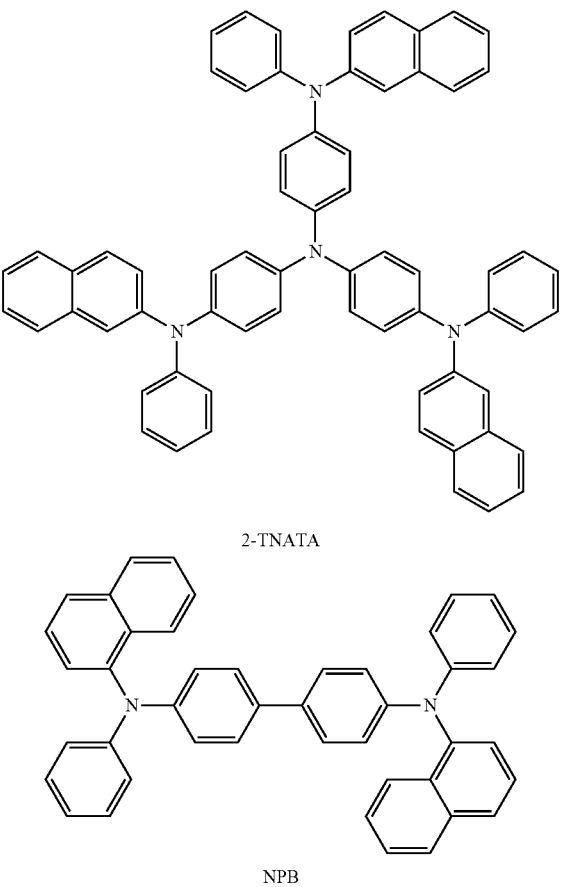

2-TNATA

NPB

-continued

H1
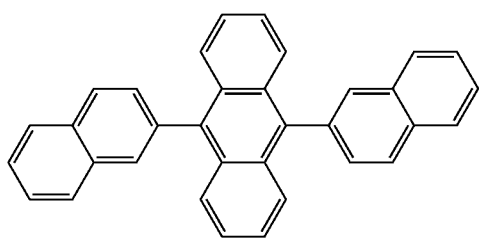

D1
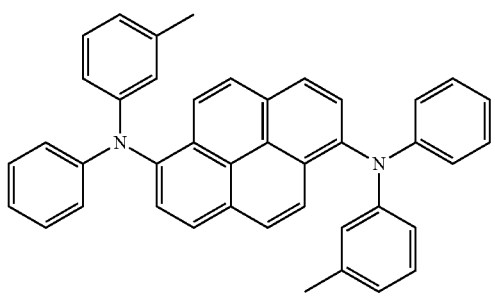

Subsequently, the compound of the following structural formula E1 was deposited to a thickness of 300 Å on the light emitting layer, thereby forming an electron transporting layer.

E1
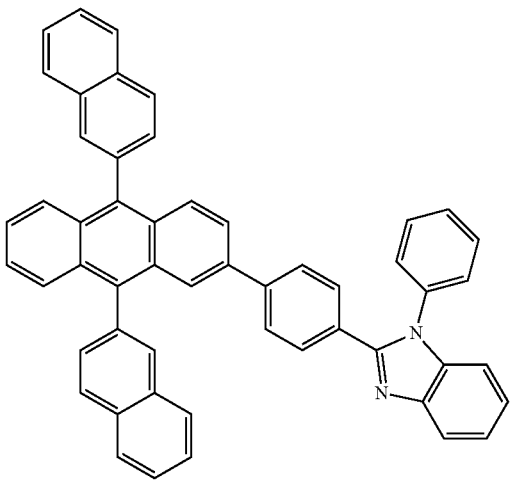

Thereafter, lithium fluoride (LiF) was deposited to a thickness of 10 Å as an electron injection layer on the electron transporting layer, and Al was deposited to a thickness of 1,000 Å on the electron injection layer to form a negative electrode, thereby manufacturing an OLED.

Meanwhile, all the organic compounds required for manufacturing an OLED were subjected to vacuum sublimed purification under $10^{-6}$ to $10^{-8}$ torr for each material, and used for the manufacture of the OLED.

EXAMPLES 1 TO 145

An organic electroluminescence device was manufactured in the same manner as in Comparative Example 1, except that the compound of the following Table 3 was used instead of E1 used when an electron transporting layer was formed in Comparative Example 1.

EXPERIMENTAL EXAMPLE

Evaluation of Organic Electroluminescence Device

For each of the organic electroluminescence devices manufactured in Comparative Examples 1 and Examples 1 to 145, the driving voltage, the efficiency, the color coordinate, and the service life were measured at a light emitting brightness of 700 cd/m² and evaluated, and the results are shown in the following Table 3. In this case, the service life was measured by using M6000PMX manufactured by Mac Science Co., Ltd.

TABLE 3

| | Electron transporting layer material | Driving voltage (V) | Efficiency (cd/A) | Color coordinate (x, y) | Service life ($T_{50}$) |
|---|---|---|---|---|---|
| Comparative Example 1 | E1 | 4.7 | 4.5 | (0.15, 0.18) | 330 |
| Example 1 | Compound 2 | 5.77 | 3.87 | (0.149, 0.182) | 355 |
| Example 2 | Compound 3 | 4.6 | 4.8 | (0.15, 0.18) | 376 |
| Example 3 | Compound 5 | 4.2 | 4.7 | (0.14, 0.18) | 355 |
| Example 4 | Compound 12 | 4.6 | 4.9 | (0.15, 0.18) | 370 |
| Example 5 | Compound 14 | 4.3 | 4.5 | (0.15, 0.17) | 354 |
| Example 6 | Compound 15 | 4.3 | 4.6 | (0.15, 0.19) | 356 |
| Example 7 | Compound 17 | 4.2 | 5.0 | (0.15, 0.17) | 421 |
| Example 8 | Compound 18 | 4.48 | 4.48 | (0.153, 0.186) | 960 |
| Example 9 | Compound 19 | 4.3 | 4.9 | (0.15, 0.17) | 520 |
| Example 10 | Compound 21 | 4.5 | 4.6 | (0.15, 0.18) | 358 |
| Example 11 | Compound 25 | 4.7 | 4.6 | (0.15, 0.19) | 346 |
| Example 12 | Compound 28 | 4.22 | 5.59 | (0.150, 0.182) | 400 |
| Example 13 | Compound 30 | 4.5 | 5.0 | (0.14, 0.19) | 334 |
| Example 14 | Compound 31 | 4.2 | 4.8 | (0.15, 0.17) | 340 |
| Example 15 | Compound 32 | 4.6 | 4.6 | (0.15, 0.18) | 336 |
| Example 16 | Compound 37 | 4.54 | 5.61 | (0.149, 0.182) | 370 |
| Example 17 | Compound 41 | 4.58 | 4.98 | (0.149, 0.180) | 288 |
| Example 18 | Compound 42 | 4.3 | 4.6 | (0.15, 0.17) | 380 |
| Example 19 | Compound 43 | 4.48 | 4.94 | (0.148, 0.182) | 192 |
| Example 20 | Compound 44 | 5.27 | 3.49 | (0.148, 0.186) | 672 |
| Example 21 | Compound 45 | 4.3 | 4.8 | (0.15, 0.17) | 370 |
| Example 22 | Compound 47 | 3.9 | 4.7 | (0.15, 0.18) | 367 |
| Example 23 | Compound 52 | 4.3 | 4.9 | (0.15, 0.18) | 370 |
| Example 24 | Compound 53 | 4.4 | 4.6 | (0.15, 0.17) | 354 |
| Example 25 | Compound 61 | 4.4 | 4.5 | (0.15, 0.17) | 336 |
| Example 26 | Compound 63 | 4.6 | 4.8 | (0.15, 0.18) | 376 |
| Example 27 | Compound 66 | 4.5 | 4.9 | (0.15, 0.18) | 379 |
| Example 28 | Compound 67 | 4.5 | 5.0 | (0.15, 0.18) | 487 |

TABLE 3-continued

| | Electron transporting layer material | Driving voltage (V) | Efficiency (cd/A) | Color coordinate (x, y) | Service life ($T_{50}$) |
|---|---|---|---|---|---|
| Example 29 | Compound 68 | 4.5 | 4.7 | (0.15, 0.18) | 343 |
| Example 30 | Compound 69 | 4.5 | 4.8 | (0.15, 0.18) | 360 |
| Example 31 | Compound 70 | 3.9 | 5.0 | (0.15, 0.18) | 401 |
| Example 32 | Compound 71 | 4.1 | 4.8 | (0.15, 0.17) | 402 |
| Example 33 | Compound 72 | 4.1 | 4.9 | (0.15, 0.17) | 489 |
| Example 34 | Compound 73 | 4.5 | 4.6 | (0.14, 0.18) | 532 |
| Example 35 | Compound 75 | 4.5 | 4.7 | (0.15, 0.19) | 344 |
| Example 36 | Compound 76 | 4.60 | 4.71 | (0.153, 0.167) | 350 |
| Example 37 | Compound 77 | 4.69 | 3.45 | (0.150, 0.177) | 420 |
| Example 38 | Compound 78 | 4.5 | 4.7 | (0.15, 0.18) | 402 |
| Example 39 | Compound 79 | 4.5 | 4.8 | (0.15, 0.18) | 390 |
| Example 40 | Compound 80 | 4.6 | 5.0 | (0.15, 0.18) | 339 |
| Example 41 | Compound 81 | 4.6 | 4.7 | (0.15, 0.18) | 419 |
| Example 42 | Compound 82 | 4.5 | 5.1 | (0.15, 0.19) | 404 |
| Example 43 | Compound 85 | 4.3 | 4.8 | (0.15, 0.18) | 355 |
| Example 44 | Compound 87 | 4.4 | 4.7 | (0.15, 0.19) | 369 |
| Example 45 | Compound 89 | 4.7 | 4.6 | (0.15, 0.17) | 343 |
| Example 46 | Compound 93 | 4.3 | 4.9 | (0.15, 0.18) | 398 |
| Example 47 | Compound 94 | 4.4 | 4.6 | (0.15, 0.18) | 389 |
| Example 48 | Compound 96 | 4.1 | 4.7 | (0.15, 0.18) | 378 |
| Example 49 | Compound 98 | 4.30 | 4.65 | (0.148, 0.182) | 380 |
| Example 50 | Compound 101 | 4.54 | 4.64 | (0.153, 0.167) | 317 |
| Example 51 | Compound 103 | 4.5 | 4.7 | (0.15, 0.18) | 342 |
| Example 52 | Compound 104 | 4.6 | 4.6 | (0.15, 0.19) | 342 |
| Example 53 | Compound 109 | 4.6 | 4.7 | (0.15, 0.19) | 342 |
| Example 54 | Compound 113 | 4.5 | 4.6 | (0.15, 0.18) | 342 |
| Example 55 | Compound 114 | 4.5 | 5.0 | (0.15, 0.19) | 334 |
| Example 56 | Compound 120 | 4.48 | 4.86 | (0.153, 0.170) | 317 |
| Example 57 | Compound 122 | 4.7 | 4.8 | (0.15, 0.18) | 356 |
| Example 58 | Compound 124 | 4.7 | 4.6 | (0.15, 0.18) | 339 |
| Example 59 | Compound 128 | 4.6 | 4.7 | (0.15, 0.18) | 342 |
| Example 60 | Compound 130 | 4.7 | 4.6 | (0.15, 0.18) | 343 |
| Example 61 | Compound 146 | 4.37 | 4.98 | (0.153, 0.171) | 576 |
| Example 62 | Compound 151 | 4.0 | 4.8 | (0.15, 0.18) | 386 |
| Example 63 | Compound 152 | 3.8 | 5.0 | (0.15, 0.19) | 389 |
| Example 64 | Compound 157 | 3.9 | 4.7 | (0.15, 0.18) | 419 |
| Example 65 | Compound 159 | 4.43 | 4.94 | (0.153, 0.169) | 480 |
| Example 66 | Compound 162 | 4.6 | 5.0 | (0.15, 0.18) | 370 |
| Example 67 | Compound 166 | 4.4 | 4.6 | (0.15, 0.19) | 342 |
| Example 68 | Compound 167 | 4.5 | 4.6 | (0.15, 0.18) | 378 |
| Example 69 | Compound 169 | 4.6 | 4.7 | (0.15, 0.19) | 346 |
| Example 70 | Compound 172 | 4.5 | 4.8 | (0.15, 0.18) | 378 |
| Example 71 | Compound 176 | 4.2 | 4.7 | (0.15, 0.18) | 355 |
| Example 72 | Compound 177 | 4.6 | 4.9 | (0.15, 0.18) | 370 |
| Example 73 | Compound 180 | 4.4 | 4.6 | (0.15, 0.17) | 354 |
| Example 74 | Compound 182 | 4.4 | 4.5 | (0.15, 0.17) | 339 |
| Example 75 | Compound 187 | 4.43 | 4.56 | (0.153, 0.166) | 576 |
| Example 76 | Compound 189 | 4.4 | 4.8 | (0.15, 0.18) | 399 |
| Example 77 | Compound 190 | 4.5 | 4.6 | (0.15, 0.18) | 358 |
| Example 78 | Compound 193 | 4.1 | 5.1 | (0.15, 0.18) | 380 |
| Example 79 | Compound 194 | 4.4 | 4.7 | (0.15, 0.18) | 389 |
| Example 80 | Compound 198 | 3.9 | 4.9 | (0.15, 0.18) | 430 |
| Example 81 | Compound 200 | 4.7 | 4.6 | (0.15, 0.17) | 343 |
| Example 82 | Compound 213 | 4.5 | 4.6 | (0.15, 0.19) | 345 |
| Example 83 | Compound 214 | 4.6 | 4.6 | (0.15, 0.19) | 335 |
| Example 84 | Compound 217 | 4.5 | 4.7 | (0.15, 0.18) | 354 |
| Example 85 | Compound 220 | 4.6 | 4.6 | (0.15, 0.19) | 348 |
| Example 86 | Compound 223 | 4.7 | 4.8 | (0.15, 0.19) | 356 |
| Example 87 | Compound 225 | 4.3 | 4.8 | (0.15, 0.18) | 355 |
| Example 88 | Compound 227 | 4.1 | 4.9 | (0.15, 0.18) | 480 |
| Example 89 | Compound 230 | 4.3 | 5.2 | (0.15, 0.18) | 402 |
| Example 90 | Compound 233 | 4.55 | 4.64 | (0.153, 0.175) | 499 |
| Example 91 | Compound 235 | 4.3 | 4.6 | (0.15, 0.18) | 368 |
| Example 92 | Compound 237 | 4.37 | 5.02 | (0.153, 0.177) | 518 |
| Example 93 | Compound 239 | 4.45 | 4.86 | (0.153, 0.180) | 499 |
| Example 94 | Compound 240 | 4.1 | 4.6 | (0.15, 0.19) | 390 |
| Example 95 | Compound 241 | 3.8 | 4.6 | (0.15, 0.17) | 489 |
| Example 96 | Compound 242 | 4.59 | 4.64 | (0.153, 0.172) | 509 |
| Example 97 | Compound 245 | 4.59 | 4.64 | (0.153, 0.172) | 509 |
| Example 98 | Compound 246 | 4.2 | 4.9 | (0.15, 0.17) | 450 |
| Example 99 | Compound 248 | 4.24 | 4.64 | (0.153, 0.172) | 345 |
| Example 100 | Compound 250 | 4.5 | 4.6 | (0.15, 0.18) | 358 |
| Example 101 | Compound 253 | 4.3 | 4.7 | (0.15, 0.19) | 433 |
| Example 102 | Compound 255 | 4.2 | 4.9 | (0.15, 0.19) | 423 |

TABLE 3-continued

| | Electron transporting layer material | Driving voltage (V) | Efficiency (cd/A) | Color coordinate (x, y) | Service life ($T_{50}$) |
|---|---|---|---|---|---|
| Example 103 | Compound 261 | 4.2 | 4.8 | (0.15, 0.18) | 478 |
| Example 104 | Compound 263 | 4.1 | 4.8 | (0.15, 0.19) | 411 |
| Example 105 | Compound 266 | 4.3 | 4.8 | (0.15, 0.18) | 498 |
| Example 106 | Compound 267 | 4.2 | 4.8 | (0.15, 0.18) | 402 |
| Example 107 | Compound 268 | 4.2 | 4.7 | (0.15, 0.18) | 412 |
| Example 108 | Compound 274 | 4.4 | 4.6 | (0.15, 0.18) | 488 |
| Example 109 | Compound 275 | 4.1 | 4.8 | (0.15, 0.18) | 423 |
| Example 110 | Compound 276 | 4.3 | 4.9 | (0.15, 0.18) | 398 |
| Example 111 | Compound 278 | 4.0 | 5.0 | (0.15, 0.17) | 452 |
| Example 112 | Compound 283 | 3.9 | 4.8 | (0.15, 0.18) | 520 |
| Example 113 | Compound 287 | 4.1 | 4.8 | (0.15, 0.18) | 403 |
| Example 114 | Compound 290 | 3.9 | 4.9 | (0.15, 0.18) | 421 |
| Example 115 | Compound 292 | 4.4 | 4.7 | (0.15, 0.18) | 580 |
| Example 116 | Compound 296 | 4.7 | 4.6 | (0.15, 0.19) | 346 |
| Example 117 | Compound 298 | 4.5 | 5.0 | (0.15, 0.19) | 334 |
| Example 118 | Compound 304 | 4.2 | 4.8 | (0.15, 0.17) | 340 |
| Example 119 | Compound 305 | 4.1 | 5.1 | (0.15, 0.18) | 470 |
| Example 120 | Compound 307 | 4.5 | 5.0 | (0.15, 0.18) | 401 |
| Example 121 | Compound 311 | 4.3 | 4.8 | (0.15, 0.18) | 440 |
| Example 122 | Compound 316 | 4.4 | 5.2 | (0.15, 0.18) | 398 |
| Example 123 | Compound 322 | 4.5 | 4.9 | (0.15, 0.18) | 560 |
| Example 124 | Compound 323 | 4.5 | 5.1 | (0.15, 0.18) | 390 |
| Example 125 | Compound 326 | 4.4 | 4.9 | (0.15, 0.18) | 450 |
| Example 126 | Compound 333 | 4.3 | 4.8 | (0.15, 0.19) | 480 |
| Example 127 | Compound 335 | 4.5 | 4.9 | (0.15, 0.18) | 388 |
| Example 128 | Compound 338 | 4.2 | 4.7 | (0.15, 0.19) | 452 |
| Example 129 | Compound 345 | 4.4 | 4.9 | (0.15, 0.19) | 474 |
| Example 130 | Compound 347 | 4.6 | 5.1 | (0.15, 0.18) | 397 |
| Example 131 | Compound 350 | 4.3 | 4.9 | (0.15, 0.19) | 447 |
| Example 132 | Compound 356 | 4.4 | 4.8 | (0.15, 0.18) | 520 |
| Example 133 | Compound 359 | 4.5 | 4.9 | (0.15, 0.18) | 401 |
| Example 134 | Compound 362 | 4.2 | 4.7 | (0.15, 0.18) | 466 |
| Example 135 | Compound 370 | 4.2 | 4.9 | (0.15, 0.18) | 512 |
| Example 136 | Compound 372 | 4.5 | 4.7 | (0.15, 0.18) | 344 |
| Example 137 | Compound 375 | 4.5 | 4.6 | (0.15, 0.19) | 365 |
| Example 138 | Compound 380 | 4.3 | 4.9 | (0.15, 0.18) | 423 |
| Example 139 | Compound 383 | 4.1 | 4.6 | (0.15, 0.19) | 355 |
| Example 140 | Compound 388 | 4.2 | 5.0 | (0.15, 0.18) | 402 |
| Example 141 | Compound 393 | 4.3 | 4.7 | (0.15, 0.18) | 365 |
| Example 142 | Compound 398 | 4.5 | 4.7 | (0.15, 0.18) | 388 |
| Example 143 | Compound 403 | 4.3 | 4.7 | (0.15, 0.18) | 382 |
| Example 144 | Compound 404 | 4.3 | 4.8 | (0.15, 0.18) | 374 |
| Example 145 | Compound 407 | 3.8 | 4.9 | (0.15, 0.18) | 498 |

As can be seen from the result of Table 3, an organic electroluminescence device using the compound of the present application as an electron transporting layer material has a low driving voltage, an improved light emitting efficiency, and a significantly improved service life as compared to Comparative Example 1.

The invention claimed is:
1. A compound represented by the following Chemical Formula 5:

[Chemical Formula 5]

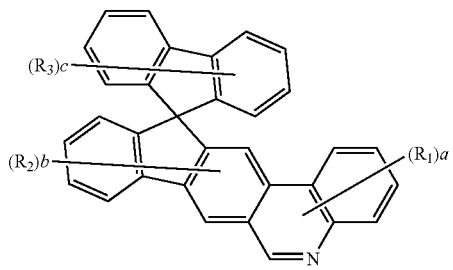

in Chemical Formula 5,
$R_1$ to $R_3$ are the same as or different from each other, and are each independently selected from the group consisting of hydrogen; halogen; a substituted or unsubstituted $C_1$ to $C_{60}$ alkyl; a substituted or unsubstituted $C_2$ to $C_{60}$ alkenyl; a substituted or unsubstituted $C_2$ to $C_{60}$ alkynyl; a substituted or unsubstituted $C_1$ to $C_{60}$ alkoxy; a substituted or unsubstituted $C_3$ to $C_{60}$ cycloalkyl; a substituted or unsubstituted $C_2$ to $C_{60}$ heterocycloalkyl; a substituted or unsubstituted $C_6$ to $C_{60}$ aryl; a substituted or unsubstituted $C_2$ to $C_{60}$ heteroaryl; —SiRR'R", and —P(=O)RR',
R, R', and R" are the same as or different from each other, and are each independently selected from the group consisting of hydrogen; deuterium; a substituted or unsubstituted $C_1$ to $C_{60}$ alkyl; a substituted or unsubstituted $C_3$ to $C_{60}$ cycloalkyl; a substituted or unsubstituted $C_6$ to $C_{60}$ aryl; and a substituted or unsubstituted $C_2$ to $C_{60}$ heteroaryl,
a is an integer of 1 to 5,
b is an integer of 0 to 6,
c is an integer of 0 to 8, and
when a, b, and c are each 2 or more, a plurality of $R_1$, $R_2$, and $R_3$ is each the same as or different from each other.

2. The compound of claim 1, wherein Chemical Formula 5 is represented by the following Chemical Formula 5-1:

[Chemical Formula 5-1]

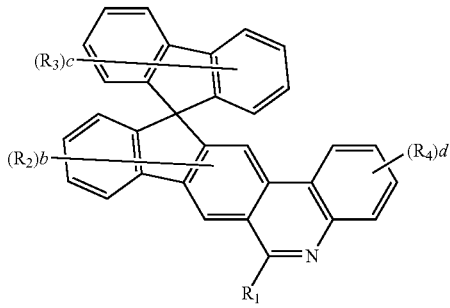

in Chemical Formula 5-1, $R_4$ is the same as the definition of $R_1$ of Chemical Formula 5, d is an integer of 0 to 4, and when d is 2 or more, a plurality of $R_4$ is the same as or different from each other, and $R_1$ to $R_3$, b, and c are the same as those defined in Chemical Formula 5.

3. The compound of claim 1, wherein $R_1$ is -(L)m-(Z)n,

L is a substituted or unsubstituted $C_6$ to $C_{60}$ arylene; or a substituted or unsubstituted $C_2$ to $C_{60}$ heteroarylene, m is an integer of 0 to 5, n is an integer of 1 to 3, Z is selected from the group consisting of a substituted or unsubstituted $C_6$ to $C_{60}$ aryl; a substituted or unsubstituted $C_2$ to $C_{60}$ heteroaryl; —SiRR'R", and —P(=O)RR', and R, R', and R" are the same as or different from each other, and are each independently selected from the group consisting of hydrogen; deuterium; a substituted or unsubstituted $C_1$ to $C_{60}$ alkyl; a substituted or unsubstituted $C_3$ to $C_{60}$ cycloalkyl; a substituted or unsubstituted $C_6$ to $C_{60}$ aryl; and a substituted or unsubstituted $C_2$ to $C_{60}$ heteroaryl.

4. The compound of claim 3, wherein Z is a substituted or unsubstituted phenyl, a substituted or unsubstituted biphenyl, a substituted or unsubstituted naphthyl, a substituted or unsubstituted chrysenyl, a substituted or unsubstituted pyrenyl, a substituted or unsubstituted triphenylenyl, a substituted or unsubstituted anthracenyl, a substituted or unsubstituted phenanthrenyl, a substituted or unsubstituted fluorenyl, or a substituted or unsubstituted spirobifluorenyl.

5. The compound of claim 3, wherein Z is a substituted or unsubstituted $C_2$ to $C_{60}$ heteroaryl, and the heteroaryl comprises at least one selected from N, O, S, Si, and Se, as a heteroatom.

6. The compound of claim 3, wherein Z is

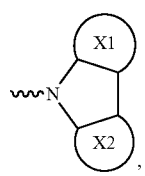

and X1 and X2 are the same as or different from each other, and are each independently a substituted or unsubstituted $C_6$ to $C_{60}$ aromatic hydrocarbon ring; or a substituted or unsubstituted $C_2$ to $C_{60}$ aromatic hetero ring.

7. The compound of claim 6, wherein

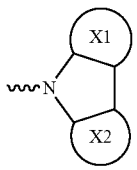

is represented by any one of the following structural formulae:

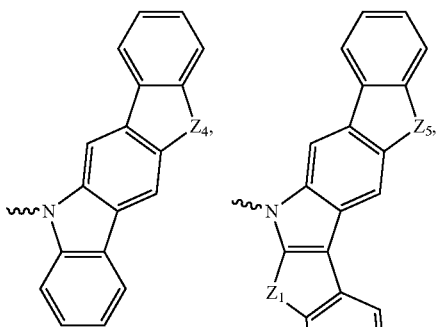

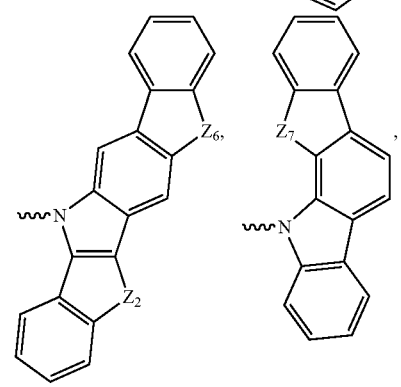

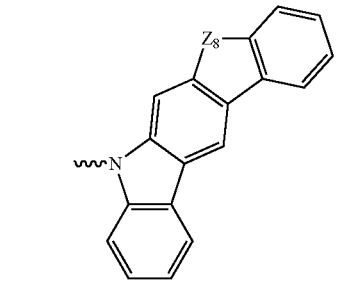

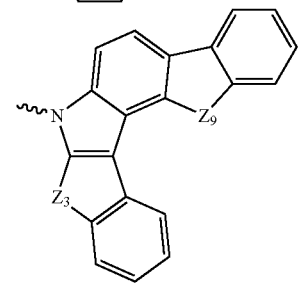

in the structural formulae, $Z_1$ to $Z_3$ are the same as or different from each other, and are each independently S or O, $Z_4$ to $Z_9$ are the same as or different from each other, and are each independently CY'Y", NY', S, or O, and Y' and Y" are the same as or different from each other, and are each independently hydrogen; deuterium; a substituted or unsubstituted $C_1$ to $C_{60}$ alkyl; or a substituted or unsubstituted $C_6$ to $C_{60}$ aryl.

8. The compound of claim 1, wherein $R_2$ and $R_3$ are the same as or different from each other, and each independently hydrogen; or a $C_6$ to $C_{60}$ aryl.

9. The compound of claim 2, wherein $R_2$ to $R_4$ are the same as or different from each other, and each independently hydrogen; or a $C_6$ to $C_{60}$ aryl.

10. The compound of claim 2, wherein b, c, and d are 0.

11. The compound of claim 1, wherein the compound of Chemical Formula 5 is selected from the following compounds:

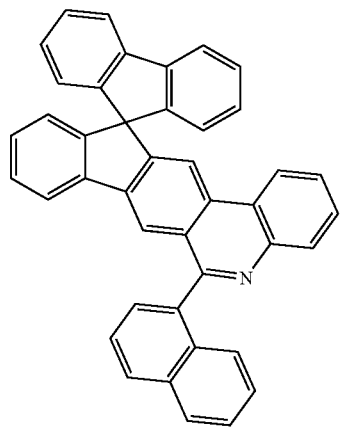
166

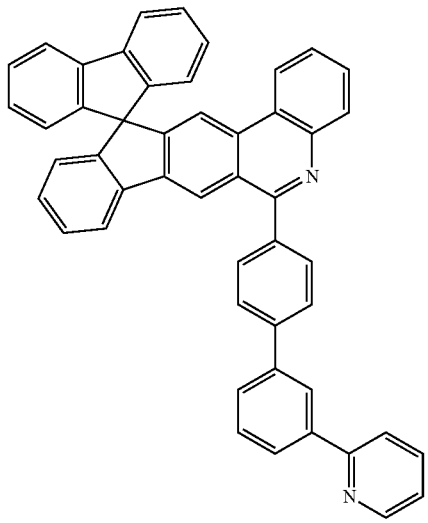
168

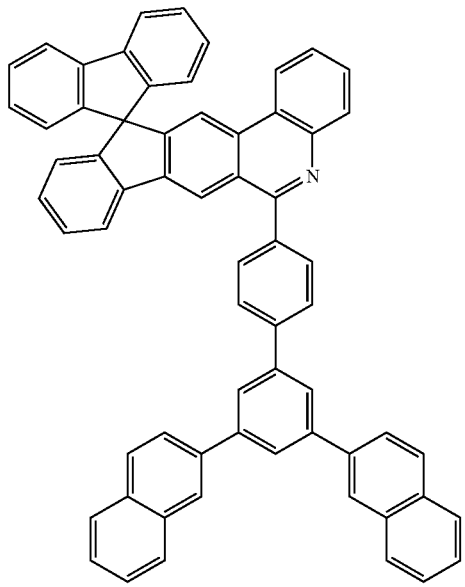
169

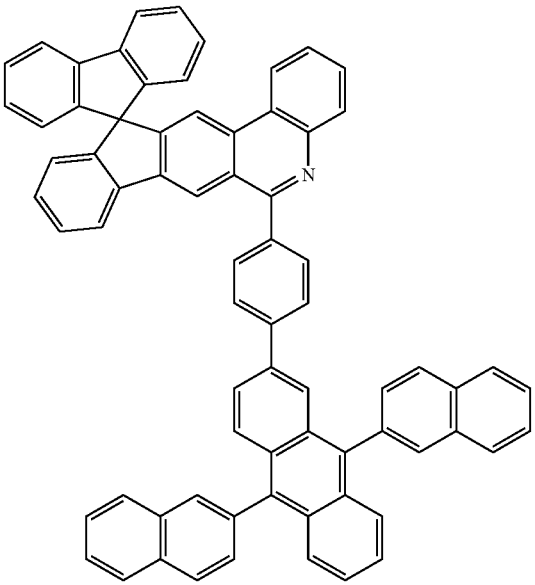
170

171
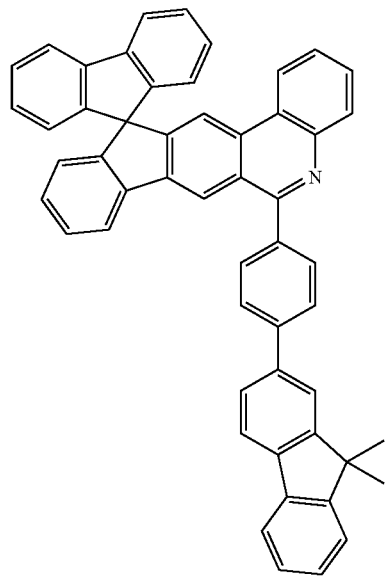
172
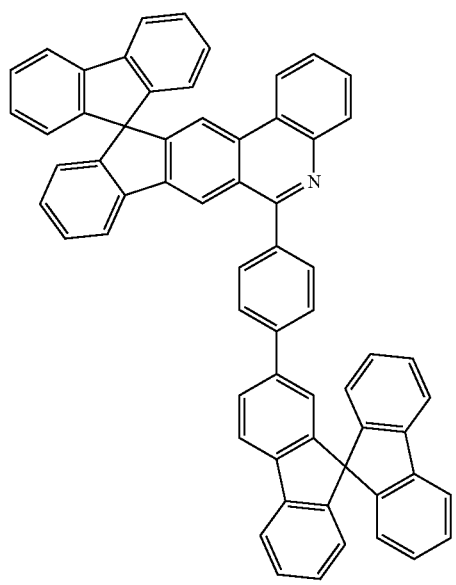
173
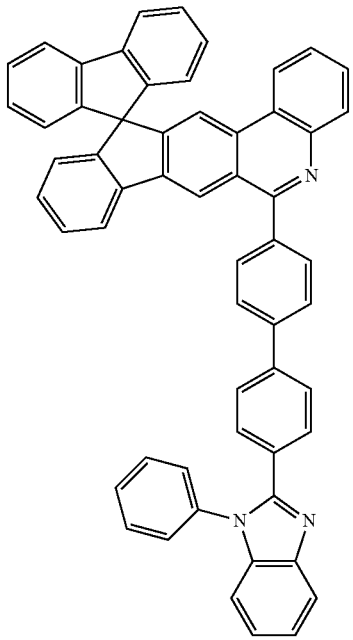
174
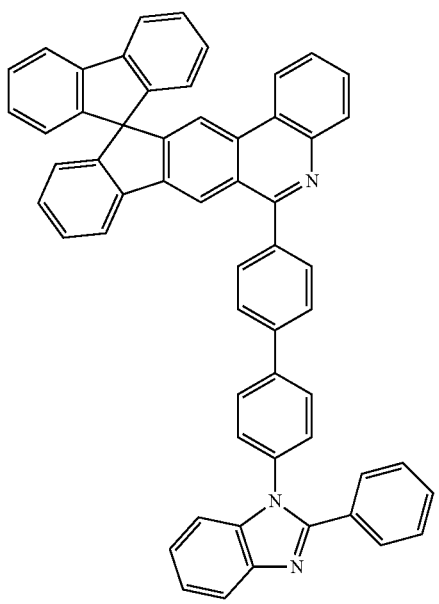
175

241
-continued
176
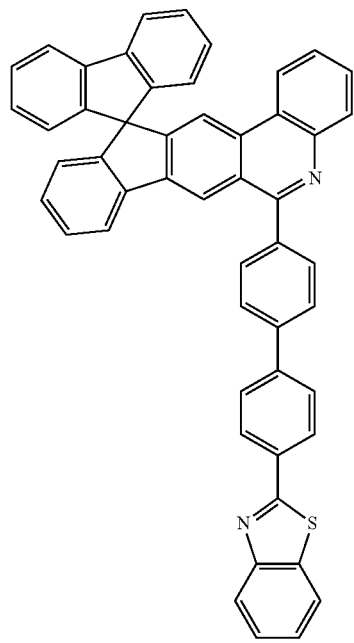
177
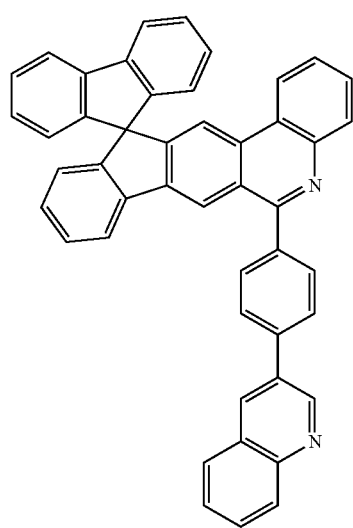
242
-continued
178
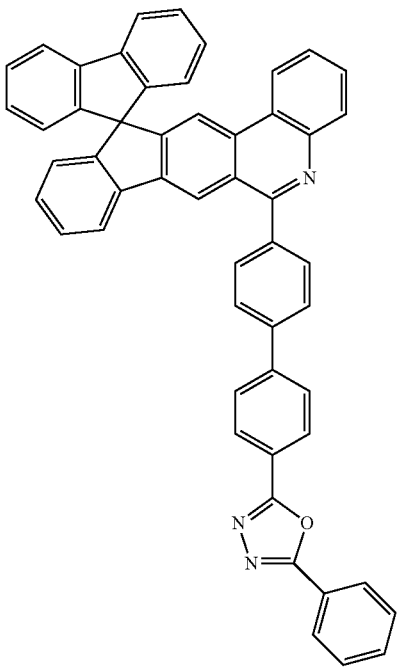
179
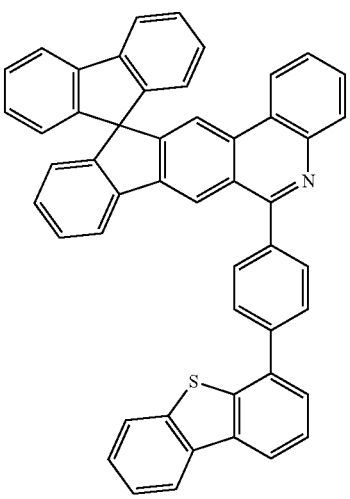

180
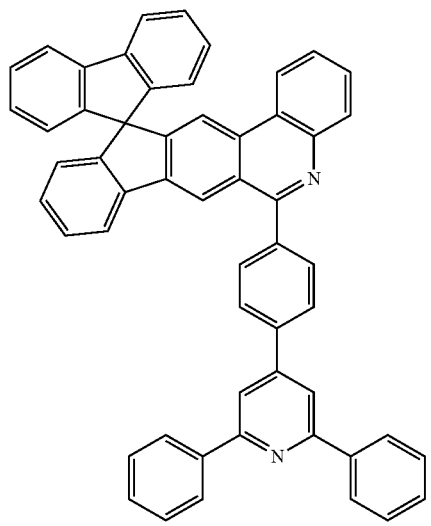
181
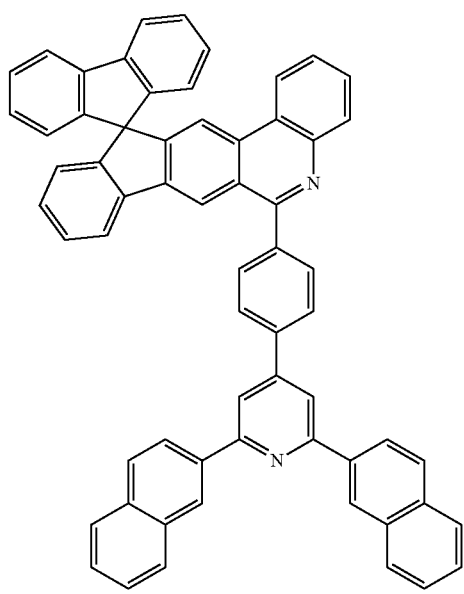
182
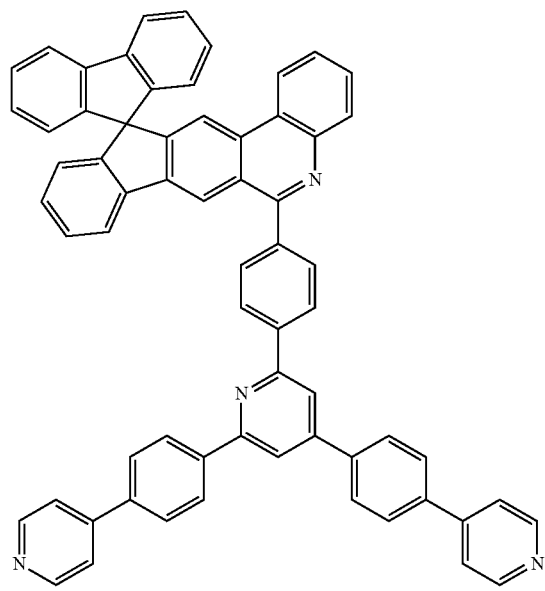
183
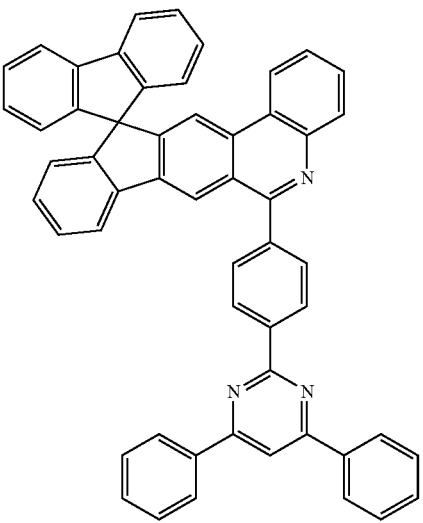

245
-continued
184
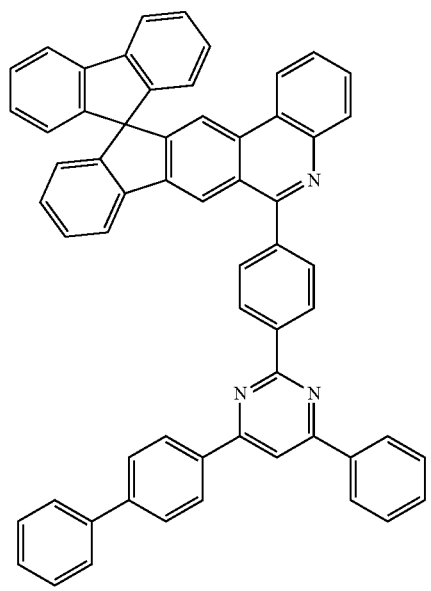
185
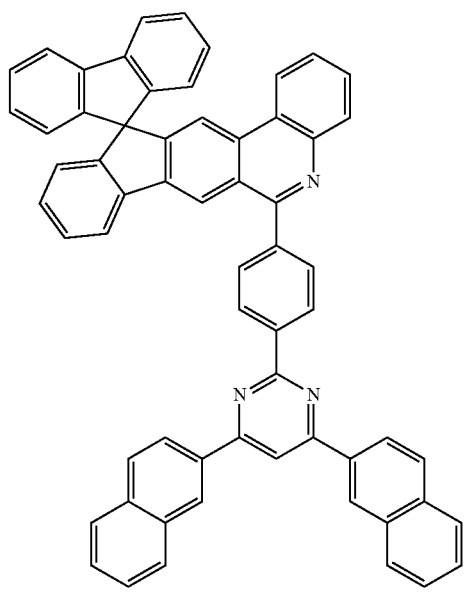
246
-continued
186
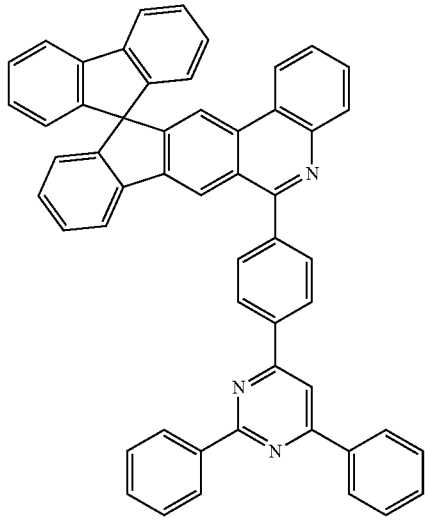
187
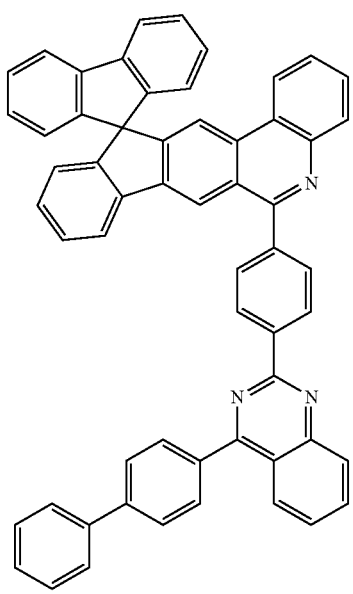
188
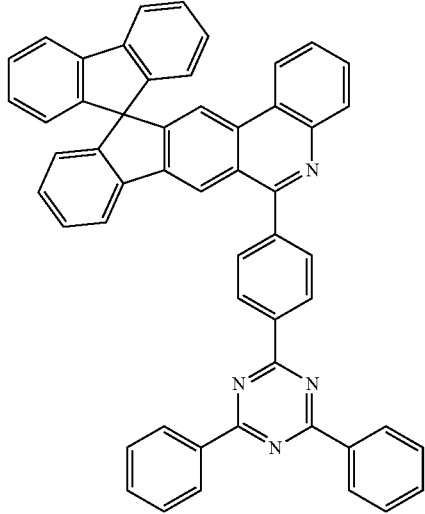

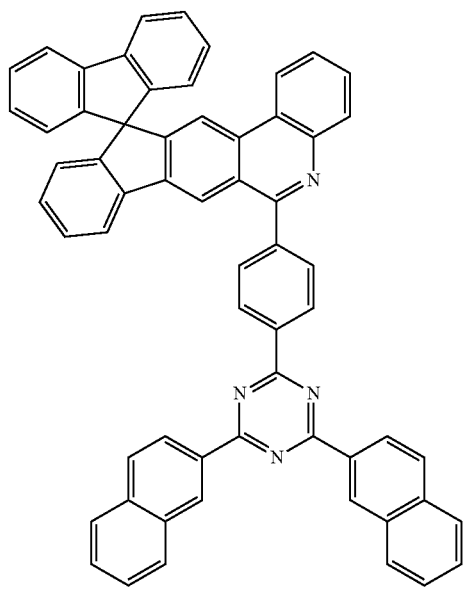
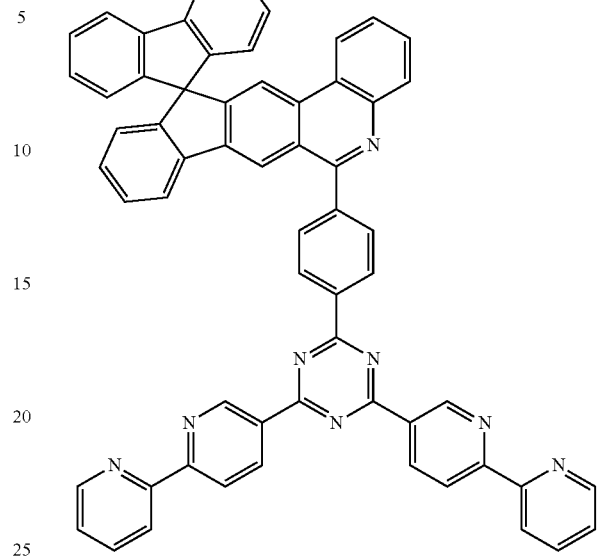
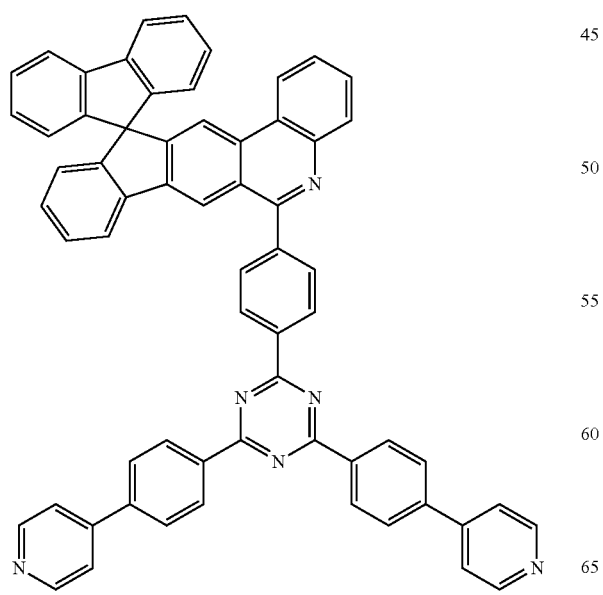
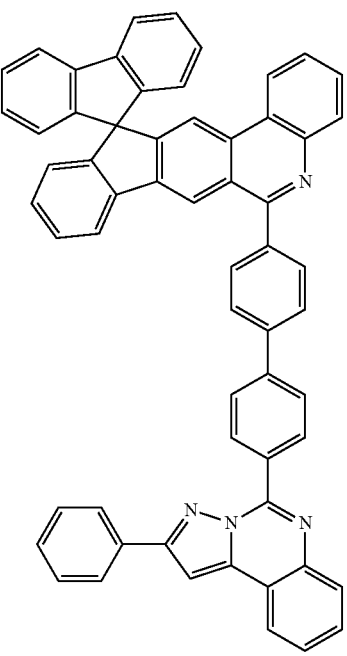

249
-continued
193
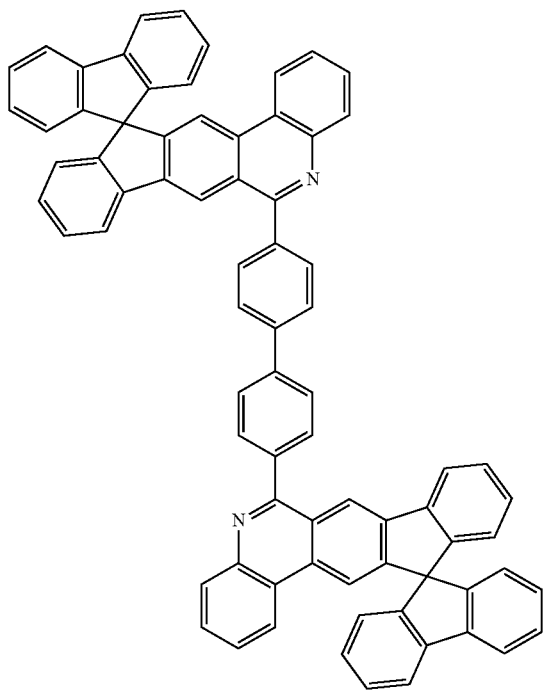
194
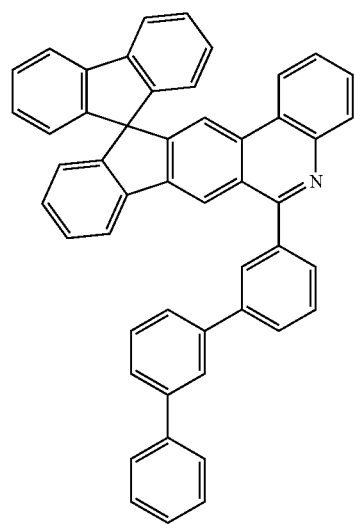
250
-continued
195
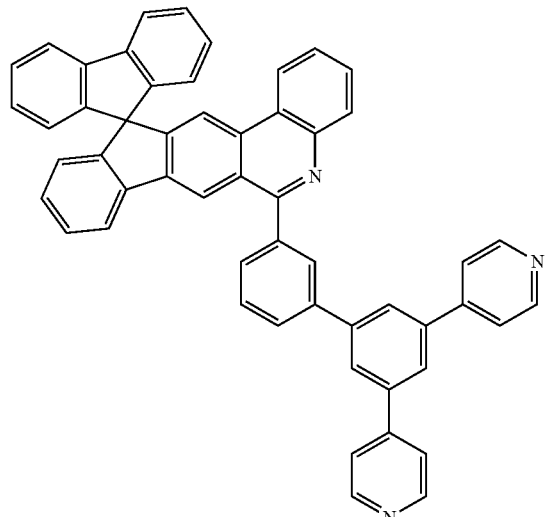
196
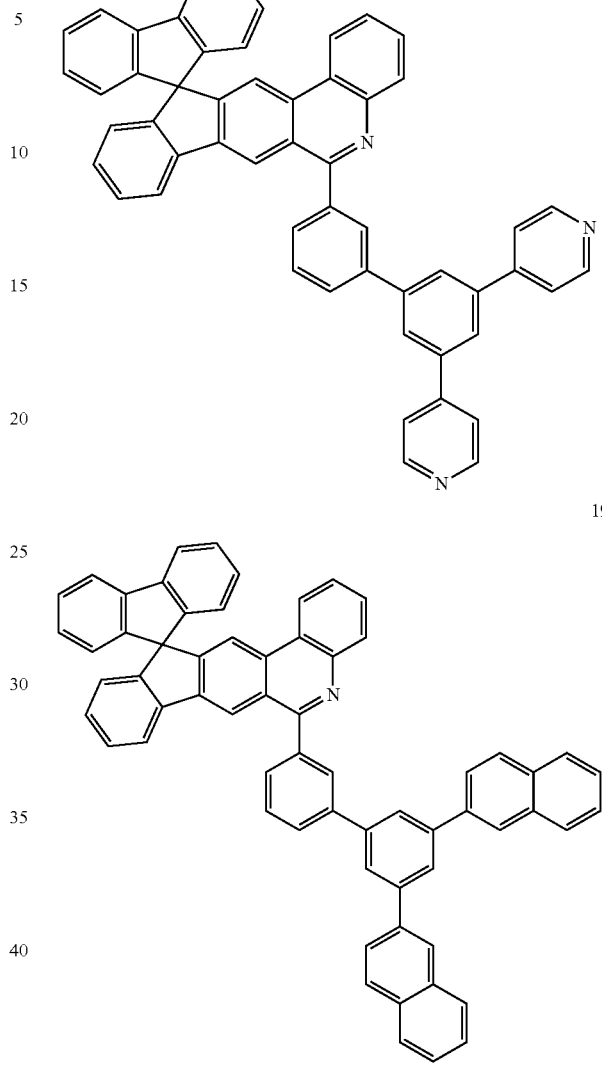
197
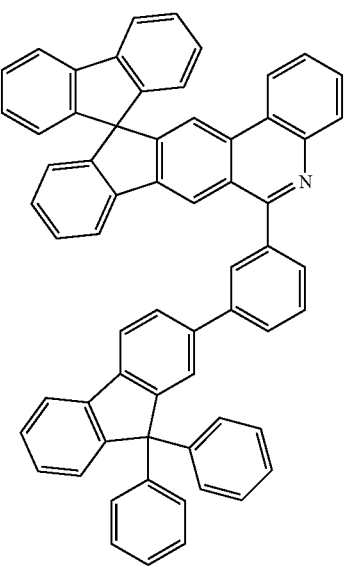

251 -continued
198
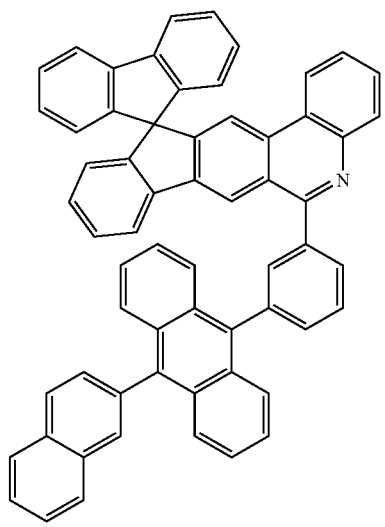
199
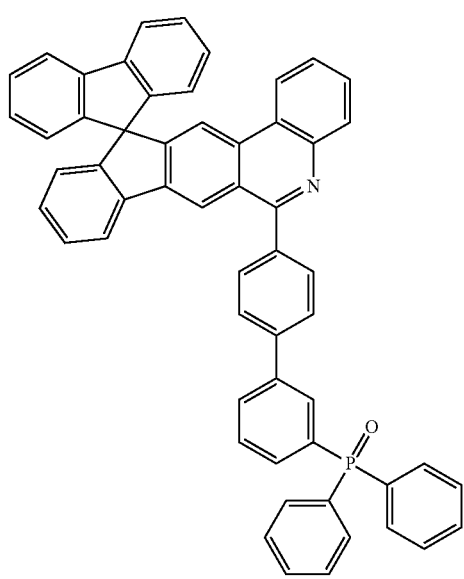
252 -continued
201
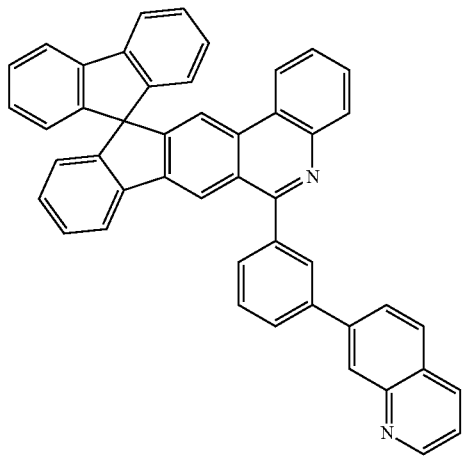
202
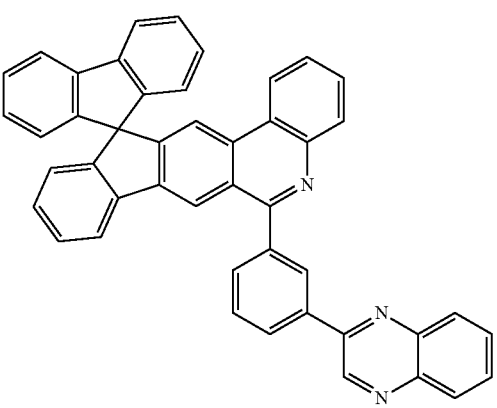
203
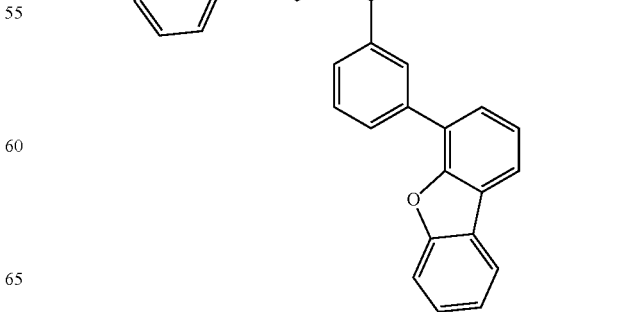

204
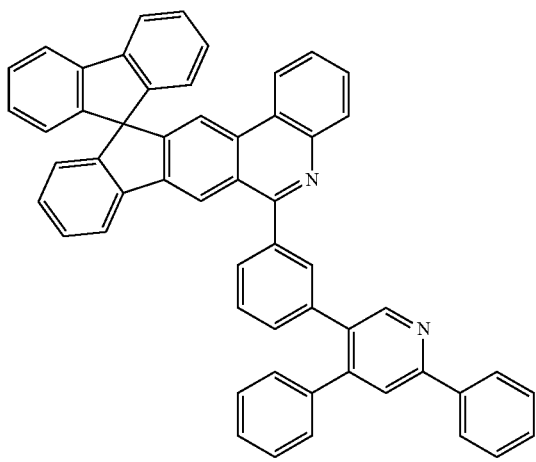
205
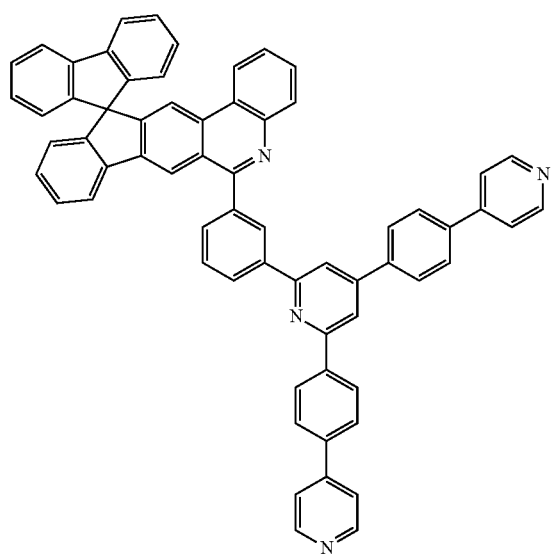
206
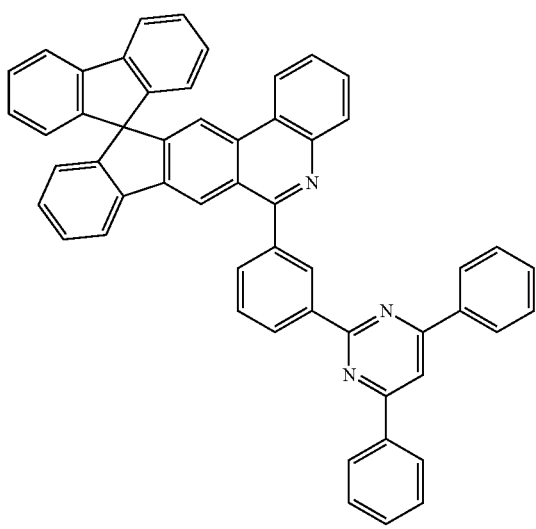
207
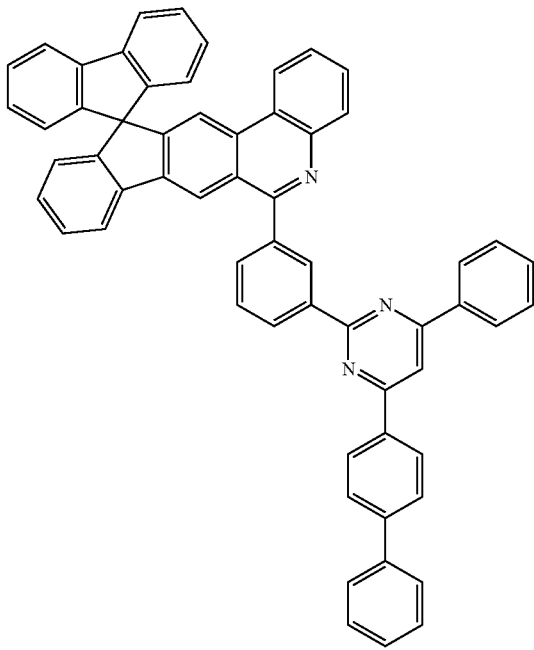
208
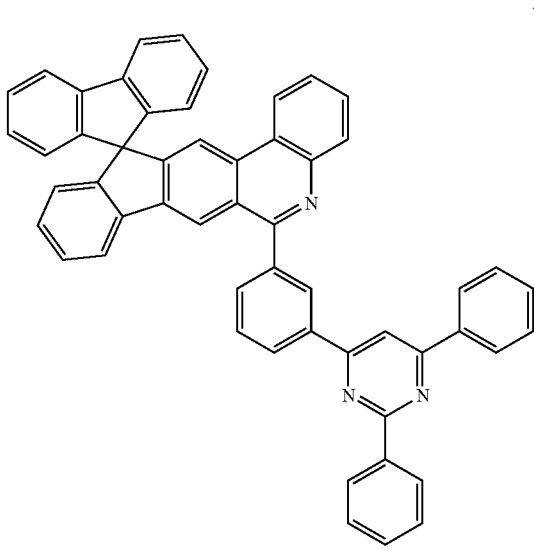
209
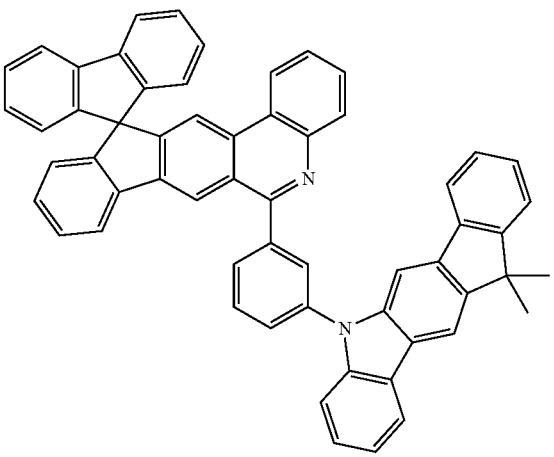

255
-continued
210
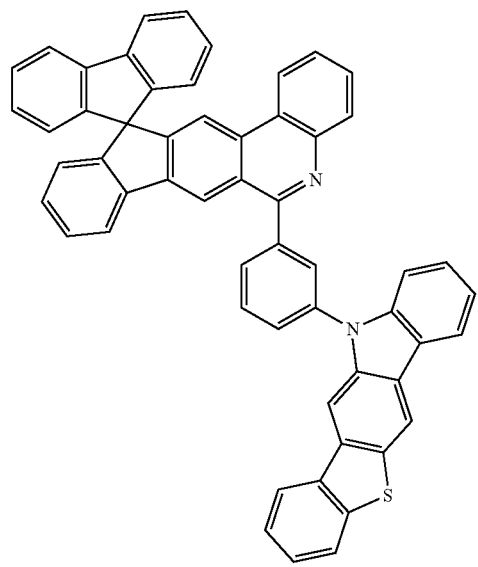
211
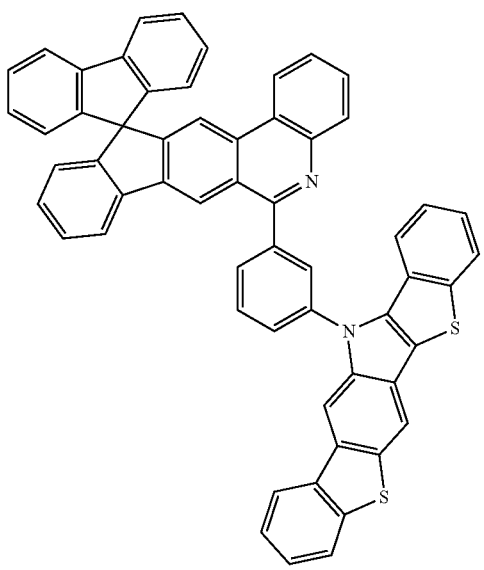
256
-continued
212
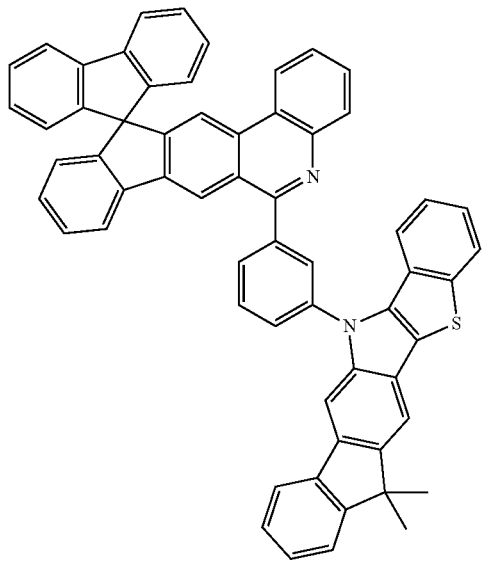
213
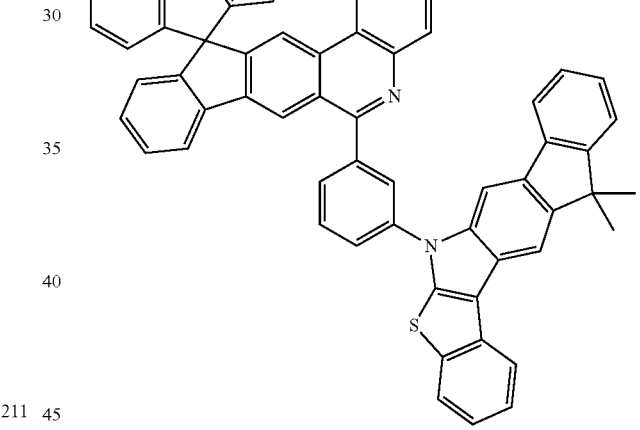
214
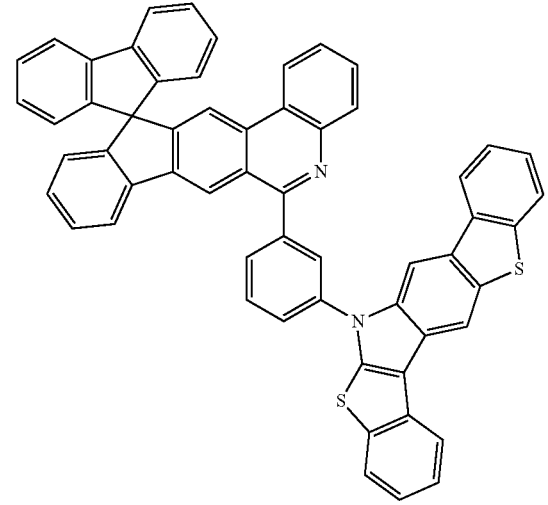

-continued
215
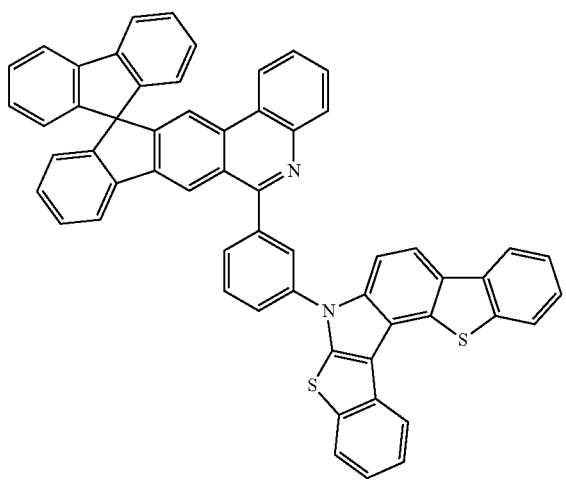
216
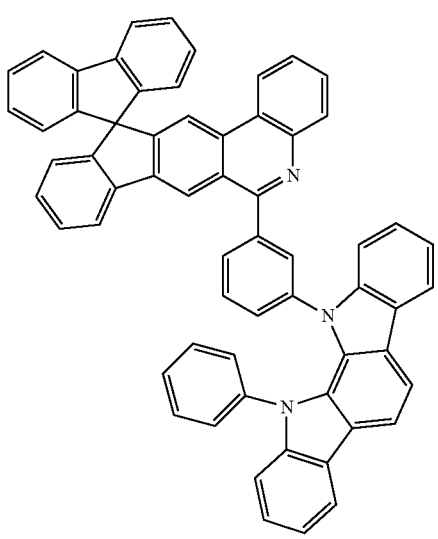
217
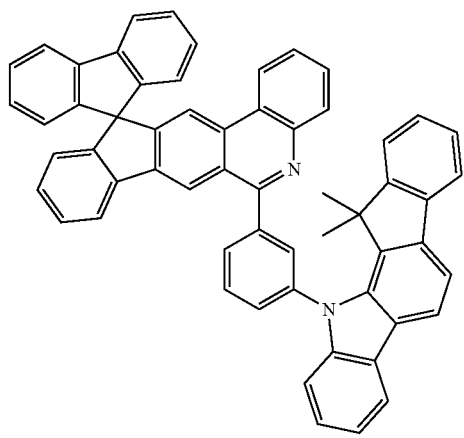
-continued
218
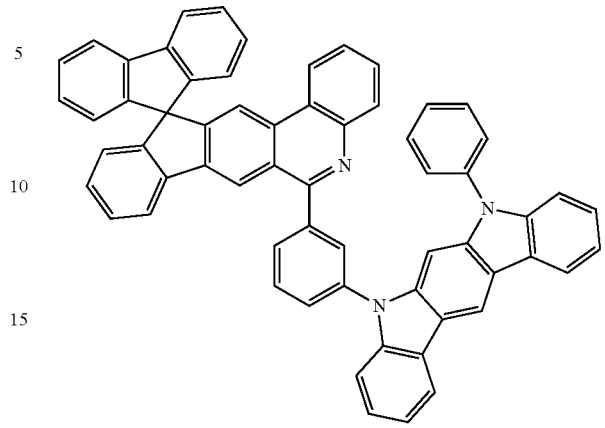
219
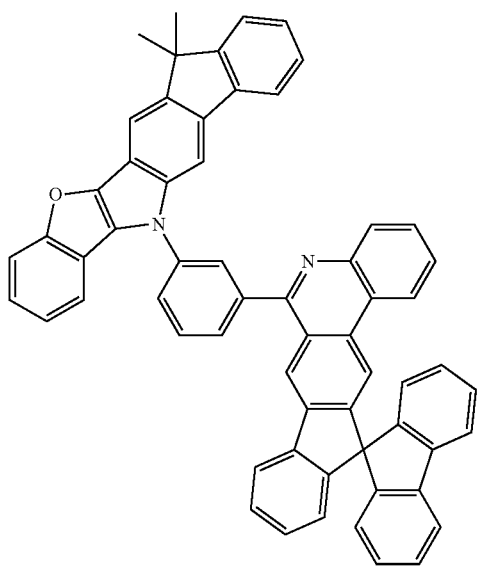
220
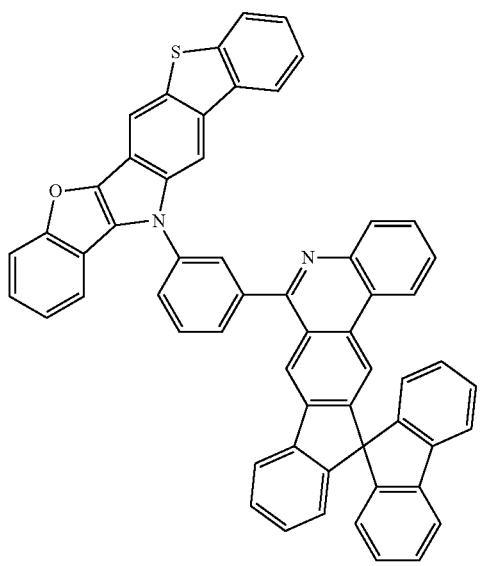

259
-continued
221
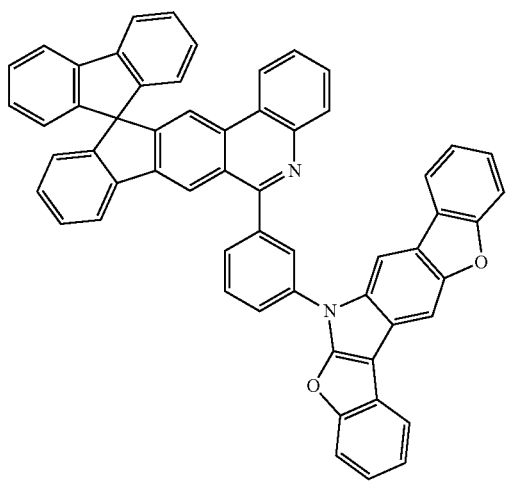
222
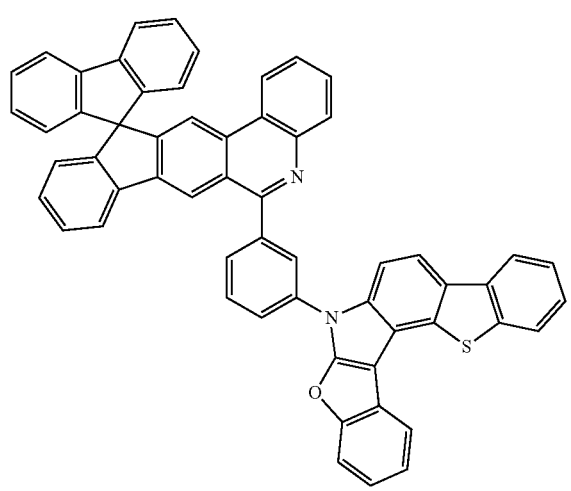
223
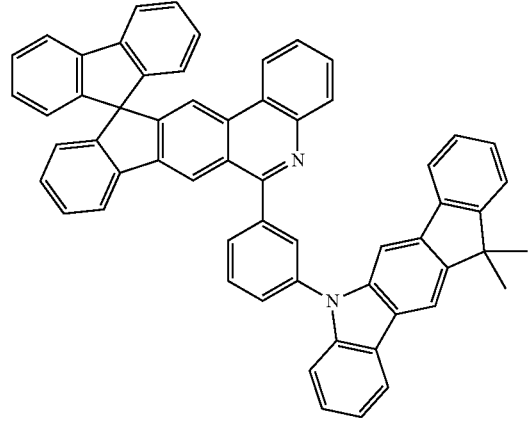
260
-continued
224
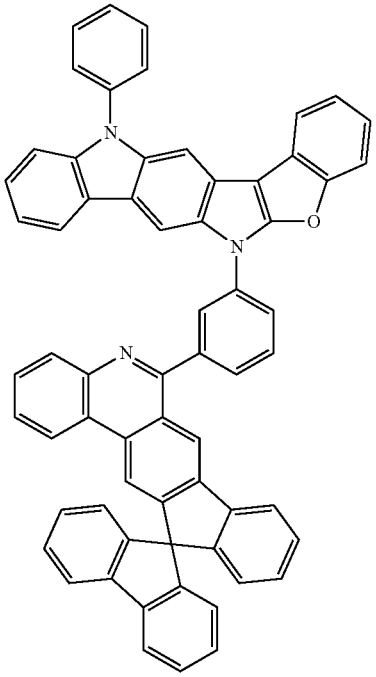
225
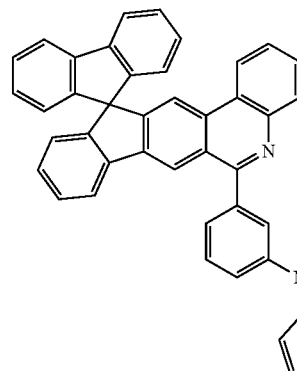
226
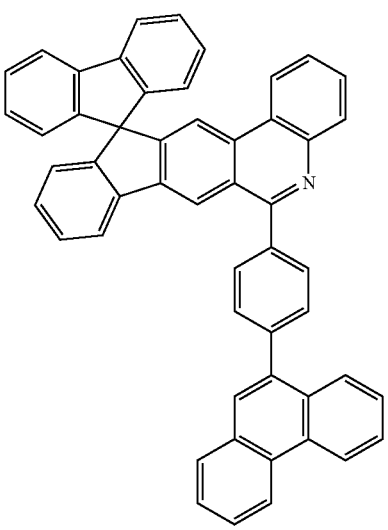

261
227
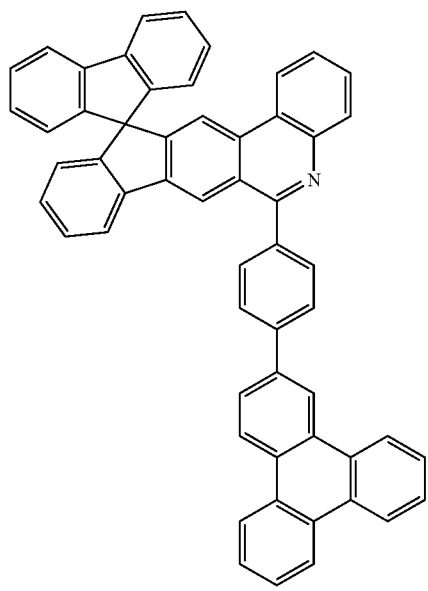
228
262
229
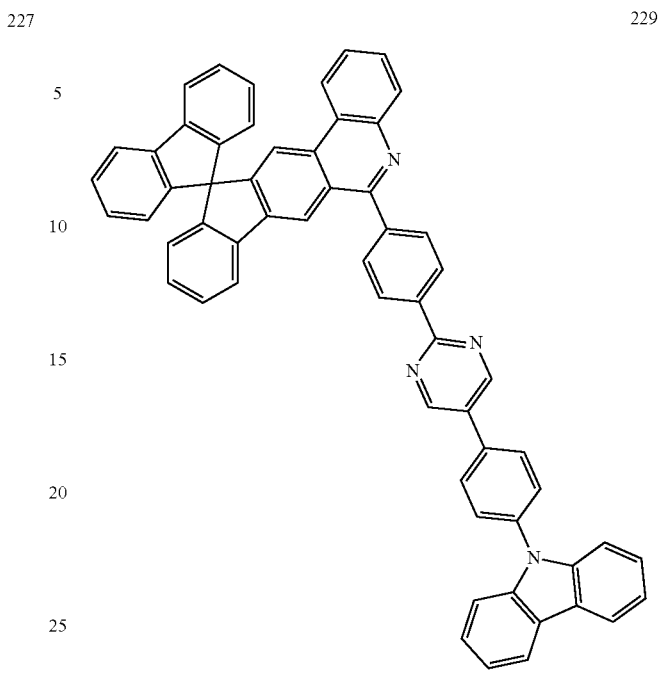
230

263
-continued
231
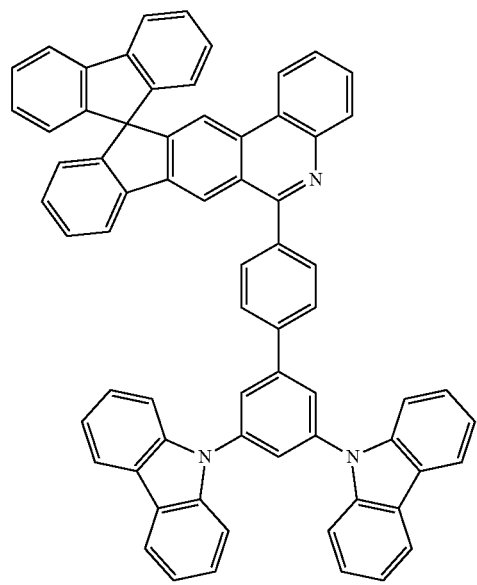
232
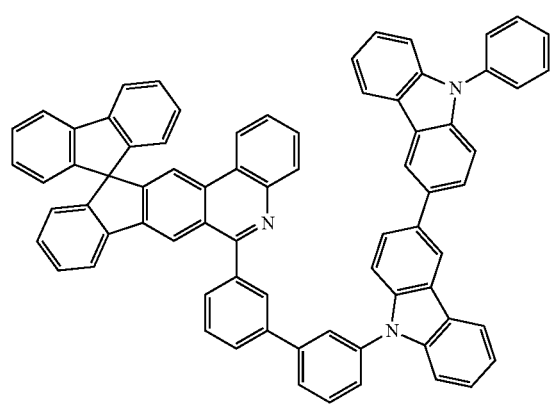
233
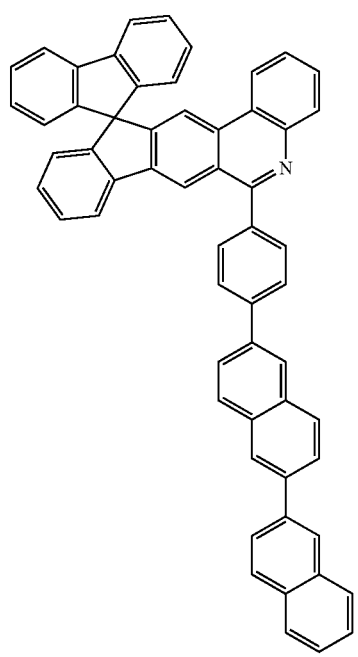
264
-continued
234
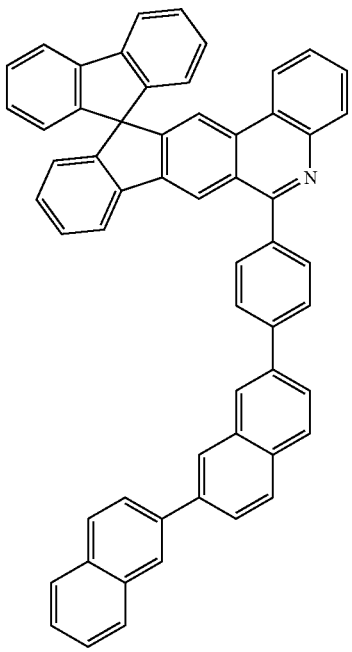
235
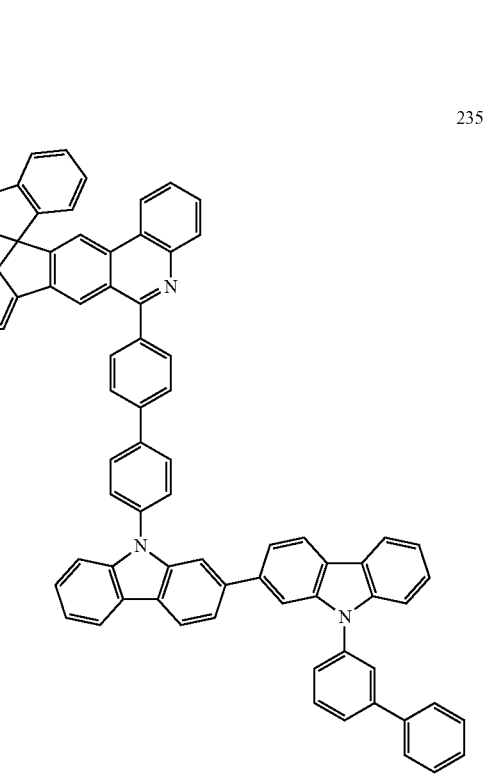

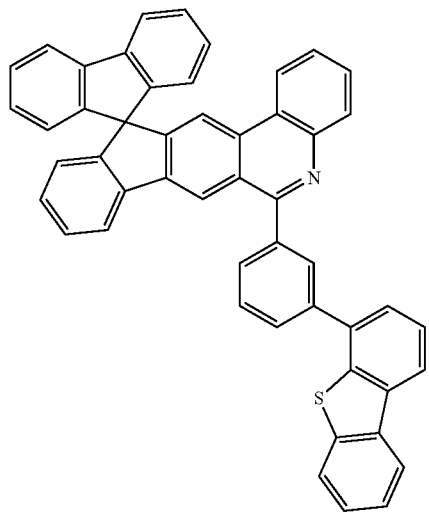
244
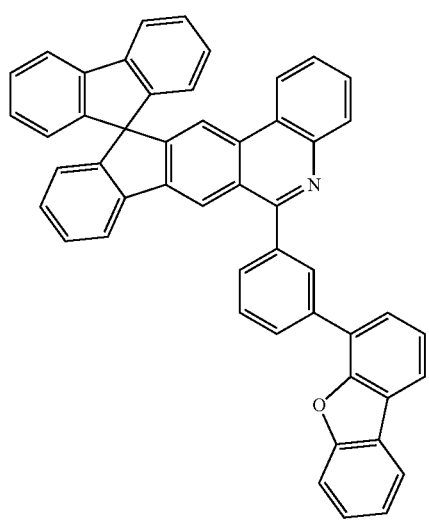
245
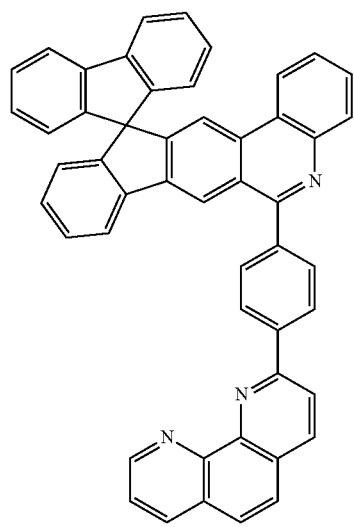
265
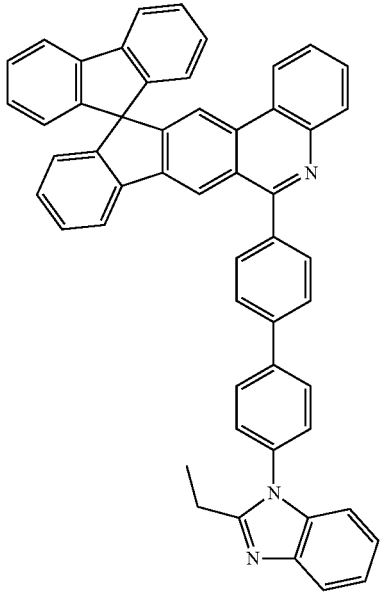
266
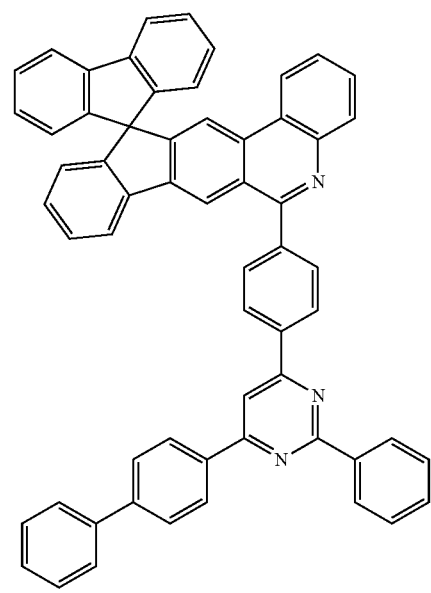
267

267
-continued
268
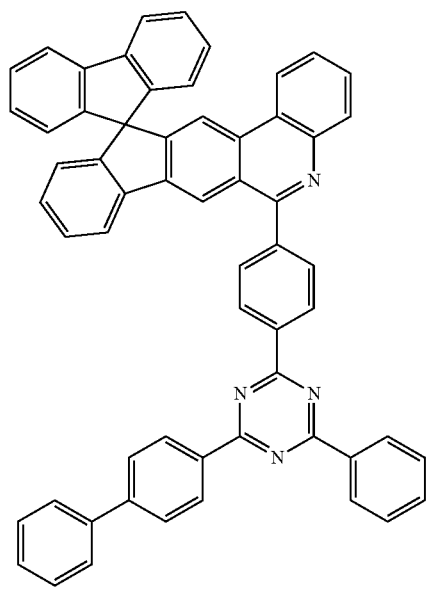
268
-continued
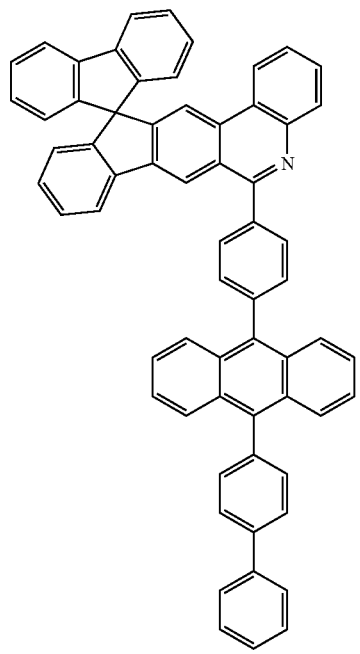
270
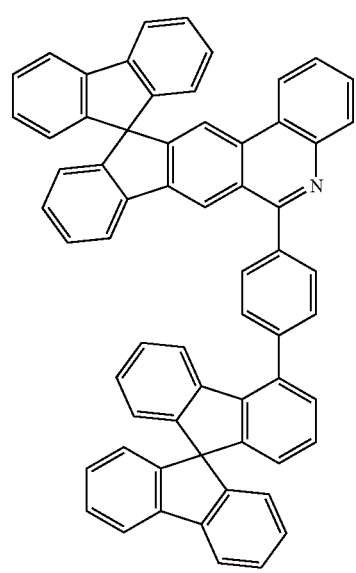
271
269
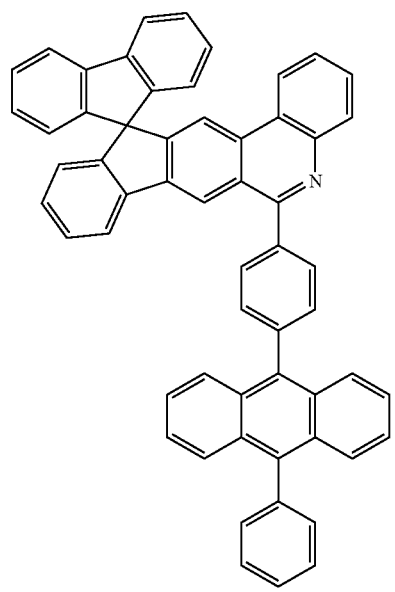
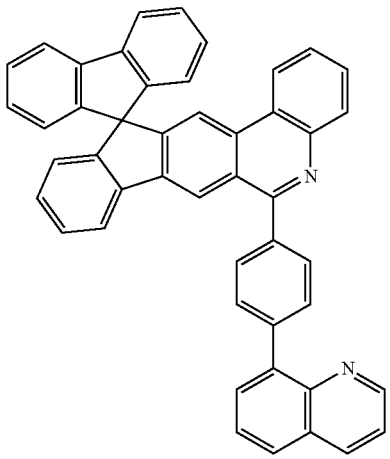
272

269
-continued
273
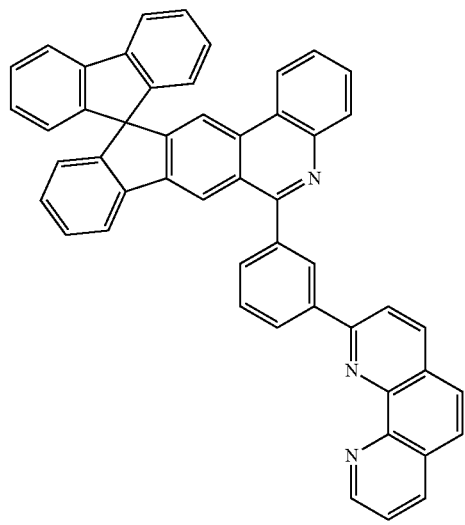
274
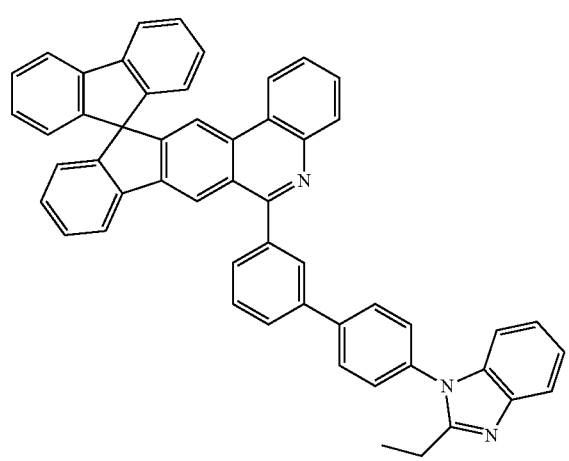
275
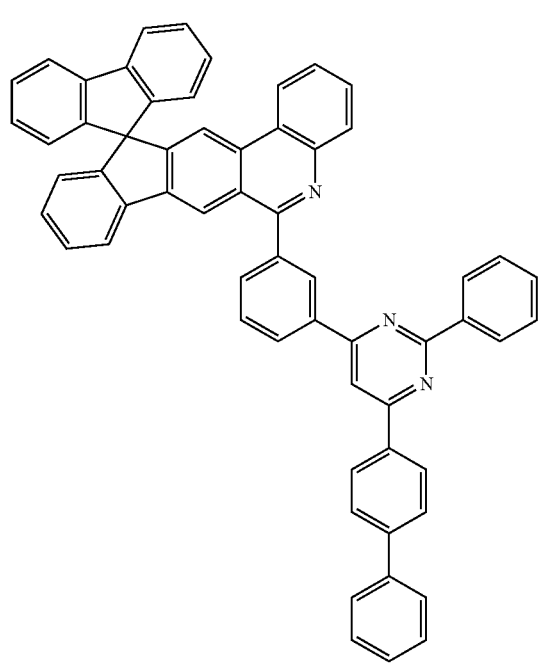
270
-continued
276
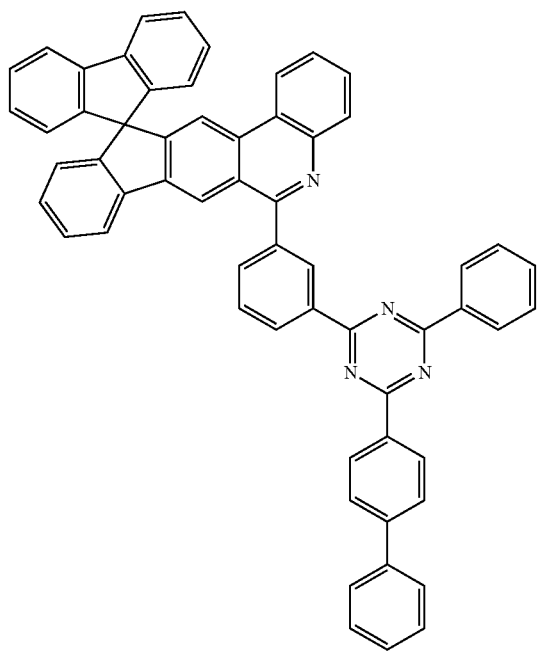
277
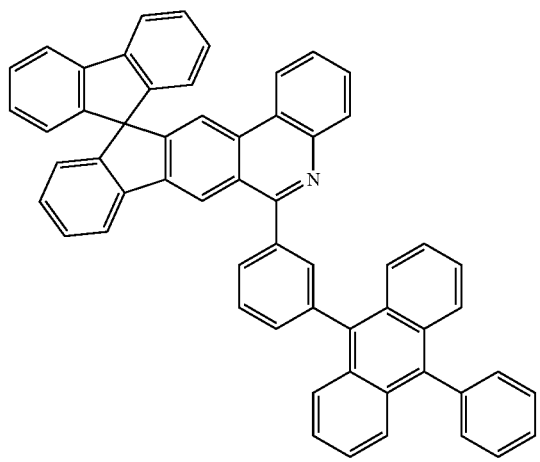
278
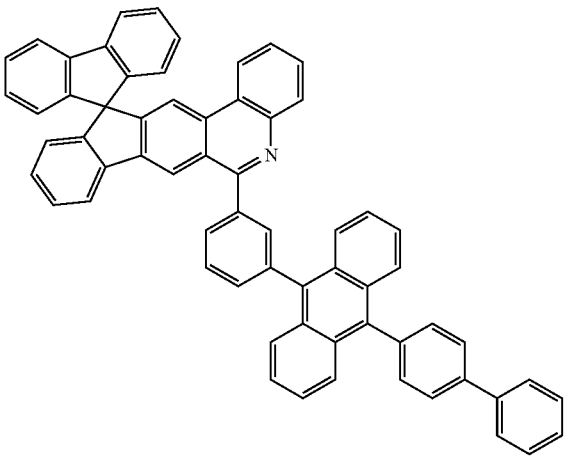

279
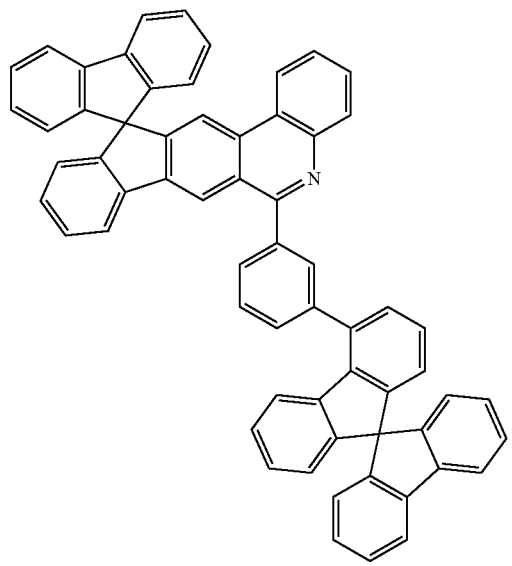
280
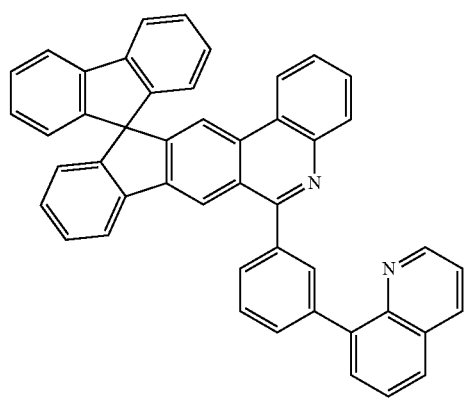
336
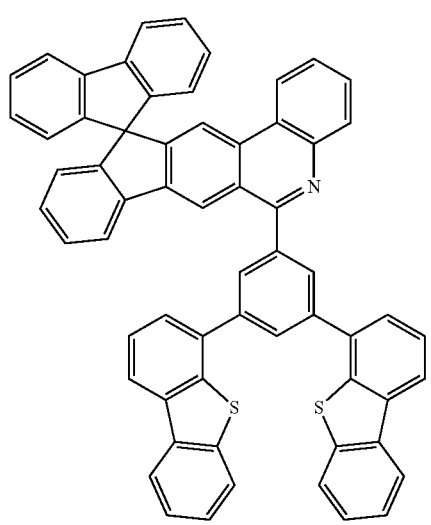
337
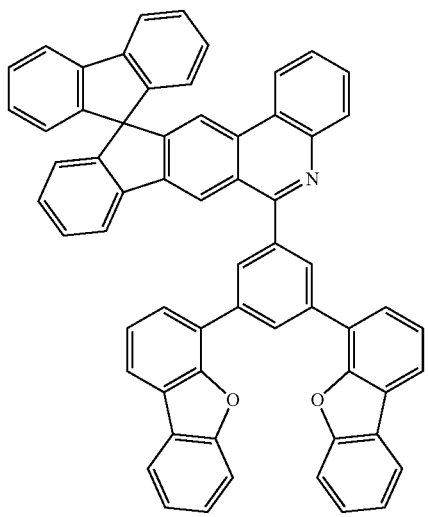
338
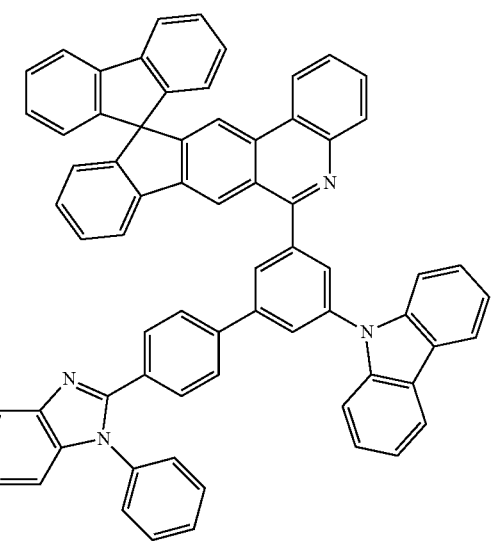
339
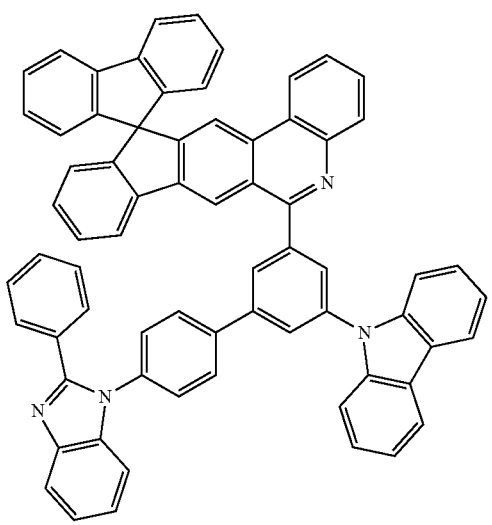

340
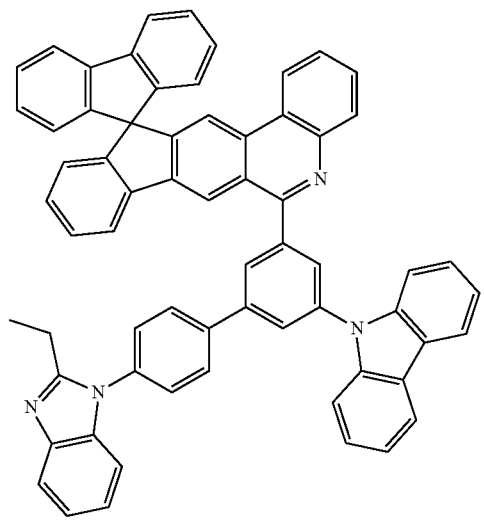
341
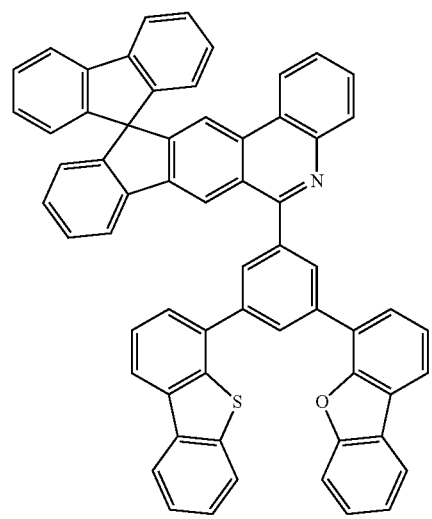
342
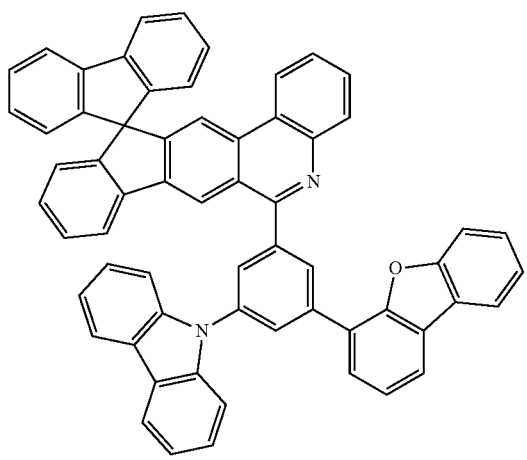
343
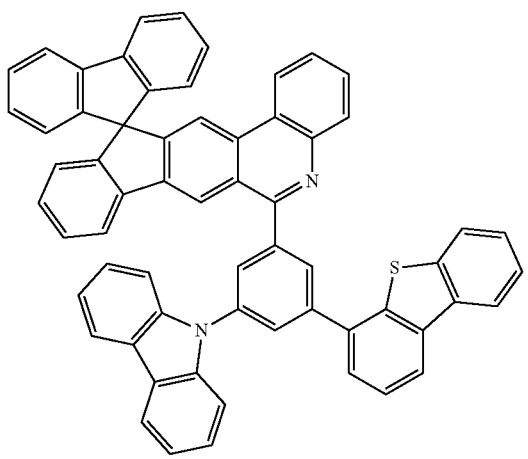
344
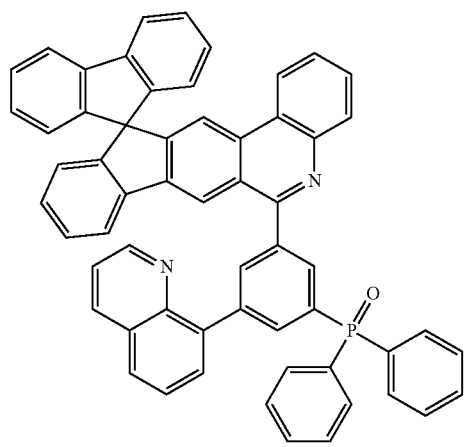
345
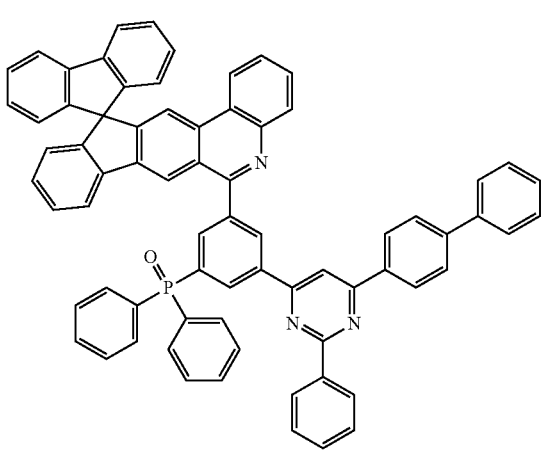

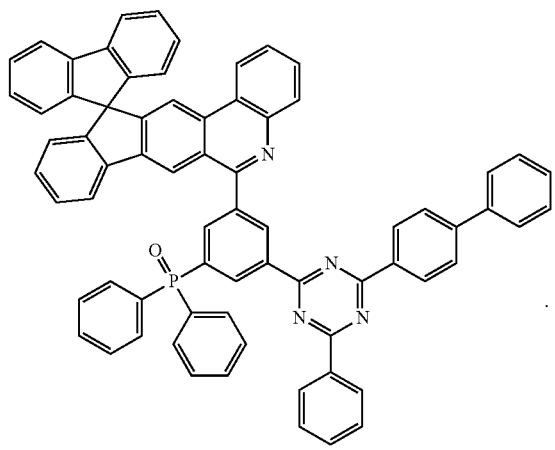

346

12. An organic light emitting device comprising: a positive electrode; a negative electrode; and one or more organic material layers provided between the positive electrode and the negative electrode, wherein one or more layers of the organic material layers comprise the compound of claim 1.

13. The organic light emitting device of claim 12, wherein the organic material layer comprising the compound is one or more layers selected from the group consisting of a hole injection layer, a hole transporting layer, a light emitting layer, a hole blocking layer, an electron transporting layer, and an electron injection layer.

14. The organic light emitting device of claim 12, wherein the organic material layer comprising the compound is an electron transporting layer.

15. The organic light emitting device of claim 12, wherein the organic material layer comprising the compound is a light emitting layer.

16. The organic light emitting device of claim 12, wherein the organic material layer comprising the compound is a hole blocking layer.

* * * * *